United States Patent
Peese et al.

(10) Patent No.: US 9,409,922 B2
(45) Date of Patent: Aug. 9, 2016

(54) IMIDAZOPYRIDINE MACROCYCLES AS INHIBITORS OF HUMAN IMMUNODEFICIENCY VIRUS REPLICATION

(71) Applicant: Bristol-Myers Squibb Company, Princeton, NJ (US)

(72) Inventors: Kevin Peese, Haddam, CT (US); Zhongyu Wang, Tolland, CT (US); John F. Kadow, Wallingford, CT (US); Prasanna Sivaprakasam, Middletown, CT (US); B. Narasimhulu Naidu, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/619,213

(22) Filed: Feb. 11, 2015

(65) Prior Publication Data
US 2015/0232480 A1    Aug. 20, 2015

Related U.S. Application Data

(60) Provisional application No. 61/941,004, filed on Feb. 18, 2014.

(51) Int. Cl.
*C07D 471/04* (2006.01)
*C07D 498/22* (2006.01)

(52) U.S. Cl.
CPC ............ *C07D 498/22* (2013.01); *C07D 471/04* (2013.01)

(58) Field of Classification Search
CPC .......................... C07D 471/04; C07D 498/22
See application file for complete search history.

(56) References Cited

U.S. PATENT DOCUMENTS

| 8,906,929 B2 | 12/2014 | Naidu et al. |
| 2010/0130737 A1* | 5/2010 | Itoh ...................... A61K 31/195 544/165 |

FOREIGN PATENT DOCUMENTS

| WO | WO 2010/130034 A1 | 11/2010 |
| WO | WO 2014/028384 A1 | 2/2014 |
| WO | WO 2014/159076 A1 | 10/2014 |
| WO | WO 2014/164409 A1 | 10/2014 |
| WO | WO 2014/164428 A1 | 10/2014 |
| WO | WO 2015/123182 A1 | 8/2015 |
| WO | WO 2015/123230 A1 | 8/2015 |
| WO | WO 2015/126737 A1 | 8/2015 |
| WO | WO 2015/126743 A1 | 8/2015 |
| WO | WO 2015/126758 A1 | 8/2015 |
| WO | WO 2015/126765 A1 | 8/2015 |
| WO | WO 2015/127003 A1 | 8/2015 |

OTHER PUBLICATIONS

Naidu et al., U.S. Appl. No. 62/042,300, filed Aug. 27, 2014.

* cited by examiner

*Primary Examiner* — Sun Jae Yoo

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection.

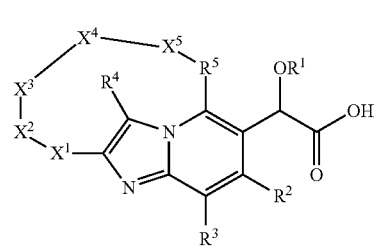

12 Claims, No Drawings

IMIDAZOPYRIDINE MACROCYCLES AS INHIBITORS OF HUMAN IMMUNODEFICIENCY VIRUS REPLICATION

CROSS-REFERENCE TO RELATED APPLICATIONS

This application claims priority to Provisional Patent Application U.S. Ser. No. 61/941,004 filed Feb. 18, 2014, hereby incorporated by reference in its entirety.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that an estimated 35.3 million people worldwide are infected with the virus (UNAIDS: Report on the Global HIV/AIDS Epidemic, 2013). In addition to the large number of individuals already infected, the virus continues to spread. Estimates from 2012 point to close to 2.3 million new infections in that year alone. In the same year there were approximately 1.6 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The nonnucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: however, the effect is only temporary as the virus readily develops resistance to all known agents used as monotherapy. However, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. N. Engl. J. Med. 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130842, WO2011076765, WO2012003497, WO2012003498, WO2012033735, WO2012065963, WO2012066442, WO2013012649, WO2013043553, WO2013062028, WO2013073875, WO2013134113, and WO2013134142.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I where:

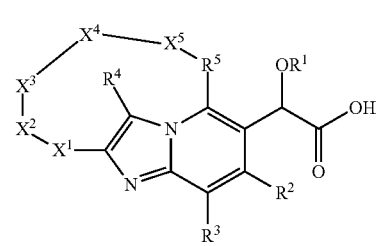

$R^1$ is hydrogen, alkyl, or cycloalkyl;
$R^2$ is hydrogen or alkyl;
$R^3$ is hydrogen, halo, alkyl, or (alkyl)SO$_2$NH—;
$R^4$ is hydrogen or alkyl;
$R^5$ is azetidinyl, pyrrolidinyl, piperidinyl, piperazinyl, morpholinyl, homopiperidinyl, homopiperazinyl, or homomorpholinyl substituted with 0-3 substituents selected from halo, alkyl, haloalkyl, hydroxy, alkoxy, and haloalkoxy;
$Ar^1$ is phenyl substituted with 0-3 substituents selected from cyano, halo, alkyl, haloalkyl, alkoxy, and haloalkoxy;
$Ar^2$ is imidazolyl or oxadiazolyl and is substituted with 0-3 substituents selected from halo and alkyl;
$X^1$ is CONHCH$_2$—, $Ar^1$, or $(Ar^2)CH_2$—;
$X^2$ is phenyl substituted with 0-3 substituents selected from cyano, halo, alkyl, haloalkyl, alkoxy, and haloalkoxy;
$X^3$ is —CH—, —CH$_2$—, or —O—;
$X^4$ is alkylene or alkenylene; and
$X^5$ is —CH—, —CH$_2$—, or —O—;
or a pharmaceutically acceptable salt thereof.

Another aspect of the invention is a compound of formula I where $R^1$ is alkyl; $R^2$ is alkyl; $R^3$ is hydrogen, halo, alkyl, or (alkyl)SO$_2$NH—; $R^4$ is hydrogen; $R^5$ is azetidinyl, pyrrolidinyl, piperidinyl, piperazinyl, morpholinyl, homopiperidinyl, homopiperazinyl, or homomorpholinyl substituted with 0-3 substituents selected from halo, alkyl, haloalkyl, hydroxy, alkoxy, and haloalkoxy; $Ar^1$ is phenyl substituted with 0-3 substituents selected from cyano, halo, alkyl, haloalkyl, alkoxy, and haloalkoxy; $Ar^2$ is imidazolyl or oxadiazolyl and is substituted with 0-3 substituents selected from halo and alkyl; $X^1$ is CONHCH$_2$—, $Ar^1$, or $(Ar^2)CH_2$—; $X^2$ is phenyl substituted with 0-3 substituents selected from cyano, halo, alkyl, haloalkyl, alkoxy, and haloalkoxy; $X^3$ is —CH—, —CH$_2$—, or —O—; $X^4$ is alkylene or alkenylene; and $X^5$ is —CH—, —CH$_2$—, or —O—; or a pharmaceutically acceptable salt thereof.

Another aspect of the invention is a compound of formula I $R^5$ is piperidinyl substituted with 0-3 alkyl substituents; $Ar^1$ is phenyl substituted with 0-3 substituents selected from cyano, halo, alkyl, haloalkyl, alkoxy, and haloalkoxy; $Ar^2$ is imidazolyl or oxadiazolyl and is substituted with 0-3 substituents selected from halo and alkyl; $X^1$ is CONHCH$_2$—, $Ar^1$, or $(Ar^2)CH_2$—; $X^2$ is phenyl substituted with 0-3 substituents selected from cyano, halo, alkyl, haloalkyl, alkoxy, and haloalkoxy; $X^3$ is —CH—, —CH$_2$—, or —O—; $X^4$ is alkylene or alkenylene; and $X^5$ is —CH—, —CH$_2$—, or —O—; or a pharmaceutically acceptable salt thereof.

Another aspect of the invention is a compound of formula I where $R^1$ is alkyl, $R^2$ is alkyl, $R^3$ is hydrogen, halo, alkyl, or (alkyl)SO$_2$NH—, and $R^4$ is hydrogen or alkyl.

Another aspect of the invention is a compound of formula I where $R^5$ is piperidinyl substituted with 0-3 substituents selected from halo, alkyl, haloalkyl, hydroxy, alkoxy, and haloalkoxy.

Another aspect of the invention is a compound of formula I where $R^5$ is piperidinyl substituted with 0-3 alkyl substituents.

Another aspect of the invention is a compound of formula I where $X^1$ is $Ar^1$.

Another aspect of the invention is a compound of formula I where $X^1$ is CONHCH$_2$— or $(Ar^2)CH_2$—;

Another aspect of the invention is a compound of formula I where $X^3$ is —O—, $X^4$ is alkylene or alkenylene; and $X^5$ is —O—.

For a compound of Formula I, the scope of any instance of a variable substituent, including $R^1$, $R^2$, $R^3$, $R^4$, $R^5$, $Ar^1$, $Ar^2$, $X^1$, $X^2$, $X^3$, $X^4$, and $X^5$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 6 carbons. "Alkenylene" means a straight or branched divalent alkene group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Alkyleneoxy" means a straight or branched divalent alkyloxy group composed of 1 to 6 carbons, for example, —CH$_2$CH$_2$CH$_2$O—. "Alkenyleneoxy" means a straight or branched divalent alkeneoxy group composed of 2 to 6 carbons with at least one double bond, for example, —CH═CHCH$_2$O—. "Halo" includes fluoro, chloro, bromo, and iodo. "Halo" includes all halogenated isomers from monohalo substituted to perhalo substituted in substituents defined with halo, for example, "Haloalkyl" "haloalkoxy", "halophenyl", and "halophenoxy." "Aryl" includes carbocyclic and heterocyclic aromatic substituents. Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication:

A recombinant NL-RLuc proviral clone was constructed in which a section of the nef gene from NL4-3 was replaced with the *Renilla* Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC 18 at the PvuII site. The NL-RLuc virus was prepared by transfection of 293T cells with the plasmid pNLR-Luc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$(Johnson V A, Byington R T. Infectivity Assay. In *Techniques in HIV Research*. ed. Aldovini A, Walker B D. 71-76. New York: Stockton Press. 1990). Results are shown in Table 1.

TABLE 1

| Example | $EC_{50}$ µM |
|---|---|
| 1 | 0.071 |
| 2 | 0.016 |
| 3 | 0.027 |
| 4 | 0.010 |
| 5 | 0.007 |
| 6 | 0.005 |
| 7 | 0.005 |
| 8 | 0.015 |
| 9 | 0.009 |
| 10 | 0.004 |
| 11 | 0.012 |
| 12 | 0.003 |
| 13 | 0.008 |
| 14 | 0.002 |
| 15 | 0.002 |
| 16 | 0.004 |
| 17 | 0.006 |
| 18 | 0.008 |
| 19 | 0.015 |
| 0.020 | 0.011 |
| 21 | 0.005 |
| 22 | 0.024 |
| 23 | 0.019 |
| 24 | 0.020 |
| 25 | 0.030 |
| 26 | 0.026 |
| 27 | 0.013 |
| 28 | 0.008 |
| 29 | 0.030 |
| 30 | 0.021 |
| 31 | 0.019 |
| 32 | 0.010 |
| 33 | 0.025 |
| 34 | 0.003 |
| 35 | 0.007 |
| 36 | 0.010 |
| 37 | 0.010 |
| 38 | 0.093 |
| 39 | 0.012 |
| 40 | nd |
| 41 | 0.013 |
| 42 | 0.060 |
| 43 | 0.011 |
| 44 | 0.331 |
| 45 | 0.047 |
| 46 | 0.004 |
| 47 | 0.007 |
| 48 | 0.024 |
| 49 | 0.002 |
| 50 | 0.010 |
| 51 | 0.0 |
| 52 | 0.0 |
| 53 | 0.008 |
| 54 | 0.004 |
| 55 | 0.009 |
| 56 | 0.072 |
| 57 | 0.013 |
| 58 | 0.0 |
| 59 | 0.0 |
| 60 | 0.0 |
| 61 | 0.015 |
| 62 | 0.0 |
| 63 | 0.018 |
| 64 | 0.006 |
| 65 | 0.006 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "DCM" for dichloromethane, "ACN" for acetonitrile; "DME" for 1,2-dimethoxyethane; "HOBt" for 1-hydroxybenzotriazole hydrate; and "DIEA" for diisopropylethylamine.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "prep-" for preparative, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I, Compounds I-1 are commercially available or synthesized by reactions well known in the art. Treatment of I-1 with sulfuric acid and nitric acid under hot conditions provided intermediates I-2 which was converted to the tert-butyl ester intermediates I-3 by reacting with tert-butyl acetate in the presence of perchloric acid. Intermediates I-3 conveniently transformed to ketoesters I-6 using conditions well-known to those skilled in the art. Intermediates I-6 were converted to intermediate I-8 via a carboxylic acid intermediates I-7 by sequence of reactions well know those skilled in the art. Amines I-9 were coupled to intermediates I-8 in the presence of organic base such as Hunig's base to provide I-10. Chiral Lewis acid mediated reduction of ketoesters I-10 with catecholborane furnished chiral alcohols I-11. Tertiary butylation of alcohols I-11 by well-known conditions, including but not limited to tertiary-butyl acetate and perchloric acid, gave intermediates I-12. Selective hydrolysis of diester intermediates I-12 by using conditions well-known in the art gave the mono carboxyliv acid intermediates I-13, HATU mediated coupling of amines I-14 with intermediates I-13 furnished amides I-15. Treatment of intermediates I-15 to ring closing metathesis, hydrogenation and hydrolysis conditions provided the macrocycles I-16.

Scheme I

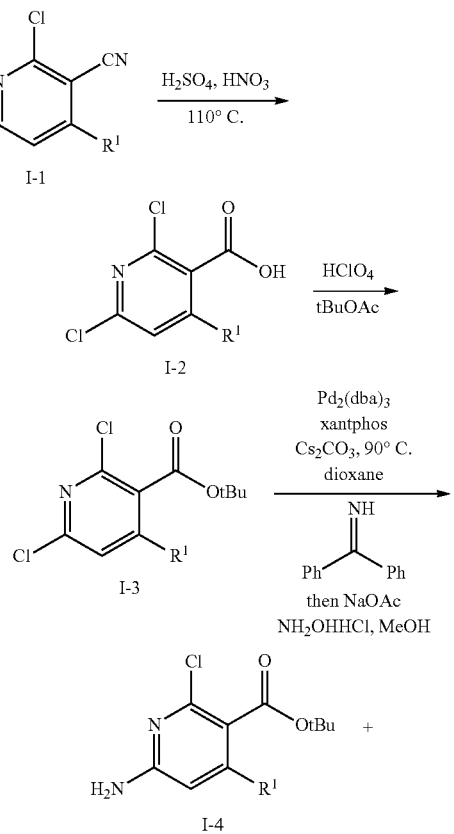

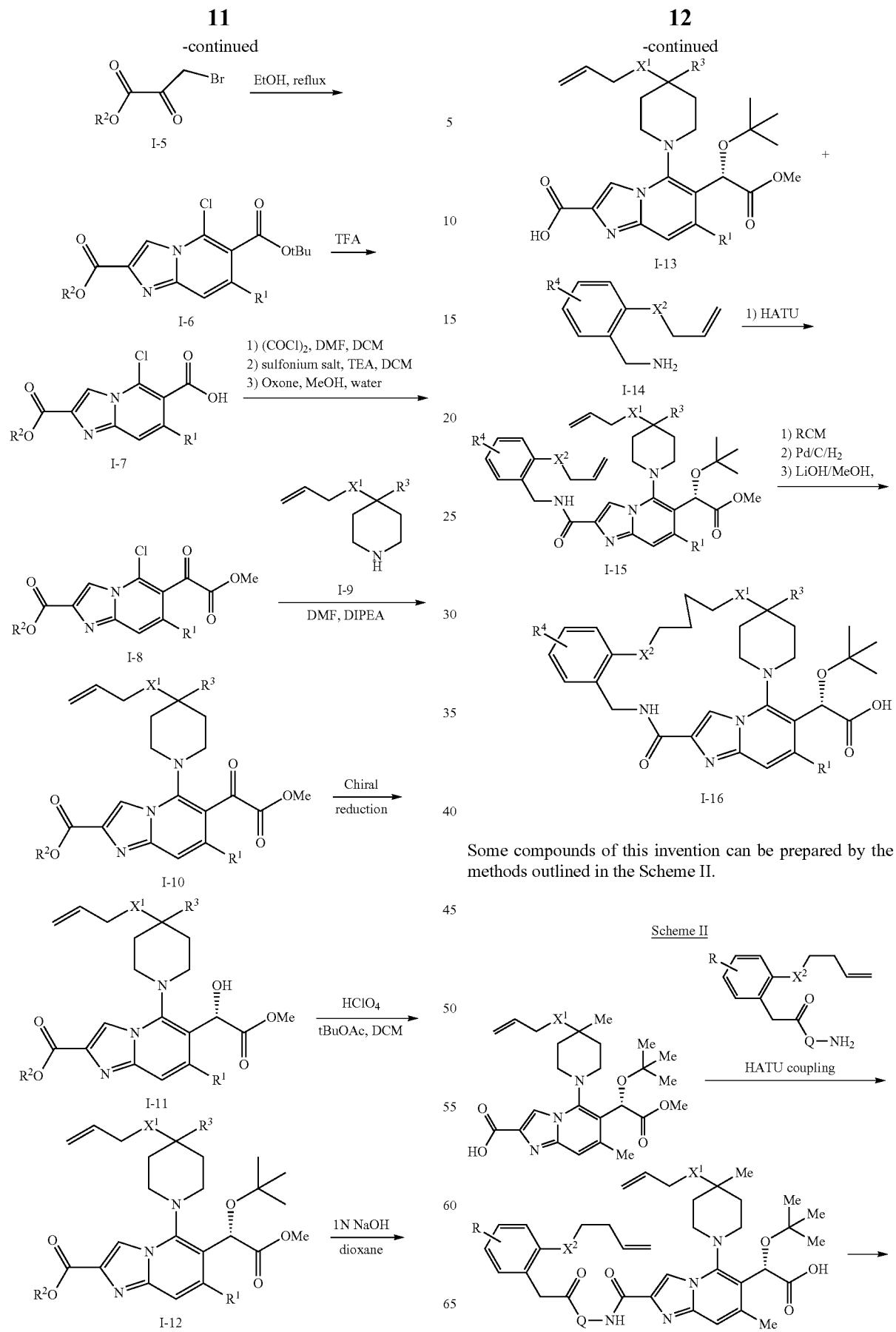
Some compounds of this invention can be prepared by the methods outlined in the Scheme II.
Scheme II

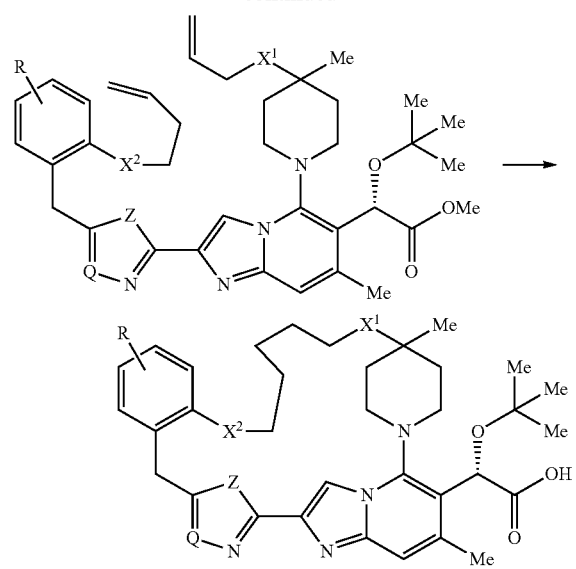
Q = C or N
Z = O or S
Some compounds of this invention can be prepared by the methods outlined in the Scheme III.
Scheme III
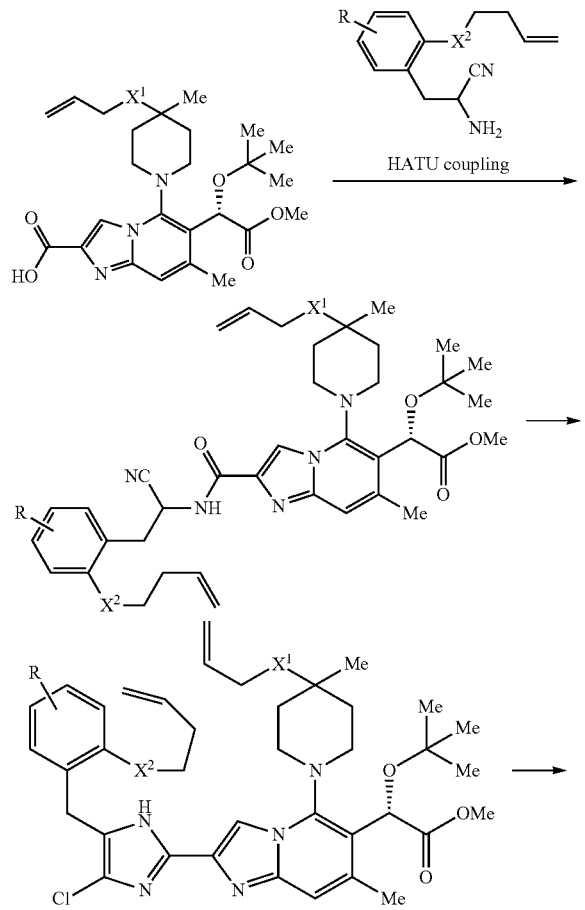
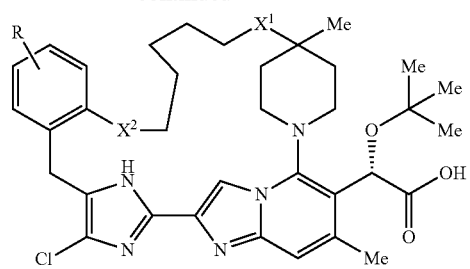
Some compounds of this invention can be prepared by the methods outlined in the Scheme IV.
Scheme IV
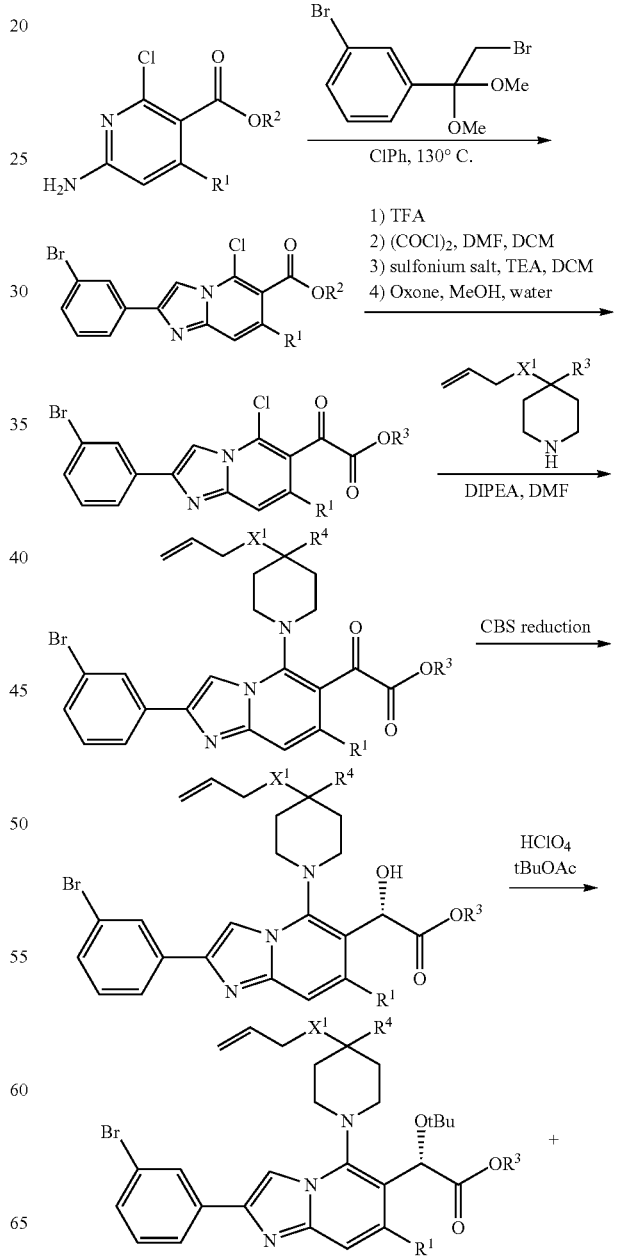

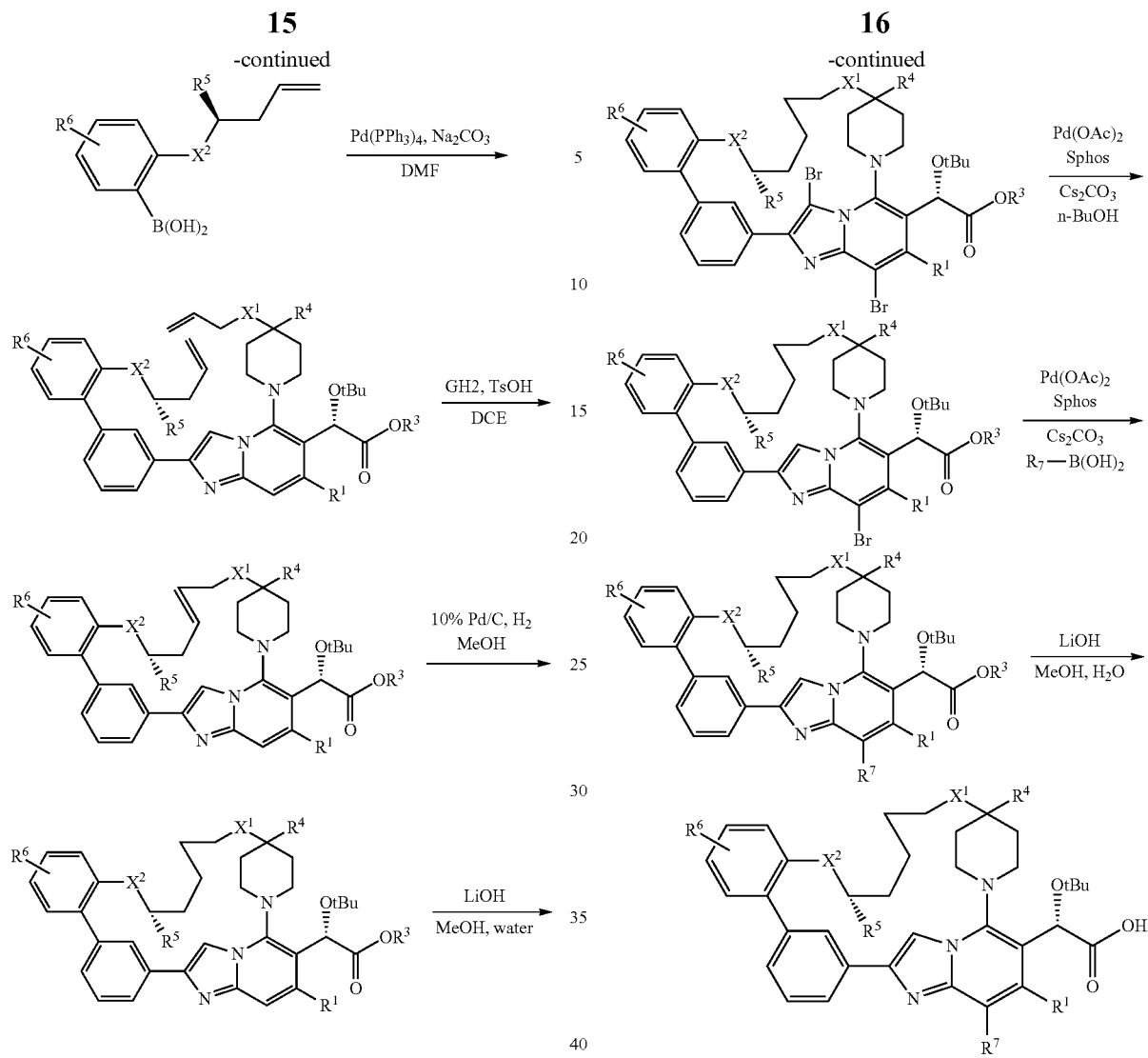
Some compounds of this invention can be prepared by the methods outlined in the Scheme V.
Scheme V
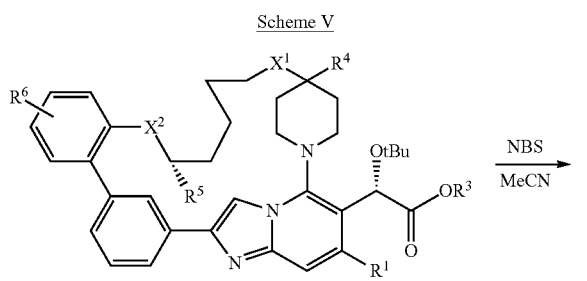
Some compounds of this invention can be prepared by the methods outlined in the Scheme VI.
Scheme VI
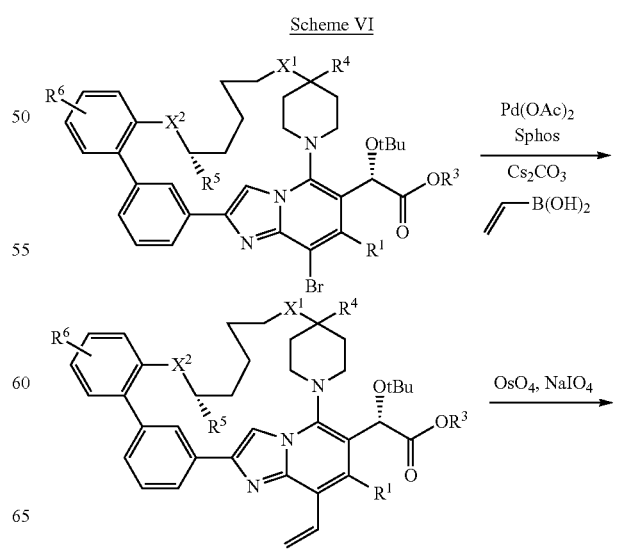

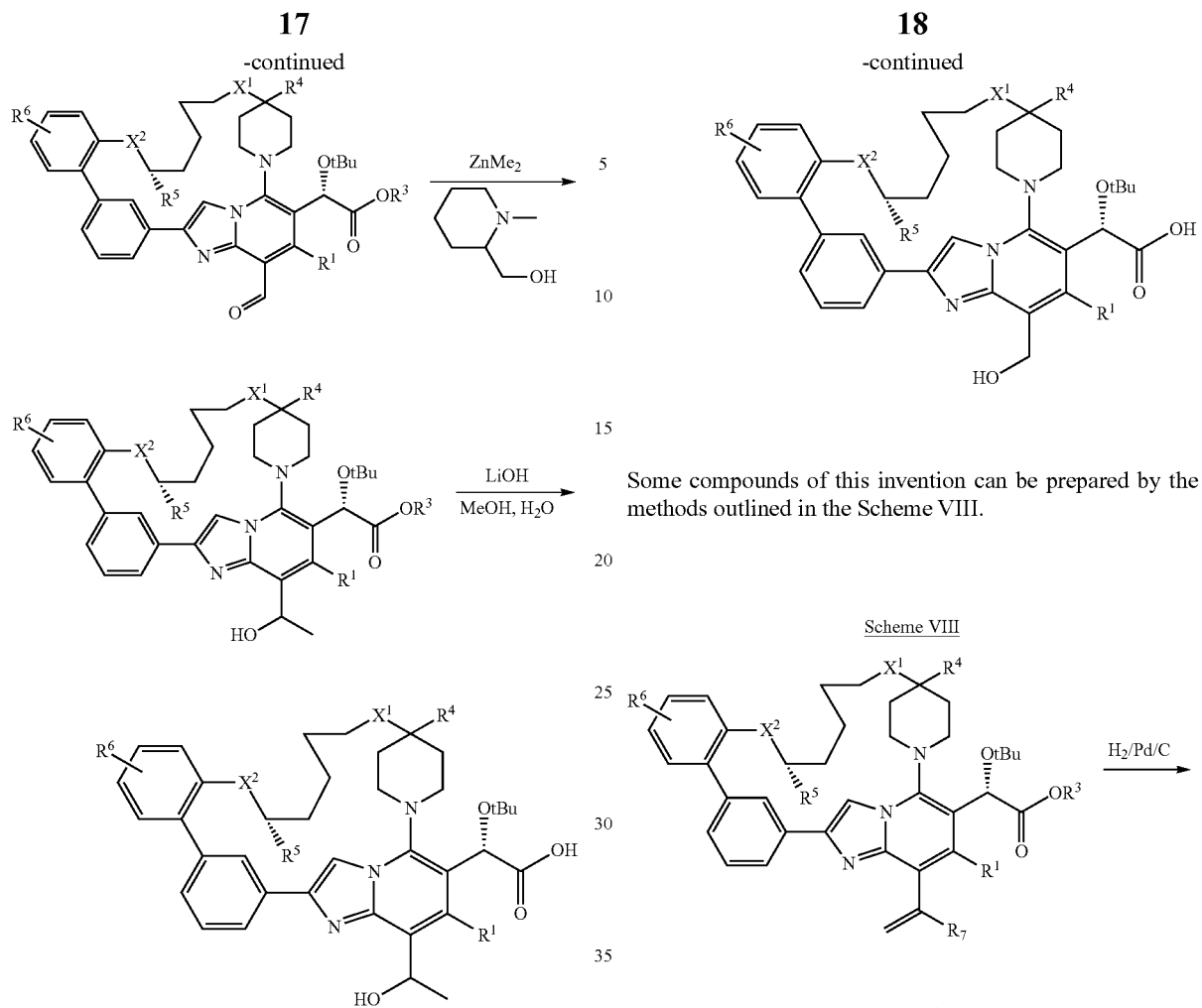
Some compounds of this invention can be prepared by the methods outlined in the Scheme VII.
Some compounds of this invention can be prepared by the methods outlined in the Scheme VIII.
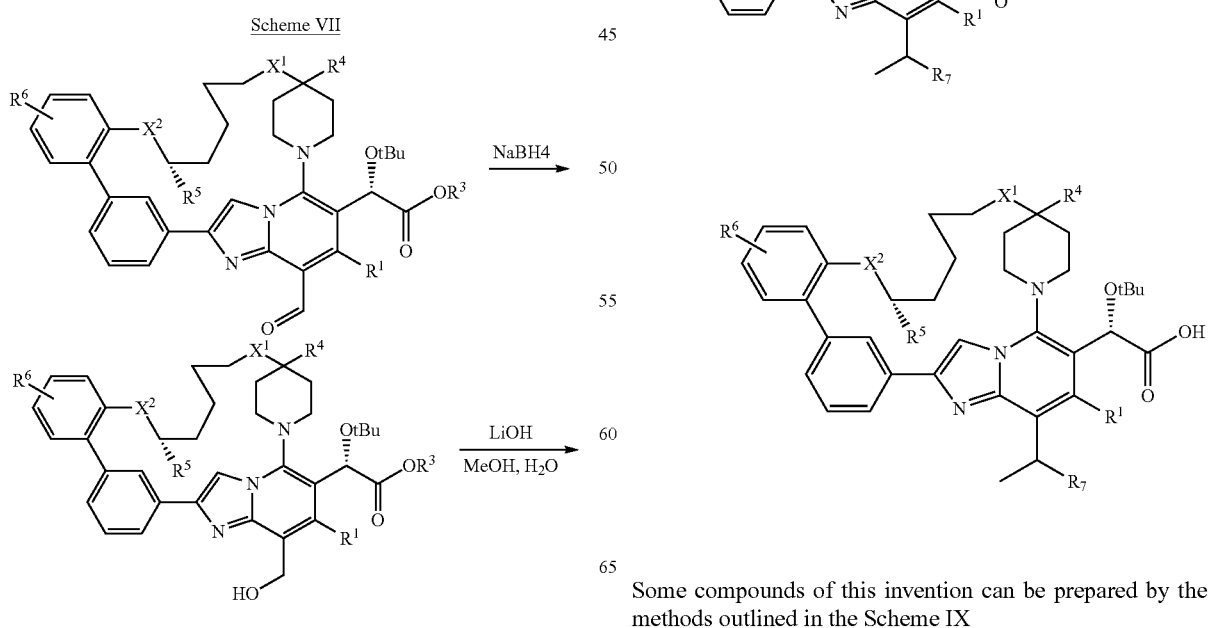
Some compounds of this invention can be prepared by the methods outlined in the Scheme IX

Scheme IX
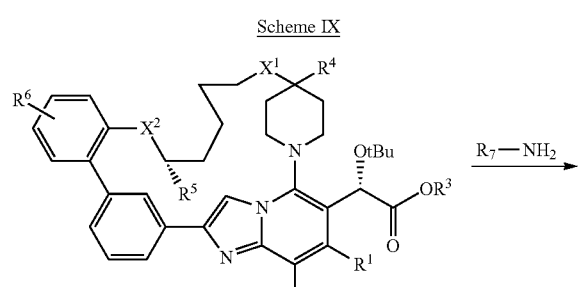
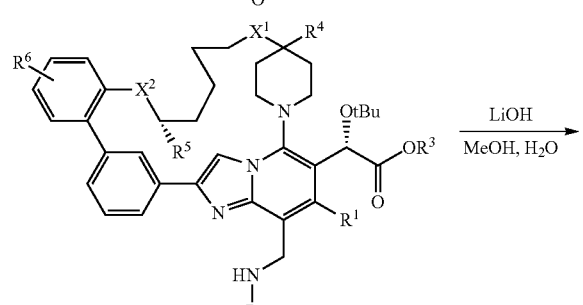
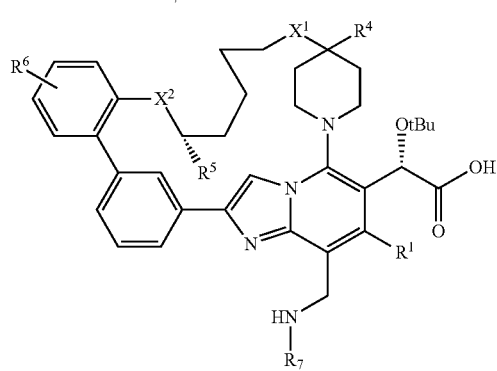
Some compounds of this invention can be prepared by the methods outlined in the Scheme X.
Scheme X
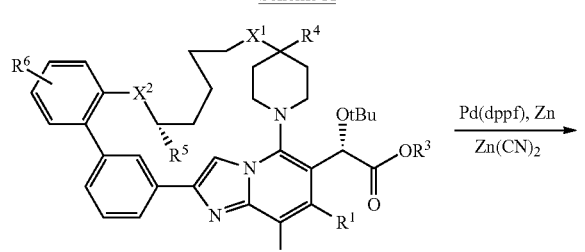
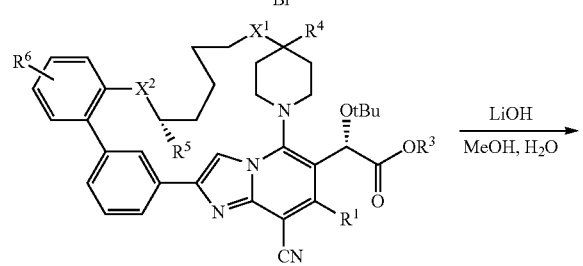
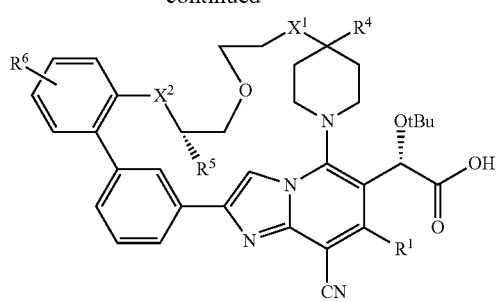
Some compounds of this invention can be prepared by the methods outlined in the Scheme XI.
Scheme XI
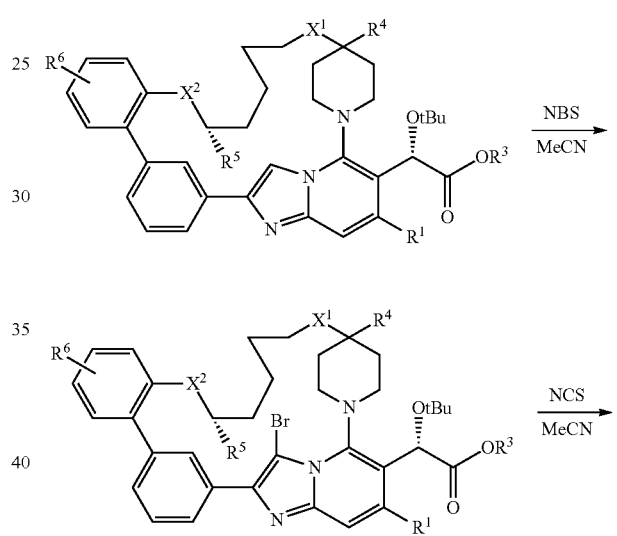

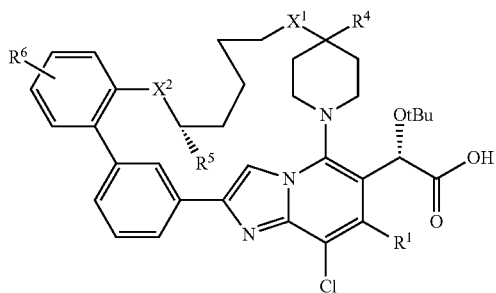
Some compounds of this invention can be prepared by the methods outlined in the Scheme XII.
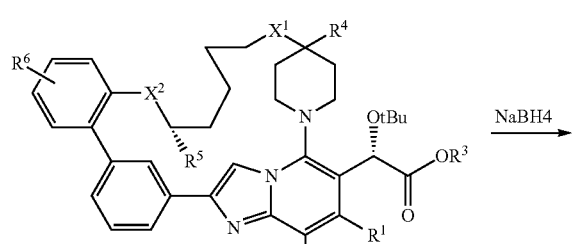
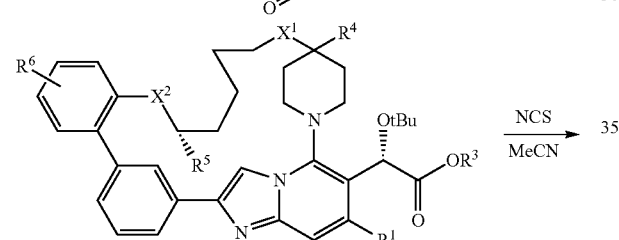
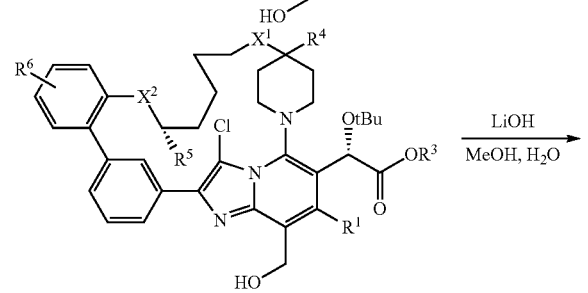
Some compounds of this invention can be prepared by the methods outlined in the Scheme XIII.
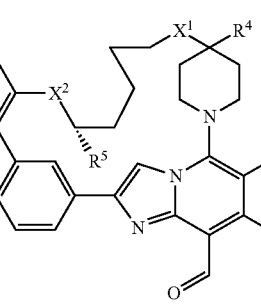
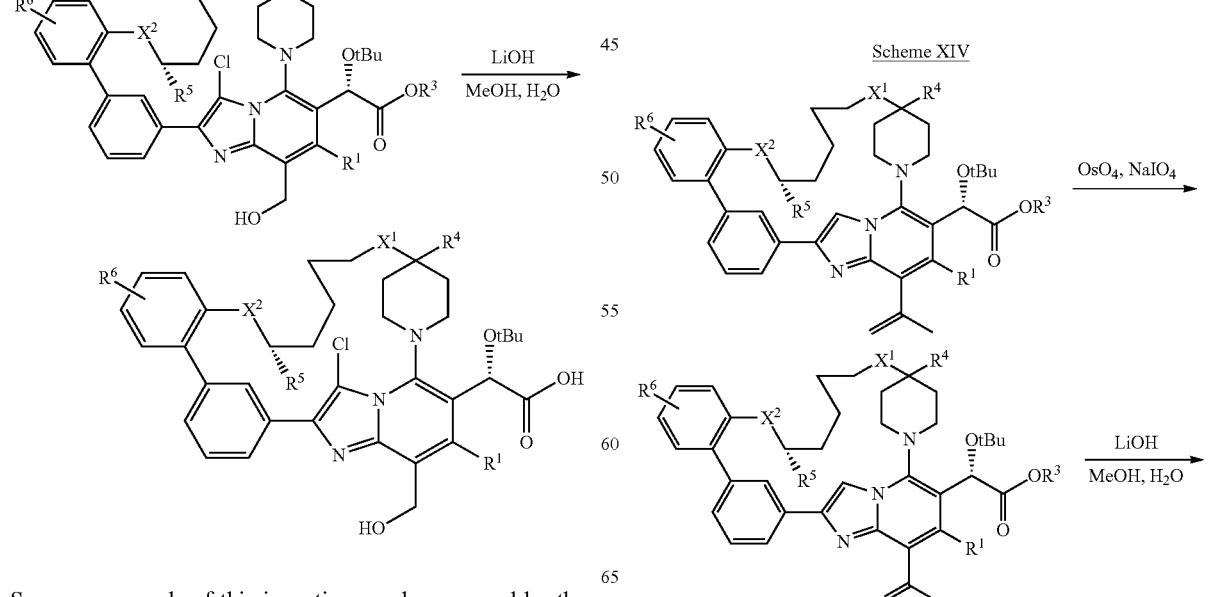
Some compounds of this invention can be prepared by the methods outlined in the Scheme XIV.

-continued

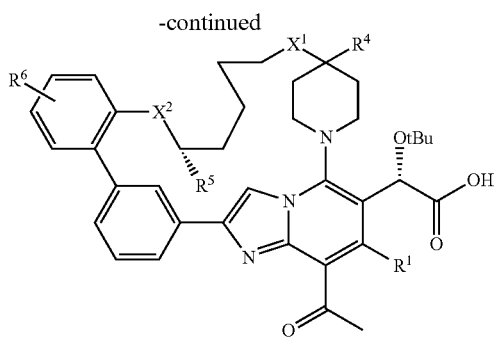

Some compounds of this invention can be prepared by the methods outlined in the Scheme XV.

Scheme XV

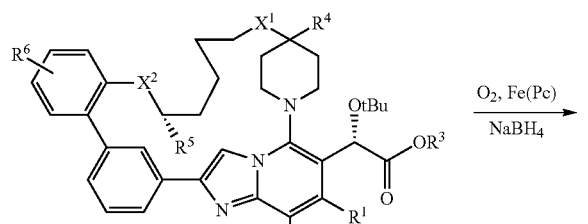

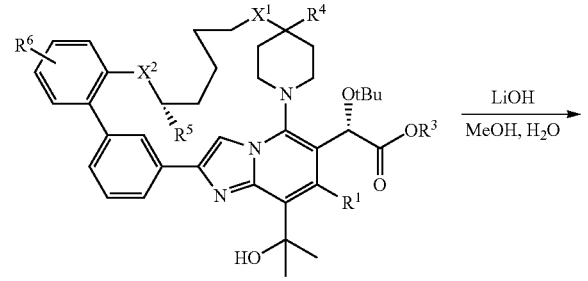

The compounds described herein were purified by the methods well known to those skilled in art by normal phase column chromatography on silica gel column using appropriate solvent system described. Preparative HPLC purifications mentioned in this experimentation section were carried out gradient elution either on Sunfire Prep C18 ODB column (5 μm; 19 or 30×100 mm) or Waters Xbridge column (5 μM; 19 or 30×100 mm) using the following mobile phases: Mobile phase A: 95:5 H$_2$O/acetonitrile with 10 mM NH$_4$OAc and mobile phase B:A: 95:5 acetonitrile/H$_2$O with: 10 mM NH$_4$OAc; or mobile phase A: 95:5 H$_2$O/acetonitrile with 0.1% TFA and mobile phase B:A: 95:5 acetonitrile/H$_2$O with: 0.1% TFA; or mobile phase A: 95:5 H$_2$O/MeOH with 20 mM NH$_4$OAc and mobile phase B: 95:5 MeOH/H$_2$O with 20 mM NH$_4$OAc.

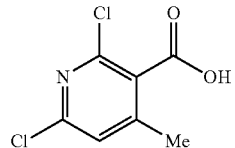 [SMILES: Cc1cc(Cl)nc(Cl)c1C(=O)O]

2,6-dichloro-4-methylnicotinic acid

Prepared from commercially available 2,6-dichloro-4-methylnicotinonitrile following procedure in U.S. Pat. No. 6,677,352 (2004).

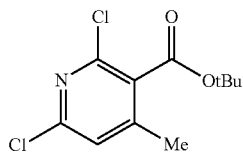 [SMILES: Cc1cc(Cl)nc(Cl)c1C(=O)OC(C)(C)C]

tert-butyl 2,6-dichloro-4-methylnicotinate

To a solution of 2,6-dichloro-4-methylnicotinic acid (1.00 g, 4.85 mmol, 1 equiv) in tert-butyl acetate (24 mL) was added 70% perchloric acid (0.88 mL, 14.56 mmol, 3 equiv). After 1 h, reaction was diluted with DCM, washed cautiously with saturated aqueous sodium bicarbonate solution, dried (Na$_2$SO$_4$), and concentrated in vacuo to provide the product (1.21 g, 95%) as a pale yellow oil. $^1$H NMR (400 MHz, CDCl$_3$) δ 7.15 (s, 1H), 2.37 (d, J=0.5 Hz, 3H), 1.62 (s, 9H); LCMS (ESI, M+1): 262.1.

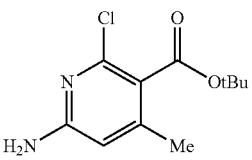

tert-butyl 6-amino-2-chloro-4-methylnicotinate tert-butyl 2,6-dichloro-4-methylnicotinate (10.5 g, 40.1 mmol, 1 equiv), Pd$_2$(dba)$_3$ (1.84 g, 2.01 mmol, 0.05 equiv), xantphos (2.32 g, 4.01 mmol, 0.1 equiv), and Cs$_2$CO$_3$ slurried in dioxane (deoxygenated by bubbling nitrogen through it for 10 min) added. Benzophenone imine (8.0 mL, 48.1 mmol, 1.2 equiv) added and the mixture was heated at 90° C. for 1 h. Upon cooling to ambient temperature, the reaction was diluted with EtOAc and washed with water, dried (Na$_2$SO$_4$), and concentrated in vacuo. The crude product was taken up in MeOH (200 mL) and NaOAc (9.87, 120 mmol, equiv) and hydroxlamine hydrochloride (5.57 g, 80 mmol, 2 equiv) was added. After 30 min, the reaction was added to 1 N NaOH and extracted with DCM (×2). The combined DCM extracts were dried (Na$_2$SO$_4$) and concentrated in vacuo. The crude product was purified by flash column chromatography (0-30% EtOAc/hex) to afford tert-butyl 6-amino-2-chloro-4-methylnicotinate (7.5 g, 77%). $^1$H NMR (400 MHz, CDCl$_3$) δ 6.22 (d, J=0.8 Hz, 1H), 4.58 (br. s., 2H), 2.27 (d, J=0.8 Hz, 3H), 1.60 (s, 9H); LCMS (ESI, M+1): 243.1.

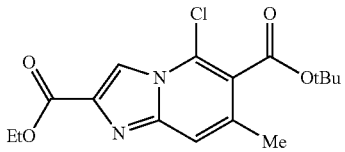 [SMILES: CCOC(=O)c1cn2c(Cl)c(C(=O)OC(C)(C)C)c(C)cc2n1]

6-tert-butyl 2-ethyl 5-chloro-7-methylimidazo[1,2-a]pyridine-2,6-dicarboxylate

A solution of tert-butyl 6-amino-2-chloro-4-methylnicotinate (9.4 g, 38.7 mmol, 1 equiv) and ethyl bromopyruvate (6.5 mL, 46.5 mmol, 1.2 equiv) in EtOH (194 mL) was heated to reflux for 2 h. Upon cooling to ambient temperature, the solution was concentrated in vacuo. The residue was triturated in ether and filtered to provide the product (11.4 g, 70%) as a cream colored solid. LCMS (ESI, M+1): 339.1.

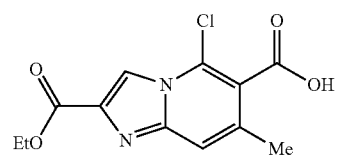 [SMILES: CCOC(=O)c1cn2c(Cl)c(C(=O)O)c(C)cc2n1]

5-chloro-2-(ethoxycarbonyl)-7-methylimidazo[1,2-a]pyridine-6-carboxylic acid 6-tert-butyl 2-ethyl 5-chloro-7-methylimidazo[1,2-a]pyridine-2,6-dicarboxylate (11.4 g, 27.2 mmol, 1 equiv) was treated with TFA (100 mL) and stirred for 2 h. Upon completion, the reaction was concentrated in vacuo. The crude product was triturated in ether and filtered to provide the product (10.8 g, 100%) as a cream colored solid. LCMS (ESI, M+1): 283.1.

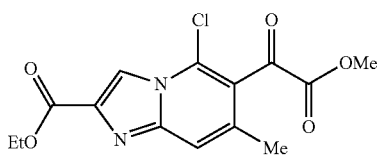 [SMILES: CCOC(=O)c1cn2c(Cl)c(C(=O)C(=O)OC)c(C)cc2n1]

ethyl 5-chloro-6-(2-methoxy-2-oxoacetyl)-7-methylimidazo[1,2-a]pyridine-2-carboxylate To a slurry of 5-chloro-2-(ethoxycarbonyl)-7-methylimidazo[1,2-a]pyridine-6-carboxylic acid (0.46 g, 1.623, 1 equiv) and 1-(cyanomethyl)tetrahydro-1H-thiophen-1-ium, bromide salt (0.47 g, 2.27 mmol, 1.4 equiv) in DCM (16 mL) was added DIPEA (1.13 mL, 6.49 mmol, 4 equiv) then HATU (0.86 g, 2.27 mmol, 1.4 equiv). After 2 h, more 1-(cyanomethyl)tetrahydro-1H-thiophen-1-ium, bromide salt (0.20 g) and DIPEA (0.5 mL) added. After stirring 18 h, the reaction was added to saturated aqueous NaHCO$_3$ and extracted with DCM (×2). The combined DCM extracts were dried (Na$_2$SO$_4$) and concentrated in vacuo. The crude sulfur ylide was taken up in MeOH (16 mL) and a solution of Oxone (2.4 g, 3.90 mmol, 2.4 equiv) in water (5 mL) was added. After 2 d, more Oxone (2.4 g, 3.90 mmol, 2.4 equiv) was added. After 6 h, the reaction was added cautiously to saturated aqueous NaHCO$_3$ and extracted with DCM (×3). The combined DCM extracts were dried (Na$_2$SO$_4$) and concentrated in vacuo. The crude product was purified by flash column chromatography (20-100% EtOAc/hex) to provide the product (0.40, 76%) as a viscous yellow oil. $^1$H NMR (500 MHz, CDCl$_3$) δ 8.37 (d, J=0.8 Hz, 1H), 7.55-7.52 (m, 1H), 4.51 (q, J=7.2 Hz, 2H), 4.01 (s, 3H), 2.40 (d, J=1.1 Hz, 3H), 1.47 (t, J=7.2 Hz, 3H); LCMS (ESI, M+1): 325.05.

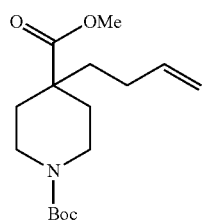 [SMILES: C=CCCC1(C(=O)OC)CCN(C(=O)OC(C)(C)C)CC1]

1-tert-Butyl 4-methyl 4-(but-3-en-1-yl)piperidine-1,4-dicarboxylate

A mixture of diisopropylamine (17.57 mL, 123 mmol) and THF (300 mL) was cooled to −78° C. and 1.6 M solution of n-BuLi (77 mL, 123 mmol) in hexane was added slowly. The mixture was stirred for 15 min, warmed to 0° C. for 20 min and cooled back to −78° C. 1-tert-Butyl 4-methyl piperidine-1,4-dicarboxylate (25 g, 103 mmol) in THF (25 mL) was added dropwise and the mixture was stirred for 40 min. Then, a mixture of HMPA (17.88 mL, 103 mmol) and 4-bromobut-1-ene (27.7 g, 206 mmol) was added and the mixture was stirred for 1 h before it was warmed to room temp and stir for 16 h. Sat. NH$_4$Cl was then added and the mixture was extracted with ether (2×500 mL), dried (Na$_2$SO$_4$), filtered and concentrated. The residue was purified by Biotage (0-20% EtOAc/hexane; 300 g column) to afford 1-tert-butyl 4-methyl 4-(but-3-en-1-yl)piperidine-1,4-dicarboxylate (22 g, 74.0 mmol, 72.0% yield) as light yellow oil. $^1$H NMR (500 MHz, CDCl$_3$) δ 5.76 (ddt, J=17.0, 10.3, 6.5 Hz, 1H), 5.06-4.92 (m, 2H), 3.94-3.85 (m, 2H), 3.73 (s, 3H), 2.95-2.80 (m, 2H), 2.13 (d, J=13.1 Hz, 2H), 2.02-1.93 (m, 2H), 1.64-1.58 (m, 2H), 1.47 (s, 9H), 1.42-1.32 (m, 2H). LCMS (M+H)=298.2.

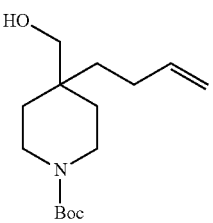 [SMILES: C=CCCC1(CO)CCN(C(=O)OC(C)(C)C)CC1]

tert-Butyl 4-(but-3-en-1-yl)-4-(hydroxymethyl)piperidine-1-carboxylate

To a solution of 1-tert-butyl 4-methyl 4-(but-3-en-1-yl)piperidine-1,4-dicarboxylate (21.2 g, 71.3 mmol) in THF (300 mL) at 0° C. was added 2M LAH/THF (35.6 mL, 71.3 mmol) and the resulting mixture was stirred at 0° C. for 1 h and then stirred at room temp for 2 h. The mixture was then recooled to 0° C. and water (2.7 mL), 1N NaOH (2.7 mL) and water (8.2 mL) were added successively and the mixture was stirred for 5 min. The solids were filtered off and the cake was washed with ethyl acetate. The filterate was washed with water (2×50 mL), brine (100 mL), dried (Na$_2$SO$_4$), filtered and concentrated under reduced pressure to give tert-butyl 4-(but-3-en-1-yl)-4-(hydroxymethyl)piperidine-1-carboxylate (16.5 g, 61.3 mmol, 86% yield) as yellow oil. $^1$H NMR (500 MHz, CDCl$_3$) δ 5.90-5.78 (m, 1H), 5.13-5.01 (m, 1H), 5.01-4.86 (m, 1H), 3.57-3.42 (m, 4H), 3.39-3.28 (m, 2H), 2.46-2.33 (m, 1H), 2.06-1.99 (m, 2H), 1.54-1.38 (m, 14H).

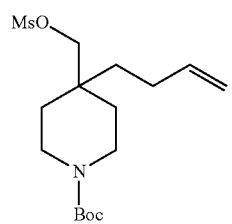

tert-Butyl 4-(but-3-en-1-yl)-4-(((methylsulfonyl)oxy)methyl)piperidine-1-carboxylate Ms-Cl (5.59 mL, 71.7 mmol) was added dropwise at 0° C. to a stirred solution of tert-butyl 4-(but-3-en-1-yl)-4-(hydroxymethyl)piperidine-1-carboxylate (16.1 g, 59.8 mmol) TEA (16.66 mL, 120 mmol) and DMAP (0.365 g, 2.99 mmol) in CH$_2$Cl$_2$ (300 mL) and the mixture was stirred at room temp for 2 h. Water was then added and the mixture was extracted with methylene chloride (100 mL), dried (Na$_2$SO$_4$), filtered and concentrated. The residue was purified by Biotage (0-40% Hex/EtOAc) to afford tert-butyl 4-(but-3-en-1-yl)-4-(((methylsulfonyl)oxy)methyl)piperidine-1-carboxylate (18 g, 51.8 mmol, 87% yield) as colorless oil. $^1$H NMR (500 MHz, CDCl$_3$) δ 5.88-5.75 (m, 1H), 5.11-4.90 (m, 2H), 4.09 (s, 2H), 3.58-3.44 (m, 2H), 3.40-3.32 (m, 2H), 3.05 (s, 3H), 2.07-2.02 (m, 2H), 1.59-1.54 (m, 2H), 1.53-1.49 (m, 4H), 1.48 (s, 9H).

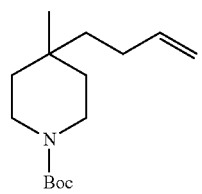 [SMILES: C=CCCC1(C)CCN(C(=O)OC(C)(C)C)CC1]

tert-Butyl 4-(but-3-en-1-yl)-4-methylpiperidine-1-carboxylate

To a solution of tert-butyl 4-(but-3-en-1-yl)-4-(((methylsulfonyl)oxy)methyl)piperidine-1-carboxylate (17 g, 48.9 mmol) in THF (250 mL) was added 1M solution of Superhydride (98 mL, 98 mmol) in THF and the resulting mixture was refluxed for 3 h. After cooling to room temp water was added and the mixture was extracted with ether (2×200 mL), washed with brine (100 mL), dried (Na$_2$SO$_4$), filtered and concentrated. The residue was purified by Biotage (0-20% EtOAc/hexane) to afford tert-butyl 4-(but-3-en-1-yl)-4-methylpiperidine-1-carboxylate (3.5 g, 13.81 mmol, 28.2% yield). $^1$H NMR (500 MHz, CDCl$_3$) δ 5.88-5.80 (m, 1H), 5.03 (dq, J=17.1, 1.7 Hz, 1H), 4.96 (ddt, J=10.2, 2.1, 1.1 Hz, 1H), 3.62-3.49 (m, 2H), 3.23 (ddd, J=13.4, 9.3, 3.8 Hz, 2H), 2.09-1.97 (m, 2H), 1.48 (s, 9H), 1.43-1.22 (m, 6H), 0.96 (s, 3H). LCMS (M+H)=254.2. 8 g of starting material was also recovered.

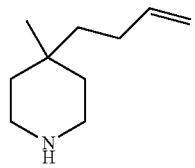

4-(But-3-en-1-yl)-4-methylpiperidine.HCl

A mixture of tert-butyl 4-(but-3-en-1-yl)-4-methylpiperidine-1-carboxylate (3.5 g, 13.81 mmol) and 4M HCl/dioxane (17.27 ml, 69.1 mmol) was stirred at room temp for 3 h. Mixture was then concentrated and dried under high vac to afford 4-(but-3-en-1-yl)-4-methylpiperidine.HCl (2.6 g, 13.70 mmol, 99% yield) as off-white solid. $^1$H NMR (500 MHz, DMSO-d$_6$) δ 5.83 (ddt, J=17.0, 10.3, 6.6 Hz, 1H), 5.05 (dq, J=17.1, 1.7 Hz, 1H), 5.00-4.80 (m, 1H), 3.11-2.90 (m, 5H), 2.05-1.90 (m, 2H), 1.56-1.42 (m, 5H), 1.38-1.26 (m, 2H), 0.95 (s, 3H). LCMS (M+H)=154.1.

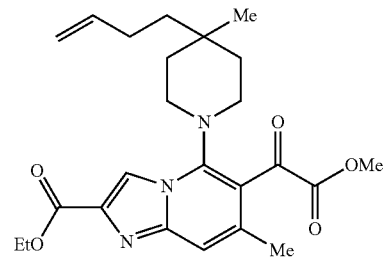 [SMILES: C=CCCC1(C)CCN(c2c(C(=O)C(=O)OC)c(C)cc3nc(C(=O)OCC)cn23)CC1]

ethyl 5-(4-(but-3-en-1-yl)-4-methylpiperidin-1-yl)-6-(2-methoxy-2-oxoacetyl)-7-methylimidazo[1,2-a]pyridine-2-carboxylate A solution of ethyl 5-chloro-6-(2-methoxy-2-oxoacetyl)-7-methylimidazo[1,2-a]pyridine-2-carboxylate (0.40 g, 1.23 mmol, 1 equiv), DIPEA (0.52 mL, 2.96 mmol, 2.4 equiv), and 4-(but-3-en-1-yl)-4-methylpiperidine, HCl (0.23 g, 1.23 mmol, 1 equiv). After 2 h, the reaction was added to saturated aqueous NaHCO$_3$ and extracted with EtOAc (×3). The combined EtOAc extracts were dried (Na$_2$SO$_4$) and concentrated in vacuo. The crude product was purified by flash column chromatography (0-100% EtOAc/hex) to provide the product (0.44, 81%) as a viscous yellow oil that slowly crystallized. $^1$H NMR (400 MHz, CDCl$_3$) δ 8.28-8.13 (m, 1H), 7.37 (br. s., 1H), 5.96-5.78 (m, 1H), 5.08 (d, J=17.6 Hz, 1H), 5.00 (d, J=10.5 Hz, 1H), 4.57-4.43 (m, 2H), 3.97 (s, 3H), 3.62-3.28 (m, 2H), 3.01-2.87 (m, 2H), 2.34 (d, J=0.8 Hz, 3H), 2.14-2.04 (m, 2H), 1.62-1.38 (m, 9H), 1.14-0.99 (m, 3H); LCMS (ESI, M+1): 442.25.

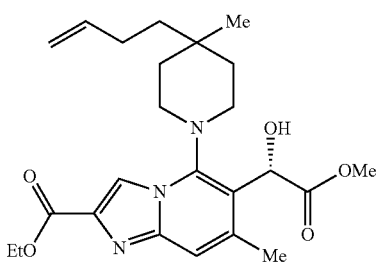 [SMILES: C=CCCC1(C)CCN(c2c([C@H](O)C(=O)OC)c(C)cc3nc(C(=O)OCC)cn23)CC1]

(S)-ethyl 5-(4-(but-3-en-1-yl)-4-methylpiperidin-1-yl)-6-(1-hydroxy-2-methoxy-2-oxoethyl)-7-methylimidazo[1,2-a]pyridine-2-carboxylate A solution of ethyl 5-(4-(but-3-en-1-yl)-4-methylpiperidin-1-yl)-6-(2-methoxy-2-oxoacetyl)-7-methylimidazo[1,2-a]pyridine-2-carboxylate (0.44 g, 1.00 mmol, 1 equiv) and R-5,5-diphenyl-2-methyl-3,4-propano-1,3,2-oxazaborlidine (1.59 mL of a 1 M solution in toluene, 1.59 mmol, 1.6 equiv) in toluene (10 mL) was cooled to −30° C. (IPA/dry ice). Catecholborane (0.34 mL, 1.59 mmol, 1.6 equiv) was added and the reaction was stirred at −15° C.-30° C. for 3 h. The reaction was then added to 10% K$_2$CO$_3$ and extracted with ether (×3). The combined ether extracts were dried (MgSO$_4$) and concentrated in vacuo. The crude product was purified by flash column chromatography (30-100% EtOAc/hex) to provide the product (0.51 g, ~100%) as a viscous colorless oil. NMR shows contamination with a CBS byproduct accounting for extra mass. $^1$H NMR (500 MHz, CDCl$_3$) δ 8.26 (s, 1H), 7.40 (s, 1H), 5.98-5.84 (m, 1H), 5.61 (d, J=11.0 Hz, 1H), 5.17-4.98 (m, 2H), 4.55-4.46 (m, 2H), 3.81 (s, 3H), 3.61 (t, J=10.9 Hz, 2H), 3.11-2.94 (m, 4H), 2.44 (d, J=0.9 Hz, 3H), 2.18-2.09 (m, 2H), 1.82-1.53 (m, 4H), 1.50-1.44 (m, 3H), 1.16 (s, 3H); LCMS (ESI, M+1): 444.25.

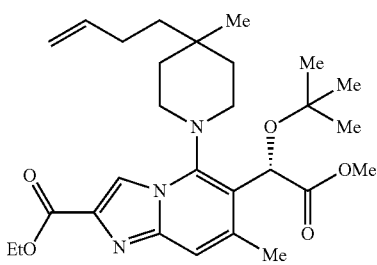 [SMILES: C=CCCC1(C)CCN(c2c([C@H](OC(C)(C)C)C(=O)OC)c(C)cc3nc(C(=O)O)cn23)CC1]

(S)-ethyl 5-(4-(but-3-en-1-yl)-4-methylpiperidin-1-yl)-6-(1-(tert-butoxy)-2-methoxy-2-oxoethyl)-7-methylimidazo[1,2-a]pyridine-2-carboxylate To a solution of (S)-ethyl 5-(4-(but-3-en-1-yl)-4-methylpiperidin-1-yl)-6-(1-hydroxy-2-methoxy-2-oxoethyl)-7-methylimidazo[1,2-a]pyridine-2-carboxylate (0.50 g, 1.13 mmolo, 1 equiv) in t-BuOAc (18 mL) was added 70% HClO$_4$ (0.48 mL, 5.64 mmol, 5 equiv). A white precipitate formed. DCM (5 mL) was added to aid solubility. After 1 h, the reaction was carefully added to saturated aqueous NaHCO$_3$ and extracted with DCM (×3). The combined DCM extracts were dried (Na$_2$SO$_4$) and concentrated in vacuo. The crude product was purified by flash column chromatography (0-100% EtOAc/hex) to provide the product (0.16 g, 28%) as a white foam. In addition, starting material (0.38 g) was recovered. $^1$H NMR (400 MHz, CDCl$_3$) [note: major rotamer transcribed, 3:2 mixture of rotamers] δ8.23 (s, 1H), 7.33 (s, 1H), 6.06 (s, 1H), 5.97-5.81 (m, 1H), 5.17-4.97 (m, 2H), 4.53-4.42 (m, 2H), 3.71 (s, 3H), 3.69-3.64 (m, 1H), 3.57-3.50 (m, 1H), 3.17-3.07 (m, 1H), 2.88 (d, J=12.0 Hz, 1H), 2.46-2.44 (m, 3H), 2.18-2.08 (m, 2H), 1.71-1.58 (m, 6H), 1.48-1.43 (m, 3H), 1.25 (s, 9H), 1.16 (s, 3H); LCMS (ESI, M+1): 500.35.

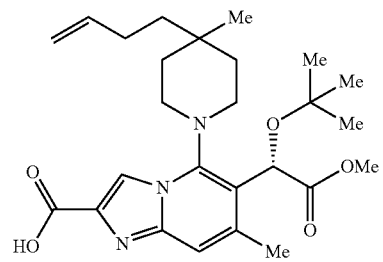

(S)-5-(4-(but-3-en-1-yl)-4-methylpiperidin-1-yl)-6-(1-(tert-butoxy)-2-methoxy-2-oxoethyl)-7-methylimidazo[1,2-a]pyridine-2-carboxylic acid sodium salt To a solution of (S)-ethyl 5-(4-(but-3-en-1-yl)-4-methylpiperidin-1-yl)-6-(1-(tert-butoxy)-2-methoxy-2-oxoethyl)-7-methylimidazo[1,2-a]pyridine-2-carboxylate (0.164 g, 0.328 mmol, 1 equiv) in MeOH (3.3 mL) was added 1 N NaOH (0.36 mL, 0.36 mmol, 1.1 equiv). After stirring 18 h, the reaction was heated to 60° C. for 2 h. Upon cooling to ambient temperature, the reaction was concentrated in vacuo. The residue was then concentrated in vacuo with toluene (×3) to remove residual MeOH to provide the product as a yellow solid (0.168 g, 100%). LCMS (ESI, M+1): 472.3.

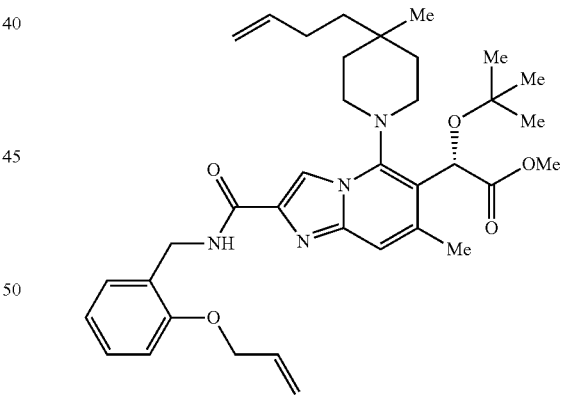

(S)-methyl 2-(2-((2-(allyloxy)benzyl)carbamoyl)-5-(4-(but-3-en-1-yl)-4-methylpiperidin-1-yl)-7-methylimidazo[1,2-a]pyridin-6-yl)-2-(tert-butoxy)acetate A yellow solution of (S)-5-(4-(but-3-en-1-yl)-4-methylpiperidin-1-yl)-6-(1-(tert-butoxy)-2-methoxy-2-oxoethyl)-7-methylimidazo[1,2-a]pyridine-2-carboxylic acid sodium salt (40 mg, 0.081 mmol, 1 equiv), 2-allyloxybenzylamine (18 mg, 0.113 mmol, 1.4 equiv), DIPEA (0.042 mL, 0.243 mmol, 3 equiv), and HATU (43 mg, 0.113 mmol, 1.4 equiv) in DMF (0.81 mL) was stirred 2 h. The reaction was then diluted with EtOAc, washed with saturated aqueous NaHCO₃, dried (Na₂SO₄), and concentrated in vacuo. The crude product was purified by flash column chromatography (0-100% EtOAc/hex) to provide the product (30 mg, 60%) as a colorless oil. ¹H NMR (400 MHz, CDCl₃) [note: appears to be at least two rotamers, only major rotamer transcribed] δ 8.21 (s, 1H), 7.81 (t, J=6.1 Hz, 1H), 7.26-7.16 (m, 2H), 6.97-6.85 (m, 2H), 6.19-6.06 (m, 2H), 5.93-5.82 (m, 1H), 5.47 (dq, J=17.3, 1.5 Hz, 1H), 5.31 (dq, J=10.5, 1.4 Hz, 1H), 5.14-4.95 (m, 2H), 4.72 (d, J=6.0 Hz, 2H), 4.63 (dt, J=5.0, 1.5 Hz, 2H), 3.70 (s, 3H), 3.61-3.48 (m, 2H), 3.07 (d, J=13.8 Hz, 1H), 2.85 (d, J=12.0 Hz, 1H), 2.45 (d, J=1.0 Hz, 3H), 2.17-2.07 (m, 2H), 1.71-1.40 (m, 6H), 1.24 (s, 9H), 1.13 (s, 3H); LCMS (ESI, M+1): 617.4.

Example 1

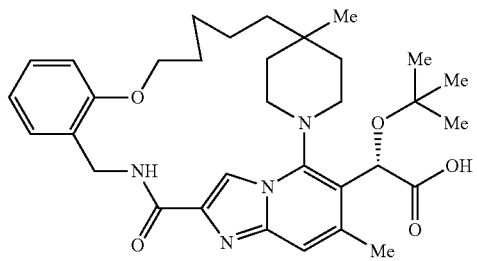 [SMILES: Cc1cc2nc3cn2c(c1[C@H](OC(C)(C)C)C(=O)O)N1CCC(C)(CCCCCOc2ccccc2CNC3=O)CC1]

(2S)-2-(tert-Butoxy)-2-{4,25-dimethyl-10-oxo-19-oxa-1,7,11,30-tetraazapentacyclo[23.2.2.1⁶,⁹.0²,⁷.0¹³,¹⁸]triaconta-2,4,6(30),8,13(18),14,16-heptaen-3-yl}acetic acid A solution of (S)-methyl 2-(2-((2-(allyloxy)benzyl)carbamoyl)-5-(4-(but-3-en-1-yl)-4-methylpiperidin-1-yl)-7-methylimidazo[1,2-a]pyridin-6-yl)-2-(tert-butoxy)acetate (0.023 g, 0.037 mmol, 1 equiv) and TsOH (7 mg, 0.037 mmol, 1 equiv) in DCE (19 mL) was heated to 80° C. The Hoveyda Grubbs 2ⁿᵈ generation catalyst (5 mg, 0.007 mmol, 0.2 equiv) was added. The pale green brown solution was stirred for 2 h. Upon cooling to ambient temperature, the reaction was washed with saturated aqueous NaHCO₃, dried (Na₂SO₄), and concentrated in vacuo. The dark residue was then taken up in MeOH (2 mL) and NaBH₄ (2 mg, 0.052 mmol, 1.4 equiv) was added. After stirring 1 h, the reaction was added to saturated aqueous NaHCO₃ and extracted with DCM (×3). The combined DCM extracts were dried (Na₂SO₄) and concentrated in vacuo. The crude product was taken up in 9:1 MeOH:water (2 mL) and LiOH.H₂O (78 mg, 1.684 mmol, 50 equiv) was added. The reaction was heated to 60° C. for 6 h. Upon cooling to ambient temperature, the reaction was filtered and purified via preparative LC/MS with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min to provide the product (7.1 mg, 31%). ¹H NMR (500 MHz, DMSO-d₆) δ 8.71-8.61 (m, 1H), 8.08 (s, 1H), 7.36 (d, J=7.0 Hz, 1H), 7.27-7.18 (m, 2H), 7.07 (d, J=8.2 Hz, 1H), 6.85 (t, J=7.3 Hz, 1H), 5.90 (m, 1H), 4.14 (td, J=10.6, 6.0 Hz, 2H), 3.68 (br. s., 2H), 3.06 (d, J=7.9 Hz, 1H), 2.57 (br. s., 1H), 2.37 (s, 3H), 2.09-1.93 (m, 3H), 1.68-1.25 (m, 9H), 1.17 (s, 9H), 0.98 (s, 3H); LCMS (ESI, M+1): 577.5.

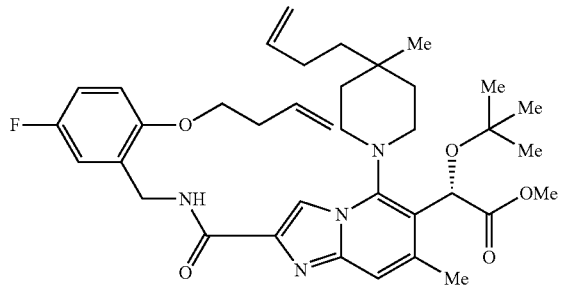 [SMILES: C=CCCOc1ccc(F)cc1CNC(=O)c1cn2c(N3CCC(C)(CCC=C)CC3)c([C@H](OC(C)(C)C)C(=O)OC)c(C)cc2n1]

Methyl(2S)-2-{5-[4-(but-3-en-1-yl)-4-methylpiperidin-1-yl]-2-({[2-(but-3-en-1-yloxy)-5-fluorophenyl]methyl}carbamoyl)-7-methylimidazo[1,2-a]pyridin-6-yl}-2-(tert-butoxy)acetate Prepared from (S)-5-(4-(but-3-en-1-yl)-4-methylpiperidin-1-yl)-6-(1-(tert-butoxy)-2-methoxy-2-oxoethyl)-7-methylimidazo[1,2-a]pyridine-2-carboxylic acid sodium salt and 2-(but-3-en-1-yloxy)-5-fluorobenzylamine in 75% yield using the same procedure as (S)-methyl 2-(2-((2-(allyloxy)benzyl)carbamoyl)-5-(4-(but-3-en-1-yl)-4-methylpiperidin-1-yl)-7-methylimidazo[1,2-a]pyridin-6-yl)-2-(tert-butoxy)acetate. ¹H NMR (500 MHz, CDCl₃) [note: appears to be 2:1 mixture of rotamers, major rotamer transcribed] δ 8.24-8.21 (m, 1H), 7.90-7.81 (m, 1H), 7.23-7.18 (m, 1H), 7.14-7.09 (m, 1H), 6.95-6.87 (m, 1H), 6.83-6.77 (m, 1H), 6.12-6.08 (m, 1H), 6.05-5.89 (m, 2H), 5.28-5.21 (m, 1H), 5.19-5.15 (m, 1H), 5.14-4.98 (m, 2H), 4.69-4.64 (m, 2H), 4.07 (s, 2H), 3.74-3.73 (m, 1H), 3.71 (s, 3H), 3.64-3.49 (m, 1H), 3.14-2.93 (m, 1H), 2.91-2.83 (m, 1H), 2.70-2.60 (m, 2H), 2.47-2.46 (m, 3H), 2.17-2.09 (m, 2H), 1.71-1.60 (m, 6H), 1.26 (s, 9H), 1.15 (s, 3H); LCMS (ESI, M+1): 649.35.

Example 2

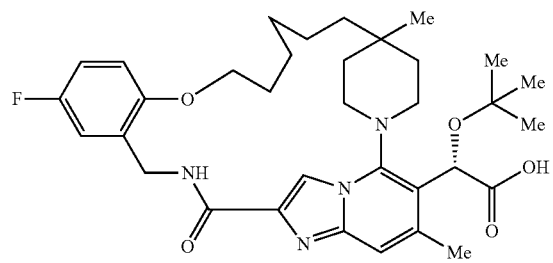 [SMILES: Cc1cc2nc3cn2c(c1[C@H](OC(C)(C)C)C(=O)O)N1CCC(C)(CCCCCCOc2ccc(F)cc2CNC3=O)CC1]

(2S)-2-(tert-Butoxy)-2-{15-fluoro-4,26-dimethyl-10-oxo-19-oxa-1,7,11,31-tetraazapentacyclo[24.2.2.1⁶,⁹.0²,⁷.0¹³,¹⁸]hentriaconta-2,4,6(31),8,13(18),14,16-heptaen-3-yl}acetic acid Prepared from methyl(2S)-2-{5-[4-(but-3-en-1-yl)-4-methylpiperidin-1-yl]-2-({[2-(but-3-en-1-yloxy)-5-fluorophenyl]methyl}carbamoyl)-7-methylimidazo[1,2-a]pyridin-6-yl}-2-(tert-butoxy)acetate in 12% yield using the same procedure as (2S)-2-(tert-butoxy)-2-{4,25-dimethyl-10-oxo-19-oxa-1,7,11,30-tetraazapentacyclo[23.2.2.1⁶,⁹.0²,⁷.0¹³,¹⁸]triaconta-2,4,6(30),8,13(18),14,16-heptaen-3-yl}acetic acid. ¹H NMR (500 MHz, DMSO-d₆) δ 8.90-8.81 (m, 1H), 8.21 (s, 1H), 7.27 (dd, J=8.9, 3.1 Hz, 1H), 7.22 (s, 1H), 7.10-7.03 (m, 1H), 6.95 (dd, J=9.0, 4.4 Hz, 1H), 5.91 (s, 1H), 4.30 (t, J=5.0 Hz, 2H), 4.05-3.95 (m, 2H), 3.79-3.71 (m, 2H), 3.01 (d, J=11.0 Hz, 1H), 2.62 (d, J=11.0 Hz, 1H), 2.37 (s, 3H), 1.82-1.33 (m, 14H), 1.17 (s, 9H), 0.96 (s, 3H); LCMS (ESI, M+1): 609.3.

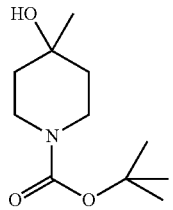

tert-Butyl 4-hydroxy-4-methylpiperidine-1-carboxylate

Under an N2 atmosphere, a 3N solution in ether of methylmagnesium bromide (1.67 mL, 5.02 mmol) was added dropwise to a cooled (−25° C.) solution of tert-butyl 4-hydroxy-4-methylpiperidine-1-carboxylate (4 g, 20.08 mmol) in ether (20 mL). The reaction mixture was allowed to warm to rt and was stirred for 2 h. It was then cooled to 0° C. and quenched by the addition of sat. aq. ammonium chloride. Another 20 mL of ether was added and the mixture was partitioned in a separatory funnel. The organic phase was set aside and the aqueous phase was extracted with another 20 mL of ether. The combined ether extracts were dried over MgSO₄, filtered and evaporated to obtain an oil, which was then purified by biotage, eluting with 0-50% EtOAc/hexane to obtain tert-butyl 4-hydroxy-4-methylpiperidine-1-carboxylate (4.30 g, 18.0 mmol, 90%) as a colorless oil. ¹H NMR (400 MHz, CDCl₃) δ 3.84-3.65 (m, 2H), 3.34-3.18 (m, 2H), 2.59-2.39 (m, 1H), 1.61-1.53 (m, 4H), 1.50-1.45 (m, 9H), 1.32-1.27 (m, 3H).

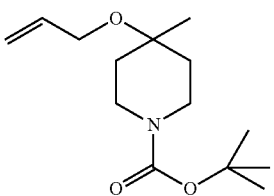 [SMILES: C=CCOC1(C)CCN(C(=O)OC(C)(C)C)CC1]

tert-Butyl 4-(allyloxy)-4-methylpiperidine-1-carboxylate

To a mixture of tert-butyl 4-hydroxy-4-methylpiperidine-1-carboxylate (4.30 g, 20.0 mmol) in DMF (50 mL) at 0° C. was added NaH (60 wt %) (1.60 g, 39.9 mmol). The mixture was then stirred at rt for 2 h. At this time allyl bromide (8.64 mL, 100 mmol) was added slowly over the course of 5 min. The reaction mixture was stirred at rt for 3 h. It was then cooled to 0° C. and quenched with sat. aq. ammonium chloride. The reaction mixture was extracted with ether. The organic phase was dried over MgSO₄, filtered and concentrated to obtain a colorless oil, which was then purified by biotage, eluting with 0-25% EtOAc/hexane to isolate 3.1 g (61%) of tert-butyl 4-(allyloxy)-4-methylpiperidine-1-carboxylate as a colorless oil. ¹H NMR (500 MHz, CDCl₃) δ 6.02-5.90 (m, 1H), 5.32 (dd, J=17.2, 1.7 Hz, 1H), 5.16 (dd, J=10.4, 1.4 Hz, 1H), 3.94-3.88 (m, 2H), 3.73 (br. s., 2H), 3.19 (br. s., 2H), 1.78 (d, J=13.1 Hz, 2H), 1.53-1.42 (m, 11H), 1.21 (s, 3H).

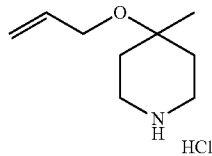

4-(Allyloxy)-4-methylpiperidine hydrogen chloride salt

A mixture of tert-butyl 4-(allyloxy)-4-methylpiperidine-1-carboxylate (3.10 g, 12.1 mmol) and 4N HCl/dioxane (15 mL, 60.0 mmol) was stirred at rt for 3 h. It was then concentrated in vacuum to obtain 2.2 g (95%) of 4-(allyloxy)-4-methylpiperidine hydrochloride as a light brown solid. ¹H NMR (500 MHz, CD₃OD) δ 6.02-5.92 (m, 1H), 5.33 (dd, J=17.2, 1.7 Hz, 1H), 5.15 (dd, J=10.6, 1.7 Hz, 1H), 3.96 (dt, J=5.1, 1.6 Hz, 2H), 3.23-3.18 (m, 4H), 2.06 (dd, J=15.3, 2.5 Hz, 2H), 1.77-1.69 (m, 2H), 1.31-1.28 (s, 3H). Free base (brown solid) is obtained by stirring HCl salt with aq Na₂CO₃ and extracting with DCM.

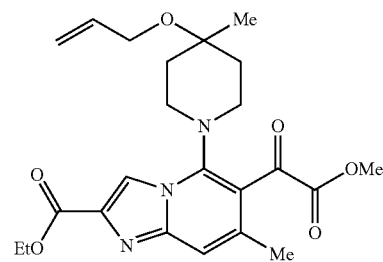

Ethyl 5-(4-(allyloxy)-4-methylpiperidin-1-yl)-6-(2-methoxy-2-oxoacetyl)-7-methylimidazo[1,2-a]pyridine-2-carboxylate A solution of ethyl 5-chloro-6-(2-methoxy-2-oxoacetyl)-7-methylimidazo[1,2-a]pyridine-2-carboxylate (0.75 g, 2.31 mmol, 1 equiv), 4-allyloxy-4-methylpiperidine, HCl (0.66 g, 3.46 mmol, 1.5 equiv), and DIPEA (1.21 mL, 6.93 mmol, 3 equiv) in DMF (11.5 mL) was stirred for 1 h. The reaction was then added to saturated aqueous NaHCO₃ and extracted with EtOAc (×2). The combined EtOAc extracts were dried (Na₂SO₄) and concentrated in vacuo. The crude product was purified via silica gel flash chromatography (0-100% EtOAc [2% TEA]/hexane) to provide the product (0.85 g, 83%). LCMS (ESI, M+1): 444.25.

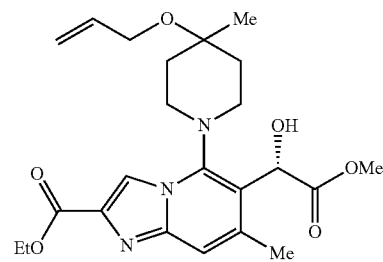

(S)-Ethyl 5-(4-(allyloxy)-4-methylpiperidin-1-yl)-6-(1-hydroxy-2-methoxy-2-oxoethyl)-7-methylimidazo[1,2-a]pyridine-2-carboxylate To a stirred yellow solution of ethyl 5-(4-(allyloxy)-4-methylpiperidin-1-yl)-6-(2-methoxy-2-oxoacetyl)-7-methylimidazo[1,2-a]pyridine-2-carboxylate (0.86 g, 1.94 mmol, 1 equiv) in toluene (19 mL) was added (R)-1-methyl-3,3-diphenylhexahydropyrrolo[1,2-c][1,3,2]oxazaborole/toluene (0.54 g, 1.94 mmol, 1 equiv). The reaction was cooled to −40° C. (acetonitrile/dry ice bath) and a solution of 50% catechoborane in toluene (0.93 mL, 3.88 mmol, 2 equiv) was added over 10 min. The reaction mixture was stirred at −15° C. for 2 h. Upon completion, the reaction was diluted with EtOAc (30 mL) and sat. NaHCO$_3$ (10 mL). The mixture was stirred vigorously for 30 min. The organic phase was washed with saturated aqueous NaHCO$_3$ (2×5 mL), dried (Na$_2$SO$_4$), and concentrated in vacuo. The crude product was purified by silica gel chromatography (0-10% MeOH/DCM) to afford desired product (0.86 g, 100%) as an off-white solid. LCMS (ESI, M+1): 446.25.

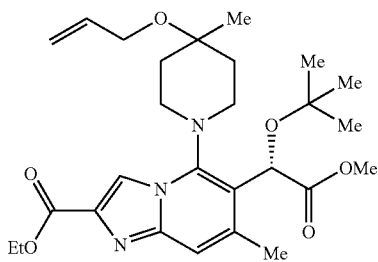

(S)-Ethyl 5-(4-(allyloxy)-4-methylpiperidin-1-yl)-6-(1-(tert-butoxy)-2-methoxy-2-oxoethyl)-7-methylimidazo[1,2-a]pyridine-2-carboxylate (S)-Ethyl 5-(4,4-dimethylpiperidin-1-yl)-6-(1-hydroxy-2-methoxy-2-oxoethyl)-7-methylimidazo[1,2-a]pyridine-2-carboxylate (1.3 g, 3.22 mmol, 1 equiv) was suspended in DCM (3 mL) and tert-butyl acetate (10 mL). To this mixture was added 70% HClO$_4$ (0.831 mL, 9.67 mmol, 3 equiv) through sealed rubber stopper. After 2 h, LCMS indicated about 60% conversion. The reaction was washed with 1 N NaOH, dried (Na$_2$SO$_4$), and concentrated in vacuo. The crude product was purified via silica gel flash chromatography (0-100% EtOAc [2% TEA]/hexane) to provide the product (0.68 g, 46%). $^1$H NMR (400 MHz, CDCl$_3$) 8.22 (d, J=0.8 Hz, 1H), 7.31 (s, 1H), 6.02 (s, 1H), 4.47 (q, J=7.2 Hz, 2H), 3.70 (s, 3H), 3.60 (td, J=11.4, 2.8 Hz, 1H), 3.49 (td, J=11.5, 2.6 Hz, 1H), 3.10 (dt, J=11.9, 3.5 Hz, 1H), 2.95-2.86 (m, 1H), 2.44 (d, J=1.0 Hz, 3H), 1.73-1.48 (m, 7H), 1.45 (t, J=7.0 Hz, 4H), 1.24 (s, 10H), 1.15 (s, 3H), 1.08 (s, 3H); LCMS (ESI, M+1): 502.35.

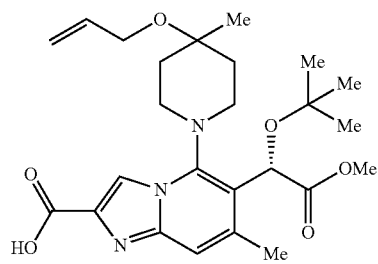

(S)-5-(4-(Allyloxy)-4-methylpiperidin-1-yl)-6-(1-(tert-butoxy)-2-methoxy-2-oxoethyl)-7-methylimidazo[1,2-a]pyridine-2-carboxylic acid sodium salt (S)-Ethyl 5-(4-(allyloxy)-4-methylpiperidin-1-yl)-6-(1-(tert-butoxy)-2-methoxy-2-oxoethyl)-7-methylimidazo[1,2-a]pyridine-2-carboxylate (450 mg, 0.923 mmol, 1 equiv) was dissolved in MeOH (9 mL). To this solution was added 1 N NaOH (1.02 mL, 1.015 mmol, 1.1 equiv). The reaction was stirred at 60° C. for 2 h. Upon cooling to ambient temperature, the reaction was concentrated in vacuo. The residue was then azeotroped with toluene to give a pale brown solid (S)-5-(4-(allyloxy)-4-methylpiperidin-1-yl)-6-(1-(tert-butoxy)-2-methoxy-2-oxoethyl)-7-methylimidazo[1,2-a]pyridine-2-carboxylic acid (400 mg, 92% yield) which was used as is for further reactions. LCMS (ESI, M+1): 474.35.

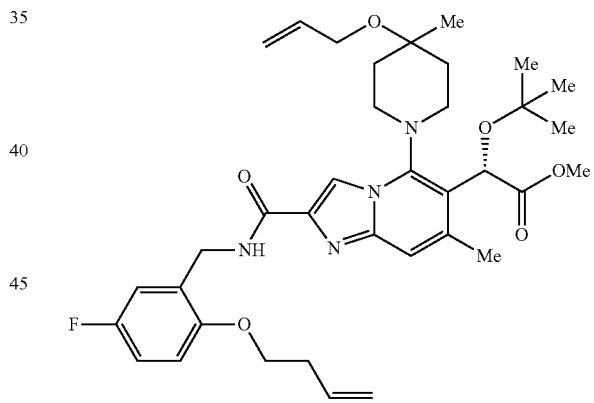

Methyl(2S)-2-[2-({[2-(but-3-en-1-yloxy)-5-fluorophenyl]methyl}carbamoyl)-7-methyl-5-[4-methyl-4-(prop-2-en-1-yloxy)piperidin-1-yl]imidazo[1,2-a]pyridin-6-yl]-2-(tert-butoxy)acetate Prepared from (S)-5-(4-(allyloxy)-4-methylpiperidin-1-yl)-6-(1-(tert-butoxy)-2-methoxy-2-oxoethyl)-7-methylimidazo[1,2-a]pyridine-2-carboxylic acid sodium salt and 2-(but-3-en-1-yloxy)-5-fluorobenzylamine in 61% yield using the same procedure as (S)-methyl 2-(2-((2-(allyloxy)benzyl)carbamoyl)-5-(4-(but-3-en-1-yl)-4-methylpiperidin-1-yl)-7-methylimidazo[1,2-a]pyridin-6-yl)-2-(tert-butoxy)acetate. LCMS (ESI, M+1):651.35.

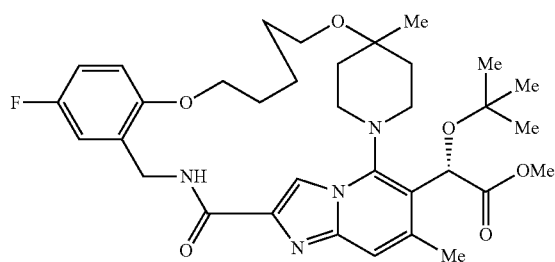 [SMILES: COC(=O)[C@@H](OC(C)(C)C)c1c(C)cc2nc3cn2c1N1CCC(C)(CC1)OCCCCCOc1ccc(F)cc1CNC3=O]

Methyl(2S)-2-(tert-butoxy)-2-{15-fluoro-4,26-dimethyl-10-oxo-19,25-dioxa-1,7,11,31-tetraazapentacyclo[24.2.2.1⁶,⁹.0²,⁷.0¹³,¹⁸]hentriaconta-2,4,6(31),8,13(18),14,16-heptaen-3-yl}acetate A solution of methyl(2S)-2-[2-({[2-(but-3-en-1-yloxy)-5-fluorophenyl]methyl}carbamoyl)-7-methyl-5-[4-methyl-4-(prop-2-en-1-yloxy)piperidin-1-yl]imidazo[1,2-a]pyridin-6-yl]-2-(tert-butoxy)acetate (0.046 g, 0.071 mmol, 1 equiv) and TsOH monohydrate (15 mg, 0.077 mmol, 1.1 equiv) in DCE (24 mL) was heated to 75° C. The Hoveyda Grubbs 2$^{nd}$ generation catalyst (9 mg, 0.014 mmol, 0.2 equiv) was added. The pale green brown solution was stirred for 1 h. Upon cooling to ambient temperature, the reaction was concentrated in vacuo. The residue was taken up in MeOH (5 mL) and 10% Pd/C (15 mg, 0.014 mmol, 0.2 equiv) was added. The reaction was then stirred under a balloon of H$_2$ for 2 h. The reaction was then filtered through Celite eluting with MeOH. The filtrate was then concentrated in vacuo. The residue was taken up in DCM and washed with saturated aqueous NaHCO$_3$, dried (Na$_2$SO$_4$), and concentrated in vacuo. The crude product was purified by flash column chromatography (0-100% EtOAc [2% TEA]/hexane) to provide the product (22 mg, 50%) as a brown film. LCMS (ESI, M+1): 625.35.

Example 3

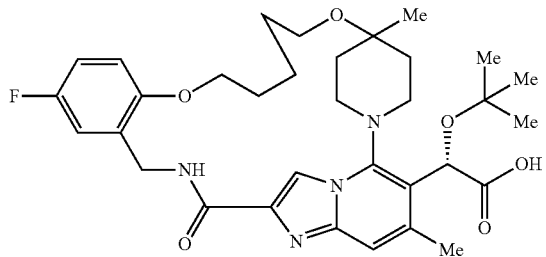 [SMILES: Cc1cc2nc3cn2c(c1[C@H](OC(C)(C)C)C(=O)O)N1CCC(C)(CC1)OCCCCCOc1ccc(F)cc1CNC3=O]

(2S)-2-(tert-Butoxy)-2-{15-fluoro-4,26-dimethyl-10-oxo-19,25-dioxa-1,7,11,31-tetraazapentacyclo[24.2.2.1⁶,⁹.0²,⁷.0¹³,¹⁸]hentriaconta-2,4,6(31),8,13(18),14,16-heptaen-3-yl}acetic acid To a solution of methyl(2S)-2-(tert-butoxy)-2-{15-fluoro-4,26-dimethyl-10-oxo-19,25-dioxa-1,7,11,31-tetraazapentacyclo[24.2.2.1⁶,⁹.0²,⁷.0¹³,¹⁸]hentriaconta-2,4,6(31),8,13(18),14,16-heptaen-3-yl}acetate (22 mg, 0.035 mmol, 1 equiv) in 9:1 MeOH:water (1 mL) was added LiOH.H$_2$O (44 mg, 1.06 mmol, 30 equiv). The reaction was heated to 60° C. for 1 h. Upon cooling to ambient temperature, the reaction was filtered and purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min to provide the product (10.2 mg, 46%). $^1$H NMR (500 MHz, DMSO-d$_6$) δ 8.72-8.62 (m, 1H), 8.01 (s, 1H), 7.29-7.18 (m, 2H), 7.05 (dd, J=8.4, 2.9 Hz, 1H), 6.97 (dd, J=8.7, 4.4 Hz, 1H), 5.91 (br. s., 1H), 4.31 (br. s., 2H), 4.08-3.95 (m, 2H), 3.86-3.79 (m, 2H), 3.50-3.40 (m, J=5.2 Hz, 2H), 2.95 (d, J=7.9 Hz, 1H), 2.60 (d, J=7.6 Hz, 1H), 2.38 (s, 3H), 1.89-1.60 (m, 10H), 1.21 (s, 3H), 1.17 (s, 9H); LCMS (ESI, M+1): 611.5. —OH

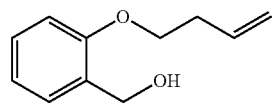

(2-(But-3-en-1-yloxy)phenyl)methanol

To a solution of salicaldehyde (10 g, 82 mmol, 1 equiv) in DMF (82 mL) was slowly added 60% NaH (3.93 g, 98 mmol, 1.2 equiv). Gas evolution. 4-bromobut-1-ene (11.6 mL, 115 mmol, 1.4 equiv) was added and the reaction was heated to 90° C. for 4 h. Upon cooling to ambient temperature, the reaction was diluted with ether and washed with 1 N NaOH, brine, dried (MgSO$_4$), and concentrated in vacuo to provide the crude alkylation product. $^1$H NMR (400 MHz, CDCl$_3$) δ 10.52 (s, 1H), 7.85 (dd, J=7.8, 1.8 Hz, 1H), 7.64-7.48 (m, 1H), 7.13-6.93 (m, 2H), 6.02-5.84 (m, 1H), 5.24-5.05 (m, 2H), 4.16 (t, J=6.5 Hz, 2H), 2.74-2.52 (m, 2H). The crude alkylation product was taken up in MeOH (100 mL) and NaBH$_4$ (4.3 g, 115 mmol, 1.4 equiv) was added. Gas evolution and some warming noted. After 30 min, the reaction was diluted with ether and washed with 1 N HCl, saturated aqueous NaHCO$_3$, brine, dried (MgSO$_4$), and concentrated in vacuo. The crude product was purified via flash column chromatography (0-50% EtOAc/hexane) to provide the product (4.35 g, 30%) as a pale yellow oil. $^1$H NMR (500 MHz, CDCl$_3$) δ 7.31-7.26 (m, 2H), 6.96 (td, J=7.4, 0.9 Hz, 1H), 6.90 (d, J=8.5 Hz, 1H), 5.93 (ddt, J=17.1, 10.3, 6.8 Hz, 1H), 5.24 (dq, J=17.2, 1.6 Hz, 1H), 5.17 (dq, J=10.2, 1.4 Hz, 1H), 4.70 (s, 2H), 4.12 (t, J=6.4 Hz, 2H), 2.61 (qt, J=6.4, 1.4 Hz, 2H), 2.50 (br. s., 1H).

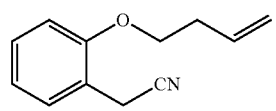

2-(2-(But-3-en-1-yloxy)phenyl)acetonitrile 2-(But-3-en-1-yloxy)phenyl)methanol (4.35 g, 24.4 mmol, 1 equiv) was taken up in thionyl chloride (81 mL) and heated to reflux for 1 h. Upon cooling to ambient temperature, the dark red purple solution was concentrated in vacuo. The residue was concentrated in vacuo with benzene (×3) to remove residual thionyl chloride and provide the crude benyl chloride as a purple oil. This was taken up in MeCN (80 mL) and NaCN (3.59 g, 73 mmol, 3 equiv) was added and the mixture was heated to reflux. After 24 h, the reaction was allowed to cool to ambient temperature. The reaction was diluted with ether, filtered, and the filtrate was concentrated in vacuo. The crude product was purified via flash column chromatography (0-100% DCM/hexane) to provide the product (3.0 g, 66%) as a pale yellow oil. ¹H NMR (400 MHz, CDCl₃) δ 7.37 (d, J=7.5 Hz, 1H), 7.34-7.28 (m, 1H), 6.98 (t, J=7.4 Hz, 1H), 6.89 (d, J=8.0 Hz, 1H), 5.92 (ddt, J=17.1, 10.3, 6.8 Hz, 1H), 5.20 (dd, J=17.1, 1.5 Hz, 1H), 5.14 (d, J=10.3 Hz, 1H), 4.08 (t, J=6.5 Hz, 2H), 3.70 (s, 2H), 2.60 (q, J=6.6 Hz, 2H).

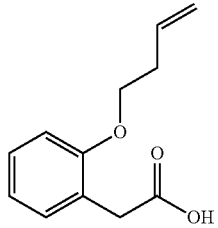

2-(2-(But-3-en-1-yloxy)phenyl)acetic acid

To a solution of 2-(2-(but-3-en-1-yloxy)phenyl)acetonitrile (1.0 g, 5.34 mmol, 1 equiv) in EtOH (27 mL) was added 10 N NaOH (27 mL). The reaction was heated at reflux for 18 h. Upon cooling to ambient temperature, the reaction was diluted with water and washed with ether. The aqueous layer was acidified with concentrated HCl and extracted with DCM (×3). The combined DCM extracts were dried (Na₂SO₄) and concentrated in vacuo to provide the product (0.98 g, 89%) as a viscous pale yellow oil. ¹H NMR (400 MHz, CDCl₃) δ 11.15-9.85 (m, 1H), 7.30-7.25 (m, 1H), 7.21 (dd, J=7.3, 1.5 Hz, 1H), 6.97-6.91 (m, 1H), 6.89 (d, J=8.3 Hz, 1H), 5.98-5.82 (m, 1H), 5.21-5.14 (m, 1H), 5.10 (dd, J=10.3, 1.5 Hz, 1H), 4.06 (t, J=6.5 Hz, 2H), 3.68 (s, 2H), 2.55 (q, J=6.6 Hz, 2H).

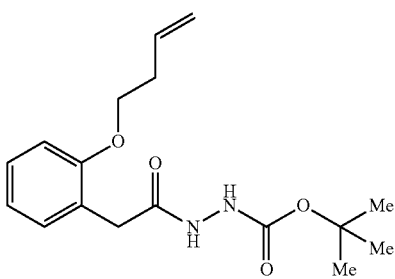 [SMILES: C=CCCOc1ccccc1CC(=O)NNC(=O)OC(C)(C)C]

tert-Butyl 2-(2-(2-(but-3-en-1-yloxy)phenyl)acetyl) hydrazinecarboxylate

To a solution of 2-(2-(but-3-en-1-yloxy)phenyl)acetic acid (0.22 g, 1.06 mmol, 1 equiv) in DCM (11 mL) was added one drop DMF followed by oxalyl chloride (0.19 mL, 2.11 mmol, 2 equiv). Gas evolution observed. After 1 h, the reaction was concentrated in vacuo to provide the crude acid chloride. The acid chloride was taken up in DCM (5 mL) and added slowly to a solution of tert-butyl hydrazinecarboxylate (168 mg, 1.27 mmol, 1.2 equiv) and DIPEA (0.55 mL, 3.17 mmol, 3 equiv) in DCM (11 mL). After stirring 1 h, the reaction was diluted with DCM, washed with saturated aqueous NaHCO₃, dried (MgSO₄), and concentrated in vacuo. The crude product was purified via flash column chromatography (0-100% EtOAc/hexane) to provide the product (0.28 g, 83%) as a viscous tan oil. ¹H NMR (400 MHz, CDCl₃) δ 7.62 (br. s., 1H), 7.31-7.23 (m, 2H), 7.00-6.87 (m, 2H), 6.48-6.26 (m, 1H), 5.99-5.85 (m, 1H), 5.23 (dd, J=17.1, 1.5 Hz, 1H), 5.17 (d, J=10.3 Hz, 1H), 4.14-4.09 (m, 2H), 3.61 (s, 2H), 2.61 (q, J=6.4 Hz, 2H), 1.48-1.36 (m, 9H).

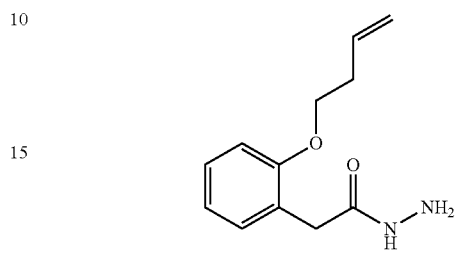

2-(2-(But-3-en-1-yloxy)phenyl)acetohydrazide HCl tert-Butyl 2-(2-(2-(but-3-en-1-yloxy)phenyl)acetyl)hydrazinecarboxylate (0.28 g, 0.874 mmol, 1 equiv) was treated with 4 N HCl in dioxane (9 mL). After stirring 18 h, the reaction was concentrated in vacuo. The crude product was triturated with ether to provide the product (0.16 g, 71%) as a yellow solid. ¹H NMR (400 MHz, CD₃OD) δ 7.28 (td, J=7.9, 1.8 Hz, 1H), 7.22 (dd, J=7.5, 1.3 Hz, 1H), 6.98 (d, J=8.3 Hz, 1H), 6.93 (t, J=7.5 Hz, 1H), 5.95 (ddt, J=17.2, 10.3, 6.8 Hz, 1H), 5.18 (dd, J=17.2, 1.6 Hz, 1H), 5.11 (d, J=10.3 Hz, 1H), 4.06 (t, J=6.7 Hz, 2H), 3.63 (s, 2H), 2.56 (q, J=6.6 Hz, 2H); LCMS (ESI, M+1): 221.15.

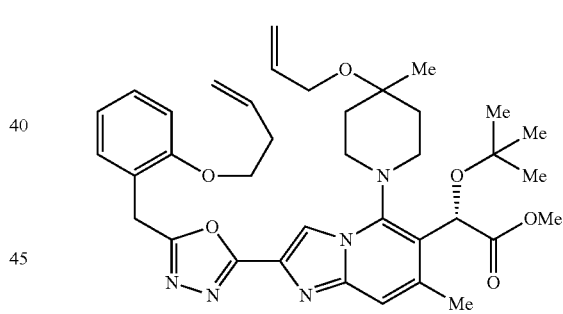

(S)-Methyl 2-(5-(4-(allyloxy)-4-methylpiperidin-1-yl)-2-(5-(2-(but-3-en-1-yloxy)benzyl)-1,3,4-oxadiazol-2-yl)-7-methylimidazo[1,2-a]pyridin-6-yl)-2-(tert-butoxy)acetate A solution of (S)-5-(4-(allyloxy)-4-methylpiperidin-1-yl)-6-(1-(tert-butoxy)-2-methoxy-2-oxoethyl)-7-methylimidazo [1,2-a]pyridine-2-carboxylic acid sodium salt (76 mg, 0.153 mmol, 1 equiv), 2-(2-(but-3-en-1-yloxy)phenyl)acetohydrazide, HCl (55 mg, 0.214 mmol, 1.4 equiv), DIPEA (0.080 mL, 0.459 mmol, 3 equiv), and HATU (43 mg, 0.113 mmol, 1.4 equiv) in DMF (1.5 mL) was stirred 1 h. The reaction was then added to saturated aqueous NaHCO₃ and extracted with DCM (×3). The combined DCM extracts were dried (Na₂SO₄), and concentrated in vacuo. The crude coupling product was taken up in THF (1.5 mL) and Burgess reagent (146 mg, 0.612 mmol, 4 equiv) was added. The reaction was then heated to 60° C. for 1.5 h. Upon cooling to ambient temperature, the reaction was diluted with DCM and washed with water, saturated aqueous NaHCO₃, dried (Na₂SO₄), and concentrated in vacuo. The crude product was purified by flash column chromatography (0-100% EtOAc [2% TEA]/hexane) to provide the product (27 mg, 27%) as a yellow film. LCMS (ESI, M+1): 658.35.

Example 4

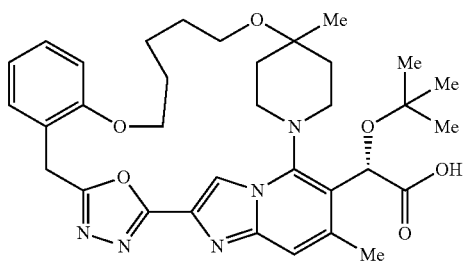 [SMILES: Cc1cc2nc3cn2c(c1[C@H](OC(C)(C)C)C(=O)O)N1CCC(C)(CC1)OCCCCCOc1ccccc1Cc1nnc-3o1]

(2S)-2-(tert-Butoxy)-2-{4,28-dimethyl-21,27,33-trioxa-1,7,11,12,34-pentaazahexacyclo[26.2.2.1⁶,⁹.1¹⁰,¹³.0²,⁷.0¹⁵,²⁰]tetratriaconta-2,4,6(34),8,10,12,15(20),16,18-nonaen-3-yl}acetic acid Prepared from (S)-methyl 2-(5-(4-(allyloxy)-4-methylpiperidin-1-yl)-2-(5-(2-(but-3-en-1-yloxy)benzyl)-1,3,4-oxadiazol-2-yl)-7-methylimidazo[1,2-a]pyridin-6-yl)-2-(tert-butoxy)acetate in 6% yield following the procedures used to prepare methyl(2S)-2-(tert-butoxy)-2-{15-fluoro-4,26-dimethyl-10-oxo-19,25-dioxa-1,7,11,31-tetraazapentacyclo[24.2.2.1⁶,⁹.0²,⁷.0¹³,¹⁸]hentriaconta-2,4,6(31),8,13(18),14,16-heptaen-3-yl}acetate and (2S)-2-(tert-butoxy)-2-{15-fluoro-4,26-dimethyl-10-oxo-19,25-dioxa-1,7,11,31-tetraazapentacyclo[24.2.2.1⁶,⁹.0²,⁷.0¹³,¹⁸]hentriaconta-2,4,6(31),8,13(18),14,16-heptaen-3-yl}acetic acid. ¹H NMR (500 MHz, DMSO-d₆) δ 8.08-8.03 (m, 1H), 7.36-7.32 (m, 2H), 7.28-7.23 (m, 1H), 7.09-7.01 (m, 1H), 6.97-6.89 (m, 1H), 5.92-5.76 (m, 1H), 4.33-4.21 (m, 2H), 4.13-4.03 (m, 2H), 3.77-3.69 (m, 2H), 3.14-3.03 (m, 2H), 2.91-2.81 (m, 1H), 2.74-2.62 (m, 1H), 2.44-2.39 (m, 3H), 1.93-1.60 (m, 10H), 1.23-1.20 (m, 3H), 1.17 (s, 9H); LCMS (ESI, M+1): 618.5.

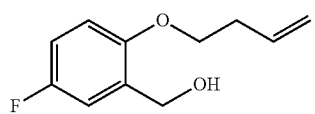

(2-(But-3-en-1-yloxy)-5-fluorophenyl)methanol

Prepared from 5-fluoro-2-hydroxybenzaldehyde in 39% yield following the same procedure as (2-(but-3-en-1-yloxy)phenyl)methanol. ¹H NMR (400 MHz, CDCl₃) δ 7.03 (dd, J=8.7, 3.1 Hz, 1H), 6.94 (td, J=8.5, 3.0 Hz, 1H), 6.80 (dd, J=9.0, 4.3 Hz, 1H), 5.90 (ddt, J=17.1, 10.3, 6.8 Hz, 1H), 5.26-5.09 (m, 2H), 4.65 (d, J=6.8 Hz, 2H), 4.06 (t, J=6.3 Hz, 2H), 2.66-2.53 (m, 2H), 2.40 (t, J=6.8 Hz, 1H).

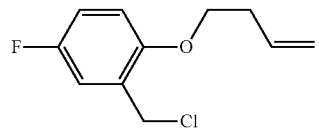

1-(But-3-en-1-yloxy)-2-(chloromethyl)-4-fluorobenzene (2-(But-3-en-1-yloxy)-5-fluorophenyl)methanol (6.3 g, 32.1 mmol, 1 equiv) was taken up in thionyl chloride (107 mL) and heated to reflux for 1 h. Upon cooling to ambient temperature, the solution was concentrated in vacuo. The residue was concentrated in vacuo with benzene (×3) to remove residual thionyl chloride and provide the benzyl chloride (6.3 g, 91%) as a yellow oil. ¹H NMR (400 MHz, CDCl₃) δ 7.12 (dd, J=8.7, 3.1 Hz, 1H), 6.98 (ddd, J=8.9, 8.0, 3.1 Hz, 1H), 6.82 (dd, J=9.0, 4.3 Hz, 1H), 5.93 (ddt, J=17.1, 10.3, 6.8 Hz, 1H), 5.25-5.09 (m, 2H), 4.62 (s, 2H), 4.05 (t, J=6.5 Hz, 2H), 2.58 (qt, J=6.6, 1.3 Hz, 2H).

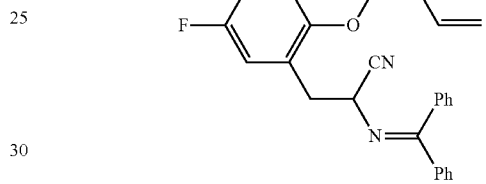

3-(2-(But-3-en-1-yloxy)-5-fluorophenyl)-2-((diphenylmethylene)amino)propanenitrile To a solution of 1-(but-3-en-1-yloxy)-2-(chloromethyl)-4-fluorobenzene (1 g, 4.66 mmol, 1 equiv), 2-((diphenylmethylene)amino)acetonitrile (1.13 g, 5.12 mmol, 1.1 equiv), and benzyltrimethylammonium chloride (87 mg, 0.466 mmol, 0.1 equiv) in DCM (8 mL) was added 10 N NaOH (0.84 mL, 8.39 mmol, 1.8 equiv). After 44 h, add to water and extract with DCM (×3). The combined DCM extracts were dried (Na₂SO₄) and concentrated in vacuo. The crude product was purified by flash column chromatography (0-30% EtOAc/hexane) to provide the product (1.39 g, 75%) as a yellow oil. ¹H NMR (400 MHz, CDCl₃) δ 7.62-7.54 (m, 2H), 7.49-7.33 (m, 5H), 6.96-6.74 (m, 5H), 6.61 (dd, J=8.8, 4.3 Hz, 1H), 5.58 (ddt, J=17.1, 10.2, 6.8 Hz, 1H), 5.18-4.97 (m, 2H), 4.65 (dd, J=9.2, 4.6 Hz, 1H), 3.81 (dt, J=8.7, 6.3 Hz, 1H), 3.62-3.45 (m, 1H), 3.37 (dd, J=13.1, 4.8 Hz, 1H), 3.15 (dd, J=13.1, 9.3 Hz, 1H), 2.24 (q, J=6.6 Hz, 2H).

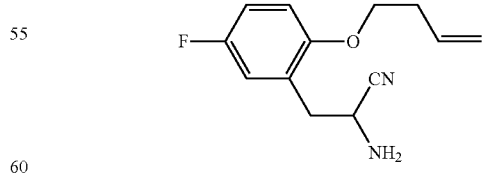

2-Amino-3-(2-(but-3-en-1-yloxy)-5-fluorophenyl)propanenitrile

To a solution of 3-(2-(but-3-en-1-yloxy)-5-fluorophenyl)-2-((diphenylmethylene)amino)propanenitrile (1.39 g, 3.49 mmol, 1 equiv) in THF (14 mL) was added 1 N HCl (3.84 mL, 3.84 mmol, 1.1 equiv). After 3 h, the reaction was diluted with water and washed with ether. The aqueous layer was then neutralized with 1 N NaOH and extracted with DCM (×3). The combined DCM extracts were dried (Na₂SO₄) and concentrated in vacuo to provide the product (0.60 g, 73%) as a yellow oil. ¹H NMR (400 MHz, CDCl₃) δ 7.00-6.92 (m, 2H), 6.85-6.77 (m, 1H), 5.90 (ddt, J=17.1, 10.2, 6.8 Hz, 1H), 5.20 (dd, J=17.1, 1.5 Hz, 1H), 5.15 (d, J=11.0 Hz, 1H), 4.12 (t, J=7.3 Hz, 1H), 4.03 (t, J=6.3 Hz, 2H), 3.05 (d, J=7.3 Hz, 2H), 2.57 (q, J=6.5 Hz, 2H), 2.19 (br. s., 2H).

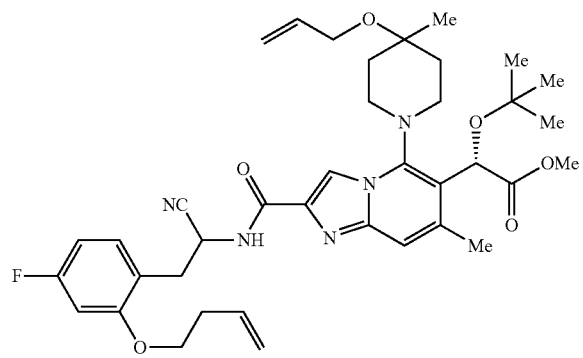 [SMILES: C=CCCOc1cc(F)ccc1CC(C#N)NC(=O)c1cn2c(N3CCC(C)(OCC=C)CC3)c([C@H](OC(C)(C)C)C(=O)OC)c(C)cc2n1]

(2S)-Methyl 2-(5-(4-(allyloxy)-4-methylpiperidin-1-yl)-2-((2-(2-(but-3-en-1-yloxy)-4-fluorophenyl)-1-cyanoethyl)carbamoyl)-7-methylimidazo[1,2-a]pyridin-6-yl)-2-(tert-butoxy)acetate Prepared from 2-amino-3-(2-(but-3-en-1-yloxy)-5-fluorophenyl)propanenitrile and (S)-5-(4-(allyloxy)-4-methylpiperidin-1-yl)-6-(1-(tert-butoxy)-2-methoxy-2-oxoethyl)-7-methylimidazo[1,2-a]pyridine-2-carboxylic acid sodium salt in 70% following the same procedure as (S)-methyl 2-(2-((2-(allyloxy)benzyl)carbamoyl)-5-(4-(but-3-en-1-yl)-4-methylpiperidin-1-yl)-7-methylimidazo[1,2-a]pyridin-6-yl)-2-(tert-butoxy)acetate. LCMS (ESI, M+1): 690.4.

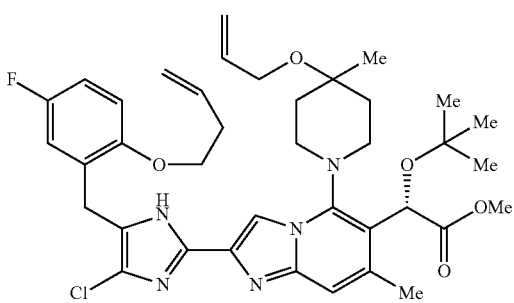 [SMILES: C=CCCOc1ccc(F)cc1Cc1[nH]c(-c2cn3c(N4CCC(C)(OCC=C)CC4)c([C@H](OC(C)(C)C)C(=O)OC)c(C)cc3n2)nc1Cl]

(S)-Methyl 2-(5-(4-(allyloxy)-4-methylpiperidin-1-yl)-2-(5-(2-(but-3-en-1-yloxy)-5-fluorobenzyl)-4-chloro-1H-imidazol-2-yl)-7-methylimidazo[1,2-a]pyridin-6-yl)-2-(tert-butoxy)acetate To a solution of (2S)-methyl 2-(5-(4-(allyloxy)-4-methylpiperidin-1-yl)-2-((2-(2-(but-3-en-1-yloxy)-4-fluorophenyl)-1-cyano ethyl)carbamoyl)-7-methylimidazo[1,2-a]pyridin-6-yl)-2-(tert-butoxy)acetate (215 mg, 0.312 mmol, 1 equiv) and carbon tetrachloride (0.075 mL, 0.7796 mmol, 2.5 equiv) in MeCN (3.1 mL) was added PPh₃ (204 mg, 0.7796 mmol, 2.5 equiv). The reaction was heated to 50° C. for 3 h. Upon cooling to ambient temperature, the reaction was diluted with DCM and washed with 1 N NaOH, dried (Na₂SO₄), and concentrated in vacuo. The crude product was purified by flash column chromatography (0-100% EtOAc [2% TEA]/hexane) to provide the product (134 mg, 61%) as a yellow film. LCMS (ESI, M+1): 708.35.

Example 5

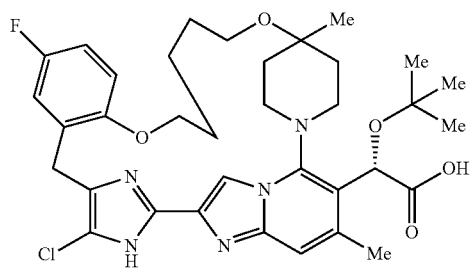 [SMILES: Cc1cc2nc3cn2c(c1[C@H](OC(C)(C)C)C(=O)O)N1CCC(C)(CC1)OCCCCCOc1ccc(F)cc1Cc1nc-3[nH]c1Cl]

((2S)-2-(tert-Butoxy)-2-{12-chloro-17-fluoro-4,28-dimethyl-21,27-dioxa-1,7,11,33,34-pentaazahexacyclo[26.2.2.1⁶,⁹.1¹⁰,¹³.0²,⁷.0¹⁵,²⁰]tetratriaconta-2,4,6 (34),8,10(33),12,15(20),16,18-nonaen-3-yl}acetic acid Prepared from (S)-methyl 2-(5-(4-(allyloxy)-4-methylpiperidin-1-yl)-2-(5-(2-(but-3-en-1-yloxy)-5-fluorobenzyl)-4-chloro-1H-imidazol-2-yl)-7-methylimidazo[1,2-a]pyridin-6-yl)-2-(tert-butoxy)acetate in 3% yield following the procedures used to prepare methyl(2S)-2-(tert-butoxy)-2-{15-fluoro-4,26-dimethyl-10-oxo-19,25-dioxa-1,7,11,31-tetraazapentacyclo[24.2.2.1⁶,⁹.0²,⁷.0¹³,¹⁸]hentriaconta-2,4,6 (31),8,13(18),14,16-heptaen-3-yl}acetate and (2S)-2-(tert-butoxy)-2-{15-fluoro-4,26-dimethyl-10-oxo-19,25-dioxa-1,7,11,31-tetraazapentacyclo[24.2.2.1⁶,⁹.0²,⁷.0¹³,¹⁸] hentriaconta-2,4,6(31),8,13(18),14,16-heptaen-3-yl}acetic acid. ¹H NMR (500 MHz, DMSO-d₆) δ 12.35-12.20 (m, 1H), 7.96 (s, 1H), 7.24 (s, 1H), 7.18 (br. s., 1H), 6.99 (br. s., 2H), 5.92 (br. s., 1H), 4.18-3.47 (m, 8H), 3.00 (br. s., 1H), 2.66 (br. s., 1H), 2.40 (br. s., 3H), 1.94-1.62 (m, 10H), 1.22 (br. s., 3H), 1.19 (s, 9H); LCMS (ESI, M+1): 668.6.

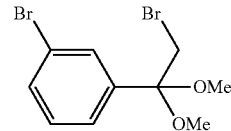

1-Bromo-3-(2-bromo-1,1-dimethoxyethyl)benzene

A solution of 2-bromo-1-(3-bromophenyl)ethanone (48.23 g, 174 mmol) in MeOH (200 ml) was treated with trimethyl orthoformate (57.5 mL) and pTsOH (1.650 g, 8.68 mmol) and heated at reflux (75° C. oil bath) under nitrogen for 2.5 hrs. The mixture was cooled, concentrated to a viscous oil, diluted with Et₂O (250 mL), and washed with 2.0 M aq. K₂CO₃ (100 mL), then brine. The organic layer was dried (MgSO₄), filtered, and concentrated under reduced pressure, affording the product (56.43 g, 174 mmol, 100% yield) as a mobile yellow oil. ¹H NMR (500 MHz, CDCl₃) δ 7.69 (t, J=1.8 Hz, 1H), 7.48 (ddd, J=7.9, 2.0, 1.0 Hz, 1H), 7.43 (dq, J=7.8, 0.9 Hz, 1H), 7.29-7.24 (m, 2H), 3.60 (s, 2H), 3.24 (s, 6H). ¹³C NMR (126 MHz, CDCl₃) δ 141.0, 131.5, 130.6, 129.6, 125.9, 122.3, 100.8, 49.5, 35.0. LCMS (M+H-MeOH)=291.97.

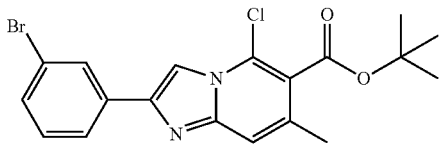 [SMILES: Cc1cc2nc(-c3cccc(Br)c3)cn2c(Cl)c1C(=O)OC(C)(C)C]

tert-Butyl 2-(3-bromophenyl)-5-chloro-7-methylimidazo[1,2-a]pyridine-6-carboxylate A flask charged with chlorobenzene (300 ml) was heated to reflux (140° C. oil bath) and to this was added sequentially 1-bromo-3-(2-bromo-1,1-dimethoxyethyl)benzene (56.05 g, 173 mmol) as an oil, and tert-butyl 6-amino-2-chloro-4-methylnicotinate (33.91 g, 140 mmol) as a powder, rinsing both with additional chlorobenzene (70 mL total) to facilitate transfer. The reaction was returned to reflux and heated for 90 min, then cooled and poured slowly into vigorously stirred Et₂O (1500 mL). The resulting suspension was stirred for 15 min, then solids were collected by vacuum filtration to afford the product (47 g, 111 mmol, 64.4% yield) as a tan powdery solid. A 3 g sample of product was first purified by biotage (80 g SiO₂, 0% (3 CV), 0-60% (15 CV), 60% (2 CV), EtOAc in hexanes), then recrystallized from hot acetonitrile to afford a high purity sample for spectra. ¹H NMR (500 MHz, CDCl₃) δ 8.14 (t, J=1.7 Hz, 1H), 8.02 (d, J=0.5 Hz, 1H), 7.89 (dq, J=7.7, 0.9 Hz, 1H), 7.48 (ddd, J=8.0, 2.0, 1.1 Hz, 1H), 7.41-7.39 (m, 1H), 7.32 (t, J=7.9 Hz, 1H), 2.45 (d, J=0.9 Hz, 3H), 1.65 (s, 9H). ¹³C NMR (126 MHz, CDCl₃) δ 164.3, 145.6, 145.2, 135.3, 133.6, 131.3, 130.3, 129.2, 124.7, 123.9, 123.0, 121.7, 115.4, 107.6, 83.9, 28.1, 19.9. LCMS (M+H)=421.3.

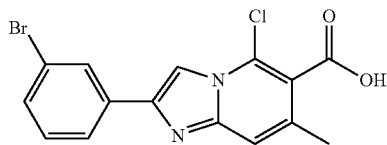 [SMILES: Cc1cc2nc(-c3cccc(Br)c3)cn2c(Cl)c1C(=O)O]

2-(3-Bromophenyl)-5-chloro-7-methylimidazo[1,2-a]pyridine-6-carboxylic acid, HCl salt A suspension of tert-butyl 2-(3-bromophenyl)-5-chloro-7-methylimidazo[1,2-a]pyridine-6-carboxylate (35.5 g, 84 mmol) in 4.0 N HCl in dioxane (800 ml) was stirred for 48 hrs. The reaction was concentrated to a thick paste, then the residue was triturated with acetonitrile, collecting solids by vacuum filtration and washing with several small portions of acetonitrile. The reside was resuspended in fresh acetonitrile, stirred for 20 min, then filtered to collect solids. The solids were dried once from Et₂O by rotary evaporator, to afford the product (23.3 g, 58.0 mmol, 68.8% yield) as an off-white powder. ¹H NMR (500 MHz, DMSO-d₆) δ 8.90 (s, 1H), 8.35 (t, J=1.7 Hz, 1H), 8.17-8.08 (m, 1H), 7.73 (s, 1H), 7.67-7.59 (m, 1H), 7.48 (t, J=8.0 Hz, 1H), 2.46 (d, J=0.9 Hz, 3H). ¹³C NMR (126 MHz, DMSO-d₆) δ 165.9, 143.1, 132.6, 131.7, 129.2, 125.6, 125.1, 125.1, 124.3, 123.0, 113.2, 110.9, 66.8, 20.0. LCMS (M+H)=367.1.

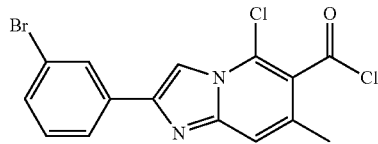 [SMILES: Cc1cc2nc(-c3cccc(Br)c3)cn2c(Cl)c1C(=O)Cl]

2-(3-Bromophenyl)-5-chloro-7-methylimidazo[1,2-a]pyridine-6-carbonyl chloride

A suspension of 2-(3-bromophenyl)-5-chloro-7-methylimidazo[1,2-a]pyridine-6-carboxylic acid, HCl salt (22.03 g, 60.3 mmol) in dry dichlormethane (600 ml) was treated with oxalyl chloride (13 ml, 149 mmol) followed by DMF (1.5 mL). The suspension was stirred for 3.5 hrs, then concentrated under reduced pressure to afford the acid-chloride as a brown powdery solid which was then used immediately in the following step.

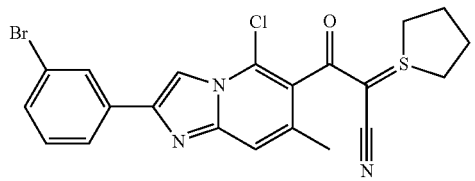 [SMILES: Cc1cc2nc(-c3cccc(Br)c3)cn2c(Cl)c1C(=O)C(C#N)=S1CCCC1]

3-[2-(3-Bromophenyl)-5-chloro-7-methylimidazo[1,2-a]pyridin-6-yl]-3-oxo-2-[(1E)-1λ⁴-thiolan-1-ylidene]propanenitrile A stirred solution of 2-(3-bromophenyl)-5-chloro-7-methylimidazo[1,2-a]pyridine-6-carbonyl chloride (23.16 g, 60.3 mmol) in dichloromethane (600 ml) was treated with 1-(cyanomethyl)tetrahydro-1H-thiophen-1-ium bromide (18.82 g, 90 mmol) followed by Hunig's Base (31.6 ml, 181 mmol). The reaction was stirred for 16 hrs at room temperature, then the mixture was washed with saturated sodium bicarbonate solution (2×200 mL) and the combined aqueous layer was back extracted (2×50 mL). The combined organic layers were dried (Na₂SO₄), filtered, and concentrated under reduced pressure to a reduced volume. The concentrated solution was purified by biotage (330 g SiO₂, 10% (3 CV), 10-100% (10 CV), 100% (2 CV), EtOAc in hexanes, then 0% (2 CV), 0-10% (10 CV), 10% (2 CV) MeOH in CH₂Cl₂). Product fractions were pooled and concentrated under reduced pressure, affording the product (24.6 g, 51.8 mmol, 86% yield) as a brown glassy solid. This material was used as-is in the following step. Separately, a small sample of column purified product was dissolved in minimal acetonitrile, then further diluted with approximately 4 volumes of Et₂O. After 10 min, the resulting crystals were collected by vacuum filtration, washing with Et₂O, to afford a higher purity sample for spectra. ¹H NMR (500 MHz, CDCl₃) δ 8.14 (t, J=1.7 Hz, 1H), 8.00 (d, J=0.5 Hz, 1H), 7.92-7.86 (m, 1H), 7.49-7.45 (m, 1H), 7.44-7.39 (m, 1H), 7.36-7.28 (m, 1H), 3.62-3.52 (m, 4H), 2.78-2.67 (m, 2H), 2.42 (d, J=1.1 Hz, 3H), 2.26-2.14 (m, 2H). LCMS (M+H)=476.1.

Methyl 2-(2-(3-bromophenyl)-5-chloro-7-methylimidazo[1,2-a]pyridin-6-yl)-2-oxoacetate A suspension of 3-[2-(3-Bromophenyl)-5-chloro-7-methylimidazo[1,2-a]pyridin-6-yl]-3-oxo-2-[(1E)-1λ⁴-thiolan-1-ylidene]propanenitrile (18.92 g, 39.8 mmol) and oxone (39.2 g, 63.8 mmol) in anhydrous MeOH (660 ml) was heated (75° C. oil bath) and stirred exposed to air. Additional oxone (12.25 g, 19.92 mmol) was added after each of 5 hrs and 7.5 hrs respectively. The temperature was reduced (40° C.) and the reaction was stirred for 16 hrs, then warmed again (80° C.) and stirred for 20 hrs. Solids were removed by filtration, and the filtrate was concentrated. The residue was dissolved in EtOAc and washed with water. The organic layer was dried (MgSO₄) and concentrated to a small volume. Solids were collected and the filtrate was further concentrated, affording a second crop of solids, both of similar purity, and combined to afford the desired product (9 g, 22.08 mmol, 55.4% yield) as a yellow powdery solid. LCMS (M+H)=409.0.

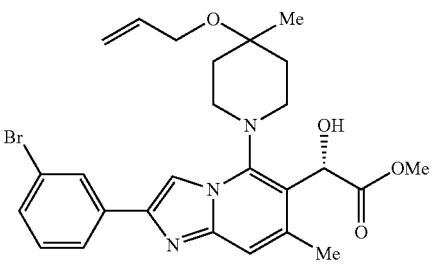

(S)-Methyl 2-(5-(4-(allyloxy)-4-methylpiperidin-1-yl)-2-(3-bromophenyl)-7-methylimidazo[1,2-a]pyridin-6-yl)-2-hydroxyacetate Prepared from methyl 2-(5-(4-(allyloxy)-4-methylpiperidin-1-yl)-2-(3-bromophenyl)-7-methylimidazo[1,2-a]pyridin-6-yl)-2-oxoacetate in 80% yield following the same procedure as (S)-ethyl 5-(4-(but-3-en-1-yl)-4-methylpiperidin-1-yl)-6-(1-hydroxy-2-methoxy-2-oxoethyl)-7-methylimidazo[1,2-a]pyridine-2-carboxylate. ¹H NMR (400 MHz, CDCl₃) δ 8.06 (s, 1H), 8.01 (s, 1H), 7.96 (br. s., 1H), 7.51-7.31 (m, 3H), 6.24-6.09 (m, 1H), 5.58-5.50 (m, 2H), 5.46-5.40 (m, 1H), 4.83-4.72 (m, 1H), 4.02 (d, J=5.0 Hz, 2H), 3.90 (t, J=11.8 Hz, 2H), 3.79 (s, 3H), 2.91 (d, J=8.0 Hz, 1H), 2.66 (d, J=10.8 Hz, 1H), 2.49 (s, 3H), 1.99 (t, J=11.8 Hz, 2H), 1.82 (qd, J=12.9, 4.8 Hz, 2H), 1.34 (s, 3H); LCMS (ESI, M+1): 528.25.

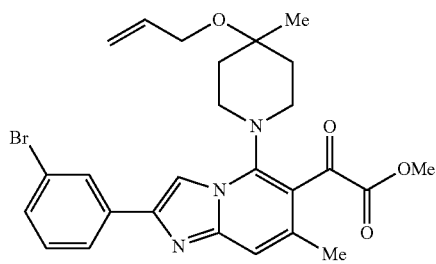 [SMILES: C=CCOC1(C)CCN(c2c(C(=O)C(=O)OC)c(C)cc3nc(-c4cccc(Br)c4)cn23)CC1]

Methyl 2-(5-(4-(allyloxy)-4-methylpiperidin-1-yl)-2-(3-bromophenyl)-7-methylimidazo[1,2-a]pyridin-6-yl)-2-oxoacetate Prepared from methyl 2-(2-(3-bromophenyl)-5-chloro-7-methylimidazo[1,2-a]pyridin-6-yl)-2-oxoacetate in 77% yield following the same procedure as ethyl 5-(4-(but-3-en-1-yl)-4-methylpiperidin-1-yl)-6-(2-methoxy-2-oxoacetyl)-7-methylimidazo[1,2-a]pyridine-2-carboxylate. ¹H NMR (500 MHz, CDCl₃) δ 8.10 (s, 1H), 8.00 (s, 1H), 7.93 (d, J=7.6 Hz, 1H), 7.53-7.49 (m, 1H), 7.41 (br. s., 1H), 7.34 (t, J=7.8 Hz, 1H), 6.24-6.09 (m, 1H), 5.53 (d, J=16.9 Hz, 1H), 5.41 (d, J=10.2 Hz, 1H), 4.03-4.00 (m, 2H), 3.97 (s, 3H), 3.86 (t, J=11.3 Hz, 2H), 2.81 (d, J=7.6 Hz, 2H), 2.42 (s, 3H), 1.96 (d, J=12.6 Hz, 2H), 1.64 (br. s., 2H), 1.32 (s, 3H); LCMS (ESI, M+1): 526.2.

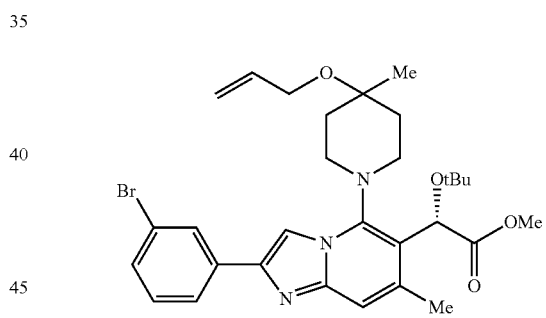

(S)-Methyl 2-(5-(4-(allyloxy)-4-methylpiperidin-1-yl)-2-(3-bromophenyl)-7-methylimidazo[1,2-a]pyridin-6-yl)-2-(tert-butoxy)acetate Prepared from (S)-methyl 2-(5-(4-(allyloxy)-4-methylpiperidin-1-yl)-2-(3-bromophenyl)-7-methylimidazo[1,2-a]pyridin-6-yl)-2-hydroxyacetate in 45% yield following the same procedure as (S)-ethyl 5-(4-(but-3-en-1-yl)-4-methylpiperidin-1-yl)-6-(1-(tert-butoxy)-2-methoxy-2-oxoethyl)-7-methylimidazo[1,2-a]pyridine-2-carboxylate. ¹H NMR (400 MHz, CDCl₃) δ 8.06 (s, 1H), 7.99 (s, 1H), 7.96 (d, J=7.8 Hz, 1H), 7.47 (d, J=7.8 Hz, 1H), 7.40 (br. s., 1H), 7.35-7.30 (m, 1H), 6.23-6.10 (m, 1H), 6.05 (s, 1H), 5.55 (dd, J=17.1, 1.8 Hz, 1H), 5.42 (dd, J=10.4, 1.4 Hz, 1H), 4.04 (d, J=5.3 Hz, 2H), 4.01-3.93 (m, 1H), 3.84-3.75 (m, 1H), 3.69 (s, 3H), 3.03 (dd, J=11.0, 3.0 Hz, 1H), 2.72 (d, J=8.0 Hz, 1H), 2.49 (s, 3H), 2.00 (dd, J=14.2, 2.6 Hz, H), 1.88-1.78 (m, 2H), 1.35 (s, 3H), 1.26 (s, 9H); LCMS (ESI, M+1): 584.25.

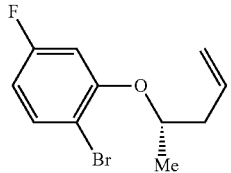

(S)-1-Bromo-4-fluoro-2-(pent-4-en-2-yloxy)benzene

To a solution of 2-bromo-5-fluorophenol (1.46 g, 7.64 mmol, 1 equiv), (R)-pent-4-en-2-ol (0.94 mL, 9.17 mmol, 1.2 equiv), and PPh$_3$ (2.40 g, 9.17 mmol, 1.2 equiv) in THF (26 mL) was added DIAD (1.78 mL, 9.17 mmol, 1.2 equiv). After stirring 2 h, the yellow solution was diluted with ether, washed with 1 N NaOH, dried (MgSO$_4$), and concentrated in vacuo. The crude product was purified by flash column chromatography (hexane) to provide the product (1.18 g, 60%) as a colorless oil. $^1$H NMR (500 MHz, CDCl$_3$) δ 7.49 (dd, J=8.7, 6.3 Hz, 1H), 6.67 (dd, J=10.6, 2.8 Hz, 1H), 6.62-6.56 (m, 1H), 5.91 (ddt, J=17.1, 10.1, 7.1 Hz, 1H), 5.22-5.12 (m, 2H), 4.49-4.38 (m, 1H), 2.62-2.52 (m, 1H), 2.49-2.40 (m, 1H), 1.39 (d, J=6.1 Hz, 3H).

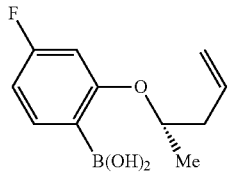

(S)-(4-Fluoro-2-(pent-4-en-2-yloxy)phenyl)boronic acid

A solution of (S)-1-bromo-4-fluoro-2-(pent-4-en-2-yloxy) benzene (0.66 mL, 2.55 mmol, 1 equiv) in THF (13 mL) was cooled to −78° C. (IPA/dry ice). nBuLi (1.9 mL of a 1.6 M solution in hexane, 3.06 mmol, 1.2 equiv) was added slowly. No color change observed. After 45 min, triisopropyl borate (0.70 mL, 3.06 mmol, 1.2 equiv) was added. The reaction was stirred 30 min. 1 N HCl (5 mL) was added and the reaction was removed from the cold bath. After 10 min, the reaction was added to water and extracted with DCM (×3). The combined DCM extracts were dried (Na$_2$SO$_4$) and concentrated in vacuo to provide the crude boronic acid (0.58 g, 100%) as a viscous pale yellow oil. Purity is ~80%. The crude boronic acid was for used as is for the Suzuki coupling. $^1$H NMR (500 MHz, CDCl$_3$) δ 7.85 (t, J=8.0 Hz, 1H), 6.74 (td, J=8.3, 2.2 Hz, 1H), 6.66-6.62 (m, 1H), 5.87 (ddt, J=17.1, 10.1, 7.1 Hz, 1H), 5.24-5.18 (m, 2H), 4.63-4.54 (m, 1H), 2.60-2.45 (m, 2H), 1.43 (d, J=6.1 Hz, 3H).

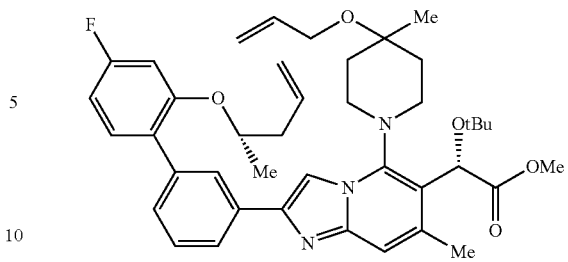

(S)-Methyl 2-(5-(4-(allyloxy)-4-methylpiperidin-1-yl)-2-(4'-fluoro-2'-((S)-pent-4-en-2-yloxy)-[1,1'-biphenyl]-3-yl)-7-methylimidazo[1,2-a]pyridin-6-yl)-2-(tert-butoxy)acetate To a solution of (S)-methyl 2-(5-(4-(allyloxy)-4-methylpiperidin-1-yl)-2-(3-bromophenyl)-7-methylimidazo[1,2-a]pyridin-6-yl)-2-(tert-butoxy)acetate (0.27 g, 0.462 mmol, 1 equiv) and (S)-(4-fluoro-2-(pent-4-en-2-yloxy)phenyl)boronic acid (207 mg, 0.924 mmol, 2 equiv) in DMF (5 mL, sparged with nitrogen for 10 min) was added Pd(PPh$_3$)$_4$ (53 mg, 0.046 mmol, 0.1 equiv) and 2 M Na$_2$CO$_3$ (0.46 mL, 0.924 mmol, 2 equiv). The reaction was heated at 90° C. for 2.5 h. Upon cooling to ambient temperature, the reaction was diluted with EtOAc, washed with water, dried (Na$_2$SO$_4$), and concentrated in vacuo. The crude product was purified by flash column chromatography (0-100% EtOAc [2% TEA]/hexane) to provide the product (210 mg, 66%) as a viscous yellow oil. LCMS (ESI, M+1): 684.35.

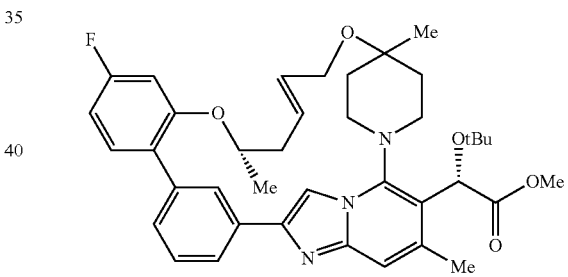

Methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate A solution of (S)-methyl 2-(5-(4-(allyloxy)-4-methylpiperidin-1-yl)-2-(4'-fluoro-2'-((S)-pent-4-en-2-yloxy)-[1,1'-biphenyl]-3-yl)-7-methylimidazo[1,2-a]pyridin-6-yl)-2-(tert-butoxy)acetate (0.21 g, 0.307 mmol, 1 equiv) and TsOH monohydrate (58 mg, 0.307 mmol, 1 equiv) in DCE (300 mL) was heated to 80° C. The Hoveyda Grubbs 2$^{nd}$ generation catalyst (19 mg, 0.031 mmol, 0.1 equiv) was added. The pale green brown solution was stirred for 2 h. Upon cooling to ambient temperature, the reaction was washed with saturated aqueous NaHCO$_3$, dried (Na$_2$SO$_4$), and concentrated in vacuo. The crude product was purified by flash column chromatography (0-100% EtOAc [2% TEA]/hexane) to provide the product (0.20 g, 99%) as a yellow glass. LCMS (ESI, M+1): 656.25.

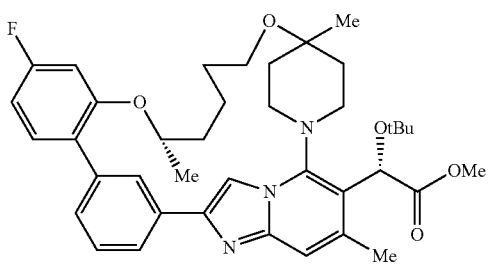 [SMILES: COC(=O)[C@@H](OC(C)(C)C)c1c(C)cc2nc3cn2c1N1CCC(C)(CC1)OCCCC[C@H](C)Oc1cc(F)ccc1-c1cccc-3c1]

Methyl(2S)-2-(tert-butoxy)-2-[(22S)-18-fluoro-4,22,
28-trimethyl-21,27-dioxa-1,7,34-triazahexacyclo
[26.2.2.1$^{6,9}$.1$^{10,14}$.0$^{2,7}$.0$^{15,20}$]tetratriaconta-2,4,6
(34),8,10(33),11,13,15(20),16,18-decaen-3-yl]
acetate To a solution of methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate (0.19 g, 0.29 mmol, 1 equiv) in MeOH (6 mL) was added 10% Pd/C (62 mg, 0.058 mmol, 0.2 equiv). The reaction was then stirred under a balloon of H$_2$ for 4 d. More 10% Pd/C (62 mg, 0.058 mmol, 0.2 equiv) was added. After 5 h, the reaction was then filtered through Celite eluting with MeOH. The filtrate was then concentrated in vacuo. The crude product was purified by flash column chromatography (0-100% EtOAc [2% TEA]/hexane) to provide the product (0.15 g, 79%) as a colorless glass. LCMS (ESI, M+1): 658.5.

Example 6

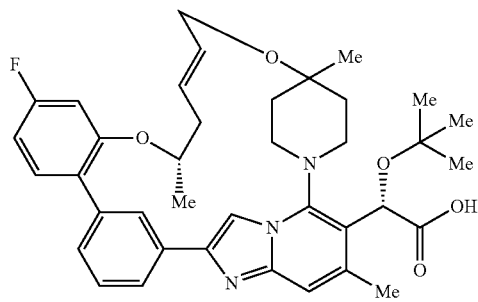 [SMILES: Cc1cc2nc3cn2c(c1[C@H](OC(C)(C)C)C(=O)O)N1CCC(C)(CC1)OC/C=C/C[C@H](C)Oc1cc(F)ccc1-c1cccc-3c1]

(2S)-2-(tert-Butoxy)-2-[(22S)-18-fluoro-4,22,28-
trimethyl-21,27-dioxa-1,7,34-triazahexacyclo
[26.2.2.1$^{6,9}$.1$^{10,14}$.0$^{2,7}$.0$^{15,20}$]tetratriaconta-2,4,6
(34),8,10(33),11,13,15(20),16,18,24-undecaen-3-yl]
acetic acid To a solution of methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (11 mg, 0.017 mmol, 1 equiv) in 9:1 MeOH:water (1.1 mL) was added LiOH·H$_2$O (28 mg, 0.671 mmol, 40 equiv). The reaction was heated to 70° C. for 1 h. Upon cooling to ambient temperature, the reaction was filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-85% B over 15 minutes, then a 5-minute hold at 100% B; Flow: 20 mL/min. Product isolated (7.2 mg, 77%). $^1$H NMR (500 MHz, DMSO-d$_6$) δ 7.84 (d, J=7.6 Hz, 1H), 7.76 (d, J=6.1 Hz, 2H), 7.28 (t, J=7.6 Hz, 1H), 7.11 (t, J=7.6 Hz, 1H), 7.06 (s, 1H), 7.03 (d, J=7.3 Hz, 1H), 6.89 (d, J=11.6 Hz, 1H), 6.62 (t, J=8.1 Hz, 1H), 5.90-5.80 (m, 1H), 5.68 (br. s., 1H), 5.54 (d, J=15.6 Hz, 1H), 4.44 (br. s., 1H), 3.80-3.65 (m, 3H), 3.39 (d, J=11.3 Hz, 1H), 2.87 (d, J=8.5 Hz, 1H), 2.37 (d, J=8.2 Hz, 1H), 2.33-2.29 (m, 1H), 2.28 (br. s., 3H), 2.08-1.98 (m, 1H), 1.76-1.58 (m, 2H), 1.52-1.40 (m, 2H), 1.01 (s, 3H), 0.94 (s, 9H), 0.83 (d, J=5.8 Hz, 3H); LCMS (ESI, M+1): 642.5.

Example 7

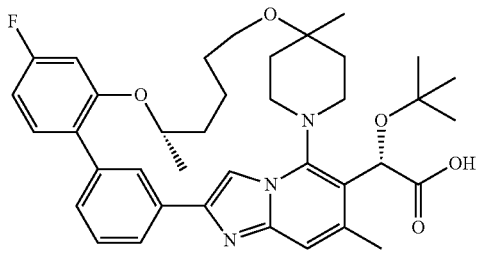 [SMILES: Cc1cc2nc3cn2c(c1[C@H](OC(C)(C)C)C(=O)O)N1CCC(C)(CC1)OCCCC[C@H](C)Oc1cc(F)ccc1-c1cccc-3c1]

(2S)-2-(tert-Butoxy)-2-[(22S)-4,17,22,28-tetram-
ethyl-21,27-dioxa-1,7,34-triazahexacyclo[26.2.
2.1$^{6,9}$.1$^{10,14}$.0$^{2,7}$.0$^{15,20}$]tetratriaconta-2,4,6(34),8,10
(33),11,13,15(20),16,18-decaen-3-yl]acetic acid To a solution of methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate (20 mg, 0.030 mmol, 1 equiv) in MeOH (2 mL) was added 10% Pd/C (6 mg, 0.006 mmol, 0.2 equiv). The reaction was then stirred under a balloon of H$_2$ for 2 h. The reaction was then filtered through Celite eluting with MeOH. The filtrate was then concentrated in vacuo. The crude hydrogenation product was taken upon in MeOH (1.5 mL), water (1 mL0, and THF (0.5 mL) and LiOH·H$_2$O (37 mg, 0.913 mmol, 30 equiv) was added. The reaction was heated to 60° C. for 2 h. Upon cooling to ambient temperature, the reaction was filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-90% B over 15 minutes, then a 5-minute hold at 100% B; Flow: 20 mL/min to provide the product (5.2 mg, 27%). $^1$H NMR (500 MHz, DMSO-d$_6$) δ 8.07 (br. s., 2H), 7.97 (s, 1H), 7.50 (t, J=7.8 Hz, 1H), 7.35 (t, J=7.6 Hz, 1H), 7.29-7.21 (m, 2H), 7.08 (d, J=11.0 Hz, 1H), 6.83 (t, J=8.1 Hz, 1H), 5.79 (br. s., 1H), 4.70 (br. s., 1H), 3.82 (t, J=11.3 Hz, 1H), 2.63 (d, J=8.2 Hz, 1H), 2.39 (s, 3H), 1.94-1.57 (m, 12H), 1.52 (br. s., 1H), 1.19 (s, 3H), 1.15 (s, 9H), 1.12 (d, J=5.8 Hz, 3H); LCMS (ESI, M+1): 644.35.

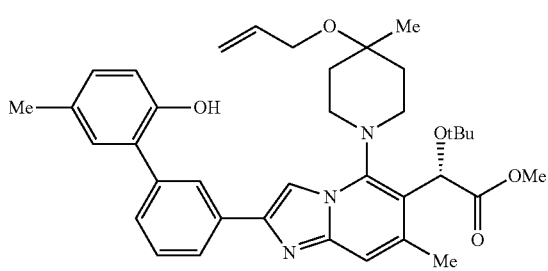 [SMILES: C=CCOC1(C)CCN(c2c([C@H](OC(C)(C)C)C(=O)OC)c(C)cc3nc(-c4cccc(-c5cc(C)ccc5O)c4)cn23)CC1]

(S)-Methyl 2-(5-(4-(allyloxy)-4-methylpiperidin-1-yl)-2-(2'-hydroxy-5'-methyl-[1,1'-biphenyl]-3-yl)-7-methylimidazo[1,2-a]pyridin-6-yl)-2-(tert-butoxy)acetate To a solution of (S)-methyl 2-(5-(4-(allyloxy)-4-methylpiperidin-1-yl)-2-(3-bromophenyl)-7-methylimidazo[1,2-a]pyridin-6-yl)-2-(tert-butoxy)acetate (84 mg, 0.144 mmol, 1 equiv) and (2-hydroxy-5-methylphenyl)boronic acid (33 mg, 0.216 mmol, 1.5 equiv) in DMF (1.4 mL, sparged with nitrogen for 10 min) was added Pd(PPh$_3$)$_4$ (17 mg, 0.014 mmol, 0.1 equiv) and 2 M Na$_2$CO$_3$ (0.144 mL, 0.287 mmol, 2 equiv). The reaction was heated at 90° C. for 3 h. Upon cooling to ambient temperature, the reaction was diluted with EtOAc, washed with water, dried (Na$_2$SO$_4$), and concentrated in vacuo. The crude product was purified by flash column chromatography (0-100% EtOAc [2% TEA]/hexane) to provide the product (51 mg, 58%) as a yellow foam. $^1$H NMR (400 MHz, CDCl$_3$) δ 8.13 (br. s., 1H), 8.08-8.01 (m, J=7.0 Hz, 1H), 7.95 (br. s., 1H), 7.62-7.56 (m, 1H), 7.51 (br. s., 1H), 7.14 (s, 1H), 7.09 (d, J=8.3 Hz, 1H), 7.01 (s, 1H), 6.96 (d, J=7.5 Hz, 1H), 6.10-5.94 (m, 2H), 5.40 (d, J=17.1 Hz, 1H), 5.03 (d, J=9.5 Hz, 1H), 3.99 (d, J=5.0 Hz, 2H), 3.90 (br. s., 1H), 3.79-3.75 (m, 1H), 3.71 (s, 3H), 3.08 (br. s., 1H), 2.79-2.70 (m, 1H), 2.56 (br. s., 3H), 2.35 (s, 3H), 2.00 (d, J=13.6 Hz, 2H), 1.88-1.77 (m, 2H), 1.34 (s, 3H), 1.26 (s, 9H); LCMS (ESI, M+1): 612.4.

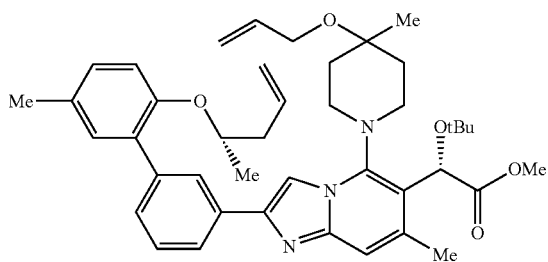 [SMILES: C=CCOC1(C)CCN(c2c([C@H](OC(C)(C)C)C(=O)OC)c(C)cc3nc(-c4cccc(-c5cc(C)ccc5O[C@@H](C)CC=C)c4)cn23)CC1]

(S)-Methyl 2-(5-(4-(allyloxy)-4-methylpiperidin-1-yl)-7-methyl-2-(5'-methyl-2'-((S)-pent-4-en-2-yloxy)-[1,1'-biphenyl]-3-yl) imidazo[1,2-a]pyridin-6-yl)-2-(tert-butoxy)acetate To a solution of (S)-methyl 2-(5-(4-(allyloxy)-4-methylpiperidin-1-yl)-2-(2'-hydroxy-5'-methyl-[1,1'-biphenyl]-3-yl)-7-methylimidazo[1,2-a]pyridin-6-yl)-2-(tert-butoxy)acetate (51 mg, 0.083 mmol, 1 equiv), (R)-pent-4-en-2-ol (22 mg, 0.250 mmol, 3 equiv), and PPh$_3$ (44 mg, 0.167 mmol, 2 equiv) in THF (0.8 mL) was added DEAD (0.066 mL of a 40% solution in toluene, 0.167 mmol, 2 equiv). After stirring 18 h, the yellow solution was diluted with ether, washed with water, dried (MgSO$_4$), and concentrated in vacuo. The crude product was purified by flash column chromatography (0-100% EtOAc [2% TEA]/hexane) to provide the product (53 mg, 94%) as a colorless film. LCMS (ESI, M+1): 680.45.

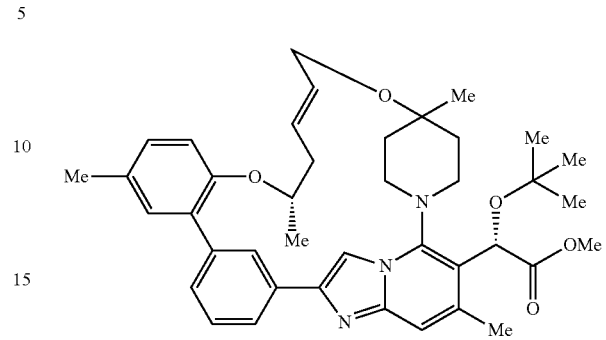

Methyl(2S)-2-(tert-butoxy)-2-[(22S)-4,17,22,28-tetramethyl-21,27-dioxa-1,7,34-triazahexacyclo [26.2.2.1$^{6,9}$.1$^{10,14}$.0$^{2,7}$.0$^{15,20}$]tetratriaconta-2,4,6 (34),8,10(33),11,13,15(20),16,18,24-undecaen-3-yl] acetate Prepared from (S)-methyl 2-(5-(4-(allyloxy)-4-methylpiperidin-1-yl)-7-methyl-2-(5'-methyl-2'-((S)-pent-4-en-2-yloxy)-[1,1'-biphenyl]-3-yl)imidazo[1,2-a]pyridin-6-yl)-2-(tert-butoxy)acetate in 83% yield following the same procedure as (2S)-2-(tert-butoxy)-2-[(22S)-18-fluoro-4,22,28-trimethyl-21,27-dioxa-1,7,34-triazahexacyclo [26.2.2.1$^{6,9}$.1$^{10,14}$.0$^{2,7}$.0$^{15,20}$]tetratriaconta-2,4,6(34),8,10 (33),11,13,15(20),16,18,24-undecaen-3-yl]acetic acid. $^1$H NMR (400 MHz, CDCl$_3$) δ 8.23-8.16 (m, 1H), 8.07 (s, 1H), 8.02 (s, 1H), 7.57-7.50 (m, 1H), 7.43-7.38 (m, 1H), 7.33 (d, J=7.5 Hz, 1H), 7.16 (d, J=1.8 Hz, 1H), 7.11 (dd, J=8.3, 2.0 Hz, 1H), 6.94 (d, J=8.3 Hz, 1H), 6.24-6.12 (m, 1H), 6.04 (br. s., 1H), 5.86-5.73 (m, 1H), 4.57-4.46 (m, 1H), 4.10-3.93 (m, 3H), 3.82-3.74 (m, 1H), 3.69 (s, 3H), 3.08 (d, J=8.0 Hz, 1H), 2.68 (d, J=7.5 Hz, 1H), 2.47 (s, 3H), 2.42-2.35 (m, 2H), 2.34 (s, 3H), 2.01-1.93 (m, 2H), 1.81-1.73 (m, 2H), 1.32 (s, 3H), 1.25 (s, 9H), 1.09 (d, J=6.0 Hz, 3H); LCMS (ESI, M+1): 652.4.

Example 8

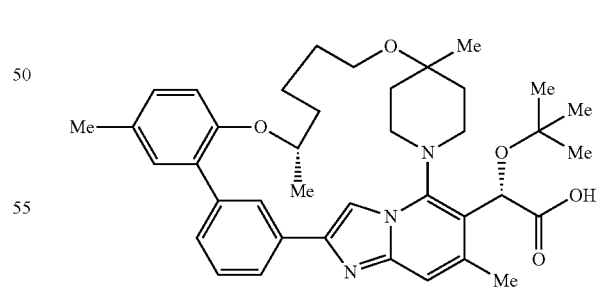

(2S)-2-(tert-Butoxy)-2-[(22S)-4,17,22,28-tetramethyl-21,27-dioxa-1,7,34-triazahexacyclo[26.2. 2.1$^{6,9}$.1$^{10,14}$.0$^{2,7}$.0$^{15,20}$]tetratriaconta-2,4,6(34),8,10 (33),11,13,15(20),16,18-decaen-3-yl]acetic acid Prepared from methyl(2S)-2-(tert-butoxy)-2-[(22S)-4,17, 22,28-tetramethyl-21,27-dioxa-1,7,34-triazahexacyclo

[26.2.2.1⁶,⁹.1¹⁰,¹⁴.0²,⁷.0¹⁵,²⁰]tetratriaconta-2,4,6(34),8,10 (33),11,13,15(20),16,18,24-undecaen-3-yl]acetate in 55% yield following the same procedure as (2S)-2-(tert-butoxy)-2-[(22S)-4,17,22,28-tetramethyl-21,27-dioxa-1,7,34-triazahexacyclo[26.2.2.1⁶,⁹.1¹⁰,¹⁴.0²,⁷.0¹⁵,²⁰]tetratriaconta-2,4,6 (34),8,10(33),11,13,15(20),16,18-decaen-3-yl]acetic acid. ¹H NMR (500 MHz, DMSO-d₆) δ 8.13 (s, 1H), 8.06 (d, J=7.6 Hz, 1H), 7.98 (s, 1H), 7.51 (t, J=7.6 Hz, 1H), 7.31 (d, J=7.3 Hz, 1H), 7.22 (s, 1H), 7.17 (s, 1H), 7.14 (d, J=8.9 Hz, 1H), 7.06 (d, J=8.5 Hz, 1H), 5.74 (br. s., 1H), 4.62 (br. s., 1H), 3.85 (t, J=11.4 Hz, 1H), 3.62-3.57 (m, 4H), 2.65 (d, J=9.5 Hz, 1H), 2.41 (s, 3H), 2.30 (s, 3H), 1.90-1.48 (m, 10H), 1.21 (s, 3H), 1.15 (s, 9H), 1.09 (d, J=6.1 Hz, 3H); LCMS (ESI, M+1): 640.6.

Example 9

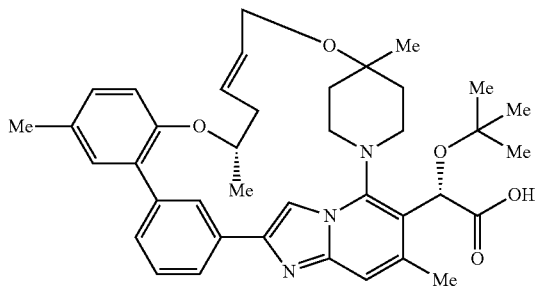 [SMILES: Cc1ccc2c(c1)-c1cccc(c1)-c1cn3c(c([C@H](OC(C)(C)C)C(=O)O)c(C)cc3n1)N1CCC(C)(CC1)OC/C=C/C[C@H](C)O2]

(2S)-2-(tert-Butoxy)-2-[(22S)-4,17,22,28-tetramethyl-21,27-dioxa-1,7,34-triazahexacyclo[26.2. 2.1⁶,⁹.1¹⁰,¹⁴.0²,⁷.0¹⁵,²⁰]tetratriaconta-2,4,6(34),8,10 (33),11,13,15(20),16,18,24-undecaen-3-yl]acetic acid Prepared from methyl(2S)-2-(tert-butoxy)-2-[(22S)-4,17, 22,28-tetramethyl-21,27-dioxa-1,7,34-triazahexacyclo [26.2.2.1⁶,⁹.1¹⁰,¹⁴.0²,⁷.0¹⁵,²⁰]tetratriaconta-2,4,6(34),8,10 (33),11,13,15(20),16,18,24-undecaen-3-yl]acetate in 60% yield following the same procedure as (2S)-2-(tert-butoxy)-2-[(22S)-18-fluoro-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18,24-undecaen-3-yl] acetic acid. ¹H NMR (500 MHz, DMSO-d₆) δ 8.06 (d, J=8.5 Hz, 1H), 8.04 (s, 1H), 8.00 (s, 1H), 7.52 (t, J=7.5 Hz, 1H), 7.36-7.28 (m, 2H), 7.18-7.13 (m, 2H), 7.12-7.07 (m, 1H), 6.17-6.06 (m, 1H), 5.92 (br. s., 1H), 5.77 (d, J=15.9 Hz, 1H), 4.57 (br. s., 1H), 4.05-3.90 (m, 3H), 3.64 (t, J=11.0 Hz, 1H), 3.13 (br. s., 1H), 2.64 (d, J=10.7 Hz, 1H), 2.58-2.53 (m, 1H), 2.41 (s, 3H), 2.30 (s, 3H), 2.28-2.20 (m, 1H), 1.96 (d, J=13.1 Hz, 1H), 1.88 (d, J=13.4 Hz, 1H), 1.72 (br. s., 2H), 1.26 (s, 3H), 1.19 (s, 9H), 1.02 (d, J=5.8 Hz, 3H); LCMS (ESI, M+1): 638.5.

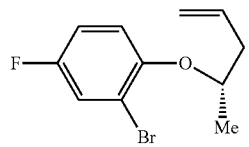

(S)-2-Bromo-4-fluoro-1-(pent-4-en-2-yloxy)benzene

Prepared from 2-bromo-4-fluorophenol in 88% yield following the same procedure as (S)-1-bromo-4-fluoro-2-(pent-4-en-2-yloxy)benzene. ¹H NMR (400 MHz, CDCl₃) δ 7.39-7.33 (m, 1H), 7.30 (dd, J=8.0, 3.0 Hz, 1H), 7.01-6.94 (m, 1H), 6.91-6.85 (m, 1H), 5.90 (ddt, J=17.2, 10.2, 7.0 Hz, 1H), 5.20-5.10 (m, 2H), 4.36 (sxt, J=6.1 Hz, 1H), 2.58-2.49 (m, 1H), 2.45-2.36 (m, 1H), 1.34 (d, J=6.0 Hz, 3H).

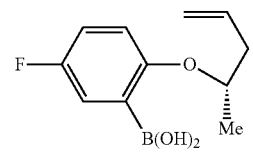

(S)-(5-Fluoro-2-(pent-4-en-2-yloxy)phenyl)boronic acid

Prepared from (S)-2-bromo-4-fluoro-1-(pent-4-en-2-yloxy)benzene in 100% yield following the same procedure as (S)-(4-fluoro-2-(pent-4-en-2-yloxy)phenyl)boronic acid. NMR is complex and suggests an oligomeric mixture. The material, however, was used as is and was fully compentent for undergoing a Suzuki coupling.

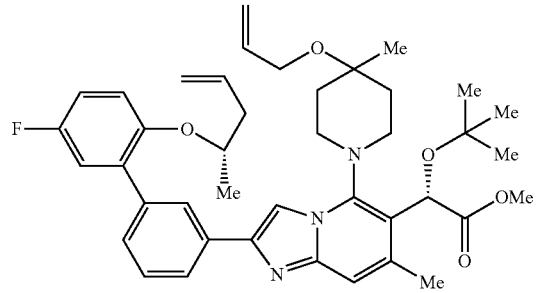 [SMILES: C=CCOC1(C)CCN(c2c([C@H](OC(C)(C)C)C(=O)OC)c(C)cc3nc(-c4cccc(-c5cc(F)ccc5O[C@@H](C)CC=C)c4)cn23)CC1]

Methyl(S)-2-(5-(4-(allyloxy)-4-methylpiperidin-1-yl)-2-(5'-fluoro-2'-((S)-pent-4-en-2-yloxy)-[1,1'-biphenyl]-3-yl)-7-methylimidazo[1,2-a]pyridin-6-yl)-2-(tert-butoxy)acetate Prepared in 82% yield from (S)-(5-fluoro-2-(pent-4-en-2-yloxy)phenyl)boronic acid and (S)-methyl 2-(5-(4-(allyloxy)-4-methylpiperidin-1-yl)-2-(3-bromophenyl)-7-methylimidazo[1,2-a]pyridin-6-yl)-2-(tert-butoxy)acetate following the procedure for (S)-methyl 2-(5-(4-(allyloxy)-4-methylpiperidin-1-yl)-2-(4'-fluoro-2'-((S)-pent-4-en-2-yloxy)-[1,1'-biphenyl]-3-yl)-7-methylimidazo[1,2-a]pyridin-6-yl)-2-(tert-butoxy)acetate. LCMS (ESI, M+1): 684.4.

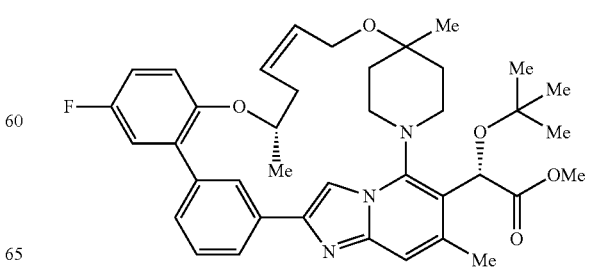

Methyl(2S)-2-(tert-butoxy)-2-[(22S)-17-fluoro-4,22, 28-trimethyl-21,27-dioxa-1,7,34-triazahexacyclo [26.2.2.1$^{6,9}$.1$^{10,14}$.0$^{2,7}$.0$^{15,20}$]tetratriaconta-2,4,6 (34),8,10(33),11,13,15(20),16,18,24-undecaen-3-yl] acetate Prepared in 93% yield from methyl(S)-2-(5-(4-(allyloxy)-4-methylpiperidin-1-yl)-2-(5'-fluoro-2'-((S)-pent-4-en-2-yloxy)-[1,1'-biphenyl]-3-yl)-7-methylimidazo[1,2-a]pyridin-6-yl)-2-(tert-butoxy)acetate following the procedure for methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15 (20),16,18,24-undecaen-3-yl]acetate. LCMS (ESI, M+1): 656.3.

Example 10

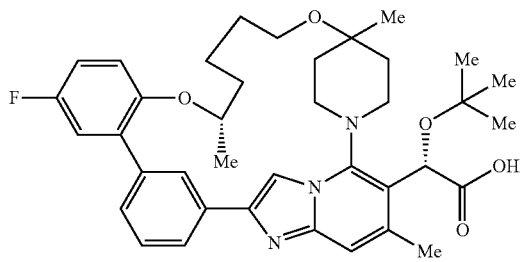 [SMILES: Cc1cc2nc3cn2c(c1[C@H](OC(C)(C)C)C(=O)O)N1CCC(C)(CC1)OCCCC[C@H](C)Oc1ccc(F)cc1-c1cccc-3c1]

(2S)-2-(tert-Butoxy)-2-[(22S)-17-fluoro-4,22,28-trimethyl-21,27-dioxa-1,7,34-triazahexacyclo [26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]acetic acid Prepared in 37% from methyl(2S)-2-(tert-butoxy)-2-[(22S)-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl] acetate following the same procedure as (2S)-2-(tert-butoxy)-2-[(22S)-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.14 (s, 1H), 8.10 (d, J=7.7 Hz, 1H), 7.99 (s, 1H), 7.53 (t, J=7.7 Hz, 1H), 7.35 (d, J=7.7 Hz, 1H), 7.30 (s, 1H), 7.24-7.19 (m, 1H), 7.17 (d, J=5.9 Hz, 2H), 5.90 (br. s., 1H), 4.61 (br. s., 1H), 3.83 (br. s., 1H), 3.64 (br. s., 1H), 3.52-3.29 (m, 2H), 3.17-3.08 (m, 1H), 2.68-2.60 (m, 1H), 2.40 (s, 3H), 1.93-1.46 (m, 10H), 1.19 (s, 3H), 1.17 (s, 9H), 1.07 (d, J=6.2 Hz, 3H); LCMS (ESI, M+1): 644.5.

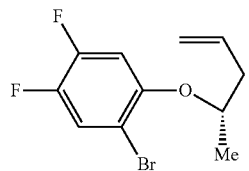

(S)-1-Bromo-4,5-difluoro-2-(pent-4-en-2-yloxy) benzene

Prepared in 61% yield from 2-bromo-4,5-difluorophenol following the same procedure as (S)-1-bromo-4-fluoro-2-(pent-4-en-2-yloxy)benzene. $^1$H NMR (400 MHz, CDCl$_3$) δ 7.42-7.35 (m, 1H), 6.77 (dd, J=11.9, 7.2 Hz, 1H), 5.88 (ddt, J=17.2, 10.1, 7.1 Hz, 1H), 5.21-5.06 (m, 2H), 4.40-4.27 (m, 1H), 2.61-2.36 (m, 2H), 1.35 (d, J=6.0 Hz, 3H).

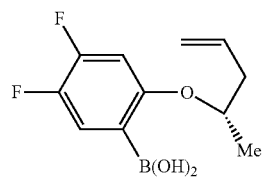 [SMILES: C=CC[C@H](C)Oc1cc(F)c(F)cc1B(O)O]

(S)-(4,5-Difluoro-2-(pent-4-en-2-yloxy)phenyl)boronic acid

Prepared from (S)-1-bromo-4,5-difluoro-2-(pent-4-en-2-yloxy)benzene in 100% yield following the same procedure as (S)-(4-fluoro-2-(pent-4-en-2-yloxy)phenyl)boronic acid. NMR is complex and suggests an oligomeric mixture. The material, however, was used as is and was fully compentent for undergoing a Suzuki coupling.

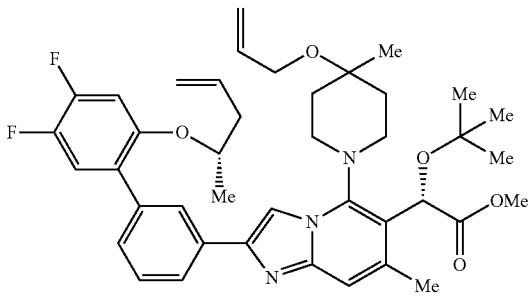 [SMILES: C=CCOC1(C)CCN(c2c([C@H](OC(C)(C)C)C(=O)OC)c(C)cc3nc(-c4cccc(-c5cc(F)c(F)cc5O[C@@H](C)CC=C)c4)cn23)CC1]

Methyl(2S)-2-(tert-butoxy)-2-[2-(3-{4,5-difluoro-2-[(2S)-pent-4-en-2-yloxy]phenyl}phenyl)-7-methyl-5-[4-methyl-4-(prop-2-en-1-yloxy)piperidin-1-yl]imidazo[1,2-a]pyridin-6-yl]acetate Prepared in 72% yield from (S)-(4,5-difluoro-2-(pent-4-en-2-yloxy)phenyl)boronic acid and (S)-methyl 2-(5-(4-(allyloxy)-4-methylpiperidin-1-yl)-2-(3-bromophenyl)-7-methylimidazo[1,2-a]pyridin-6-yl)-2-(tert-butoxy)acetate following the procedure for (S)-methyl 2-(5-(4-(allyloxy)-4-methylpiperidin-1-yl)-2-(4'-fluoro-2'-((S)-pent-4-en-2-yloxy)-[1,1'-biphenyl]-3-yl)-7-methylimidazo[1,2-a]pyridin-6-yl)-2-(tert-butoxy)acetate. $^1$H NMR (400 MHz, CDCl$_3$) δ 8.07-7.88 (m, 3H), 7.51-7.38 (m, 3H), 7.32 (br. s., 1H), 6.92-6.74 (m, 1H), 6.14-6.00 (m, 2H), 5.80-5.65 (m, 1H), 5.51-5.40 (m, 1H), 5.12-4.97 (m, 3H), 4.28-4.17 (m, 1H), 4.05-3.95 (m, 3H), 3.86-3.77 (m, 1H), 3.69 (s, 3H), 3.07-2.97 (m, 1H), 2.79-2.65 (m, 1H), 2.47 (s, 3H), 2.41-2.30 (m, 1H), 2.29-2.18 (m, 1H), 2.04-1.92 (m, 2H), 1.88-1.68 (m, 2H), 1.33 (s, 3H), 1.27 (s, 9H), 1.19 (d, J=6.0 Hz, 3H); $^{19}$F NMR (376 MHz, CDCl$_3$) δ −137.17−−137.33 (d, J=23 Hz, 1F), −147.78−−147.92 (d, J=23 Hz, 1F); LCMS (ESI, M+1): 702.25.

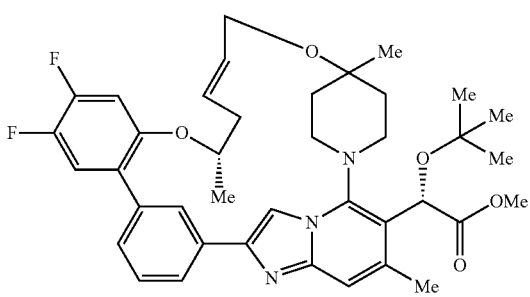 [SMILES: COC(=O)[C@@H](OC(C)(C)C)c1c(C)cc2nc3cn2c1N1CCC(C)(CC1)OC/C=C/C[C@H](C)Oc1cc(F)c(F)cc1-c1cccc-3c1]

Methyl(2S)-2-(tert-butoxy)-2-[(22S)-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate Prepared in 92% yield from (S)-methyl 2-(5-(4-(allyloxy)-4-methylpiperidin-1-yl)-2-(5'-fluoro-2'-((S)-pent-4-en-2-yloxy)-[1,1'-biphenyl]-3-yl)-7-methylimidazo[1,2-a]pyridin-6-yl)-2-(tert-butoxy)acetate following the same procedure as (2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid. $^1$H NMR (500 MHz, CDCl$_3$) δ 8.21 (d, J=8.0 Hz, 1H), 8.06-8.03 (m, 2H), 7.54 (t, J=7.6 Hz, 1H), 7.33 (s, 1H), 7.26 (s, 1H), 7.22-7.16 (m, 1H), 6.89-6.83 (m, 1H), 6.23-6.14 (m, 1H), 6.07-6.02 (m, 1H), 5.85-5.77 (m, 1H), 4.48-4.40 (m, 1H), 4.08-3.95 (m, 3H), 3.83-3.75 (m, 1H), 3.71 (s, 3H), 3.16-3.06 (m, 1H), 2.75-2.66 (m, 1H), 2.50 (dt, J=2.4, 1.2 Hz, 1H), 2.48 (d, J=0.8 Hz, 3H), 2.43-2.35 (m, 1H), 2.04-1.95 (m, 2H), 1.84-1.73 (m, 2H), 1.35 (s, 3H), 1.27 (s, 9H), 1.12 (d, J=6.1 Hz, 3H); $^{19}$F NMR (471 MHz, CDCl$_3$) δ −137.12-−137.54 (m, 1F), −147.87-−148.37 (m, 1F); LCMS (ESI, M+1): 674.3.

Example 11

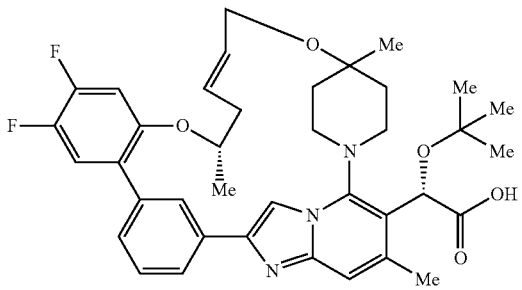 [SMILES: Cc1cc2nc3cn2c(c1[C@H](OC(C)(C)C)C(=O)O)N1CCC(C)(CC1)OC/C=C/C[C@H](C)Oc1cc(F)c(F)cc1-c1cccc-3c1]

(2S)-2-(tert-Butoxy)-2-[(22S)-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid Prepared in 59% yield from Methyl(2S)-2-(tert-butoxy)-2-[(22S)-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate following the procedure for (2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid. $^1$H NMR (500 MHz, DMSO-d$_6$) δ 8.10 (d, J=7.3 Hz, 1H), 8.02 (s, 1H), 7.99 (s, 1H), 7.53 (t, J=7.7 Hz, 1H), 7.46-7.37 (m, 2H), 7.31 (d, J=7.7 Hz, 1H), 7.25 (s, 1H), 6.15-6.07 (m, 1H), 5.85-5.75 (m, 2H), 4.64 (br. s., 1H), 4.08-3.88 (m, 3H), 3.59 (t, J=11.4 Hz, 1H), 3.28 (br. s., 1H), 2.68-2.53 (m, 2H), 2.40 (s, 3H), 2.30-2.20 (m, 1H), 1.97-1.85 (m, 2H), 1.79-1.62 (m, 2H), 1.25 (s, 3H), 1.17 (s, 9H), 1.04 (d, J=5.9 Hz, 3H); LCMS (ESI, M): 659.3.

Example 12

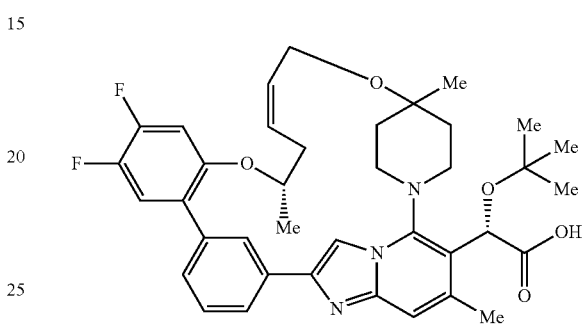

(2S)-2-(tert-Butoxy)-2-[(22S)-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid The minor isomer from the previous reaction was also isolated in 31%. $^1$H NMR (500 MHz, DMSO-d$_6$) δ 8.15 (d, J=7.3 Hz, 1H), 8.07 (s, 1H), 7.88 (s, 1H), 7.62 (br. s., 1H), 7.60-7.55 (m, 1H), 7.32 (br. s., 1H), 7.28 (s, 1H), 7.06 (dd, J=11.9, 3.5 Hz, 1H), 6.04-5.94 (m, 1H), 5.88-5.77 (m, 2H), 4.81 (br. s., 1H), 4.01-3.88 (m, 3H), 3.59 (t, J=11.4 Hz, 1H), 3.18 (br. s., 1H), 2.69 (d, J=8.8 Hz, 1H), 2.63 (br. s., 1H), 2.42 (s, 3H), 2.14-2.01 (m, 1H), 1.95-1.87 (m, 2H), 1.72 (d, J=11.7 Hz, 2H), 1.32 (d, J=5.9 Hz, 3H), 1.25 (s, 3H), 1.19 (s, 9H); LCMS (ESI, M): 659.3.

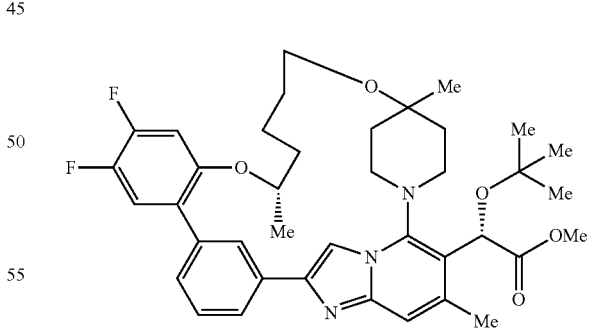

Methyl(2S)-2-(tert-butoxy)-2-[(22S)-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 75% yield from methyl(2S)-2-(tert-butoxy)-2-[(22S)-17,18-difluoro-4,22,28-trimethyl-21,27-dioxa-1,7, 34-triazahexacyclo[26.2.2.1$^{6,9}$.1$^{10,14}$.0$^{2,7}$.0$^{15,20}$]tetratria-conta-2,4,6(34),8,10(33),11,13,15(20),16,18,24-undecaen-3-yl]acetate following the same procedure as methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. $^1$H NMR (400 MHz, CDCl$_3$) δ 8.21 (d, J=8.0 Hz, 1H), 8.08 (s, 1H), 8.02 (s, 1H), 7.53 (t, J=7.7 Hz, 1H), 7.32 (s, 1H), 7.27-7.16 (m, 2H), 6.82 (dd, J=12.7, 6.9 Hz, 1H), 6.04 (br. s., 1H), 4.44 (d, J=5.0 Hz, 1H), 3.96 (t, J=11.0 Hz, 1H), 3.81-3.72 (m, 1H), 3.70 (s, 3H), 3.57-3.42 (m, 2H), 3.10 (d, J=10.5 Hz, 1H), 2.70 (d, J=10.8 Hz, 1H), 2.46 (s, 3H), 2.00-1.70 (m, 10H), 1.29 (s, 3H), 1.25 (s, 9H), 1.16 (d, J=6.0 Hz, 3H); $^{19}$F NMR (376 MHz, CDCl$_3$) δ −137.12−−137.51 (m, 1F), −148.56−−149.02 (m, 1F); LCMS (ESI, M+1): 676.25.

Example 13

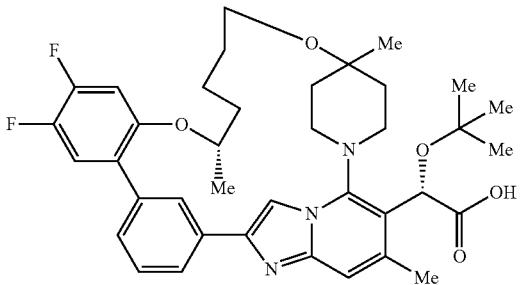 [SMILES: Cc1cc2nc3cn2c(c1[C@H](OC(C)(C)C)C(=O)O)N1CCC(C)(CC1)OCCCC[C@H](C)Oc1cc(F)c(F)cc1-c1cccc-3c1]

(2S)-2-(tert-Butoxy)-2-[(22S)-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid $^1$H NMR (500 MHz, DMSO-d$_6$) δ 8.12-8.07 (m, 2H), 7.99 (s, 1H), 7.52 (t, J=7.9 Hz, 1H), 7.45 (t, J=10.3 Hz, 1H), 7.38-7.30 (m, 2H), 7.27 (s, 1H), 5.84 (br. s., 1H), 4.67 (br. s., 1H), 3.84 (t, J=11.6 Hz, 1H), 3.69-3.57 (m, 1H), 3.52-3.28 (m, 2H), 3.23 (br. s., 1H), 2.65 (d, J=8.4 Hz, 1H), 2.40 (s, 3H), 1.94-1.58 (m, 10H), 1.20 (s, 3H), 1.17 (s, 9H), 1.10 (d, J=5.9 Hz, 3H); LCMS (ESI, M): 661.3.

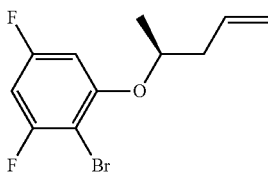

(S)-2-Bromo-1,5-difluoro-3-(pent-4-en-2-yloxy)benzene

Prepared in 75% yield from 2-bromo-3,5-difluorophenol following the same procedure as (S)-1-bromo-4-fluoro-2-(pent-4-en-2-yloxy)benzene. $^1$H NMR (400 MHz, CDCl$_3$) δ 6.59-6.43 (m, 2H), 5.94-5.80 (m, 1H), 5.22-5.09 (m, 2H), 4.47-4.36 (m, 1H), 2.59-2.37 (m, 2H), 1.37 (d, J=6.3 Hz, 3H).

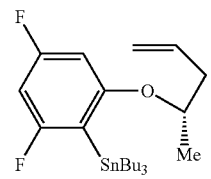

(S)-Tributyl(2,4-difluoro-6-(pent-4-en-2-yloxy)phenyl)stannane

A solution of (S)-2-bromo-1,5-difluoro-3-(pent-4-en-2-yloxy)benzene (0.28 g, 1.01 mmol, 1 equiv) in THF (5 mL) was cooled to −78° C. (IPA/dry ice). nBuLi (0.76 mL of a 1.6 M solution in hexane, 1.21 mmol, 1.2 equiv) was added slowly. Orange color observed. After 30 min, tributyltin chloride (0.33 mL, 1.21 mmol, 1.2 equiv) was added. The reaction was stirred 30 min. The reaction was remove from the cold bath, diluted with ether, and washed with saturated aqueous NaHCO$_3$. The ether layer was dried (MgSO$_4$) and concentrated in vacuo to provide the crude stannane (0.60 g, 100%) as a yellow oil. Contaminated with tin byproducts, used as is. $^1$H NMR (400 MHz, CDCl$_3$) δ 6.44-6.25 (m, 2H), 5.95-5.62 (m, 1H), 5.21-5.06 (m, 2H), 4.52-4.28 (m, 1H), 2.62-2.43 (m, 1H), 2.31 (dd, J=13.9, 6.7 Hz, 1H), 1.70-0.74 (m, 27H).

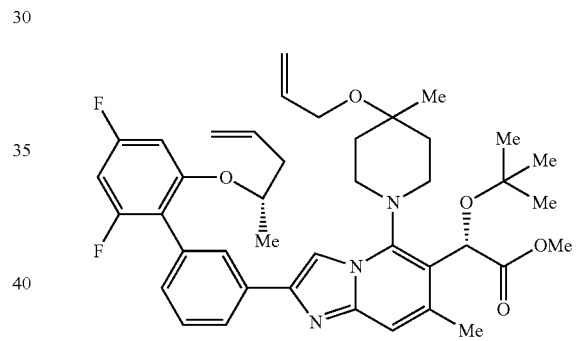

(S)-Methyl 2-(5-(4-(allyloxy)-4-methylpiperidin-1-yl)-2-(2',4'-difluoro-6'-((S)-pent-4-en-2-yloxy)-[1,1'-biphenyl]-3-yl)-7-methylimidazo[1,2-a]pyridin-6-yl)-2-(tert-butoxy)acetate To a solution of (S)-methyl 2-(5-(4-(allyloxy)-4-methylpiperidin-1-yl)-2-(3-bromophenyl)-7-methylimidazo[1,2-a]pyridin-6-yl)-2-(tert-butoxy)acetate (0.25 g, 0.428 mmol, 1 equiv) and (S)-tributyl(2,4-difluoro-6-(pent-4-en-2-yloxy)phenyl)stannane (0.25 g, 0.513 mmol, 1.2 equiv) in DMF (2 mL, sparged with nitrogen for 10 min) was added Pd(PPh$_3$)$_4$ (49 mg, 0.043 mmol, 0.1 equiv), CsF (195 mg, 1.28 mmol, 3 equiv), and CuI (20 mg, 0.107 mmol, 0.25 equiv). The reaction was heated at 80° C. for 2 h. After 2 h, more stannane (300 mg) was added. Stir for 2 h and remove from heat. Upon cooling to ambient temperature, the reaction was diluted with EtOAc, washed with water, dried (Na$_2$SO$_4$), and concentrated in vacuo. The crude product was purified by flash column chromatography (0-100% EtOAc [2% TEA]/hexane) to provide the product (160 mg, 53%) as a film. LCMS (ESI, M+1): 702.25.

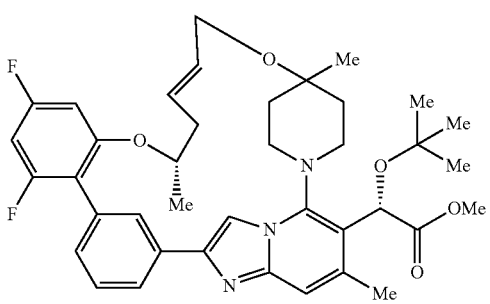 [SMILES: COC(=O)[C@@H](OC(C)(C)C)c1c(C)cc2nc3cn2c1N1CCC(C)(CC1)OCC/C=C/C[C@H](C)Oc1cc(F)cc(F)c1-c1cccc-3c1]

Methyl(2S)-2-(tert-butoxy)-2-[(22S)-16,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate Prepared in 65% yield from (S)-methyl 2-(5-(4-(allyloxy)-4-methylpiperidin-1-yl)-2-(2',4'-difluoro-6'-((S)-pent-4-en-2-yloxy)-[1,1'-biphenyl]-3-yl)-7-methylimidazo[1,2-a]pyridin-6-yl)-2-(tert-butoxy)acetate following the same procedure as methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate. $^1$H NMR (400 MHz, CDCl$_3$) δ 8.16 (d, J=8.0 Hz, 1H), 8.01 (s, 1H), 7.79 (s, 1H), 7.72 (dd, J=5.6, 3.4 Hz, 1H), 7.58-7.49 (m, 1H), 7.33 (s, 1H), 6.63-6.49 (m, 2H), 6.18-6.00 (m, 2H), 5.77 (d, J=15.1 Hz, 1H), 4.49 (br. s., 1H), 4.18-4.08 (m, 1H), 4.05-3.92 (m, 2H), 3.80-3.71 (m, 1H), 3.69 (s, 3H), 3.07 (d, J=10.5 Hz, 1H), 2.69 (d, J=12.0 Hz, 1H), 2.51-2.45 (m, 4H), 2.41 (br. s., 1H), 1.97 (t, J=11.7 Hz, 1H), 1.86-1.64 (m, 2H), 1.51-1.39 (m, 1H), 1.33 (s, 3H), 1.26 (s, 9H), 1.15 (d, J=6.3 Hz, 3H); LCMS (ESI, M+1): 674.3.

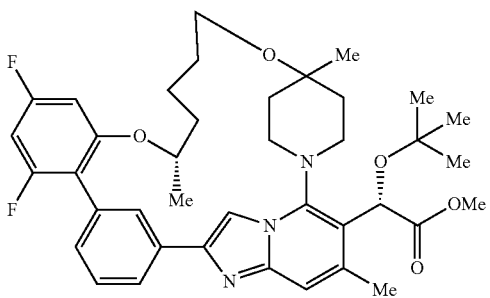 [SMILES: COC(=O)[C@@H](OC(C)(C)C)c1c(C)cc2nc3cn2c1N1CCC(C)(CC1)OCCCCC[C@H](C)Oc1cc(F)cc(F)c1-c1cccc-3c1]

Methyl(2S)-2-(tert-butoxy)-2-[(22S)-16,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 83% yield from methyl(2S)-2-(tert-butoxy)-2-[(22S)-16,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate following the same procedure as methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$] tetratriaconta-2,4,6(34),8,10(33),11,13,15(20),16,18-decaen-3-yl]acetate. LCMS (ESI, M+1): 676.25.

Example 14

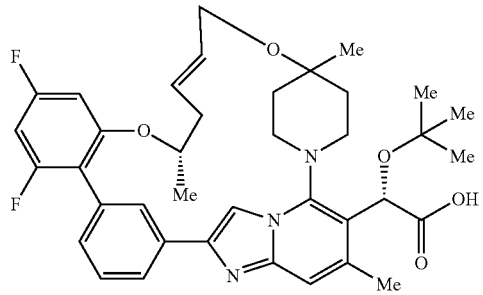 [SMILES: Cc1cc2nc3cn2c(c1[C@H](OC(C)(C)C)C(=O)O)N1CCC(C)(CC1)OCC/C=C/C[C@H](C)Oc1cc(F)cc(F)c1-c1cccc-3c1]

(2S)-2-(tert-Butoxy)-2-[(22S)-16,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid Prepared in 53% yield from methyl(2S)-2-(tert-butoxy)-2-[(22S)-16,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate following the same procedure as (2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$] tetratriaconta-2,4,6(34),8,10(33),11,13,15(20),16,18,24-undecaen-3-yl]acetic acid. $^1$H NMR (500 MHz, DMSO-d$_6$) δ 8.05 (d, J=7.7 Hz, 1H), 7.98 (s, 1H), 7.76 (s, 1H), 7.51 (t, J=7.7 Hz, 1H), 7.29 (s, 1H), 7.24 (d, J=7.3 Hz, 1H), 7.07 (d, J=11.0 Hz, 1H), 6.91 (t, J=8.4 Hz, 1H), 6.07-5.98 (m, 1H), 5.91 (br. s., 1H), 5.74 (d, J=15.4 Hz, 1H), 4.70 (d, J=5.9 Hz, 1H), 4.03 (t, J=11.2 Hz, 1H), 3.95 (br. s., 2H), 3.61 (t, J=11.0 Hz, 1H), 3.11 (br. s., 1H), 2.61 (d, J=8.8 Hz, 1H), 2.49-2.43 (m, 1H), 2.40 (s, 3H), 2.27-2.16 (m, 1H), 1.97-1.84 (m, 2H), 1.70 (d, J=7.3 Hz, 2H), 1.24 (s, 3H), 1.18 (s, 9H), 1.08 (d, J=5.9 Hz, 3H); LCMS (ESI, M): 659.3.

Example 15

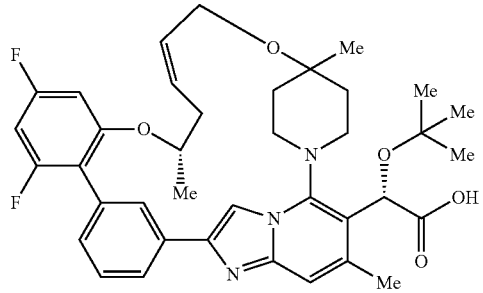 [SMILES: Cc1cc2nc3cn2c(c1[C@H](OC(C)(C)C)C(=O)O)N1CCC(C)(CC1)OCC/C=C\C[C@H](C)Oc1cc(F)cc(F)c1-c1cccc-3c1]

(2S)-2-(tert-Butoxy)-2-[(22S)-16,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid Isolated in 8% yield from the previous reaction as a minor product. $^1$H NMR (400 MHz, CD$_3$OD) δ 7.96-7.88 (m, 3H), 7.54 (t, J=7.8 Hz, 1H), 7.37 (dd, J=7.7, 3.5 Hz, 1H), 7.29 (s, 1H), 6.91 (d, J=10.8 Hz, 1H), 6.73-6.61 (m, 1H), 6.01 (s, 1H), 5.91-5.72 (m, 2H), 4.77-4.64 (m, 1H), 4.12 (dd, J=10.6, 7.9 Hz, 1H), 4.02-3.91 (m, 2H), 3.81-3.66 (m, 1H), 2.98-2.83 (m, 2H), 2.73-2.59 (m, 1H), 2.56 (s, 3H), 2.06 (d, J=13.0 Hz, 1H), 1.98-1.77 (m, 4H), 1.32 (s, 3H), 1.29-1.27 (m, 12H); LCMS (ESI, M): 659.3.

Example 16

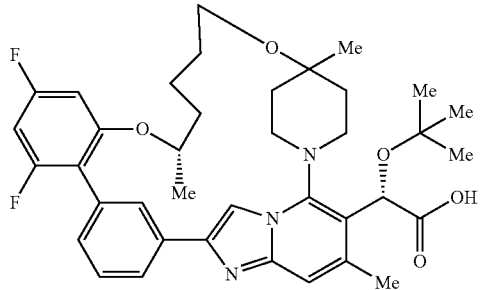 [SMILES: Cc1cc2nc3cn2c(c1[C@H](OC(C)(C)C)C(=O)O)N1CCC(C)(CC1)OCCCCC[C@H](C)Oc1cc(F)cc(F)c1-c1cccc-3c1]

(2S)-2-(tert-Butoxy)-2-[(22S)-16,18-difluoro-4,22, 28-trimethyl-21,27-dioxa-1,7,34-triazahexacyclo [26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]acetic acid Prepared in 49% yield from methyl(2S)-2-(tert-butoxy)-2-[(22S)-16,18-difluoro-4,22,28-trimethyl-21,27-dioxa-1,7, 34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl] acetate following the same procedure as (2S)-2-(tert-butoxy)-2-[(22S)-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.06 (d, J=7.7 Hz, 1H), 7.97 (s, 1H), 7.85 (s, 1H), 7.50 (t, J=7.7 Hz, 1H), 7.25 (s, 2H), 7.01 (d, J=11.4 Hz, 1H), 6.89 (t, J=9.5 Hz, 1H), 5.81 (br. s., 1H), 4.69 (t, J=5.3 Hz, 1H), 3.93-3.82 (m, 1H), 3.59 (t, J=11.2 Hz, 1H), 3.49-3.40 (m, 1H), 3.26 (d, J=7.0 Hz, 1H), 2.63 (d, J=9.9 Hz, 1H), 2.40 (s, 3H), 1.89-1.57 (m, 10H), 1.50 (d, J=7.7 Hz, 1H), 1.19 (s, 3H), 1.16 (s, 9H), 1.11 (d, J=5.9 Hz, 3H); LCMS (ESI, M): 661.3.

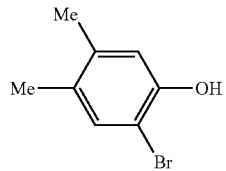

2-Bromo-4,5-dimethylphenol

To a solution of 3,4-dimethylphenol (2.48 g, 20.3 mmol, 1 equiv) in DCM (200 mL) at −78° C. (IPA/dry ice) was added dropwise bromine (1.05 mL, 20.3 mmol, 1 equiv). After 1 h, 1 N Na$_2$SO$_3$ was added and the cold bath was removed. After warming to ambient temperature, the DCM layer was separated, dried (Na$_2$SO$_4$), and concentrated in vacuo to provide the product (4.09 g, 100%) as a yellow solid. Regioselectivity>10:1, use as is. $^1$H NMR (400 MHz, CDCl$_3$) δ 7.21 (s, 1H), 6.83 (s, 1H), 5.26 (s, 1H), 2.20 (s, 3H), 2.18 (s, 3H).

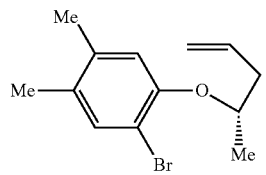

(S)-1-Bromo-4,5-dimethyl-2-(pent-4-en-2-yloxy) benzene

Prepared in 59% yield from 2-bromo-4,5-dimethylphenol following the same procedure as (S)-1-bromo-4-fluoro-2-(pent-4-en-2-yloxy)benzene. $^1$H NMR (400 MHz, CDCl$_3$) δ 7.30 (s, 1H), 6.73 (s, 1H), 5.92 (ddt, J=17.2, 10.1, 7.1 Hz, 1H), 5.19-5.09 (m, 2H), 4.44-4.33 (m, 1H), 2.59-2.49 (m, 1H), 2.45-2.37 (m, 1H), 2.21 (s, 3H), 2.18 (s, 3H), 1.34 (d, J=6.0 Hz, 3H).

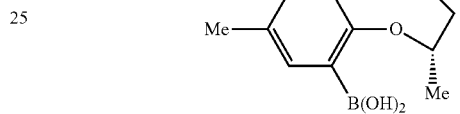

(S)-(4,5-Dimethyl-2-(pent-4-en-2-yloxy)phenyl) boronic acid

Prepared in 85% yield from (S)-1-bromo-4,5-dimethyl-2-(pent-4-en-2-yloxy)benzene following the procedure for (S)-(4-fluoro-2-(pent-4-en-2-yloxy)phenyl)boronic acid. $^1$H NMR (400 MHz, CDCl$_3$) δ 7.57 (s, 1H), 6.72 (s, 1H), 5.93-5.82 (m, 1H), 5.81 (d, J=5.8 Hz, 2H), 5.22-5.13 (m, 2H), 4.68-4.55 (m, 1H), 2.60-2.42 (m, 2H), 2.28 (s, 3H), 2.22 (s, 3H), 1.38 (d, J=6.3 Hz, 3H).

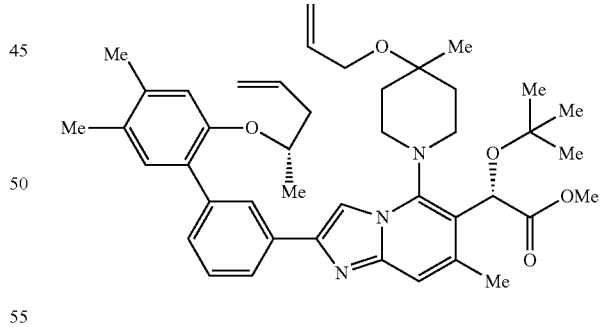

(S)-Methyl 2-(5-(4-(allyloxy)-4-methylpiperidin-1-yl)-2-(4',5'-dimethyl-2'-((S)-pent-4-en-2-yloxy)-[1, 1'-biphenyl]-3-yl)-7-methylimidazo[1,2-a]pyridin-6-yl)-2-(tert-butoxy)acetate Prepared in 77% yield from (S)-(4,5-dimethyl-2-(pent-4-en-2-yloxy)phenyl)boronic acid and (S)-methyl 2-(5-(4-(allyloxy)-4-methylpiperidin-1-yl)-2-(3-bromophenyl)-7-methylimidazo[1,2-a]pyridin-6-yl)-2-(tert-butoxy)acetate following the procedure for (S)-methyl 2-(5-(4-(allyloxy)-4-methylpiperidin-1-yl)-2-(4'-fluoro-2'-((S)-pent-4-en-2- yloxy)-[1,1'-biphenyl]-3-yl)-7-methylimidazo[1,2-a]pyridin-6-yl)-2-(tert-butoxy)acetate. $^1$H NMR (400 MHz, CDCl$_3$) δ 8.03 (d, J=11.5 Hz, 2H), 7.92-7.87 (m, 1H), 7.58-7.52 (m, 1H), 7.43 (s, 1H), 7.32 (s, 1H), 7.22 (s, 1H), 6.81 (s, 1H), 6.11-5.99 (m, 2H), 5.82-5.68 (m, 1H), 5.48-5.38 (m, 1H), 5.10-4.94 (m, 3H), 4.27-4.19 (m, 1H), 4.07-3.92 (m, J=5.0 Hz, 3H), 3.87-3.76 (m, 1H), 3.69 (s, 3H), 3.06-2.97 (m, 1H), 2.79-2.68 (m, 1H), 2.47 (s, 3H), 2.42-2.34 (m, 1H), 2.30 (s, 3H), 2.26 (s, 3H), 2.25-2.18 (m, 1H), 2.02-1.95 (m, 2H), 1.86-1.75 (m, 2H), 1.29 (s, 3H), 1.27 (s, 9H), 1.16 (d, J=6.3 Hz, 3H); LCMS (ESI, M+1): 694.35.

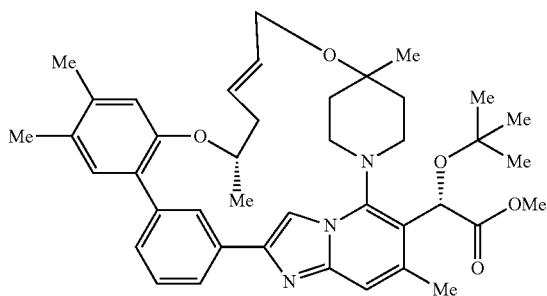 [SMILES: COC(=O)[C@@H](OC(C)(C)C)c1c(C)cc2nc3cn2c1N1CCC(C)(CC1)OCC/C=C/C[C@H](C)Oc1cc(C)c(C)cc1-c1cccc-3c1]

Methyl(2S)-2-(tert-butoxy)-2-[(22S)-4,17,18,22,28-pentamethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl] acetate Prepared in 80% yield from (S)-methyl 2-(5-(4-(allyloxy)-4-methylpiperidin-1-yl)-2-(4',5'-dimethyl-2'-((S)-pent-4-en-2-yloxy)-[1,1'-biphenyl]-3-yl)-7-methylimidazo[1,2-a]pyridin-6-yl)-2-(tert-butoxy)acetate following the procedure for methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate. $^1$H NMR (400 MHz, CDCl$_3$) δ 8.14 (d, J=7.8 Hz, 1H), 8.07 (s, 1H), 8.03 (s, 1H), 7.55-7.47 (m, 1H), 7.35-7.29 (m, 2H), 7.12 (s, 1H), 6.84 (s, 1H), 6.26-6.14 (m, 1H), 6.06 (br. s., 1H), 5.89-5.74 (m, 1H), 4.57-4.44 (m, 1H), 4.10-4.05 (m, 1H), 4.03-3.93 (m, 2H), 3.84-3.73 (m, 1H), 3.69 (s, 3H), 3.07 (d, J=8.3 Hz, 1H), 2.68 (d, J=7.5 Hz, 1H), 2.51 (br. s., 1H), 2.46 (s, 3H), 2.43-2.34 (m, 1H), 2.31 (s, 3H), 2.25 (s, 3H), 1.97 (t, J=12.5 Hz, 2H), 1.75 (td, J=12.9, 4.5 Hz, 2H), 1.32 (s, 3H), 1.25 (s, 9H), 1.10 (d, J=6.3 Hz, 3H); LCMS (ESI, M+1): 666.3.

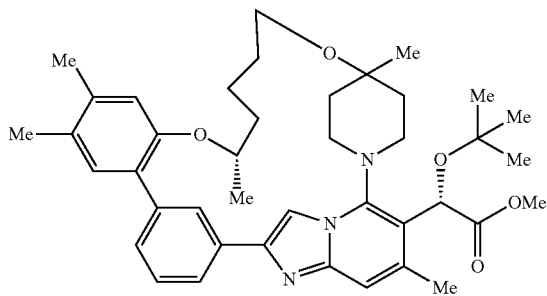 [SMILES: COC(=O)[C@@H](OC(C)(C)C)c1c(C)cc2nc3cn2c1N1CCC(C)(CC1)OCCCCC[C@H](C)Oc1cc(C)c(C)cc1-c1cccc-3c1]

Methyl(2S)-2-(tert-butoxy)-2-[(22S)-4,17,18,22,28-pentamethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl] acetate Prepared in 43% yield from methyl(2S)-2-(tert-butoxy)-2-[(22S)-4,17,18,22,28-pentamethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl] acetate following the procedure for methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. $^1$H NMR (400 MHz, CDCl$_3$) δ 8.16 (d, J=8.0 Hz, 1H), 8.13 (s, 1H), 8.02 (s, 1H), 7.51 (t, J=7.7 Hz, 1H), 7.35-7.30 (m, 2H), 7.15 (s, 1H), 6.82 (s, 1H), 6.05 (br. s., 1H), 4.55 (br. s., 1H), 3.93 (t, J=10.9 Hz, 1H), 3.77 (t, J=11.0 Hz, 1H), 3.69 (s, 3H), 3.54-3.43 (m, 2H), 3.10 (d, J=11.3 Hz, 1H), 2.69 (d, J=9.8 Hz, 1H), 2.45 (s, 3H), 2.32 (s, 3H), 2.26 (s, 3H), 1.99-1.70 (m, 10H), 1.28 (s, 3H), 1.25 (s, 9H), 1.15 (d, J=6.0 Hz, 3H); LCMS (ESI, M+1): 668.35.

Example 17

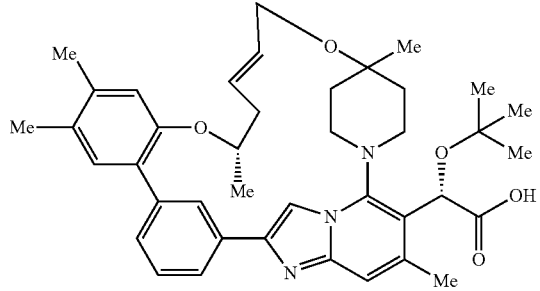 [SMILES: Cc1cc2c(cc1C)-c1cccc(c1)-c1cn3c(c([C@H](OC(C)(C)C)C(=O)O)c(C)cc3n1)N1CCC(C)(CC1)OCC/C=C/C[C@H](C)O2]

(2S)-2-(tert-Butoxy)-2-[(22S)-4,17,18,22,28-pentamethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid Prepared in 69% from methyl(2S)-2-(tert-butoxy)-2-[(22S)-4,17,18,22,28-pentamethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl] acetate following the procedure of (2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl] acetic acid. $^1$H NMR (500 MHz, DMSO-d$_6$) δ 8.06-7.97 (m, 3H), 7.50 (t, J=7.7 Hz, 1H), 7.31-7.26 (m, 2H), 7.10 (s, 1H), 7.00 (s, 1H), 6.10 (dd, J=14.3, 7.3 Hz, 1H), 5.92 (br. s., 1H), 5.77 (d, J=15.4 Hz, 1H), 4.57 (s, 1H), 4.03-3.89 (m, 3H), 3.64 (t, J=10.8 Hz, 1H), 3.10 (t, J=7.7 Hz, 1H), 2.63 (d, J=8.1 Hz, 1H), 2.56-2.53 (m, 1H), 2.40 (s, 3H), 2.27 (s, 3H), 2.23 (d, J=7.7 Hz, 1H), 2.20 (s, 3H), 1.98-1.91 (m, 1H), 1.87 (d, J=13.2 Hz, 1H), 1.77-1.67 (m, 2H), 1.25 (s, 3H), 1.18 (s, 9H), 1.01 (d, J=5.9 Hz, 3H); LCMS (ESI, M):651.4.

Example 18

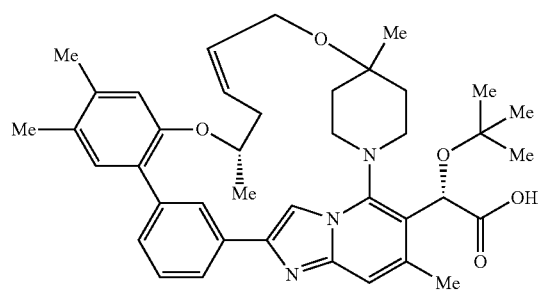 [SMILES: Cc1cc2c(cc1C)-c1cccc(c1)-c1cn3c(c([C@H](OC(C)(C)C)C(=O)O)c(C)cc3n1)N1CCC(C)(CC1)OC/C=C\C[C@H](C)O2]

(2S)-2-(tert-Butoxy)-2-[(22S)-4,17,18,22,28-pentamethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid Isolated in 6% yield as a minor product from the previous reaction. $^1$H NMR (500 MHz, DMSO-d$_6$) δ 8.20 (s, 1H), 7.98 (d, J=7.7 Hz, 1H), 7.91 (s, 1H), 7.50 (t, J=7.7 Hz, 1H), 7.37 (d, J=7.7 Hz, 1H), 7.28 (s, 1H), 7.23 (s, 1H), 7.08 (s, 1H), 5.85 (br. s., 1H), 5.78 (br. s., 2H), 4.76-4.64 (m, 1H), 4.00 (d, J=5.1 Hz, 1H), 3.91-3.78 (m, 2H), 3.61 (br. s., 1H), 3.18 (s, 1H), 2.78 (d, J=10.3 Hz, 2H), 2.58 (d, J=7.0 Hz, 1H), 2.42 (s, 3H), 2.28 (s, 3H), 2.22 (s, 3H), 1.96 (d, J=13.2 Hz, 1H), 1.80 (br. s., 2H), 1.72-1.63 (m, 1H), 1.24 (s, 3H), 1.19 (s, 9H), 1.17 (d, J=6.2 Hz, 3H); LCMS (ESI, M): 651.4.

Example 19

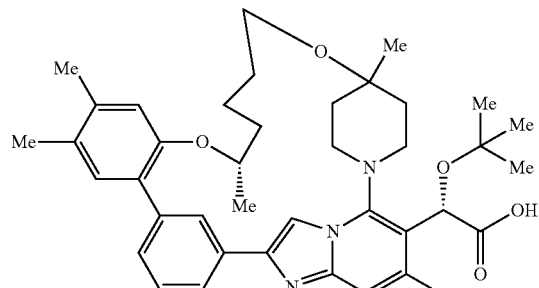

(2S)-2-(tert-Butoxy)-2-[(22S)-4,17,18,22,28-pentamethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 37% yield from methyl(2S)-2-(tert-butoxy)-2-[(22S)-4,17,18,22,28-pentamethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid. $^1$H NMR (400 MHz, CD$_3$OD) δ 8.12 (s, 1H), 8.05 (s, 1H), 7.96 (d, J=8.1 Hz, 1H), 7.52 (t, J=7.8 Hz, 1H), 7.35 (d, J=7.6 Hz, 1H), 7.30 (s, 1H), 7.11 (s, 1H), 6.92 (s, 1H), 6.04 (s, 1H), 4.57 (dt, J=6.2, 3.2 Hz, 1H), 3.98 (t, J=11.1 Hz, 1H), 3.80-3.74 (m, 1H), 3.58-3.50 (m, 2H), 3.31-3.28 (m, 1H), 2.78 (d, J=8.3 Hz, 1H), 2.55 (s, 3H), 2.32 (s, 3H), 2.26 (s, 3H), 2.00-1.65 (m, 10H), 1.28 (s, 3H), 1.26 (s, 9H), 1.09 (d, J=6.1 Hz, 3H); LCMS (ESI, M): 653.4.

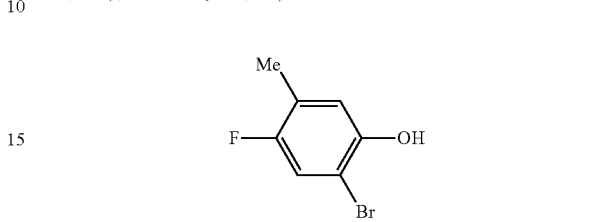

2-Bromo-4-fluoro-5-methylphenol

Prepared in 94% yield from 4-fluoro-3-methylphenol following the procedure for 2-bromo-4,5-dimethylphenol. $^1$H NMR (400 MHz, CDCl$_3$) δ 7.14 (d, J=8.5 Hz, 3H), 6.86 (d, J=7.0 Hz, 3H), 5.23 (s, 3H), 2.22 (d, J=1.8 Hz, 9H).

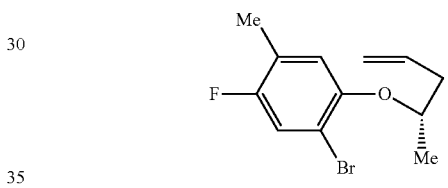

(S)-1-Bromo-5-fluoro-4-methyl-2-(pent-4-en-2-yloxy)benzene

Prepared in 59% yield from 2-bromo-4-fluoro-5-methylphenol following the same procedure as (S)-1-bromo-4-fluoro-2-(pent-4-en-2-yloxy)benzene. $^1$H NMR (400 MHz, CDCl$_3$) δ 7.21 (d, J=8.8 Hz, 1H), 6.75 (d, J=6.8 Hz, 1H), 5.91 (ddt, J=17.2, 10.2, 7.2 Hz, 1H), 5.20-5.07 (m, 2H), 4.42-4.26 (m, 1H), 2.60-2.48 (m, 1H), 2.45-2.37 (m, 1H), 2.23 (d, J=1.8 Hz, 3H), 1.33 (d, J=6.3 Hz, 3H).

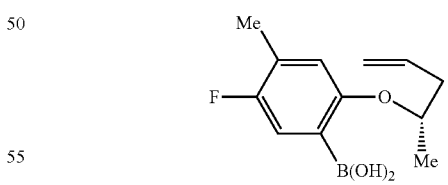

(S)-(5-Fluoro-4-methyl-2-(pent-4-en-2-yloxy)phenyl) boronic acid

Prepared in 100% yield from (S)-1-bromo-5-fluoro-4-methyl-2-(pent-4-en-2-yloxy)benzene following the procedure for (S)-(4-fluoro-2-(pent-4-en-2-yloxy)phenyl)boronic acid. NMR is complex and suggests an oligomeric mixture. The material, however, was used as is and was fully compentent for undergoing a Suzuki coupling.

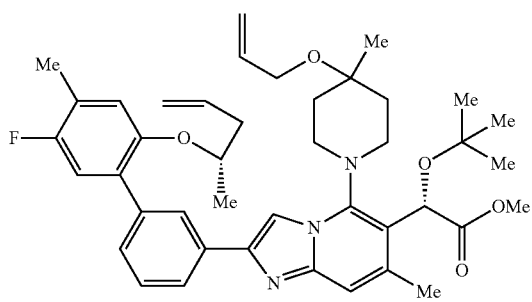 [SMILES: C=CCOC1(C)CCN(c2c([C@H](OC(C)(C)C)C(=O)OC)c(C)cc3nc(-c4cccc(-c5cc(F)c(C)cc5O[C@@H](C)CC=C)c4)cn23)CC1]

(S)-Methyl 2-(5-(4-(allyloxy)-4-methylpiperidin-1-yl)-2-(5'-fluoro-4'-methyl-2'-((S)-pent-4-en-2-yloxy)-[1,1'-biphenyl]-3-yl)-7-methylimidazo[1,2-a]pyridin-6-yl)-2-(tert-butoxy)acetate Prepared in 72% yield from (S)-(5-fluoro-4-methyl-2-(pent-4-en-2-yloxy)phenyl)boronic acid and (S)-methyl 2-(5-(4-(allyloxy)-4-methylpiperidin-1-yl)-2-(3-bromophenyl)-7-methylimidazo[1,2-a]pyridin-6-yl)-2-(tert-butoxy)acetate following the procedure for (S)-methyl 2-(5-(4-(allyloxy)-4-methylpiperidin-1-yl)-2-(4'-fluoro-2'-((S)-pent-4-en-2-yloxy)-[1,1'-biphenyl]-3-yl)-7-methylimidazo[1,2-a]pyridin-6-yl)-2-(tert-butoxy)acetate. $^1$H NMR (400 MHz, CDCl$_3$) δ 8.02 (s, 2H), 7.96-7.92 (m, 1H), 7.56-7.51 (m, 1H), 7.48-7.41 (m, 1H), 7.32 (s, 1H), 7.14-7.09 (m, 1H), 6.81 (d, J=6.5 Hz, 1H), 6.14-5.96 (m, 2H), 5.72 (ddt, J=17.1, 10.2, 7.0 Hz, 1H), 5.43 (dd, J=17.3, 1.8 Hz, 1H), 5.12-4.95 (m, 3H), 4.22-4.10 (m, 1H), 4.07-3.94 (m, 3H), 3.82 (t, J=10.5 Hz, 1H), 3.69 (s, 3H), 3.02 (d, J=7.8 Hz, 1H), 2.73 (d, J=8.5 Hz, 1H), 2.47 (d, J=0.8 Hz, 3H), 2.40-2.33 (m, 1H), 2.31 (d, J=1.5 Hz, 3H), 2.28-2.17 (m, 1H), 1.98 (dd, J=13.9, 2.6 Hz, 2H), 1.86-1.72 (m, 2H), 1.33 (s, 3H), 1.27 (s, 9H), 1.14 (d, J=6.0 Hz, 3H); LCMS (ESI, M+1): 698.35.

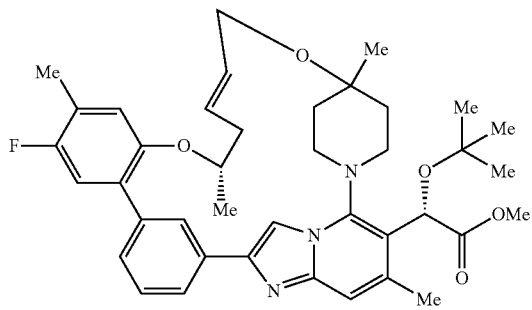 [SMILES: COC(=O)[C@@H](OC(C)(C)C)c1c(C)cc2nc3cn2c1N1CCC(C)(CC1)OC/C=C/C[C@H](C)Oc1cc(C)c(F)cc1-c1cccc-3c1]

Methyl(2S)-2-(tert-butoxy)-2-[(22S)-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate Prepared in 82% yield from (S)-methyl 2-(5-(4-(allyloxy)-4-methylpiperidin-1-yl)-2-(5'-fluoro-4'-methyl-2'-((S)-pent-4-en-2-yloxy)-[1,1'-biphenyl]-3-yl)-7-methylimidazo[1,2-a]pyridin-6-yl)-2-(tert-butoxy)acetate following the procedure for ethyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate. $^1$H NMR (400 MHz, CDCl$_3$) δ 8.16 (d, J=7.8 Hz, 1H), 8.08 (s, 1H), 8.04 (s, 1H), 7.54-7.49 (m, 1H), 7.32 (s, 1H), 7.29 (d, J=1.3 Hz, 1H), 7.03 (d, J=10.3 Hz, 1H), 6.83 (d, J=6.5 Hz, 1H), 6.25-6.14 (m, 1H), 6.05 (br. s., 1H), 5.86-5.75 (m, 1H), 4.51-4.40 (m, 1H), 4.10-3.93 (m, 3H), 3.78 (t, J=10.9 Hz, 1H), 3.69 (s, 3H), 3.07 (d, J=7.8 Hz, 1H), 2.69 (d, J=7.5 Hz, 1H), 2.51-2.47 (m, 1H), 2.46 (s, 3H), 2.41-2.35 (m, 1H), 2.32 (d, J=1.5 Hz, 3H), 1.98 (t, J=12.8 Hz, 2H), 1.82-1.70 (m, 2H), 1.33 (s, 3H), 1.25 (s, 9H), 1.06 (d, J=6.0 Hz, 3H); LCMS (ESI, M+1): 670.25.

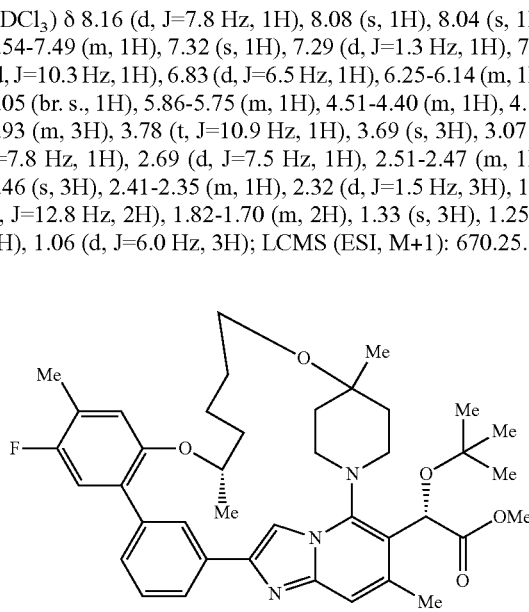

Methyl(2S)-2-(tert-butoxy)-2-[(22S)-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 94% yield from methyl(2S)-2-(tert-butoxy)-2-[(22S)-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate following the procedure for methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. $^1$H NMR (500 MHz, CDCl$_3$) δ 8.20 (dt, J=7.9, 1.4 Hz, 1H), 8.15 (t, J=1.5 Hz, 1H), 8.03 (s, 1H), 7.53 (t, J=7.7 Hz, 1H), 7.33 (s, 1H), 7.30 (dt, J=7.8, 1.3 Hz, 1H), 7.10-7.05 (m, 1H), 6.81 (d, J=6.5 Hz, 1H), 6.06 (br. s., 1H), 4.49 (td, J=6.3, 3.1 Hz, 1H), 3.97 (t, J=10.7 Hz, 1H), 3.81-3.77 (m, 1H), 3.76 (s, 3H), 3.57-3.47 (m, 2H), 3.15-3.08 (m, 1H), 2.71 (d, J=7.6 Hz, 1H), 2.47 (d, J=0.8 Hz, 3H), 2.34 (d, J=1.4 Hz, 3H), 2.00-1.69 (m, 10H), 1.30 (s, 3H), 1.26 (s, 9H), 1.12 (d, J=6.1 Hz, 3H); LCMS (ESI, M+1): 672.4.

Example 20

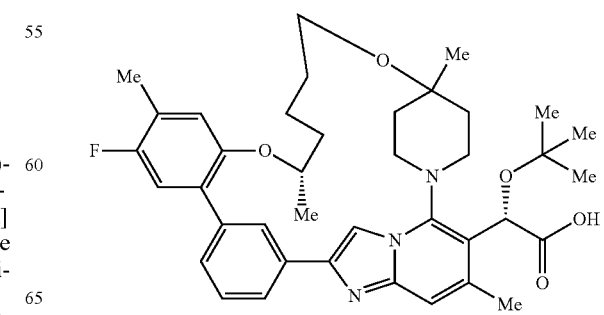

(2S)-2-(tert-Butoxy)-2-[(22S)-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 100% yield from methyl(2S)-2-(tert-butoxy)-2-[(22S)-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid. $^1$H NMR (600 MHz, DMSO-$d_6$) δ 8.15 (s, 1H), 8.05 (d, J=7.3 Hz, 1H), 7.96 (s, 1H), 7.50 (t, J=7.7 Hz, 1H), 7.31 (d, J=7.7 Hz, 1H), 7.15 (t, J=5.0 Hz, 2H), 7.09 (d, J=6.6 Hz, 1H), 5.64 (br. s., 1H), 4.62 (br. s., 1H), 3.95-3.13 (m, 5H), 2.67 (d, J=9.2 Hz, 1H), 2.40 (s, 3H), 2.29 (s, 3H), 2.00-1.53 (m, 10H), 1.20 (s, 3H), 1.13 (s, 9H), 1.08 (d, J=5.5 Hz, 3H); LCMS (ESI, M): 657.4.

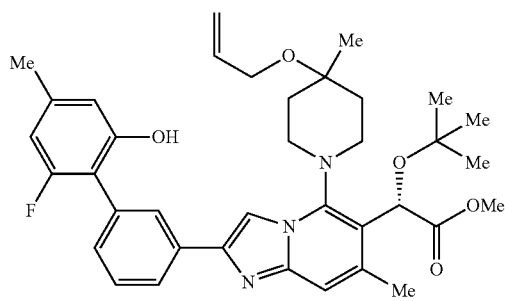 [SMILES: C=CCOC1(C)CCN(c2c([C@H](OC(C)(C)C)C(=O)OC)c(C)cc3nc(-c4cccc(-c5c(O)cc(C)cc5F)c4)cn23)CC1]

(S)-Methyl 2-(5-(4-(allyloxy)-4-methylpiperidin-1-yl)-2-(2'-fluoro-6'-hydroxy-4'-methyl-[1,1'-biphenyl]-3-yl)-7-methylimidazo[1,2-a]pyridin-6-yl)-2-(tert-butoxy)acetate Prepared in 100% yield from (2-fluoro-6-hydroxy-4-methylphenyl)boronic acid and (S)-methyl 2-(5-(4-(allyloxy)-4-methylpiperidin-1-yl)-2-(3-bromophenyl)-7-methylimidazo[1,2-a]pyridin-6-yl)-2-(tert-butoxy)acetate following the procedure of (S)-methyl 2-(5-(4-(allyloxy)-4-methylpiperidin-1-yl)-2-(2'-hydroxy-5'-methyl-[1,1'-biphenyl]-3-yl)-7-methylimidazo[1,2-a]pyridin-6-yl)-2-(tert-butoxy)acetate. LCMS (ESI, M+1): 630.3.

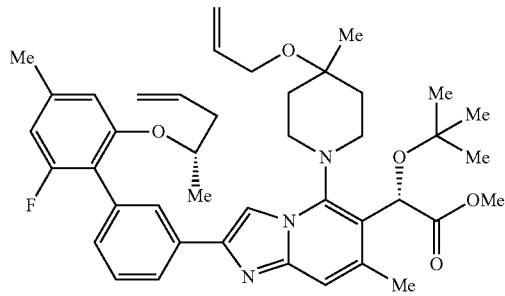 [SMILES: C=CCOC1(C)CCN(c2c([C@H](OC(C)(C)C)C(=O)OC)c(C)cc3nc(-c4cccc(-c5c(F)cc(C)cc5O[C@@H](C)CC=C)c4)cn23)CC1]

Methyl(2S)-2-(tert-butoxy)-2-[2-(3-{2-fluoro-4-methyl-6-[(2S)-pent-4-en-2-yloxy]phenyl}phenyl)-7-methyl-5-[4-methyl-4-(prop-2-en-1-yloxy)piperidin-1-yl]imidazo[1,2-a]pyridin-6-yl]acetate Prepared in 90% yield from (S)-methyl 2-(5-(4-(allyloxy)-4-methylpiperidin-1-yl)-2-(2'-fluoro-6'-hydroxy-4'-methyl-[1,1'-biphenyl]-3-yl)-7-methylimidazo[1,2-a]pyridin-6-yl)-2-(tert-butoxy)acetate following the procedure for (S)-methyl 2-(5-(4-(allyloxy)-4-methylpiperidin-1-yl)-7-methyl-2-(5'-methyl-2'-((S)-pent-4-en-2-yloxy)-[1,1'-biphenyl]-3-yl)imidazo[1,2-a]pyridin-6-yl)-2-(tert-butoxy)acetate. LCMS (ESI, M+1): 698.35.

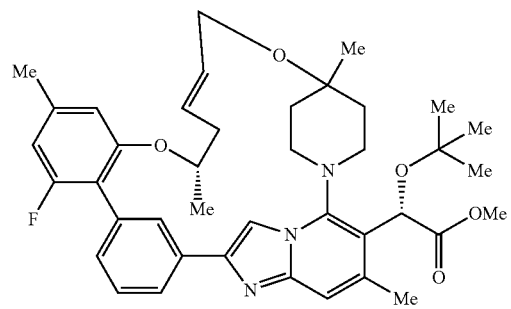 [SMILES: COC(=O)[C@@H](OC(C)(C)C)c1c(C)cc2nc3cn2c1N1CCC(C)(CC1)OC/C=C/C[C@H](C)Oc1cc(C)cc(F)c1-c1cccc-3c1]

Methyl(2S)-2-(tert-butoxy)-2-[(22S)-16-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate Prepared in 70% yield from methyl(2S)-2-(tert-butoxy)-2-[2-(3-{2-fluoro-4-methyl-6-[(2S)-pent-4-en-2-yloxy]phenyl}phenyl)-7-methyl-5-[4-methyl-4-(prop-2-en-1-yloxy)piperidin-1-yl]imidazo[1,2-a]pyridin-6-yl]acetate following the procedure for ethyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate. LCMS (ESI, M+1): 670.25.

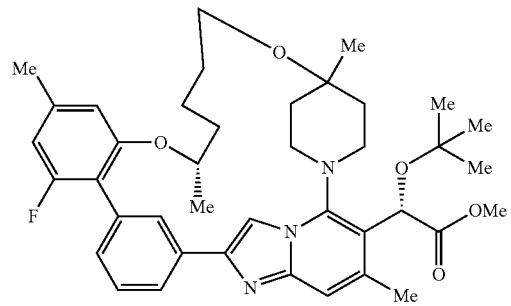 [SMILES: COC(=O)[C@@H](OC(C)(C)C)c1c(C)cc2nc3cn2c1N1CCC(C)(CC1)OCCCC[C@H](C)Oc1cc(C)cc(F)c1-c1cccc-3c1]

Methyl(2S)-2-(tert-butoxy)-2-[(22S)-16-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 100% yield from methyl(2S)-2-(tert-butoxy)-2-[(22S)-16-fluoro-4,18,22,28-tetramethyl-21,27-dioxa-1,7, 34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate following the procedure for methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. LCMS (ESI, M+1):672.35.

Example 21

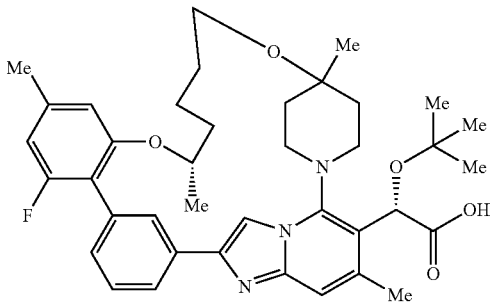 [SMILES: Cc1cc(F)c2c(c1)O[C@@H](C)CCCCOC1(C)CCN(CC1)c1c([C@H](OC(C)(C)C)C(=O)O)c(C)cc3nc(cn13)-c1cccc-2c1]

(2S)-2-(tert-Butoxy)-2-[(22S)-16-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 41% yield from methyl(2S)-2-(tert-butoxy)-2-[(22S)-16-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid. $^1$H NMR (500 MHz, DMSO-d$_6$) δ 8.04 (d, J=7.7 Hz, 1H), 7.98 (s, 1H), 7.85 (s, 1H), 7.49 (t, J=7.5 Hz, 1H), 7.30 (s, 1H), 7.24 (d, J=7.3 Hz, 1H), 6.86 (s, 1H), 6.71 (d, J=10.6 Hz, 1H), 5.90 (br. s., 1H), 4.66 (br. s., 1H), 3.87 (br. s., 1H), 3.63 (br. s., 1H), 3.49-3.42 (m, 2H), 3.12 (br. s., 1H), 2.64 (d, J=10.6 Hz, 1H), 2.40 (s, 3H), 2.37 (s, 3H), 1.93-1.51 (m, 10H), 1.20 (s, 3H), 1.18 (s, 9H), 1.10 (d, J=5.9 Hz, 3H) LCMS (ESI, M): 657.4.

Example 22

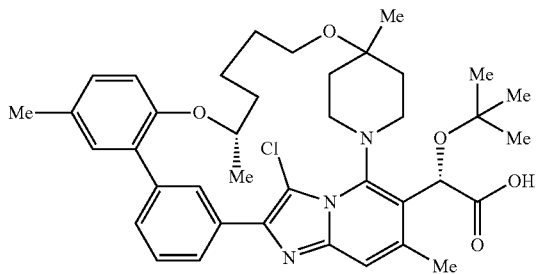 [SMILES: Cc1ccc2c(c1)-c1cccc(c1)-c1nc3cc(C)c([C@H](OC(C)(C)C)C(=O)O)c(n3c1Cl)N1CCC(C)(CC1)OCCCC[C@H](C)O2]

(2S)-2-(tert-Butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid To a solution of methyl(2S)-2-(tert-butoxy)-2-[(22S)-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (20 mg, 0.031 mmol, 1 equiv) in MeCN (1 mL) was added NCS (4 mg, 0.031 mmol, 1 equiv). After 1 h, the reaction was concentrated in vacuo. The crude chloride was taken up in 9:1 MeOH:water (1.1 mL) and LiOH.H$_2$O (39 mg, 0.918 mmol, 30 equiv) was added. A few drops of THF were added to aid solubility. The reaction was heated to 70° C. for 1.5 h. Upon cooling to ambient temperature, the reaction was filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 60-100% B over 15 minutes, then a 5-minute hold at 100% B; Flow: 20 mL/min to provide the product (10 mg, 48%). $^1$H NMR (500 MHz, DMSO-d$_6$) δ 8.30 (s, 1H), 7.81 (d, J=7.7 Hz, 1H), 7.56 (t, J=7.7 Hz, 1H), 7.41 (d, J=7.7 Hz, 1H), 7.36 (s, 1H), 7.16-7.08 (m, 3H), 6.02-5.67 (m, 1H), 4.60 (d, J=3.3 Hz, 1H), 3.96 (d, J=10.6 Hz, 2H), 3.52 (d, J=8.4 Hz, 1H), 3.42-3.30 (m, 1H), 2.44 (s, 3H), 2.40-2.31 (m, 2H), 2.29 (s, 3H), 2.05-1.51 (m, 10H), 1.20 (br. s., 3H), 1.19 (s, 9H), 1.03 (d, J=5.9 Hz, 3H); LCMS (ESI, M): 673.3.

Example 23

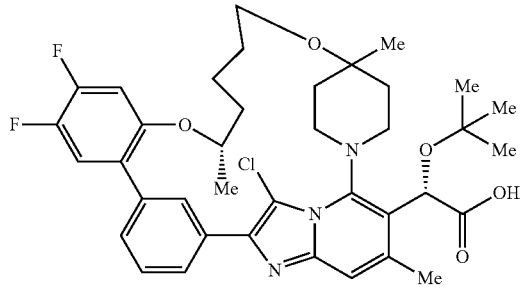 [SMILES: Cc1cc2nc3c(Cl)n2c(c1[C@H](OC(C)(C)C)C(=O)O)N1CCC(C)(CC1)OCCCC[C@H](C)Oc1cc(F)c(F)cc1-c1cccc-3c1]

(2S)-2-(tert-Butoxy)-2-[(22S)-8-chloro-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 42% yield from methyl(2S)-2-(tert-butoxy)-2-[(22S)-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ

8.28 (s, 1H), 7.85 (d, J=7.7 Hz, 1H), 7.57 (t, J=7.7 Hz, 1H), 7.45-7.36 (m, 3H), 7.32 (s, 1H), 5.91-5.64 (m, 1H), 4.65 (d, J=4.8 Hz, 1H), 4.01-3.86 (m, 2H), 3.55-3.48 (m, 1H), 3.40-3.30 (m, 1H), 2.55 (s, 1H), 2.43 (br. s., 3H), 2.33 (br. s., 1H), 2.00-1.48 (m, 10H), 1.19 (br. s., 3H), 1.17 (s, 9H), 1.06 (d, J=5.9 Hz, 3H) LCMS (ESI, M): 695.3.

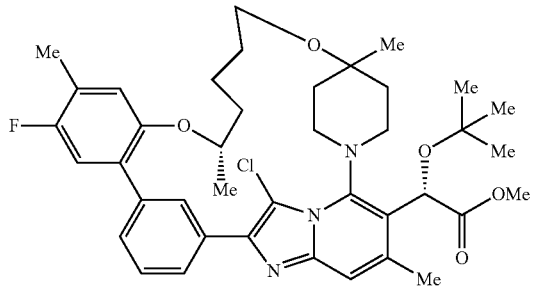 [SMILES: COC(=O)[C@@H](OC(C)(C)C)c1c(C)cc2nc3c(Cl)n2c1N1CCC(C)(CC1)OCCCC[C@H](C)Oc1cc(C)c(F)cc1-c1cccc-3c1]

Methyl(2S)-2-(tert-butoxy)-2-[(22S)-8-chloro-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate To a solution of methyl(2S)-2-(tert-butoxy)-2-[(22S)-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (56 mg, 0.083 mmol, 1 equiv) in MeCN (1 mL) was added NCS (11 mg, 0.083 mmol, 1 equiv). After 1 h, the reaction was concentrated in vacuo. The crude product was purified by flash column chromatography (0-100% EtOAc [2% TEA]/hexane) to provide the product (51 mg, 87%) as a yellow foam. $^1$H NMR (400 MHz, CDCl$_3$) δ 8.40 (t, J=1.5 Hz, 1H), 7.92 (d, J=7.8 Hz, 1H), 7.54 (t, J=7.8 Hz, 1H), 7.36 (d, J=7.8 Hz, 1H), 7.31 (s, 1H), 7.03 (d, J=10.3 Hz, 1H), 6.87 (d, J=6.8 Hz, 1H), 6.28-5.83 (m, 1H), 4.54-4.46 (m, 1H), 4.12-4.06 (m, 1H), 3.71 (s, 3H), 3.62-3.57 (m, 1H), 3.49-3.42 (m, 1H), 3.31 (br. s., 1H), 2.48 (s, 3H), 2.48-2.36 (m, 1H), 2.31 (d, J=1.3 Hz, 3H), 2.17-2.09 (m, J=6.0 Hz, 1H), 2.00-1.61 (m, 10H), 1.29 (s, 3H), 1.26 (s, 9H), 1.11 (d, J=6.0 Hz, 3H); LCMS (ESI, M+1):706.25.

Example 24

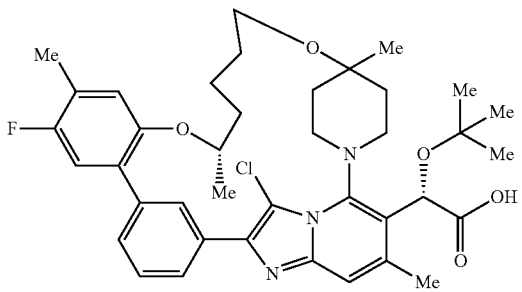 [SMILES: Cc1cc2c(cc1F)-c1cccc(c1)-c1nc3cc(C)c([C@H](OC(C)(C)C)C(=O)O)c(n3c1Cl)N1CCC(C)(CC1)OCCCC[C@H](C)O2]

(2S)-2-(tert-Butoxy)-2-[(22S)-8-chloro-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 97% yield from methyl(2S)-2-(tert-butoxy)-2-[(22S)-8-chloro-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid. $^1$H NMR (600 MHz, DMSO-d$_6$) δ 8.31 (s, 1H), 7.83 (d, J=7.7 Hz, 1H), 7.55 (t, J=7.7 Hz, 1H), 7.41 (d, J=7.3 Hz, 1H), 7.30 (br. s., 1H), 7.14 (d, J=6.2 Hz, 1H), 7.10 (d, J=10.3 Hz, 1H), 5.86-5.58 (m, 1H), 4.60 (d, J=4.4 Hz, 1H), 4.00-3.95 (m, 1H), 3.90 (br. s., 1H), 3.84-3.77 (m, 1H), 3.47-3.41 (m, 1H), 3.38-3.32 (m, 1H), 2.43 (br. s., 3H), 2.34 (br. s., 1H), 2.28 (s, 3H), 2.01-1.49 (m, 10H), 1.19 (br. s., 3H), 1.16 (s, 9H), 1.03 (d, J=5.5 Hz, 3H); LCMS (ESI, M): 691.3.

Example 25

(2S)-2-(tert-Butoxy)-2-[(22S)-8-chloro-4,17,18,22,28-pentamethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 61% yield from methyl(2S)-2-(tert-butoxy)-2-[(22S)-4,17,18,22,28-pentamethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.29 (s, 1H), 7.79 (d, J=7.7 Hz, 1H), 7.54 (t, J=7.7 Hz, 1H), 7.39 (d, J=7.3 Hz, 1H), 7.33 (s, 1H), 7.09 (s, 1H), 7.02 (s, 1H), 5.79 (br. s., 1H), 4.60 (d, J=4.8 Hz, 1H), 4.02-3.86 (m, 2H), 3.51 (br. s., 1H), 3.36 (br. s., 1H), 2.55 (s, 1H), 2.43 (br. s., 3H), 2.36 (br. s., 1H), 2.25 (s, 3H), 2.19 (s, 3H), 2.00-1.52 (m, 10H), 1.20 (br. s., 3H), 1.17 (s, 9H), 1.03 (d, J=5.5 Hz, 3H); LCMS (ESI, M): 687.3.

Example 26

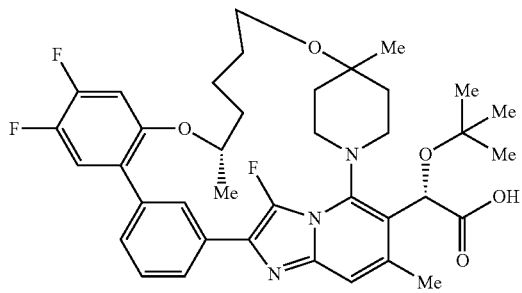 [SMILES: Cc1cc2nc3c(F)n2c(c1[C@H](OC(C)(C)C)C(=O)O)N1CCC(C)(CC1)OCCCC[C@H](C)Oc1cc(F)c(F)cc1-c1cccc-3c1]

(2S)-2-(tert-Butoxy)-2-[(22S)-8,17,18-trifluoro-4,22, 28-trimethyl-21,27-dioxa-1,7,34-triazahexacyclo [26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]acetic acid To a solution of methyl(2S)-2-(tert-butoxy)-2-[(22S)-17, 18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]acetate (22 mg, 0.033 mmol, 1 equiv) in MeCN (0.33 mL) was added 2,6-dichloro-1-fluoropyridin-1-ium, tetrafluoroborate salt (8 mg, 0.031 mmol, 1 equiv). The reaction turned dark orange. After 3 h, the reaction was concentrated in vacuo. The crude fluoride product was taken up in 9:1 MeOH:water (1.8 mL) and LiOH.H$_2$O (27 mg, 0.651 mmol, 20 equiv) was added. The reaction was heated to 60° C. for 4 h. Upon cooling to ambient temperature, the reaction was filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-90% B over 20 minutes, then a 5-minute hold at 100% B; Flow: 20 mL/min to provide the product (1.1 mg, 5%) $^1$H NMR (400 MHz, CD$_3$OD) δ 8.33 (d, J=1.5 Hz, 1H), 7.97 (d, J=8.1 Hz, 1H), 7.57 (t, J=7.7 Hz, 1H), 7.37-7.33 (m, 1H), 7.32-7.27 (m, 1H), 7.19 (s, 1H), 7.11 (dd, J=12.8, 7.0 Hz, 1H), 6.04 (br. s., 1H), 4.56 (d, J=5.9 Hz, 1H), 3.76-3.48 (m, 4H), 3.28 (d, J=11.0 Hz, 1H), 2.71 (d, J=6.8 Hz, 1H), 2.53 (s, 3H), 2.09-1.64 (m, 10H), 1.28 (s, 9H), 1.27 (s, 3H), 1.19 (d, J=6.1 Hz, 3H); LCMS (ESI, M): 679.3.

Methyl(2S)-2-[(22S)-8-bromo-17-fluoro-4,18,22,28-tetramethyl-21,27-dioxa-1,7,34-triazahexacyclo [26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]-2-(tert-butoxy)acetate To a solution of methyl(2S)-2-(tert-butoxy)-2-[(22S)-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]acetate (50 mg, 0.074 mmol, 1 equiv) in MeCN (1.5 mL) was added NBS (13 mg, 0.074 mmol, 1 equiv). After 1 h, the reaction was concentrated in vacuo. The crude product was purified by flash column chromatography (0-100% EtOAc [2% TEA]/hexane) to provide the product (40 mg, 72%). $^1$H NMR (400 MHz, CHLOROFORM-d) δ 8.16 (s, 1H), 7.82 (d, J=7.8 Hz, 1H), 7.54 (t, J=7.7 Hz, 1H), 7.37 (d, J=7.8 Hz, 1H), 7.29 (s, 1H), 6.97 (d, J=10.3 Hz, 1H), 6.85 (d, J=6.5 Hz, 1H), 4.58-4.37 (m, 2H), 3.82-3.66 (m, 4H), 3.64-3.55 (m, 1H), 3.46-3.38 (m, 1H), 2.47 (br. s., 3H), 2.30 (d, J=0.8 Hz, 4H), 1.98-1.69 (m, 8H), 1.66-1.48 (m, 4H), 1.31-1.26 (m, 7H), 1.24 (d, J=5.8 Hz, 8H), 1.15 (d, J=6.0 Hz, 3H).

Example 27

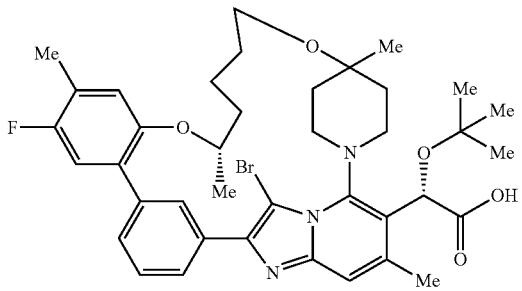

(2S)-2-[(22S)-8-Bromo-17-fluoro-4,18,22,28-tetramethyl-21,27-dioxa-1,7,34-triazahexacyclo[26.2. 2.1$^{6,9}$.1$^{10,14}$.0$^{2,7}$.0$^{15,20}$]tetratriaconta-2,4,6(34),8,10 (33),11,13,15(20),16,18-decaen-3-yl]-2-(tert-butoxy) acetic acid, 1$^{st}$ isomer Prepared in 24% from methyl(2S)-2-[(22S)-8-bromo-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]-2-(tert-butoxy)acetate following the procedure for (2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$] tetratriaconta-2,4,6(34),8,10(33),11,13,15(20),16,18,24-undecaen-3-yl]acetic acid. $^1$H NMR (600 MHz, DMSO-d$_6$) δ 8.09 (s, 1H), 7.73 (d, J=7.3 Hz, 1H), 7.56 (t, J=7.7 Hz, 1H), 7.43 (d, J=7.3 Hz, 1H), 7.33-7.29 (m, 1H), 7.14 (d, J=6.2 Hz, 1H), 7.04 (d, J=9.9 Hz, 1H), 5.75-5.61 (m, 1H), 4.69-4.59 (m, 1H), 4.31-2.61 (m, 6H), 2.43 (br. s., 3H), 2.27 (s, 3H), 1.94-

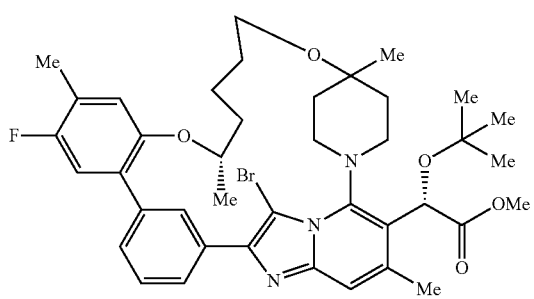 [SMILES: COC(=O)[C@@H](OC(C)(C)C)c1c(C)cc2nc3c(Br)n2c1N1CCC(C)(CC1)OCCCC[C@H](C)Oc1cc(C)c(F)cc1-c1cccc-3c1]

1.39 (m, 10H), 1.20 (br. s., 3H), 1.15 (br. s., 9H), 1.08 (d, J=5.5 Hz, 3H); LCMS (ESI, M): 735.3.

Example 28

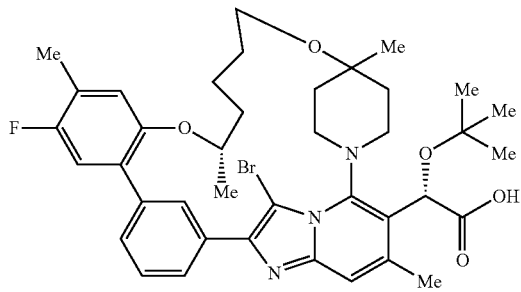 [SMILES: Cc1cc2c(cc1F)-c1cccc(c1)-c1nc3cc(C)c([C@H](OC(C)(C)C)C(=O)O)c(n3c1Br)N1CCC(C)(CC1)OCCCC[C@H](C)O2]

(2S)-2-[(22S)-8-Bromo-17-fluoro-4,18,22,28-tetramethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]-2-(tert-butoxy) acetic acid, 2$^{nd}$ isomer Isolated as the second isomer from the previous reaction. Appears to be an atropisomer that is slowly interconverting. LCMS (ESI, M): 735.3.

Example 29

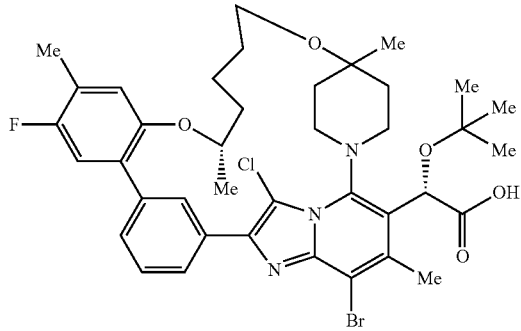 [SMILES: Cc1cc2c(cc1F)-c1cccc(c1)-c1nc3c(Br)c(C)c([C@H](OC(C)(C)C)C(=O)O)c(n3c1Cl)N1CCC(C)(CC1)OCCCC[C@H](C)O2]

(2S)-2-[(22S)-5-Bromo-8-chloro-17-fluoro-4,18,22,28-tetramethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]-2-(tert-butoxy)acetic acid To a solution of methyl(2S)-2-(tert-butoxy)-2-[(22S)-8-chloro-17-fluoro-4,18,22,28-tetramethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetate (9.5 mg, 0.013 mmol, 1 equiv) in MeCN (0.7 mL) was added NBS (2.4 mg, 0.013 mmol, 1 equiv). After 1 h, the reaction was concentrated in vacuo. The crude bromide product was taken up in 9:1 MeOH:water (1 mL) and LiOH.H₂O (23 mg, 0.538 mmol, 40 equiv) was added. The reaction was heated to 70° C. for 2 h. Upon cooling to ambient temperature, the reaction was filtered and purified via preparative LC/MS with the following conditions: The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 60-100% B over 15 minutes, then a 5-minute hold at 100% B; Flow: 20 mL/min to provide the product (5.9 mg, 55%). Methyl(2S)-2-[(22S)-5-bromo-8-chloro-17-fluoro-4,18,22,28-tetramethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]-2-(tert-butoxy)acetate. ¹H NMR (400 MHz, CDCl₃) δ 8.35 (s, 1H), 8.02 (d, J=8.0 Hz, 1H), 7.54 (t, J=7.8 Hz, 1H), 7.37 (d, J=7.8 Hz, 1H), 7.03 (d, J=10.3 Hz, 1H), 6.87 (d, J=6.8 Hz, 1H), 6.22-6.06 (m, 1H), 4.53-4.43 (m, 1H), 4.12-4.07 (m, 1H), 3.74 (br. s., 3H), 3.63-3.54 (m, 1H), 3.50-3.42 (m, 1H), 3.29 (br. s., 1H), 2.57 (br. s., 3H), 2.47 (br. s., 1H), 2.31 (d, J=1.0 Hz, 3H), 2.10-1.60 (m, 10H), 1.29 (s, 3H), 1.25 (s, 9H), 1.10 (d, J=6.3 Hz, 3H); LCMS (ESI, M+1): 784.10. (2S)-2-[(22S)-5-bromo-8-chloro-17-fluoro-4,18,22,28-tetramethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]-2-(tert-butoxy)acetic acid. ¹H NMR (600 MHz, DMSO-d₆) δ 8.31 (s, 1H), 7.87 (d, J=7.3 Hz, 1H), 7.58 (t, J=7.7 Hz, 1H), 7.44 (d, J=7.7 Hz, 1H), 7.15 (d, J=6.6 Hz, 1H), 7.11 (d, J=9.9 Hz, 1H), 5.63 (br. s., 1H), 4.61 (d, J=4.0 Hz, 1H), 4.00-3.92 (m, 1H), 3.84 (br. s., 1H), 3.74-3.65 (m, 1H), 3.38-3.27 (m, 1H), 2.51 (br. s., 3H), 2.34 (br. s., 2H), 2.28 (s, 3H), 1.99-1.50 (m, 10H), 1.17 (br. s., 3H), 1.12 (br. s., 9H), 1.03 (d, J=5.1 Hz, 3H);

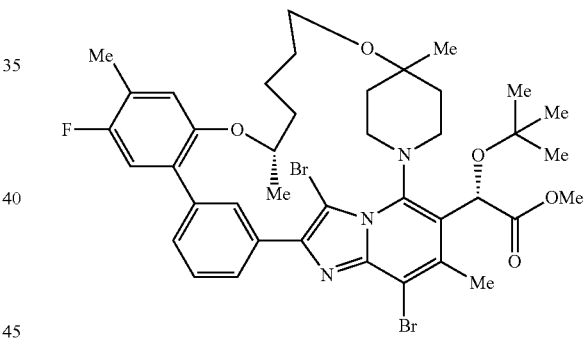

Methyl(2S)-2-(tert-butoxy)-2-[(22S)-5,8-dibromo-17-fluoro-4,18,22,28-tetramethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetate To a solution of methyl(2S)-2-(tert-butoxy)-2-[(22S)-17-fluoro-4,18,22,28-tetramethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetate (160 mg, 0.238, 1 equiv) in MeCN (5 mL) was added NBS (93 mg, 0.524 mmol, 2.2 equiv). After 1 h, the reaction was concentrated in vacuo. The crude product was purified by flash column chromatography (0-100% EtOAc [2% TEA]/hexane) to provide the product (170 mg, 86%) as a pale yellow foam. LCMS (ESI, M+1): 830.0.

Example 30

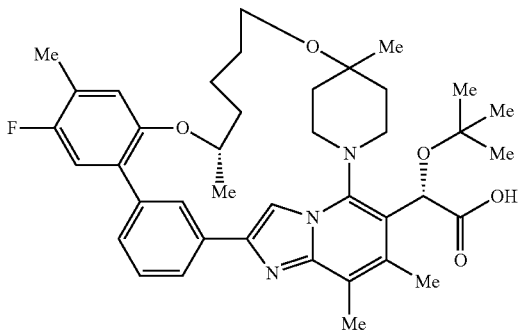 [SMILES: Cc1cc2c(cc1F)-c1cccc(c1)-c1cn3c(c([C@H](OC(C)(C)C)C(=O)O)c(C)c(C)c3n1)N1CCC(C)(CC1)OCCCC[C@H](C)O2]

(2S)-2-(tert-Butoxy)-2-[(22S)-17-fluoro-4,5,18,22,28-pentamethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid A solution of methyl(2S)-2-(tert-butoxy)-2-[(22S)-5,8-dibromo-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (21 mg, 0.025 mmol, 1 equiv), methylboronicacid (6 mg, 0.101 mmol, 4 equiv), Pd(OAc)$_2$ (0.6 mg, 0.003 mmol, 0.1 equiv), Sphos (2 mg, 0.005 mmol, 0.2 equiv), and Cs$_2$CO$_3$ (12 mg, 0.038 mmol, 1.5 equiv) in DMF (0.46 mL) and water (0.046 mL) was heated to 80° C. for 20 h. More methylboronicacid (6 mg, 0.101 mmol, 4 equiv) and Cs$_2$CO$_3$ (12 mg, 0.038 mmol, 1.5 equiv) were added. After 6 h, remove from heat. Upon cooling to ambient temperature, the reaction was diluted with EtOAc and washed with water. The EtOAc was dried (Na$_2$SO$_4$) and concentrated in vacuo. The crude product was taken up in MeOH (2 mL) was added 10% Pd/C (5 mg, 0.005 mmol, 0.2 equiv). The reaction was then stirred under a balloon of H$_2$ for 1 h. The reaction was then filtered through Celite eluting with MeOH. The filtrate was then concentrated in vacuo. The crude hydrogenation product was taken up in 10:1 MeOH:water (1 mL) and LiOH.H$_2$O (32 mg, 0.759 mmol, 30 equiv) was added. The reaction was heated to 70° C. for 3 h. Upon cooling to ambient temperature, the reaction was filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 70-100% B over 15 minutes, then a 5-minute hold at 100% B; Flow: 20 mL/min to provide the product (4.1 mg, 24%). $^1$H NMR (500 MHz, DMSO-d$_6$) δ 8.13 (d, J=1.8 Hz, 2H), 7.97 (s, 1H), 7.51 (t, J=8.1 Hz, 1H), 7.31 (d, J=7.7 Hz, 1H), 7.15 (d, J=10.3 Hz, 1H), 7.09 (d, J=6.6 Hz, 1H), 5.80 (br. s., 1H), 4.62 (br. s., 1H), 3.84 (t, J=10.3 Hz, 1H), 3.60-3.52 (m, 1H), 3.44 (br. s., 3H), 2.64 (d, J=9.2 Hz, 1H), 2.47 (s, 3H), 2.30 (br. s., 3H), 2.29 (br. s., 3H), 1.93-1.51 (m, 10H), 1.20 (s, 3H), 1.14 (s, 9H), 1.08 (d, J=6.2 Hz, 3H); LCMS (ESI, M): 671.4.

Example 31

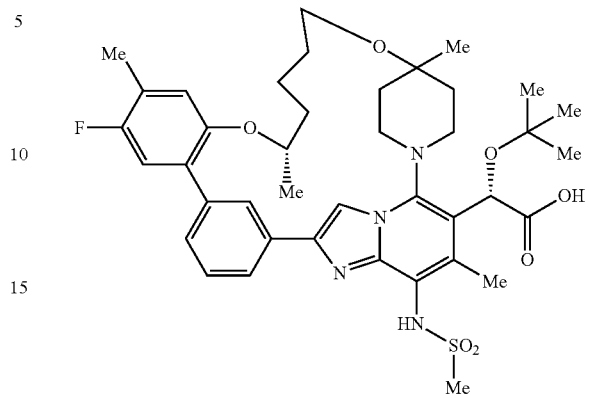

(2S)-2-(tert-Butoxy)-2-[(22S)-17-fluoro-5-methanesulfonamido-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid To a solution of methyl(2S)-2-(tert-butoxy)-2-[(22S)-5,8-dibromo-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (21 mg, 0.025 mmol, 1 equiv), methanesulfonamide (7 mg, 0.076 mmol, 3 equiv), CuI (7 mg, 0.038 mmol, 1.5 equiv), and K$_2$CO$_3$ (14 mg, 0.101 mmol, 4 equiv) in DMF (1.3 mL) was added (1S,2S)-(+)-N,N'-dimethylcyclohexanr-1,2-diamine (0.012 mL, 0.076 mmol, 3 equiv). The now blue reaction was heated to 100° C. for 24 h. More methanesulfonamide (7 mg, 0.076 mmol, 3 equiv), CuI (7 mg, 0.038 mmol, 1.5 equiv), and (1S,2S)-(+)-N,N'-dimethylcyclohexanr-1,2-diamine (0.012 mL, 0.076 mmol, 3 equiv) was added and the temperature was raised to 120° C. After 24 h, the reaction was removed from heat. Upon cooling to ambient temperature, the reaction was diluted with EtOAc and washed with water. The EtOAc was dried (Na$_2$SO$_4$) and concentrated in vacuo. The crude product was taken up in 9:1 MeOH:water (1 mL) and LiOH.H$_2$O (32 mg, 0.759 mmol, 30 equiv) was added. The reaction was heated to 70° C. for 2 h. Upon cooling to ambient temperature, the reaction was filtered and purified via preparative LC/MS with the following conditions: The crude material was purified via preparative LC/MS with the following conditions: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-100% B over 25 minutes, then a 5-minute hold at 100% B; Flow: 20 mL/min to provide the product (2.4 mg, 12% yield). $^1$H NMR (500 MHz, DMSO-d$_6$) δ 8.16 (s, 1H), 8.08 (d, J=7.7 Hz, 1H), 8.04 (s, 1H), 7.54 (t, J=7.7 Hz, 1H), 7.35 (d, J=8.1 Hz, 1H), 7.15 (d, J=10.3 Hz, 1H), 7.10 (d, J=6.2 Hz, 1H), 6.00-5.82 (m, 1H), 4.63 (br. s., 1H), 3.89-3.80 (m, 1H), 3.70-3.59 (m, 1H), 3.52-3.42 (m, 5H), 3.37-3.19 (m, 1H), 2.72-2.64 (m, 1H), 2.41 (s, 3H), 2.29 (s, 3H), 1.97-1.50 (m, 10H), 1.22 (s, 3H), 1.18 (s, 9H), 1.08 (d, J=5.9 Hz, 3H); LCMS (ESI, M): 750.3.

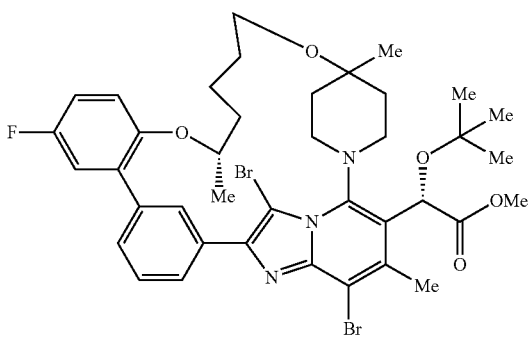 [SMILES: COC(=O)[C@@H](OC(C)(C)C)c1c(C)c(Br)c2nc3c(Br)n2c1N1CCC(C)(CC1)OCCCC[C@H](C)Oc1ccc(F)cc1-c1cccc-3c1]

Methyl(2S)-2-(tert-butoxy)-2-[(22S)-5,8-dibromo-17-fluoro-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetate Prepared in 73% yield from methyl(2S)-2-(tert-butoxy)-2-[(22S)-17-fluoro-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetate following the procedure for methyl(2S)-2-(tert-butoxy)-2-[(22S)-5,8-dibromo-17-fluoro-4,18,22,28-tetramethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetate. LCMS (ESI, M+1): 816.05.

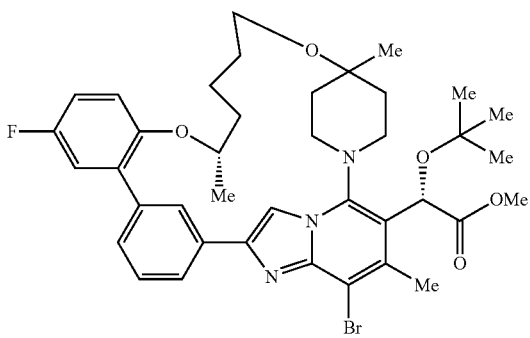 [SMILES: COC(=O)[C@@H](OC(C)(C)C)c1c(C)c(Br)c2nc3cn2c1N1CCC(C)(CC1)OCCCC[C@H](C)Oc1ccc(F)cc1-c1cccc-3c1]

Methyl(2S)-2-[(22S)-5-bromo-17-fluoro-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2, 4,6(34),8,10(33),11,13,15(20),16,18-decaen-3-yl]-2-(tert-butoxy)acetate A solution of methyl(2S)-2-(tert-butoxy)-2-[(22S)-5,8-dibromo-17-fluoro-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetate (150 mg, 0.184 mmol, 1 equiv), SPhos (15 mg, 0.037 mmol, 0.2 equiv), Pd(OAc)₂ (8 mg, 0.037 mmol, 0.2 equiv), n-BuOH (0.055 mL, 0.74 mmol, 4 equiv), and Cs₂CO₃ (90 mg, 0.276 mmol, 1.5 equiv) in 10:1 DMF:water (3.6 mL) was heated to 80° C. for 2 h. More Pd(OAc)₂ (41 mg) was added and the reaction was stirred for 3 h. The reaction was then removed from heat and stirred at ambient temperature for 4 d. More Pd(OAc)₂ (10 mg) was heated to 85° C. for 5 h. The reaction was then removed from heat. Upon cooling to ambient temperature, the reaction was diluted with EtOAc and washed with water. The EtOAc was dried (Na₂SO₄) and concentrated in vacuo. The crude product was purified by flash column chromatography (0-100% EtOAc [2% TEA]/hexane) to provide the product (63 mg, 47%). ¹H NMR (400 MHz, CDCl₃) δ 8.33 (d, J=8.0 Hz, 1H), 8.11 (d, J=6.8 Hz, 2H), 7.54 (t, J=7.7 Hz, 1H), 7.31 (d, J=7.8 Hz, 1H), 7.11 (dd, J=9.0, 3.0 Hz, 1H), 7.03-6.90 (m, 2H), 6.15 (br. s., 1H), 4.47 (d, J=6.3 Hz, 1H), 3.95 (t, J=11.2 Hz, 1H), 3.80-3.66 (m, 5H), 3.57-3.42 (m, 2H), 3.09 (d, J=11.3 Hz, 1H), 2.71 (d, J=11.8 Hz, 1H), 2.57 (s, 3H), 2.01-1.66 (m, 10H), 1.28 (s, 3H), 1.24 (s, 9H), 1.11 (d, J=6.0 Hz, 3H). LCMS (ESI, M+1): 736.20.

Example 32

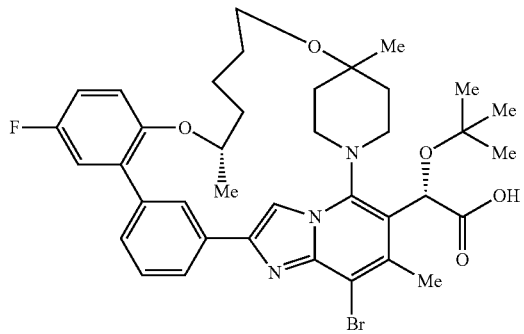 [SMILES: Cc1c([C@H](OC(C)(C)C)C(=O)O)c2n3cc(nc3c1Br)-c1cccc(c1)-c1cc(F)ccc1O[C@@H](C)CCCCOC1(C)CCN2CC1]

(2S)-2-[(22S)-5-Bromo-17-fluoro-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]-2-(tert-butoxy)acetic acid Prepared in 47% yield from methyl(2S)-2-[(22S)-5-bromo-17-fluoro-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]-2-(tert-butoxy)acetate following the procedure for (2S)-2-(tert-butoxy)-2-[(22S)-18-fluoro-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18,24-undecaen-3-yl]acetic acid. Prepared in 47% yield from methyl(2S)-2-[(22S)-5-bromo-17-fluoro-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]-2-(tert-butoxy)acetate following the procedure for (2S)-2-(tert-butoxy)-2-[(22S)-18-fluoro-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18,24-undecaen-3-yl]acetic acid. ¹H NMR (500 MHz, DMSO-d₆) δ 8.18-8.13 (m, 2H), 8.09 (s, 1H), 7.56 (t, J=7.7 Hz, 1H), 7.38 (d, J=7.3 Hz, 1H), 7.23 (d, J=9.9 Hz, 1H), 7.18 (d, J=5.5 Hz, 2H), 5.82 (br. s., 1H), 4.63 (br. s., 1H), 3.86-3.77 (m, 1H), 3.60-3.54 (m, J=11.4 Hz, 1H), 3.49-3.40

(m, 3H), 2.67 (d, J=8.8 Hz, 1H), 2.50 (s, 3H), 1.94-1.48 (m, 10H), 1.19 (s, 3H), 1.15 (s, 9H), 1.08 (d, J=5.9 Hz, 3H); LCMS (ESI, M): 721.3.

Example 33

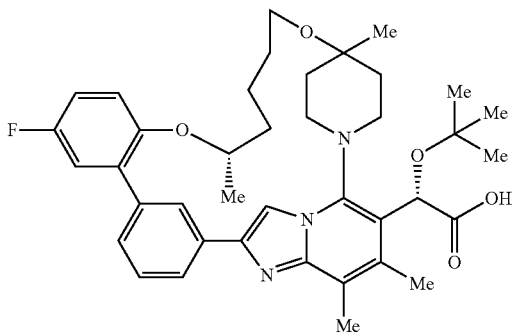 [SMILES: Cc1c([C@H](OC(C)(C)C)C(=O)O)c2n3cc(nc3c1C)-c1cccc(c1)-c1cc(F)ccc1O[C@@H](C)CCCCOC1(C)CCN2CC1]

(2S)-2-(tert-Butoxy)-2-[(22S)-17-fluoro-4,5,22,28-tetramethyl-21,27-dioxa-1,7,34-triazahexacyclo [26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]acetic acid A solution of methyl(2S)-2-[(22S)-5-bromo-17-fluoro-4, 22,28-trimethyl-21,27-dioxa-1,7,34-triazahexacyclo [26.2.2.1$^{6,9}$.1$^{10,14}$.0$^{2,7}$.0$^{15,20}$]tetratriaconta-2,4,6(34),8,10 (33),11,13,15(20),16,18-decaen-3-yl]-2-(tert-butoxy)acetate (60 mg, 0.081 mmol, 1 equiv), methylboronicacid (20 mg, 0.326 mmol, 4 equiv), Pd(OAc)$_2$ (2 mg, 0.008 mmol, 0.1 equiv), Sphos (7 mg, 0.017 mmol, 0.2 equiv), and Cs$_2$CO$_3$ (40 mg, 0.122 mmol, 1.5 equiv) in DMF (1.5 mL) and water (0.15 mL) was heated to 80° C. for 2 h. More methylboronicacid (20 mg, 0.326 mmol, 4 equiv) was added. After 1 h, remove from heat. Upon cooling to ambient temperature, the reaction was diluted with EtOAc and washed with water. The EtOAc was dried (Na$_2$SO$_4$) and concentrated in vacuo. The crude methylation product was purified by flash column chromatography (0-100% EtOAc [2% TEA]/hexane to provide the purified methylation product (35 mg). LCMS (ESI, M+1): 672.40. This product was taken up in MeOH (2 mL), water (0.5 mL), and THF (1.5 mL) and LiOH.H$_2$O (103 mg, 2.44 mmol, 30 equiv) was added. The reaction was heated to 60° C. for 2 h. Upon cooling to ambient temperature, the reaction was filtered and purified via preparative LC/MS with the following conditions: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-85% B over 15 minutes, then a 5-minute hold at 100% B; Flow: 20 mL/min to provide the product (16.1 mg, 30%). $^1$H NMR (500 MHz, DMSO-d$_6$) δ 8.16 (d, J=7.7 Hz, 1H), 8.13 (s, 1H), 8.01 (s, 1H), 7.55 (t, J=7.7 Hz, 1H), 7.36 (d, J=7.7 Hz, 1H), 7.21 (d, J=9.2 Hz, 1H), 7.19-7.15 (m, 2H), 6.11-5.97 (m, 1H), 4.63 (br. s., 1H), 3.89-3.81 (m, 1H), 3.65 (t, J=10.5 Hz, 1H), 3.50-3.41 (m, 2H), 3.12-3.04 (m, 1H), 2.65 (br. s., 1H), 2.51 (s, 3H), 2.32 (s, 3H), 1.93-1.63 (m, 9H), 1.57-1.48 (m, 1H), 1.21 (s, 3H), 1.18 (s, 9H), 1.08 (d, J=5.9 Hz, 3H). LCMS (ESI, M): 657.4.

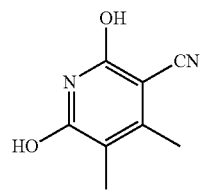

2,6-Dihydroxy-4,5-dimethylnicotinonitrile

To a slurry of ethyl 2-methyl-3-oxobutanoate (10 g, 69.4 mmol, 1 equiv) and 2-cyanoacetamide (5.8 g, 69.4 mmol, 1 equiv) was slowly added a solution of KOH (4.9 g, 87 mmol, 1.25 equiv) in MeOH (35 mL). Stir for 1 h during which time solution became homogenous yellow before developing a cream colored precipitate. Heat at reflux for 3 h. Upon cooling to ambient temperature, concentrated HCl (9 mL) was added. The off white solid was filtered and washed with ether to provide the product (10.7 g, 94%) as a cream colored solid. $^1$H NMR (500 MHz, DMSO-d$_6$) δ 2.22 (s, 3H), 1.90 (s, 3H); LCMS (ESI, M+1): 165.05.

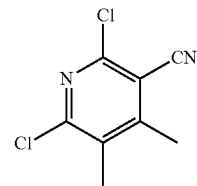

2,6-Dichloro-4,5-dimethylnicotinonitrile

A mixture of 2,6-dihydroxy-4,5-dimethylnicotinonitrile (18 g, 110 mmol, 1 equiv) and tetramethylammonium chloride (24 g, 219 mmol, 2 equiv) in phosphorousoxychloride (120 mL) was heated in a sealed tube at 200° C. for 18 h. Upon cooling to ambient temperature, the reaction mixture was partially concentrated in vacuo and then carefully poured over ice. The mixture was stirred 20 min to allow full quenching of the phosphorousoxychloride. The solid was filtered to provide the product (10.9 g, 49%). $^1$H NMR (400 MHz, DMSO-d$_6$) δ 2.55 (s, 3H), 2.34 (s, 3H).

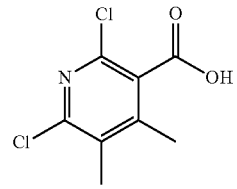

2,6-Dichloro-4,5-dimethylnicotinic acid

To a solution of 2,6-dichloro-4,5-dimethylnicotinonitrile (3.0 g, 14.9 mmol, 1 equiv) in concentrated sulfuric acid (7 mL) was added concentrated nitric acid (2.3 mL). The reaction solution was heated at 110° C. for 2 h. Upon cooling to ambient temperature, the reaction mixture was poured over ice and the precipitated solid was filtered to provide the product (2.75 g, 84%) as a tan solid. $^1$H NMR (400 MHz, DMSO-$d_6$) δ 2.32 (s, 3H), 2.31 (s, 3H); LCMS (ESI, M+1): 219.90.

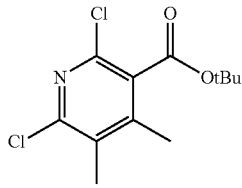 [SMILES: Cc1c(Cl)nc(Cl)c(C(=O)OC(C)(C)C)c1C]

tert-Butyl 2,6-dichloro-4,5-dimethylnicotinate

To a solution of 2,6-dichloro-4,5-dimethylnicotinic acid (2.75 g, 12.5 mmol, 1 equiv) in tertbutyl acetate (83 mL) was added concentrated perchloric acid (3.2 mL, 37.5 mmol, 3 equiv). The reaction was stirred 1 h and then diluted with EtOAc. The organic solution was then washed with 10% potassium carbonate, dried (Na$_2$SO$_4$), and concentrated in vacuo. The crude product was purified by silica gel flash column chromatography (0-100% DCM/hexane) to provide the product (2.50 g, 72%) as a waxy white solid. $^1$H NMR (400 MHz, CDCl$_3$) δ 2.35 (s, 3H), 2.32 (s, 3H), 1.62 (s, 9H); LCMS (ESI, M+1): 276.00.

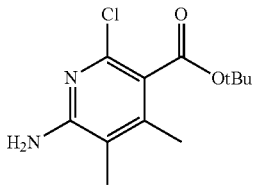 [SMILES: Cc1c(N)nc(Cl)c(C(=O)OC(C)(C)C)c1C]

tert-Butyl 6-amino-2-chloro-4,5-dimethylnicotinate tert-Butyl 2,6-dichloro-4,5-dimethylnicotinate (1.9 g, 6.9 mmol, 1 equiv), Pd$_2$(dba)$_3$ (0.63 g, 0.69 mmol, 0.1 equiv), xantphos (0.80 g, 1.38 mmol, 0.2 equiv), and Cs$_2$CO$_3$ (5.4 g, 16.5 mmol, 2.4 equiv) was slurried in dioxane (deoxygenated by bubbling nitrogen through it for 10 min) added. Benzophenone imine (1.4 mL, 8.3 mmol, 1.2 equiv) was added and the mixture was heated at 90° C. for 2 h. Upon cooling to ambient temperature, the reaction was diluted with EtOAc and washed with water, dried (Na$_2$SO$_4$), and concentrated in vacuo. The crude product was taken up in MeOH (80 mL) and NaOAc (1.69, 20.6 mmol, 3 equiv) and hydroxylamine hydrochloride (0.96 g, 13.8 mmol, 2 equiv) was added. After 18 h, the reaction was added to 1 N NaOH and extracted with DCM (×2). The combined DCM extracts were dried (Na$_2$SO$_4$) and concentrated in vacuo. The crude product was purified by flash column chromatography (0-100% EtOAc/hex) to afford the product (1.1 g, 62%) as a yellow solid. $^1$H NMR (400 MHz, CDCl$_3$) δ 4.57 (br. s., 2H), 2.24 (s, 3H), 2.03 (s, 3H), 1.60 (s, 9H); LCMS (ESI, M+1): 257.15.

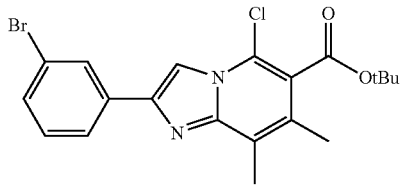 [SMILES: Cc1c(C(=O)OC(C)(C)C)c(Cl)n2cc(-c3cccc(Br)c3)nc2c1C]

tert-Butyl 2-(3-bromophenyl)-5-chloro-7,8-dimethylimidazo[1,2-a]pyridine-6-carboxylate A slurry of tert-butyl 6-amino-2-chloro-4,5-dimethylnicotinate (1.2 g, 4.7 mmol, 1 equiv) and 1-bromo-3-(2-bromo-1,1-dimethoxyethyl)benzene (2.3 g, 7.0 mmol, 1.5 equiv) in chlorobenzene (23 mL) was heated at reflux for 1.5 h. Upon cooling to ambient temperature, the reaction was added slowly to ether. The slurry was stirred for 15 min and the filtered to provide the product as a HBr salt (1.86 g, 85%). $^1$H NMR (400 MHz, DMSO-$d_6$) δ 8.73 (s, 1H), 8.32 (s, 1H), 8.12 (d, J=7.8 Hz, 1H), 7.56 (d, J=8.0 Hz, 1H), 7.47-7.40 (m, 1H), 2.56 (s, 3H), 2.30 (s, 3H), 1.60 (s, 9H); LCMS (ESI, M+1): 435.05.

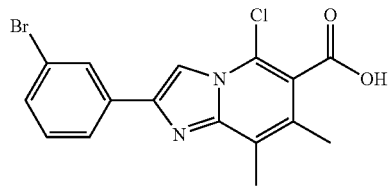 [SMILES: Cc1c(C(=O)O)c(Cl)n2cc(-c3cccc(Br)c3)nc2c1C]

2-(3-Bromophenyl)-5-chloro-7,8-dimethylimidazo[1,2-a]pyridine-6-carboxylic acid

A solution of tert-butyl 2-(3-bromophenyl)-5-chloro-7,8-dimethylimidazo[1,2-a]pyridine-6-carboxylate (1 g, 2.30 mmol, 1 equiv) in TFA (5 mL) was stirred 3 h. The reaction mixture was then concentrated in vacuo and the residue was triturated with ether. The solid was filtered and washed with ether to provide the product (0.70 g, 80%). LCMS (ESI, M+1): 379.0.

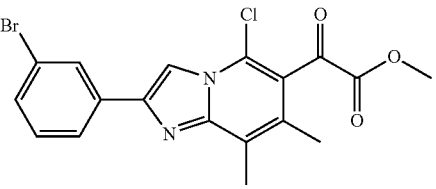 [SMILES: COC(=O)C(=O)c1c(C)c(C)c2nc(-c3cccc(Br)c3)cn2c1Cl]

Methyl 2-(2-(3-bromophenyl)-5-chloro-7,8-dimethylimidazo[1,2-a]pyridin-6-yl)-2-oxoacetate Prepared from 2-(3-bromophenyl)-5-chloro-7,8-dimethylimidazo[1,2-a]pyridine-6-carboxylic acid following the same procedure as methyl 2-(2-(3-bromophenyl)-5-chloro-7-methylimidazo[1,2-a]pyridin-6-yl)-2-oxoacetate. LCMS (ESI, M+1): 420.85.

91

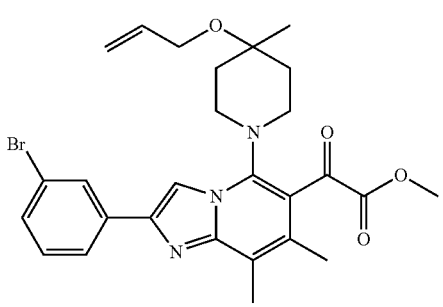 [SMILES: C=CCOC1(C)CCN(c2c(C(=O)C(=O)OC)c(C)c(C)c3nc(-c4cccc(Br)c4)cn23)CC1]

Methyl 2-(5-(4-(allyloxy)-4-methylpiperidin-1-yl)-2-(3-bromophenyl)-7,8-dimethylimidazo[1,2-a]pyridin-6-yl)-2-oxoacetate Prepared from methyl 2-(2-(3-bromophenyl)-5-chloro-7,8-dimethylimidazo[1,2-a]pyridin-6-yl)-2-oxoacetate in 60% yield following the same procedure as methyl 2-(5-(4-(allyloxy)-4-methylpiperidin-1-yl)-2-(3-bromophenyl)-7-methylimidazo[1,2-a]pyridin-6-yl)-2-oxoacetate. LCMS (ESI, M+1): 540.20.

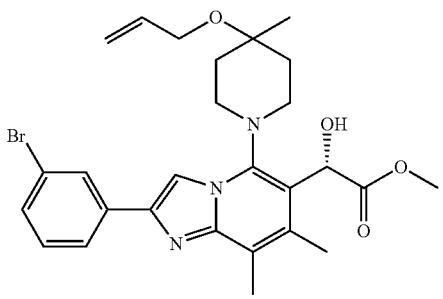 [SMILES: C=CCOC1(C)CCN(c2c([C@H](O)C(=O)OC)c(C)c(C)c3nc(-c4cccc(Br)c4)cn23)CC1]

(S)-Methyl 2-(5-(4-(allyloxy)-4-methylpiperidin-1-yl)-2-(3-bromophenyl)-7,8-dimethylimidazo[1,2-a]pyridin-6-yl)-2-hydroxyacetate Prepared from methyl 2-(5-(4-(allyloxy)-4-methylpiperidin-1-yl)-2-(3-bromophenyl)-7,8-dimethylimidazo[1,2-a]pyridin-6-yl)-2-oxoacetate in 72% yield following the same procedure as (S)-methyl 2-(5-(4-(allyloxy)-4-methylpiperidin-1-yl)-2-(3-bromophenyl)-7-methylimidazo[1,2-a]pyridin-6-yl)-2-hydroxyacetate. LCMS (ESI, M+1): 542.30.

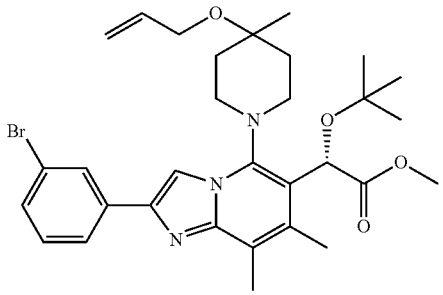 [SMILES: C=CCOC1(C)CCN(c2c([C@H](OC(C)(C)C)C(=O)OC)c(C)c(C)c3nc(-c4cccc(Br)c4)cn23)CC1]

92

(S)-Methyl 2-(5-(4-(allyloxy)-4-methylpiperidin-1-yl)-2-(3-bromophenyl)-7,8-dimethylimidazo[1,2-a]pyridin-6-yl)-2-(tert-butoxy)acetate Prepared from (S)-methyl 2-(5-(4-(allyloxy)-4-methylpiperidin-1-yl)-2-(3-bromophenyl)-7,8-dimethylimidazo[1,2-a]pyridin-6-yl)-2-hydroxyacetate in 21% yield following the same procedure as (S)-methyl 2-(5-(4-(allyloxy)-4-methylpiperidin-1-yl)-2-(3-bromophenyl)-7-methylimidazo[1,2-a]pyridin-6-yl)-2-(tert-butoxy)acetate. LCMS (ESI, M+1): 598.15.

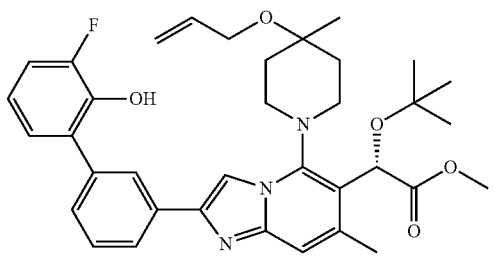 [SMILES: C=CCOC1(C)CCN(c2c([C@H](OC(C)(C)C)C(=O)OC)c(C)cc3nc(-c4cccc(-c5cccc(F)c5O)c4)cn23)CC1]

(S)-Methyl 2-(5-(4-(allyloxy)-4-methylpiperidin-1-yl)-2-(3'-fluoro-2'-hydroxy-[1,1'-biphenyl]-3-yl)-7-methylimidazo[1,2-a]pyridin-6-yl)-2-(tert-butoxy)acetate Prepared from (S)-methyl 2-(5-(4-(allyloxy)-4-methylpiperidin-1-yl)-2-(3-bromophenyl)-7,8-dimethylimidazo[1,2-a]pyridin-6-yl)-2-(tert-butoxy)acetate and (3-fluoro-2-hydroxyphenyl)boronic acid in 100% following the same procedure as (S)-methyl 2-(5-(4-(allyloxy)-4-methylpiperidin-1-yl)-2-(2'-hydroxy-5'-methyl-[1,1'-biphenyl]-3-yl)-7-methylimidazo[1,2-a]pyridin-6-yl)-2-(tert-butoxy)acetate. LCMS (ESI, M+1): 616.20.

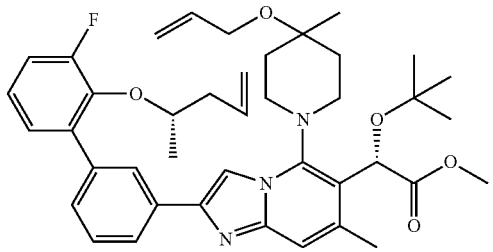 [SMILES: C=CCOC1(C)CCN(c2c([C@H](OC(C)(C)C)C(=O)OC)c(C)cc3nc(-c4cccc(-c5cccc(F)c5O[C@@H](C)CC=C)c4)cn23)CC1]

(S)-Methyl 2-(5-(4-(allyloxy)-4-methylpiperidin-1-yl)-2-(3'-fluoro-2'-((S)-pent-4-en-2-yloxy)-[1,1'-biphenyl]-3-yl)-7-methylimidazo[1,2-a]pyridin-6-yl)-2-(tert-butoxy)acetate Prepared from (S)-methyl 2-(5-(4-(allyloxy)-4-methylpiperidin-1-yl)-2-(3'-fluoro-2'-hydroxy-[1,1'-biphenyl]-3-yl)-7-methylimidazo[1,2-a]pyridin-6-yl)-2-(tert-butoxy)acetate in 70% yield following the same procedure as (S)-methyl 2-(5-(4-(allyloxy)-4-methylpiperidin-1-yl)-7-methyl-2-(5'-methyl-2'-((S)-pent-4-en-2-yloxy)-[1,1'-biphenyl]-3-yl)imidazo[1,2-a]pyridin-6-yl)-2-(tert-butoxy)acetate. LCMS (ESI, M+1): 684.20.

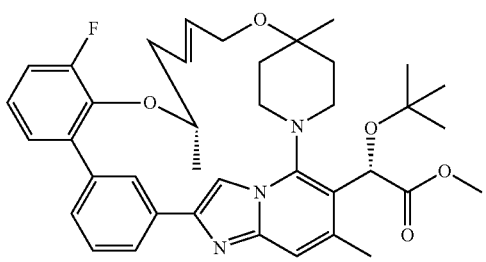 [SMILES: COC(=O)[C@@H](OC(C)(C)C)c1c(C)cc2nc3cn2c1N1CCC(C)(CC1)OC/C=C/C[C@H](C)Oc1c(F)cccc1-c1cccc-3c1]

Methyl(2S)-2-(tert-butoxy)-2-[(22S,24E)-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl] acetate Prepared in 69% from (S)-methyl 2-(5-(4-(allyloxy)-4-methylpiperidin-1-yl)-2-(3'-fluoro-2'-((S)-pent-4-en-2-yloxy)-[1,1'-biphenyl]-3-yl)-7-methylimidazo[1,2-a]pyridin-6-yl)-2-(tert-butoxy)acetate following the same procedure as methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate. $^{1}$H NMR (400 MHz, CDCl$_{3}$) δ 8.13 (br. s., 1H), 8.06 (s, 1H), 8.01 (s, 1H), 7.56 (br. s., 1H), 7.38 (d, J=7.3 Hz, 2H), 7.19-7.13 (m, 1H), 7.09 (d, J=7.3 Hz, 2H), 6.19-6.11 (m, 1H), 6.08 (br. s., 1H), 5.83 (dt, J=15.4, 4.5 Hz, 1H), 5.05-4.94 (m, 1H), 4.48-4.36 (m, 1H), 4.06-3.93 (m, 2H), 3.82-3.74 (m, 1H), 3.69 (s, 3H), 3.08-3.01 (m, 1H), 2.77-2.68 (m, 1H), 2.56-2.51 (m, 1H), 2.49 (br. s., 3H), 2.25-2.14 (m, 1H), 2.05-1.95 (m, 2H), 1.77 (br. s., 2H), 1.34 (s, 3H), 1.26 (s, 9H), 0.88 (d, J=6.0 Hz, 3H); LCMS (ESI, M+1): 656.70.

Example 34

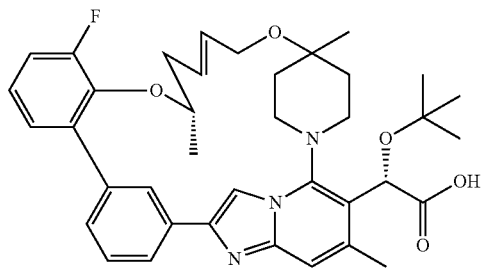 [SMILES: Cc1cc2nc3cn2c(c1[C@H](OC(C)(C)C)C(=O)O)N1CCC(C)(CC1)OC/C=C/C[C@H](C)Oc1c(F)cccc1-c1cccc-3c1]

(2S)-2-(tert-Butoxy)-2-[(22S,24E)-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl] acetic acid Prepared in 95% yield from methyl(2S)-2-(tert-butoxy)-2-[(22S,24E)-19-fluoro-4,22,28-trimethyl-21,27-34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^{1}$H NMR (500 MHz, DMSO-d$_{6}$) δ 8.01 (s, 1H), 7.99 (d, J=7.7 Hz, 1H), 7.95 (s, 1H), 7.56 (t, J=7.5 Hz, 1H), 7.40 (d, J=7.7 Hz, 1H), 7.33-7.24 (m, 2H), 7.21 (dd, J=8.1, 5.1 Hz, 1H), 7.17 (s, 1H), 6.14 (dt, J=14.4, 7.3 Hz, 1H), 5.78 (d, J=14.7 Hz, 1H), 5.73 (br. s., 1H), 4.36 (br. s., 1H), 4.09 (t, J=11.0 Hz, 1H), 4.01-3.92 (m, 2H), 3.64-3.41 (m, 2H), 2.69 (d, J=10.6 Hz, 1H), 2.41 (s, 3H), 2.14-2.05 (m, 1H), 1.99-1.89 (m, 2H), 1.72-1.67 (m, 3H), 1.25 (s, 3H), 1.15 (s, 9H), 0.80 (d, J=5.9 Hz, 3H); LCMS (ESI, M): 641.3.

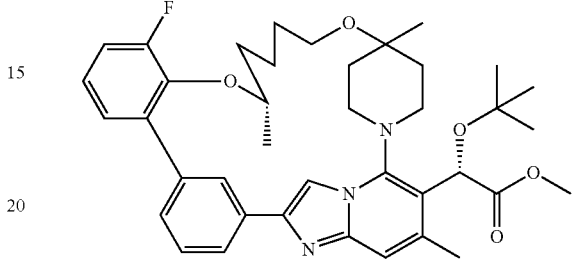

Methyl(2S)-2-(tert-butoxy)-2-[(22S)-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl] acetate Prepared in 100% yield from methyl(2S)-2-(tert-butoxy)-2-[(22S,24E)-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate following the same procedure as methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. $^{1}$H NMR (400 MHz, CDCl$_{3}$) δ 8.13 (s, 1H), 8.10 (d, J=7.0 Hz, 1H), 8.00 (s, 1H), 7.54 (t, J=7.8 Hz, 1H), 7.39 (d, J=7.5 Hz, 1H), 7.36 (br. s., 1H), 7.22-7.18 (m, 1H), 7.11-7.05 (m, 2H), 6.10 (br. s., 1H), 4.99 (dt, J=12.5, 6.3 Hz, 1H), 4.38 (br. s., 1H), 4.07 (t, J=10.5 Hz, 1H), 3.70 (s, 3H), 3.56-3.42 (m, 2H), 3.04 (d, J=10.5 Hz, 1H), 2.76 (d, J=8.5 Hz, 1H), 2.47 (s, 3H), 2.04-1.58 (m, 10H), 1.29 (s, 3H), 1.26 (s, 9H), 0.84 (d, J=6.0 Hz, 3H); LCMS (ESI, M+1): 658.20.

Example 35

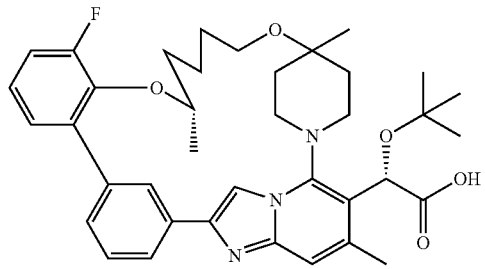 [SMILES: Cc1cc2nc3cn2c(c1[C@H](OC(C)(C)C)C(=O)O)N1CCC(C)(CC1)OCCCC[C@H](C)Oc1c(F)cccc1-c1cccc-3c1]

(2S)-2-(tert-Butoxy)-2-[(22S)-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 58% yield from methyl(2S)-2-(tert-butoxy)-2-[(22S)-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^{1}$H NMR (500 MHz, DMSO-d$_{6}$) δ 8.09 (s, 1H), 7.99-7.95 (m, 2H), 7.56 (t, J=7.7 Hz, 1H), 7.44 (d, J=7.7 Hz, 1H), 7.31 (s, 1H), 7.30-7.26 (m, 2H), 7.22-7.16 (m, 1H), 5.94 (br. s., 1H), 4.31 (br. s., 1H), 3.99-3.89 (m, 1H), 3.57 (t, J=11.4 Hz, 1H), 3.49-3.39 (m, 2H), 3.07 (d, J=9.5 Hz, 1H), 2.75-2.70 (m, 1H), 2.41 (s, 3H), 1.98-1.53 (m, 10H), 1.22 (s, 3H), 1.19 (s, 9H), 0.77 (d, J=6.2 Hz, 3H); LCMS (ESI, M): 643.3.

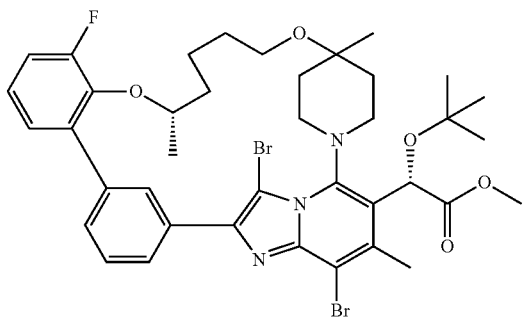 [SMILES: COC(=O)[C@@H](OC(C)(C)C)c1c(C)c(Br)c2nc3c(Br)n2c1N1CCC(C)(CC1)OCCCC[C@H](C)Oc1c(F)cccc1-c1cccc-3c1]

Methyl(2S)-2-(tert-butoxy)-2-[(22S)-5,8-dibromo-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Methyl(2S)-2-(tert-butoxy)-2-[(22S)-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (0.18 g, 0.274 mmol, 1.0 equiv) was dissolved in ACN (2.74 mL). To this solution was added NBS (0.117 g, 0.657 mmol, 2.4 equiv) and stirred for 2 hours. The mixture was diluted by 10 mL DCM, washed by 1 N Na$_{2}$S$_{2}$O$_{3}$, dried over MgSO$_{4}$, concentrated to load onto 24 g ISCO column and purified with (0-100% EtOAc[2% TEA]/hexane) to give the product (0.13 g, 58.2%). $^{1}$H NMR (500 MHz, CDCl$_{3}$) δ 8.14 (s, 1H), 7.87 (d, J=7.6 Hz, 1H), 7.57 (t, J=7.6 Hz, 1H), 7.49 (d, J=7.7 Hz, 1H), 7.15 (d, J=6.9 Hz, 1H), 7.11-7.03 (m, 2H), 6.06 (br. s., 1H), 4.65-4.58 (m, 1H), 4.42 (t, J=11.9 Hz, 1H), 4.33 (br. s., 1H), 3.76 (s, 3H), 3.75-3.70 (m, 1H), 3.64-3.58 (m, 1H), 3.46 (td, J=8.2, 3.0 Hz, 1H), 3.33 (br. s., 1H), 2.58 (br. s., 3H), 2.03-1.50 (m, 10H), 1.31 (s, 3H), 1.25 (s, 9H), 0.98 (d, J=6.1 Hz, 3H); LCMS (ESI, M+): 815.9.

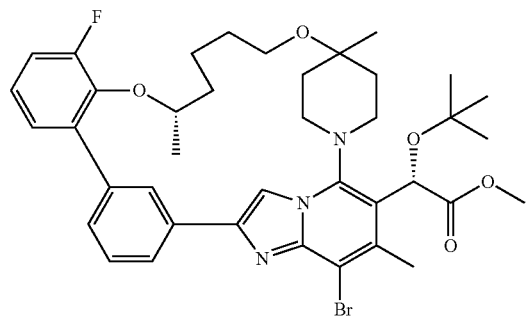 [SMILES: COC(=O)[C@@H](OC(C)(C)C)c1c(C)c(Br)c2nc3cn2c1N1CCC(C)(CC1)OCCCC[C@H](C)Oc1c(F)cccc1-c1cccc-3c1]

Methyl(2S)-2-[(22S)-5-bromo-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2, 4,6(34),8,10(33),11,13,15(20),16,18-decaen-3-yl]-2-(tert-butoxy)acetate Methyl(2S)-2-(tert-butoxy)-2-[(22S)-5,8-dibromo-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (0.13 g, 0.16 mmol, 1.0 equiv) and ammonium formate (0.101 g, 1.6 mmol, 10.0 equiv) were dissolved in DMF (3.19 mL). To this solution was added tetrakis (0.018 g, 0.016 mmol, 0.1 equiv). The mixture was heated at 40° C. overnight. Then it was diluted with ethyl acetate, washed by NaHCO$_{3}$, dried over MgSO$_{4}$, concentrated and purified by flash column (24 g, 0-100% EtOAc[2% TEA]/Hex) to afford the product (70 mg, 59.6%). LCMS (ESI, M+1): 736.3.

Example 36

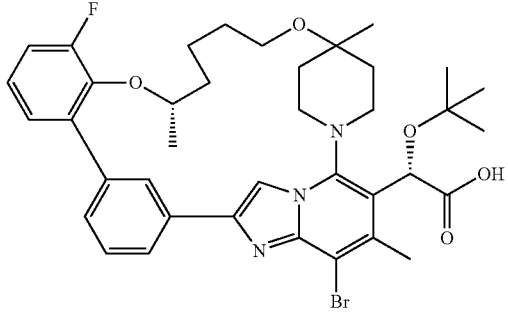 [SMILES: Cc1c([C@H](OC(C)(C)C)C(=O)O)c2n3cc(nc3c1Br)-c1cccc(c1)-c1cccc(F)c1O[C@@H](C)CCCCOC1(C)CCN2CC1]

(2S)-2-[(22S)-5-Bromo-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetic acid Prepared in 5% yield from methyl(2S)-2-[(22S)-5-bromo-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^{1}$H NMR (500 MHz, DMSO-d$_{6}$) δ 8.09 (s, 1H), 8.06 (s, 1H), 8.02 (d, J=7.7 Hz, 1H), 7.60 (t, J=7.7 Hz, 1H), 7.47 (d, J=7.7 Hz, 1H), 7.33-7.27 (m, 2H), 7.23-7.16 (m, 1H), 6.03 (br. s., 1H), 4.31 (br. s., 1H), 3.96-3.90 (m, 1H), 3.55 (t, J=11.2 Hz, 1H), 3.45 (br. s., 2H), 3.08 (d, J=8.4 Hz, 1H), 2.77 (br. s., 1H), 2.51 (s, 3H), 1.98-1.65 (m, 10H), 1.22 (s, 3H), 1.18 (s, 9H), 0.77 (d, J=5.9 Hz, 3H); LCMS (ESI, M): 721.3.

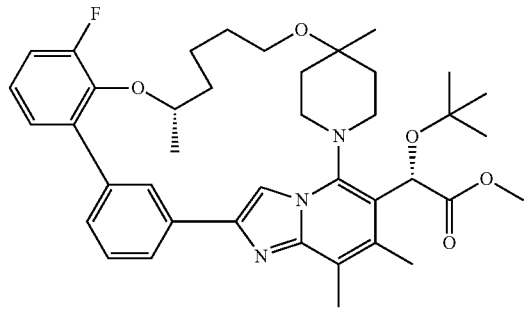 [SMILES: COC(=O)[C@@H](OC(C)(C)C)c1c(C)c(C)c2nc3cn2c1N1CCC(C)(CC1)OCCCC[C@H](C)Oc1c(F)cccc1-c1cccc-3c1]

Methyl(2S)-2-(tert-butoxy)-2-[(22S)-19-fluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Methyl(2S)-2-[(22S)-5-bromo-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetate (0.070 g, 0.095 mmol, 1.0 equiv), Pd(OAc)$_2$ (0.013 g, 0.057 mmol, 0.6 equiv), Sphos (0.047 g, 0.114 mmol, 1.2 equiv), methylboronic acid (0.057 g, 0.095 mmol, 10.0 equiv) and cesium carbonate (0.124 g, 0.380 mmol, 4.0 equiv) were mixed in DMF (1.73 mL) and water (0.17 mL). The solution was degassed for five minutes by N$_2$. Then it was stirred at 80° C. for 2 hours. It was diluted by ethyl acetate (15 mL), washed by water, dried over MgSO$_4$ and concentrated to afford the pure enough product for the next reaction. LCMS (ESI, M+1): 658.4.

Example 37

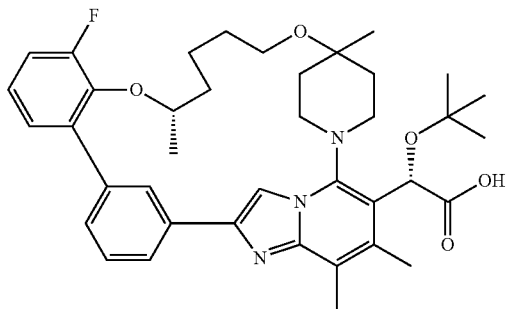 [SMILES: Cc1c([C@H](OC(C)(C)C)C(=O)O)c2n3cc(nc3c1C)-c1cccc(c1)-c1cccc(F)c1O[C@@H](C)CCCCOC1(C)CCN2CC1]

(2S)-2-(tert-Butoxy)-2-[(22S)-19-fluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 7.14% yield from methyl(2S)-2-(tert-butoxy)-2-[(22S)-19-fluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.08 (s, 1H), 8.02 (d, J=7.7 Hz, 1H), 7.94 (s, 1H), 7.60-7.54 (m, 1H), 7.43 (d, J=7.3 Hz, 1H), 7.33-7.26 (m, 2H), 7.22-7.15 (m, 1H), 5.87 (br. s., 1H), 4.32 (br. s., 1H), 4.01-3.92 (m, 1H), 3.58-3.38 (m, 4H), 2.70 (d, J=9.9 Hz, 1H), 2.47 (s, 3H), 2.31 (s, 3H), 1.94-1.54 (m, 10H), 1.20 (s, 3H), 1.15 (s, 9H), 0.78 (d, J=5.9 Hz, 3H); LCMS (ESI, M): 657.4.

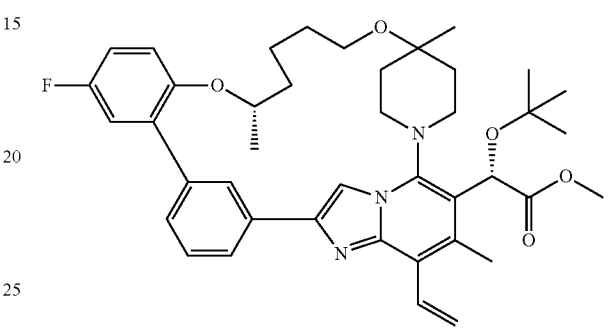

Methyl(2S)-2-(tert-butoxy)-2-[(22S)-5-ethenyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Methyl(2S)-2-[(22S)-5-bromo-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetate (40 mg, 0.054 mmol, 1.0 equiv), potassium trifluoro(vinyl)borate (36.4 mg, 0.271 mmol, 5 equiv) were mixed in DMF (1.0 mL) and water (0.10 mL). To this solution was added Pd(OAc)$_2$ (1.21 mg, 0.005 mmol, 0.1 equiv), Sphos (4.46 mg, 0.011 mmol, 0.2 equiv) and cesium carbonate (35.4 mg, 0.11 mmol, 2.0 equiv). The solution was degassed by N2 for five minutes. Then it was stirred at 80° C. for 2 hours. The mixture was loaded onto 12 g ISCO column and purified by 0-100% Ethyl Acetate [2% TEA]/Hexane to provide the product (35 mg, 94.3%) as a brown oil. LCMS (ESI, M+1): 684.4.

Example 38

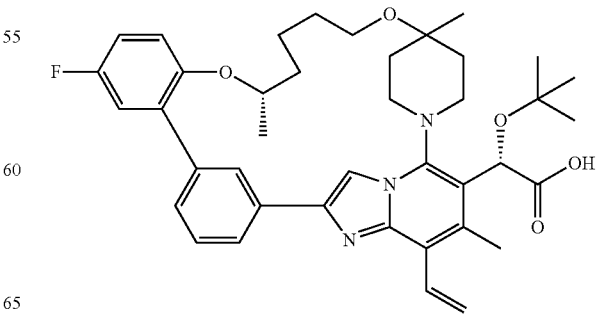

(2S)-2-(tert-Butoxy)-2-[(22S)-5-ethenyl-17-fluoro-4, 22,28-trimethyl-21,27-dioxa-1,7,34-triazahexacyclo [26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]acetic acid Prepared in 64.7% yield from methyl(2S)-2-(tert-butoxy)-2-[(22S)-5-ethenyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.21-8.11 (m, 2H), 7.98 (s, 1H), 7.53 (t, J=7.7 Hz, 1H), 7.34 (d, J=7.7 Hz, 1H), 7.26-7.21 (m, 1H), 7.20-7.15 (m, 2H), 7.12-7.04 (m, 1H), 7.00-6.94 (m, 1H), 5.75-5.65 (m, 2H), 4.64 (br. s., 1H), 3.89-3.75 (m, 2H), 3.60-3.37 (m, 4H), 2.54 (s, 3H), 1.97-1.70 (m, 10H), 1.20 (s, 3H), 1.13 (s, 9H), 1.09 (d, J=5.9 Hz, 3H). LCMS (ESI, M+): 669.4.

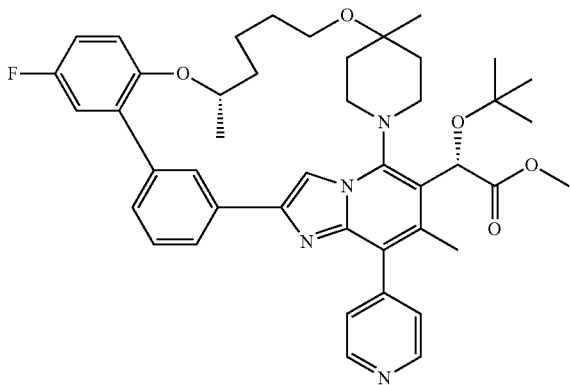 [SMILES: COC(=O)[C@@H](OC(C)(C)C)c1c(C)c(-c2ccncc2)c2nc3cn2c1N1CCC(C)(CC1)OCCCC[C@H](C)Oc1ccc(F)cc1-c1cccc-3c1]

Methyl(2S)-2-(tert-butoxy)-2-[(22S)-17-fluoro-4,22,28-trimethyl-5-(pyridin-4-yl)-21,27-dioxa-1,7,34-triazahexacyclo[26.2.2.1$^{6,9}$.1$^{10,14}$.0$^{2,7}$.0$^{15,20}$]tetratriaconta-2,4,6(34),8, 10(33),11,13,15(20),16,18-decaen-3-yl]acetate 2-Dicyclohexylphosphino-2',6'-dimethoxybiphenyl (1.672 mg, 4.07 μmol, 0.2 equiv), Pd(OAc)$_2$ (0.457 mg, 2.036 μmol, 0.1 equiv), 6-methyl-2-(pyridin-4-yl)-1,3,6,2-dioxazaborocane-4,8-dione (5.72 mg, 0.024 mmol, 1.2 equiv) and methyl (2S)-2-[(22S)-5-bromo-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetate (15 mg, 0.020 mmol, 1.0 equiv) were mixed in a one drum vial with a stir bar. The vial was vacuumed and back filled with N2 triple times. Then to this mixture was added dioxane (339 μl) and potassium phosphate tribasic (76 μl, 0.153 mmol, 7.5 equiv). The resulted solution was degassed by N2 for 5 mins. Then it was stirred at 80° C. for 1.5 hours. It was diluted by EA and washed by NaHCO$_3$. concentrated, to afford the pure enough product. LCMS (ESI, M+1): 735.4.

Example 39

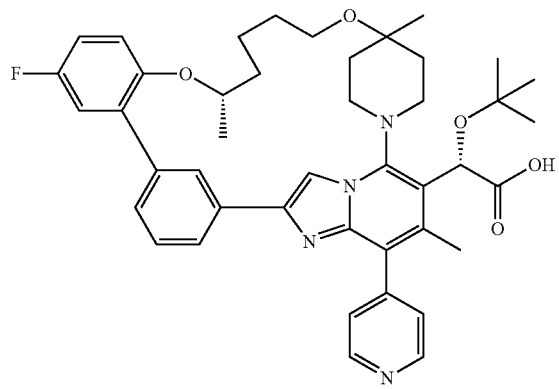 [SMILES: Cc1c([C@H](OC(C)(C)C)C(=O)O)c2n3cc(nc3c1-c1ccncc1)-c1cccc(c1)-c1cc(F)ccc1O[C@@H](C)CCCCOC1(C)CCN2CC1]

(2S)-2-(tert-Butoxy)-2-[(22S)-17-fluoro-4,22,28-trimethyl-5-(pyridin-4-yl)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 27.2% yield from methyl(2S)-2-(tert-butoxy)-2-[(22S)-17-fluoro-4,22,28-trimethyl-5-(pyridin-4-yl)-21, 27-dioxa-1,7,34-triazahexacyclo[26.2.2.1$^{6,9}$.1$^{10,14}$.0$^{2,7}$. 0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$] tetratriaconta-2,4,6(34),8,10(33),11,13,15(20),16,18-decaen-3-yl]acetic acid. $^1$H NMR (500 MHz, DMSO-d$_6$) δ 8.70 (d, J=5.5 Hz, 2H), 8.13 (s, 1H), 8.05 (s, 1H), 7.87 (d, J=7.7 Hz, 1H), 7.45 (d, J=5.5 Hz, 3H), 7.31 (d, J=7.7 Hz, 1H), 7.22-7.12 (m, 3H), 5.91 (br. s., 1H), 4.60 (br. s., 1H), 3.92-3.81 (m, 1H), 3.62 (d, J=12.1 Hz, 1H), 3.44 (br. s., 4H), 2.19 (s, 3H), 1.93-1.65 (m, 9H), 1.54 (br. s., 1H), 1.20 (s, 3H), 1.18 (s, 9H), 1.06 (d, J=6.2 Hz, 3H). LCMS (ESI, M): 720.4.

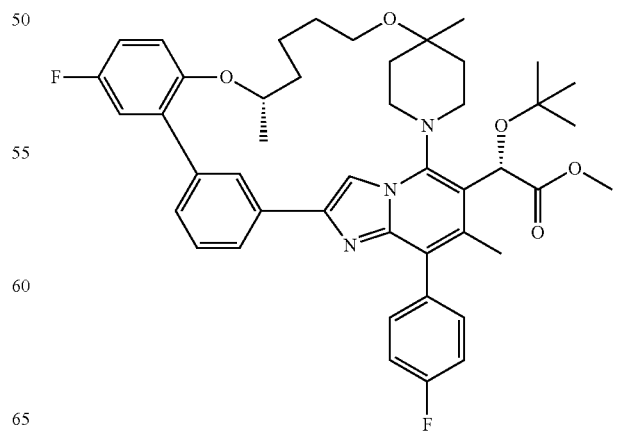

Methyl(2S)-2-(tert-butoxy)-2-[(22S)-17-fluoro-5-(4-fluorophenyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 66.7% yield from methyl(2S)-2-[(22S)-5-bromo-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetate following the procedure for Methyl(2S)-2-(tert-butoxy)-2-[(22S)-17-fluoro-4,22,28-trimethyl-5-(pyridin-4-yl)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. LCMS (ESI, M+1): 752.4.

Example 40

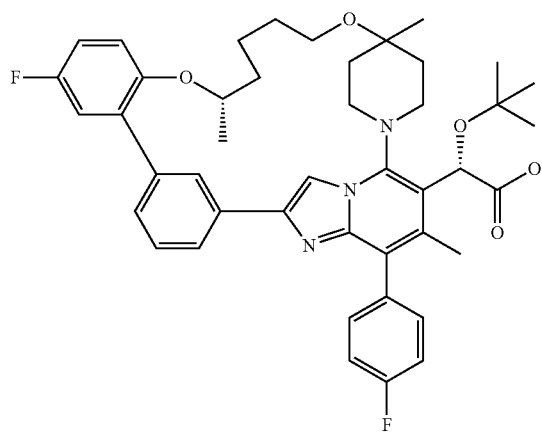

(2S)-2-(tert-Butoxy)-2-[(22S)-17-fluoro-5-(4-fluorophenyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 5.1% yield from methyl(2S)-2-(tert-butoxy)-2-[(22S)-17-fluoro-5-(4-fluorophenyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.12 (s, 1H), 8.05 (s, 1H), 7.88 (d, J=7.7 Hz, 1H), 7.48-7.41 (m, 3H), 7.36-7.29 (m, 3H), 7.22-7.12 (m, 3H), 5.98 (br. s., 1H), 4.61 (br. s., 1H), 3.93-3.81 (m, 1H), 3.66 (t, J=11.0 Hz, 1H), 3.38 (br. s., 4H), 2.18 (s, 3H), 1.95-1.63 (m, 9H), 1.55 (br. s., 1H), 1.22 (s, 3H), 1.19 (s, 9H), 1.07 (d, J=5.9 Hz, 3H). LCMS (ESI, M): 737.4.

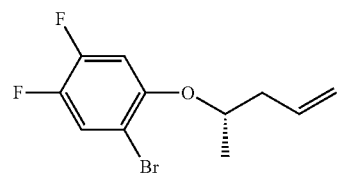

(S)-1-Bromo-4,5-difluoro-2-(pent-4-en-2-yloxy)benzene

To a solution of 2-bromo-4,5-difluorophenol (1.47 g, 7.03 mmol, 1 equiv), triphenylphosphine (2.58 g, 9.85 mmol, 1.4 equiv), and (R)-pent-4-en-2-ol (0.85 g, 9.85 mmol, 1.4 equiv), in THF (23 mL) was added DIAD (1.9 mL, 9.85 mmol, 1.4 equiv). The dark orange solution quickly turned yellow. After 3 h, the reaction mixture was diluted with ether, washed with 1 N NaOH, dried (MgSO$_4$), and concentrated in vacuo. The crude product was purified by silica gel flash column chromatography (0-10% EtOAc/hexane) to provide the product (1.18 g, 61%) as a colorless oil. $^1$H NMR (400 MHz, CDCl$_3$) δ 7.42-7.35 (m, 1H), 6.77 (dd, J=11.9, 7.2 Hz, 1H), 5.88 (ddt, J=17.2, 10.1, 7.1 Hz, 1H), 5.21-5.06 (m, 2H), 4.40-4.27 (m, 1H), 2.61-2.36 (m, 2H), 1.35 (d, J=6.0 Hz, 3H).

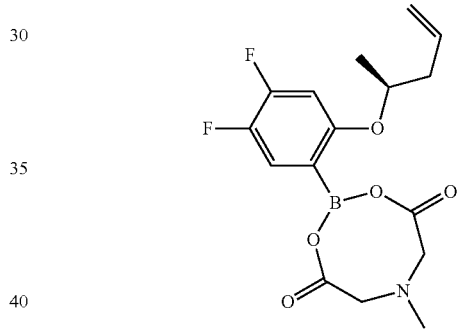

(S)-2-(4,5-Difluoro-2-(pent-4-en-2-yloxy)phenyl)-6-methyl-1,3,6,2-dioxazaborocane-4,8-dione A solution of(S)-1-bromo-4,5-difluoro-2-(pent-4-en-2-yloxy)benzene (1.24 g, 4.47 mmol, 1 equiv) in THF (45 mL) was cooled to −105° C. (ether/liquid nitrogen). nBuLi (3.4 mL of a 1.6 M solution in hexane, 5.37 mmol, 1.2 equiv) was added dropwise. After stirring 5 min, trimethylborate (0.60 mL, 5.37 mmol, 1.2 equiv) was added dropwise. The reaction was stirred 80 min and then quenched by addition of 1 N HCl (10 mL). Upon warming to ambient temperature, the mixture was added to water and extracted with EtOAc (×3). The combined EtOAc extracts were dried (Na$_2$SO$_4$) and concentrated in vacuo to give the crude boronic acid. This was taken up in toluene (60 mL) and DMSO (30 mL) and N-methyliminodiacetic acid (0.79 g, 5.37 mmol, 1.2 equiv) was added. The reaction mixture was heated at 140° C. with a Dean-Stark trap for 2 h. Upon cooling to ambient temperature, the reaction mixture was diluted with EtOAc and washed with brine. The EtOAc layer was dried (Na$_2$SO$_4$) and concentrated in vacuo. The crude MIDA product was purified by silica gel flash column chromatography (0-60% acetone/DCM) to provide the product (0.94 g, 60%) as a white solid. $^1$H NMR (400 MHz, CDCl$_3$) δ 7.56-7.48 (m, 1H), 6.77 (dd, J=12.5, 6.0 Hz, 1H), 5.89-5.75 (m, 1H), 5.20-5.10 (m, 2H), 4.54-4.47 (m, 1H), 4.12-4.05 (m, 1H), 3.94-3.85 (m, 3H), 2.70 (s, 3H), 2.55-2.46 (m, 1H), 2.42-2.32 (m, 1H), 1.30-1.27 (m, 3H); $^{19}$F NMR (376 MHz, CDCl$_3$) δ −132.78 (d, J=20.8 Hz, 1F), −147.78 (d, J=22.5 Hz, 1F).

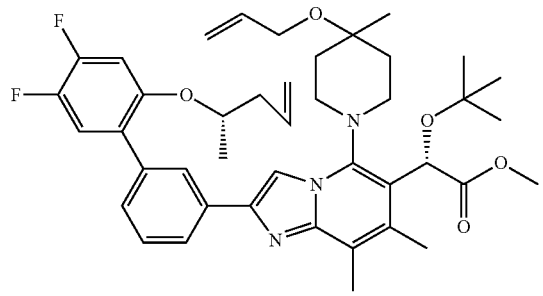 [SMILES: C=CCOC1(C)CCN(c2c([C@H](OC(C)(C)C)C(=O)OC)c(C)c(C)c3nc(-c4cccc(-c5cc(F)c(F)cc5O[C@@H](C)CC=C)c4)cn23)CC1]

(S)-Methyl 2-(5-(4-(allyloxy)-4-methylpiperidin-1-yl)-2-(4',5'-difluoro-2'-((S)-pent-4-en-2-yloxy)-[1,1'-biphenyl]-3-yl)-7,8-dimethylimidazo[1,2-a]pyridin-6-yl)-2-(tert-butoxy)acetate A mixture of (S)-methyl 2-(5-(4-(allyloxy)-4-methylpiperidin-1-yl)-2-(3-bromophenyl)-7,8-dimethylimidazo[1,2-a]pyridin-6-yl)-2-(tert-butoxy)acetate (0.25 g, 0.42 mmol, 1 equiv), Sphos (34 mg, 0.084 mmol, 0.2 equiv), (S)-2-(4,5-difluoro-2-(pent-4-en-2-yloxy)phenyl)-6-methyl-1,3,6,2-dioxazaborocane-4,8-dione (0.18 g, 0.52 mmol, 1.25 equiv), K$_3$PO$_4$ (1.05 g, 4.59 mmol, 11 equiv), and Pd(OAc)$_2$ (9 mg, 0.042 mmol, 0.1 equiv) in dioxane (5 mL) and water (1 mL) was heated at 80° C. for 1.5 h. Upon cooling to ambient temperature, the reaction mixture was diluted with EtOAc, washed with saturated aqueous sodium bicarbonate, dried (Na$_2$SO$_4$), and concentrated in vacuo. The crude product was purified by silica gel flash column chromatography (0-100% EtOAc [2% TEA]/hexane) to provide the product (0.25 g, 84%) as a white solid. LCMS (ESI, M+1): 716.70.

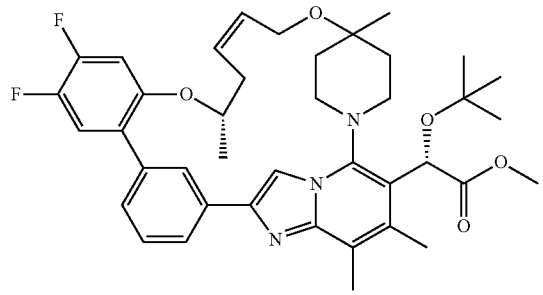 [SMILES: COC(=O)[C@@H](OC(C)(C)C)c1c(C)c(C)c2nc3cn2c1N1CCC(C)(CC1)OC/C=C\C[C@H](C)Oc1cc(F)c(F)cc1-c1cccc-3c1]

Methyl(2S)-2-(tert-butoxy)-2-[(22S,24Z)-17,18-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate Prepared in 83% yield from (S)-methyl 2-(5-(4-(allyloxy)-4-methylpiperidin-1-yl)-2-(4',5'-difluoro-2'-((S)-pent-4-en-2-yloxy)-[1,1'-biphenyl]-3-yl)-7,8-dimethylimidazo[1,2-a]pyridin-6-yl)-2-(tert-butoxy)acetate following the procedure for methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate. LCMS (ESI, M+1): 688.80.

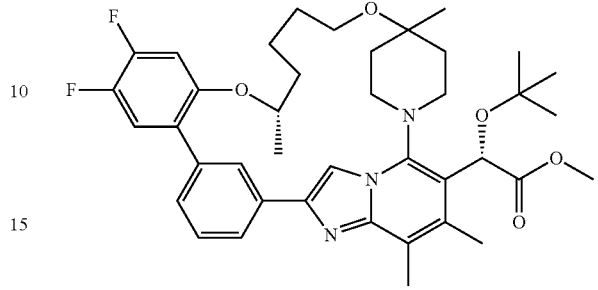

Methyl(2S)-2-(tert-butoxy)-2-[(22S)-17,18-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 85% yield from methyl(2S)-2-(tert-butoxy)-2-[(22S,24Z)-17,18-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate following the procedure for methyl (2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. LCMS (ESI, M+1): 690.4.

Example 41

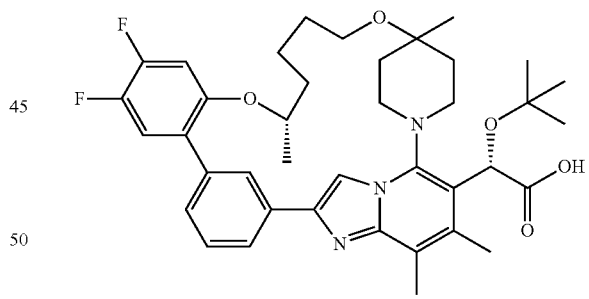

(2S)-2-(tert-Butoxy)-2-[(22S)-17,18-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 52.5% yield from methyl(2S)-2-(tert-butoxy)-2-[(22S)-17,18-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7, 34-triazahexacyclo[26.2.2.1⁶,⁹.1¹⁰,¹⁴.0²,⁷.0¹⁵,²⁰]tetratria-
conta-2,4,6(34),8,10(33),11,13,15(20),16,18-decaen-3-yl]
acetic acid. ¹H NMR (500 MHz, DMSO-d₆) δ 8.17 (d, J=7.7
Hz, 1H), 8.09 (s, 1H), 8.00 (s, 1H), 7.53 (t, J=7.7 Hz, 1H),
7.48-7.42 (m, 1H), 7.38-7.29 (m, 2H), 6.01 (br. s., 1H), 4.67
(br. s., 1H), 3.84 (t, J=11.0 Hz, 1H), 3.64 (t, J=11.6 Hz, 1H),
3.49-3.41 (m, 2H), 3.12 (d, J=7.7 Hz, 1H), 2.64 (d, J=9.2 Hz,
1H), 2.51 (s, 3H), 2.31 (s, 3H), 1.93-1.47 (m, 10H), 1.20 (s,
3H), 1.17 (s, 9H), 1.10 (d, J=5.9 Hz, 3H); LCMS (ESI, M):
675.3.

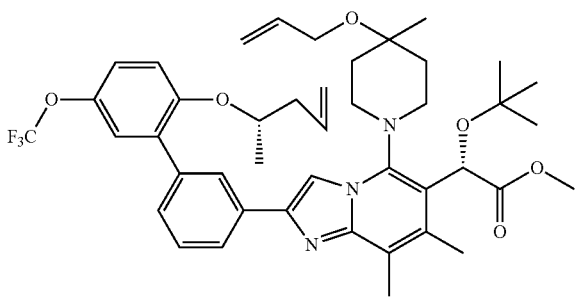

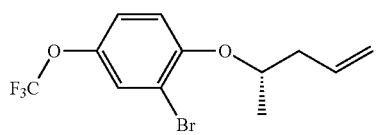 [SMILES: C=CC[C@H](C)Oc1ccc(OC(F)(F)F)cc1Br]

(S)-2-Bromo-1-(pent-4-en-2-yloxy)-4-(trifluoromethoxy)benzene

Prepared in 88% yield from 2-bromo-4-(trifluoromethoxy)
phenol following the same procedure as (S)-1-bromo-4,5-
difluoro-2-(pent-4-en-2-yloxy)benzene. ¹H NMR (400 MHz,
CDCl₃) δ 7.45 (d, J=2.3 Hz, 1H), 7.13 (dd, J=8.9, 2.1 Hz, 1H),
6.90 (d, J=9.0 Hz, 1H), 5.90 (ddt, J=17.2, 10.1, 7.1 Hz, 1H),
5.22-5.09 (m, 2H), 4.50-4.35 (m, 1H), 2.63-2.48 (m, 1H),
2.48-2.36 (m, 1H), 1.37 (d, J=6.0 Hz, 3H).

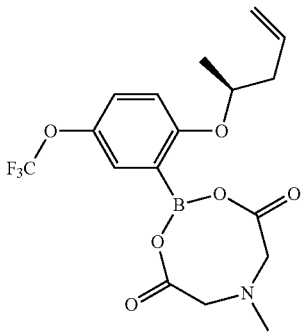 [SMILES: C=CC[C@H](C)Oc1ccc(OC(F)(F)F)cc1B1OC(=O)CN(C)CC(=O)O1]

(S)-6-Methyl-2-(2-(pent-4-en-2-yloxy)-5-(trifluoromethoxy)phenyl)-1,3,6,2-dioxazaborocane-4,8-dione Prepared in 68% yield from (S)-2-bromo-1-(pent-4-en-2-
yloxy)-4-(trifluoromethoxy)benzene following the same procedure as (S)-2-(4,5-difluoro-2-(pent-4-en-2-yloxy)phenyl)-
6-methyl-1,3,6,2-dioxazaborocane-4,8-dione. ¹H NMR (400
MHz, CDCl₃) δ 7.57 (d, J=3.0 Hz, 1H), 7.23 (dd, J=8.8, 3.0
Hz, 1H), 6.93 (d, J=8.8 Hz, 1H), 5.90-5.77 (m, 1H), 5.19-5.11
(m, 2H), 4.69-4.60 (m, 1H), 4.12 (d, J=16.1 Hz, 1H), 4.01-
3.85 (m, 3H), 2.71 (s, 3H), 2.53 (dt, J=14.4, 7.1 Hz, 1H),
2.44-2.34 (m, 1H), 1.32 (d, J=6.0 Hz, 3H); ¹⁹F NMR (376
MHz, CDCl₃) δ −58.20 (s, 3F).

(S)-Methyl 2-(5-(4-(allyloxy)-4-methylpiperidin-1-
yl)-7,8-dimethyl-2-(2'-((S)-pent-4-en-2-yloxy)-5'-
(trifluoromethoxy)-[1,1'-biphenyl]-3-yl)imidazo[1,2-
a]pyridin-6-yl)-2-(tert-butoxy)acetate Prepared from (S)-6-methyl-2-(2-(pent-4-en-2-yloxy)-5-
(trifluoromethoxy)phenyl)-1,3,6,2-dioxazaborocane-4,8-dione and (S)-methyl 2-(5-(4-(allyloxy)-4-methylpiperidin-1-
yl)-2-(3-bromophenyl)-7,8-dimethylimidazo[1,2-a]pyridin-
6-yl)-2-(tert-butoxy)acetate in 92% yield following the same
procedure as (S)-methyl 2-(5-(4-(allyloxy)-4-methylpiperidin-1-yl)-2-(4',5'-difluoro-2'-((S)-pent-4-en-2-yloxy)-[1,1'-
biphenyl]-3-yl)-7,8-dimethylimidazo[1,2-a]pyridin-6-yl)-2-
(tert-butoxy)acetate. LCMS (ESI, M+1): 746.85.

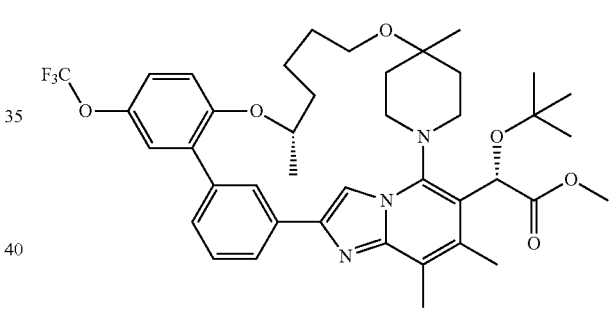

Methyl(2S)-2-(tert-butoxy)-2-[(22S)-4,5,22,28-tet-
ramethyl-17-(trifluoromethoxy)-21,27-dioxa-1,7,34-
triazahexacyclo[26.2.2.1⁶,⁹.1¹⁰,¹⁴.0²,⁷.0¹⁵,²⁰]tetra-
triaconta-2,4,6(34),8,10(33),11,13,15(20),16,18-
decaen-3-yl]acetate A solution of (S)-methyl 2-(5-(4-(allyloxy)-4-methylpiperidin-1-yl)-7,8-dimethyl-2-(2'-((S)-pent-4-en-2-yloxy)-5'-
(trifluoromethoxy)-[1,1'-biphenyl]-3-yl)imidazo[1,2-a]pyridin-6-yl)-2-(tert-butoxy)acetate (0.20 g, 0.262 mmol, 1
equiv) and TsOH monohydrate (50 mg, 0.262 mmol, 1 equiv)
in DCE (100 mL) was heated to 80° C. The Hoveyda Grubbs
2ⁿᵈ generation catalyst (16 mg, 0.026 mmol, 0.1 equiv) was
added. The pale green brown solution was stirred for 3 h.
Upon cooling to ambient temperature, the reaction was
washed with saturated aqueous NaHCO₃, dried (Na₂SO₄),
and concentrated in vacuo. The crude product was taken up in
20:1 DCE:water (2.8 mL) and tetrabutylammonium borohydride (135 mg, 0.524 mmol, 2 equiv) was added. After 1 h, the
reaction mixture was diluted with DCM, washed with water,
dried (Na₂SO₄), and concentrated in vacuo. The crude product was purified by silica gel flash column chromatography (0-100% EtOAc [2% TEA]/hexane) to provide the product (74 mg, 38%) as a tan foam. LCMS (ESI, M+1): 738.80.

Example 42

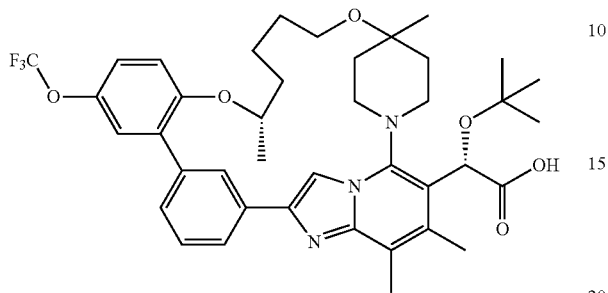

(2S)-2-(tert-Butoxy)-2-[(22S)-4,5,22,28-tetramethyl-17-(trifluoromethoxy)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 15.0% yield from methyl(2S)-2-(tert-butoxy)-2-[(22S)-4,5,22,28-tetramethyl-17-(trifluoromethoxy)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.19 (d, J=8.1 Hz, 1H), 8.13 (s, 1H), 8.01 (s, 1H), 7.55 (t, J=7.7 Hz, 1H), 7.37-7.30 (m, 3H), 7.29-7.24 (m, 1H), 6.01 (br. s., 1H), 4.70 (br. s., 1H), 3.85 (t, J=10.8 Hz, 1H), 3.64 (t, J=11.6 Hz, 1H), 3.46 (br. s., 2H), 3.10 (d, J=8.4 Hz, 1H), 2.63 (d, J=8.8 Hz, 1H), 2.51 (br. s., 3H), 2.31 (s, 3H), 1.93-1.51 (m, 10H), 1.19 (s, 3H), 1.16 (s, 9H), 1.12 (d, J=5.9 Hz, 3H); LCMS (ESI, M+1): 724.4.

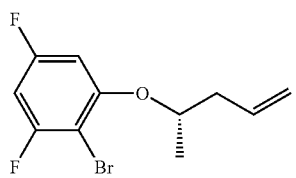

(S)-2-Bromo-1,5-difluoro-3-(pent-4-en-2-yloxy)benzene

Prepared from 2-bromo-3,5-difluorophenol in 80% yield following the procedure for (S)-2-(4,5-difluoro-2-(pent-4-en-2-yloxy)phenyl)-6-methyl-1,3,6,2-dioxazaborocane-4,8-dione. $^1$H NMR (400 MHz, CDCl$_3$) δ 6.59-6.43 (m, 2H), 5.94-5.80 (m, 1H), 5.22-5.09 (m, 2H), 4.47-4.36 (m, 1H), 2.59-2.37 (m, 2H), 1.37 (d, J=6.3 Hz, 3H).

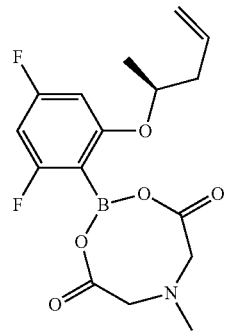 [SMILES: C=CC[C@H](C)Oc1cc(F)cc(F)c1B1OC(=O)CN(C)CC(=O)O1]

(S)-2-(2,4-Difluoro-6-(pent-4-en-2-yloxy)phenyl)-6-methyl-1,3,6,2-dioxazaborocane-4,8-dione Prepared from (S)-2-bromo-1,5-difluoro-3-(pent-4-en-2-yloxy)benzene in 58% yield following the same procedure as (S)-2-(4,5-difluoro-2-(pent-4-en-2-yloxy)phenyl)-6-methyl-1,3,6,2-dioxazaborocane-4,8-dione. $^1$H NMR (400 MHz, DMSO-d$_6$) 6.84 (d, J=11.5 Hz, 1H), 6.67-6.59 (m, 1H), 5.89-5.78 (m, 1H), 5.16-5.02 (m, 2H), 4.71-4.60 (m, 1H), 4.35 (dd, J=17.2, 5.6 Hz, 2H), 4.05-3.92 (m, 2H), 2.65 (s, 3H), 2.46-2.36 (m, 1H), 2.25 (dt, J=14.3, 6.9 Hz, 1H), 1.17 (d, J=6.0 Hz, 3H).

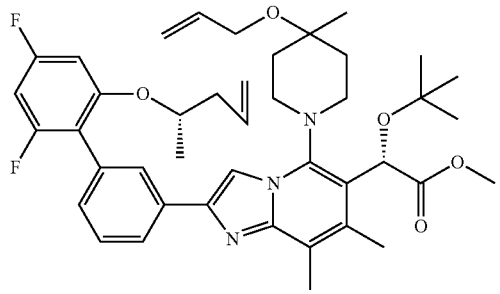 [SMILES: C=CCOC1(C)CCN(c2c([C@H](OC(C)(C)C)C(=O)OC)c(C)c(C)c3nc(-c4cccc(-c5c(F)cc(F)cc5O[C@@H](C)CC=C)c4)cn23)CC1]

(S)-Methyl 2-(5-(4-(allyloxy)-4-methylpiperidin-1-yl)-2-(2',4'-difluoro-6'-((S)-pent-4-en-2-yloxy)-[1,1'-biphenyl]-3-yl)-7,8-dimethylimidazo[1,2-a]pyridin-6-yl)-2-(tert-butoxy)acetate Prepared from (S)-methyl 2-(5-(4-(allyloxy)-4-methylpiperidin-1-yl)-2-(3-bromophenyl)-7,8-dimethylimidazo[1,2-a]pyridin-6-yl)-2-(tert-butoxy)acetate and (S)-2-(2,4-difluoro-6-(pent-4-en-2-yloxy)phenyl)-6-methyl-1,3,6,2-dioxazaborocane-4,8-dione in 99% yield following the same procedure as (S)-methyl 2-(5-(4-(allyloxy)-4-methylpiperidin-1-yl)-2-(4',5'-difluoro-2'-((S)-pent-4-en-2-yloxy)-[1,1'-biphenyl]-3-yl)-7,8-dimethylimidazo[1,2-a]pyridin-6-yl)-2-(tert-butoxy)acetate. LCMS (ESI, M+1): 716.4.

109

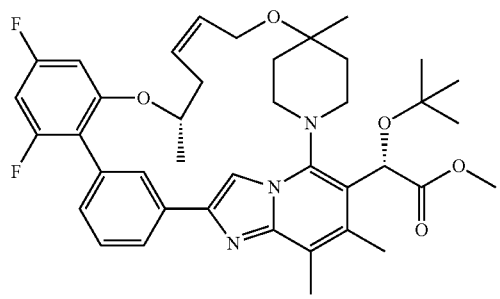 [SMILES: COC(=O)[C@@H](OC(C)(C)C)c1c(C)c(C)c2nc3cn2c1N1CCC(C)(CC1)OC/C=C\C[C@H](C)Oc1cc(F)cc(F)c1-c1cccc-3c1]

Methyl(2S)-2-(tert-butoxy)-2-[(22S,24Z)-16,18-
difluoro-4,5,22,28-tetramethyl-21,27-dioxa-1,7,34-
triazahexacyclo[26.2.2.1$^{6,9}$.1$^{10,14}$.0$^{2,7}$.0$^{15,20}$]tetra-
triaconta-2,4,6(34),8,10(33),11,13,15(20),16,18,24-
undecaen-3-yl]acetate Prepared in 85% yield from (S)-methyl 2-(5-(4-(allyloxy)-4-methylpiperidin-1-yl)-2-(2',4'-difluoro-6'-((S)-pent-4-en-2-yloxy)-[1,1'-biphenyl]-3-yl)-7,8-dimethylimidazo[1,2-a]pyridin-6-yl)-2-(tert-butoxy)acetate following the procedure for methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate. LCMS (ESI, M+1): 688.4.

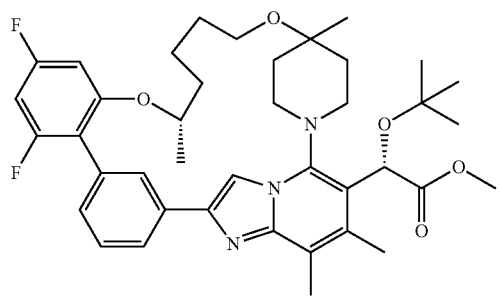 [SMILES: COC(=O)[C@@H](OC(C)(C)C)c1c(C)c(C)c2nc3cn2c1N1CCC(C)(CC1)OCCCC[C@H](C)Oc1cc(F)cc(F)c1-c1cccc-3c1]

Methyl(2S)-2-(tert-butoxy)-2-[(22S)-16,18-difluoro-
4,5,22,28-tetramethyl-21,27-dioxa-1,7,34-triaza-
hexacyclo[26.2.2.1$^{6,9}$.1$^{10,14}$.0$^{2,7}$.0$^{15,20}$]tetratria-
conta-2,4,6(34),8,10(33),11,13,15(20),16,18-decaen-
3-yl]acetate Prepared in 69.8% yield from methyl(2S)-2-(tert-butoxy)-2-[(22S,24Z)-16,18-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate following the procedure for methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. LCMS (ESI, M+1): 690.30.

110

Example 43

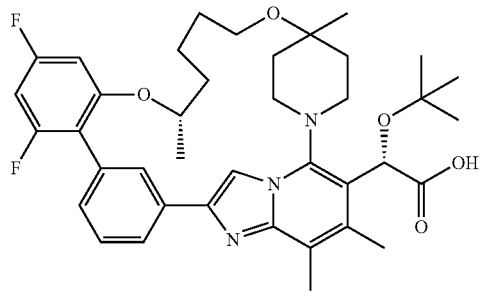 [SMILES: Cc1c([C@H](OC(C)(C)C)C(=O)O)c2n3cc(nc3c1C)-c1cccc(c1)-c1c(F)cc(F)cc1O[C@@H](C)CCCCOC1(C)CCN2CC1]

(2S)-2-(tert-Butoxy)-2-[(22S)-16,18-difluoro-4,5,22,
28-tetramethyl-21,27-dioxa-1,7,34-triazahexacyclo
[26.2.2.1$^{6,9}$.1$^{10,14}$.0$^{2,7}$.0$^{15,20}$]tetratriaconta-2,4,6
(34),8,10(33),11,13,15(20),16,18-decaen-3-yl]acetic
acid Prepared in 57.5% yield from Methyl(2S)-2-(tert-butoxy)-2-[(22S)-16,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.12 (d, J=8.1 Hz, 1H), 7.99 (s, 1H), 7.83 (s, 1H), 7.52 (t, J=7.7 Hz, 1H), 7.25 (d, J=7.7 Hz, 1H), 7.01 (d, J=11.4 Hz, 1H), 6.88 (t, J=8.8 Hz, 1H), 6.05 (br. s., 1H), 4.69 (br. s., 1H), 3.92-3.81 (m, 1H), 3.63 (t, J=10.6 Hz, 1H), 3.51-3.38 (m, 2H), 3.05 (d, J=8.4 Hz, 1H), 2.63 (d, J=7.7 Hz, 1H), 2.51 (br. s., 3H), 2.31 (s, 3H), 1.93-1.81 (m, 2H), 1.80-1.58 (m, 7H), 1.50 (br. s., 1H), 1.20 (s, 3H), 1.17 (s, 9H), 1.11 (d, J=5.9 Hz, 3H); LCMS (ESI, M): 675.3.

Example 44

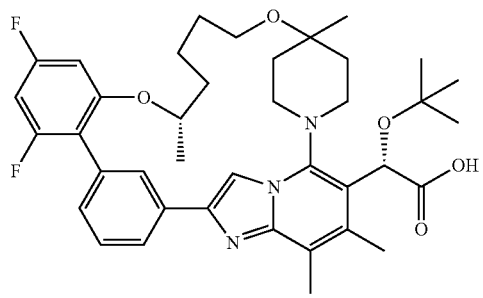 [SMILES: Cc1c([C@H](OC(C)(C)C)C(=O)O)c2n3cc(nc3c1C)-c1cccc(c1)-c1c(F)cc(F)cc1O[C@@H](C)CCCCOC1(C)CCN2CC1]

Unidentified diastereomer of (2S)-2-(tert-butoxy)-2-
[(22S)-16,18-difluoro-4,5,22,28-tetramethyl-21,27-
dioxa-1,7,34-triazahexacyclo[26.2.2.1$^{6,9}$.1$^{10,14}$.
0$^{2,7}$.0$^{15,20}$]tetratriaconta-2,4,6(34),8,10(33),11,13,15
(20),16,18-decaen-3-yl]acetic acid Prepared in 7.2% yield from Methyl(2S)-2-(tert-butoxy)-2-[(22S)-16,18-difluoro-4,22,28-trimethyl-21,27-dioxa-1,7, 34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl] acetate following the procedure for (2S)-2-(tert-butoxy)-2-[(22S)-8-chloro-4,17,22,28-tetramethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetic acid. ¹H NMR (500 MHz, DMSO-d₆) δ 8.09 (d, J=7.7 Hz, 1H), 7.93 (s, 1H), 7.74 (s, 1H), 7.53 (t, J=7.7 Hz, 1H), 7.25 (d, J=7.3 Hz, 1H), 7.01 (d, J=12.1 Hz, 1H), 6.92-6.84 (m, 1H), 6.08 (br. s., 1H), 4.69 (br. s., 1H), 3.87-3.78 (m, 1H), 3.70 (t, J=10.3 Hz, 1H), 3.50-3.40 (m, 2H), 2.89 (br. s., 1H), 2.69 (d, J=9.5 Hz, 1H), 2.49 (s, 3H), 2.33 (s, 3H), 1.93-1.46 (m, 10H), 1.20 (s, 12H), 1.13 (d, J=5.9 Hz, 3H); LCMS (ESI, M): 675.3.

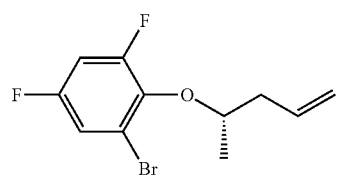

(S)-1-bromo-3,5-difluoro-2-(pent-4-en-2-yloxy)benzene

Prepared in 92% yield from 2-bromo-4,6-difluorophenol following the procedure for (S)-1-bromo-4,5-difluoro-2-(pent-4-en-2-yloxy)benzene. ¹H NMR (400 MHz, CDCl₃) δ 7.19-7.06 (m, 1H), 6.85 (ddd, J=10.9, 8.2, 3.0 Hz, 1H), 5.90 (ddt, J=17.2, 10.1, 7.0 Hz, 1H), 5.19-5.07 (m, 2H), 4.46-4.30 (m, 1H), 2.65-2.48 (m, 1H), 2.48-2.39 (m, 1H), 1.31 (dd, J=6.1, 0.6 Hz, 3H).

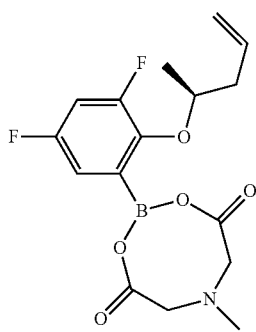 [SMILES: C=CC[C@H](C)Oc1c(F)cc(F)cc1B1OC(=O)CN(C)CC(=O)O1]

(S)-2-(3,5-Difluoro-2-(pent-4-en-2-yloxy)phenyl)-6-methyl-1,3,6,2-dioxazaborocane-4,8-dione Prepared from (S)-1-bromo-3,5-difluoro-2-(pent-4-en-2-yloxy)benzene in 40% yield following the procedure for (S)-2-(4,5-difluoro-2-(pent-4-en-2-yloxy)phenyl)-6-methyl-1,3,6,2-dioxazaborocane-4,8-dione. ¹H NMR (400 MHz, CDCl₃) δ 7.21 (dd, J=8.5, 1.8 Hz, 1H), 6.89 (ddd, J=12.5, 7.8, 3.3 Hz, 1H), 5.91-5.73 (m, 1H), 5.17-5.03 (m, 2H), 4.88-4.75 (m, 1H), 4.10-3.95 (m, 1H), 3.92-3.83 (m, 3H), 2.66 (s, 3H), 2.53-2.41 (m, 1H), 2.39-2.28 (m, 1H), 1.24 (d, J=6.3 Hz, 3H); ¹⁹F NMR (376 MHz, CDCl₃) δ -117.18 (d, J=5.2 Hz, 1F), -122.14 (d, J=5.2 Hz, 1F).

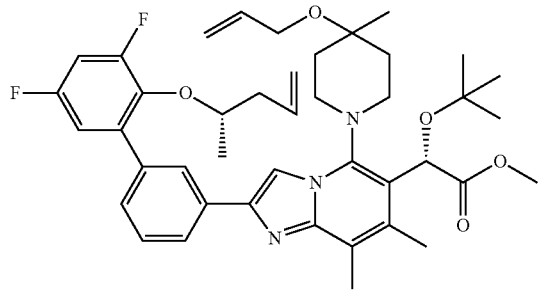 [SMILES: C=CCOC1(C)CCN(c2c([C@H](OC(C)(C)C)C(=O)OC)c(C)c(C)c3nc(-c4cccc(-c5cc(F)cc(F)c5O[C@@H](C)CC=C)c4)cn23)CC1]

(S)-Methyl 2-(5-(4-(allyloxy)-4-methylpiperidin-1-yl)-2-(3',5'-difluoro-2'-((S)-pent-4-en-2-yloxy)-[1,1'-biphenyl]-3-yl)-7,8-dimethylimidazo[1,2-a]pyridin-6-yl)-2-(tert-butoxy)acetate Prepared from (S)-methyl 2-(5-(4-(allyloxy)-4-methylpiperidin-1-yl)-2-(3-bromophenyl)-7,8-dimethylimidazo[1,2-a]pyridin-6-yl)-2-(tert-butoxy)acetate and (S)-2-(3,5-difluoro-2-(pent-4-en-2-yloxy)phenyl)-6-methyl-1,3,6,2-dioxazaborocane-4,8-dione in 99% yield following the same procedure as (S)-methyl 2-(5-(4-(allyloxy)-4-methylpiperidin-1-yl)-2-(4',5'-difluoro-2'-((S)-pent-4-en-2-yloxy)-[1,1'-biphenyl]-3-yl)-7,8-dimethylimidazo[1,2-a]pyridin-6-yl)-2-(tert-butoxy)acetate. LCMS (ESI, M+1): 716.9.

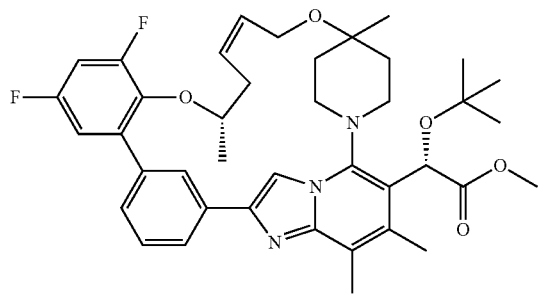 [SMILES: COC(=O)[C@@H](OC(C)(C)C)c1c(C)c(C)c2nc3cn2c1N1CCC(C)(CC1)OC/C=C\C[C@H](C)Oc1c(F)cc(F)cc1-c1cccc-3c1]

Methyl(2S)-2-(tert-butoxy)-2-[(22S,24Z)-17,19-difluoro-4,5,22,28-tetramethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18,24-undecaen-3-yl]acetate Prepared in 41.6% yield from (S)-methyl 2-(5-(4-(allyloxy)-4-methylpiperidin-1-yl)-2-(3',5'-difluoro-2'-((S)-pent-4-en-2-yloxy)-[1,1'-biphenyl]-3-yl)-7,8-dimethylimidazo[1,2-a]pyridin-6-yl)-2-(tert-butoxy)acetate following the procedure for methyl(2S)-2-(tert-butoxy)-2-[(22S)-18-fluoro-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18,24-undecaen-3-yl]acetate. LCMS (ESI, M+1): 688.2.

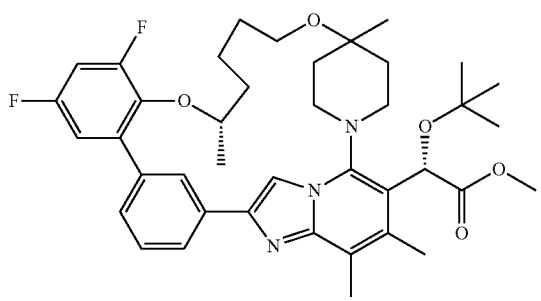 [SMILES: COC(=O)[C@@H](OC(C)(C)C)c1c(C)c(C)c2nc3cn2c1N1CCC(C)(CC1)OCCCC[C@H](C)Oc1c(F)cc(F)cc1-c1cccc-3c1]

Methyl(2S)-2-(tert-butoxy)-2-[(22S)-17,19-difluoro-4,5,22,28-tetramethyl-21,27-dioxa-1,7,34-triaza-hexacyclo[26.2.2.1$^{6,9}$.1$^{10,14}$.0$^{2,7}$.0$^{15,20}$]tetratria-conta-2,4,6(34),8,10(33),11,13,15(20),16,18-decaen-3-yl]acetate Prepared in 85% yield from Methyl(2S)-2-(tert-butoxy)-2-[(22S,24Z)-17,19-difluoro-4,5,22,28-tetramethyl-21,27-di-oxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate following the procedure for Methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. LCMS (ESI, M+1): 690.30.

Example 45

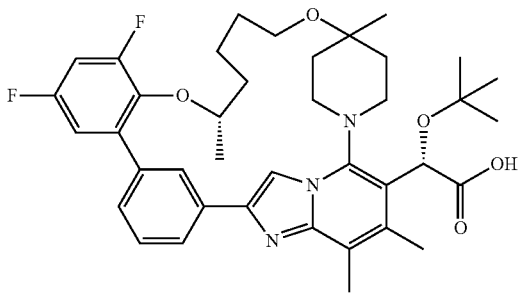 [SMILES: Cc1c([C@H](OC(C)(C)C)C(=O)O)c2n3cc(nc3c1C)-c1cccc(c1)-c1cc(F)cc(F)c1O[C@@H](C)CCCCOC1(C)CCN2CC1]

(2S)-2-(tert-Butoxy)-2-[(22S)-17,19-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 17.2% yield from methyl(2S)-2-(tert-butoxy)-2-[(22S)-17,19-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.07 (s, 1H), 8.03 (d, J=7.3 Hz, 1H), 7.94 (br. s., 1H), 7.57 (t, J=7.5 Hz, 1H), 7.46 (d, J=7.7 Hz, 1H), 7.34 (t, J=9.2 Hz, 1H), 7.19 (d, J=9.2 Hz, 1H), 6.04 (br. s., 1H), 4.20 (br. s., 1H), 3.92 (t, J=10.6 Hz, 1H), 3.55 (t, J=11.2 Hz, 1H), 3.41 (br. s., 4H), 2.48 (s, 3H), 2.31 (s, 3H), 1.93 (d, J=13.6 Hz, 1H), 1.88-1.79 (m, 2H), 1.69 (d, J=12.5 Hz, 5H), 1.54 (br. s., 2H), 1.20 (s, 3H), 1.17 (s, 9H), 0.73 (d, J=5.9 Hz, 3H); LCMS (ESI, M): 675.3.

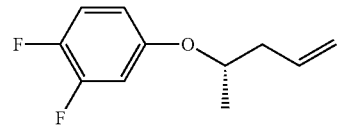

(S)-1,2-Difluoro-4-(pent-4-en-2-yloxy)benzene

Prepared in 69% from 3,4-difluorophenol following the procedure for (S)-2-(4,5-difluoro-2-(pent-4-en-2-yloxy)phenyl)-6-methyl-1,3,6,2-dioxazaborocane-4,8-dione. $^1$H NMR (400 MHz, CDCl$_3$) δ 7.11-6.97 (m, 1H), 6.72 (ddd, J=12.1, 6.6, 2.9 Hz, 1H), 6.64-6.54 (m, 1H), 5.85 (ddt, J=17.2, 10.2, 7.0 Hz, 1H), 5.19-5.09 (m, 2H), 4.38-4.23 (m, 1H), 2.48 (qd, J=7.0, 5.9 Hz, 1H), 2.40-2.28 (m, 1H), 1.31 (d, J=6.0 Hz, 3H); $^{19}$F NMR (376 MHz, CDCl$_3$) δ −135.75 (d, J=20.8 Hz, 1F), −148.32 (d, J=22.5 Hz, 1F).

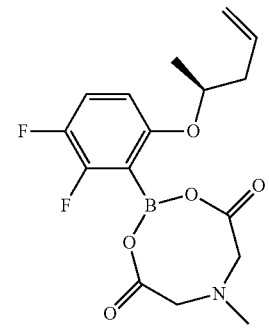 [SMILES: C=CC[C@H](C)Oc1ccc(F)c(F)c1B1OC(=O)CN(C)CC(=O)O1]

(S)-2-(2,3-Difluoro-6-(pent-4-en-2-yloxy)phenyl)-6-methyl-1,3,6,2-dioxazaborocane-4,8-dione To a solution of (S)-1,2-difluoro-4-(pent-4-en-2-yloxy)benzene (1 g, 5.05 mmol, 1 equiv) and TMEDA (0.76 mL, 5.05 mmol, 1 equiv) in THF (17 mL) at −78° C. (IPA/dry ice) was added dropwise sBuLi (4.0 mL of a 1.4 M solution in cyclohexane, 5.55 mmol, 1.1 equiv). After 2 h, the solution is clear orange. Triisopropyl borate (1.4 mL, 6.05 mmol, 1.2 equiv) is added dropwise and the reaction is stirred 1 h during which time the color faded to pale yellow. The reaction was quenched by addition of 1 N HCl (10 mL). Upon warming to ambient temperature, the mixture was added to water and extracted with EtOAc (×3). The combined EtOAc extracts were dried (Na$_2$SO$_4$) and concentrated in vacuo to give the crude boronic acid. This was taken up in toluene (15 mL) and DMSO (5 mL) and N-methyliminodiacetic acid (0.89 g, 6.05 mmol, 1.2 equiv) was added. The reaction mixture was heated at 140° C. with a Dean-Stark trap for 2 h. Upon cooling to ambient temperature, the reaction mixture was diluted with EtOAc and washed with brine. The EtOAc layer was dried (Na$_2$SO$_4$) and concentrated in vacuo. The crude MIDA product was purified by silica gel flash column chromatography (0-70% acetone/DCM) to provide the product (1.0 g, 56%) as a white solid. Product is contaminated with ~20% of a fluorine positional isomer. $^1$H NMR (400 MHz, DMSO-d$_6$) δ 7.34

(d, J=9.5 Hz, 1H), 6.85 (d, J=9.3 Hz, 1H), 5.89-5.75 (m, 1H), 5.17-5.03 (m, 2H), 4.65-4.56 (m, 1H), 4.37 (dd, J=17.3, 6.5 Hz, 2H), 4.10-4.00 (m, 2H), 2.68 (s, 3H), 2.45-2.36 (m, 1H), 2.25 (d, J=7.3 Hz, 1H), 1.16 (d, J=5.0 Hz, 3H); $^{19}$F NMR (376 MHz, DMSO-$d_6$) δ −128.84 (d, J=24.3 Hz, 1F), −148.61 (d, J=24.3 Hz, 1F).

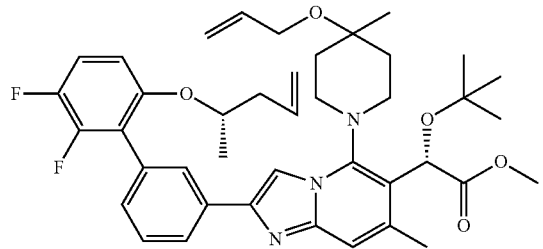 [SMILES: C=CCOC1(C)CCN(c2c([C@H](OC(C)(C)C)C(=O)OC)c(C)cc3nc(-c4cccc(-c5c(O[C@@H](C)CC=C)ccc(F)c5F)c4)cn23)CC1]

(S)-Methyl 2-(5-(4-(allyloxy)-4-methylpiperidin-1-yl)-2-(2',3'-difluoro-6'-((S)-pent-4-en-2-yloxy)-[1,1'-biphenyl]-3-yl)-7-methylimidazo[1,2-a]pyridin-6-yl)-2-(tert-butoxy)acetate Prepared from (S)-methyl 2-(5-(4-(allyloxy)-4-methylpiperidin-1-yl)-2-(3-bromophenyl)-7-methylimidazo[1,2-a]pyridin-6-yl)-2-(tert-butoxy)acetate and (S)-2-(2,3-difluoro-6-(pent-4-en-2-yloxy)phenyl)-6-methyl-1,3,6,2-dioxazaborocane-4,8-dione in 99% yield following the same procedure as (S)-methyl 2-(5-(4-(allyloxy)-4-methylpiperidin-1-yl)-2-(4',5'-difluoro-2'-((S)-pent-4-en-2-yloxy)-[1,1'-biphenyl]-3-yl)-7,8-dimethylimidazo[1,2-a]pyridin-6-yl)-2-(tert-butoxy)acetate. LCMS (ESI, M+1): 702.20.

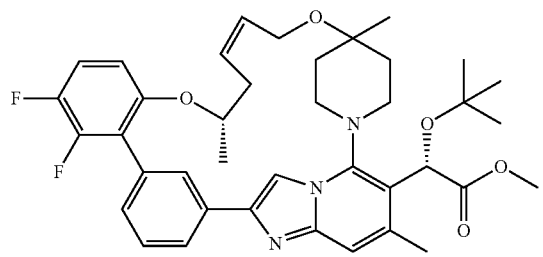 [SMILES: COC(=O)[C@@H](OC(C)(C)C)c1c(C)cc2nc3cn2c1N1CCC(C)(CC1)OC/C=C\C[C@H](C)Oc1ccc(F)c(F)c1-c1cccc-3c1]

Methyl(2S)-2-(tert-butoxy)-2-[(22S,24Z)-16,17-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate Prepared in 81.0% yield from (S)-methyl 2-(5-(4-(allyloxy)-4-methylpiperidin-1-yl)-2-(2',3'-difluoro-6'-((S)-pent-4-en-2-yloxy)-[1,1'-biphenyl]-3-yl)-7-methylimidazo[1,2-a]pyridin-6-yl)-2-(tert-butoxy)acetate following the procedure for methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate. LCMS (ESI, M+1): 674.6.

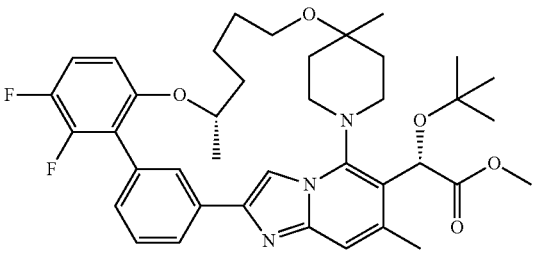 [SMILES: COC(=O)[C@@H](OC(C)(C)C)c1c(C)cc2nc3cn2c1N1CCC(C)(CC1)OCCCC[C@H](C)Oc1ccc(F)c(F)c1-c1cccc-3c1]

Methyl(2S)-2-(tert-butoxy)-2-[(22S)-16,17-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 69.8% yield from methyl(2S)-2-(tert-butoxy)-2-[(22S,24Z)-16,17-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate following the procedure for methyl (2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. $^1$H NMR (500 MHz, CDCl$_3$) δ 8.21 (dt, J=7.9, 1.3 Hz, 1H), 8.01 (s, 1H), 7.90 (t, J=1.5 Hz, 1H), 7.56 (t, J=7.7 Hz, 1H), 7.38-7.33 (m, 2H), 7.14-7.06 (m, 1H), 6.72-6.68 (m, 1H), 6.07 (br. s., 1H), 4.51-4.45 (m, 1H), 4.04-3.95 (m, 1H), 3.77 (t, J=10.8 Hz, 1H), 3.71 (s, 3H), 3.56-3.50 (m, 1H), 3.50-3.45 (m, 1H), 3.09 (d, J=10.1 Hz, 1H), 2.71 (d, J=7.7 Hz, 1H), 2.48 (d, J=0.9 Hz, 3H), 2.00-1.92 (m, 2H), 1.85-1.71 (m, 8H), 1.30 (s, 3H), 1.27 (s, 9H), 1.13 (d, J=6.1 Hz, 3H); LCMS (ESI, M+1): 676.80.

Example 46

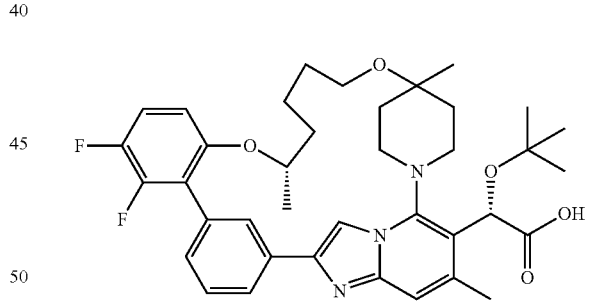

(2S)-2-(tert-butoxy)-2-[(22S)-16,17-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 78% yield from methyl(2S)-2-(tert-butoxy)-2-[(22S)-16,17-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18- decaen-3-yl]acetic acid. $^1$H NMR (500 MHz, DMSO-$d_6$) δ 8.08 (d, J=7.7 Hz, 1H), 7.97 (s, 1H), 7.88 (s, 1H), 7.54 (t, J=7.7 Hz, 1H), 7.42-7.35 (m, 1H), 7.32 (d, J=6.2 Hz, 1H), 7.29 (s, 1H), 6.99 (d, J=7.3 Hz, 1H), 5.89 (br. s., 1H), 4.62 (br. s., 1H), 3.92-3.81 (m, 1H), 3.61 (t, J=11.2 Hz, 1H), 3.46-3.41 (m, 2H), 3.12 (d, J=9.9 Hz, 1H), 2.64 (d, J=8.4 Hz, 1H), 2.40 (s, 3H), 1.93-1.50 (m, 10H), 1.19 (s, 3H), 1.16 (s, 9H), 1.07 (d, J=6.2 Hz, 3H); LCMS (ESI, M+): 661.3.

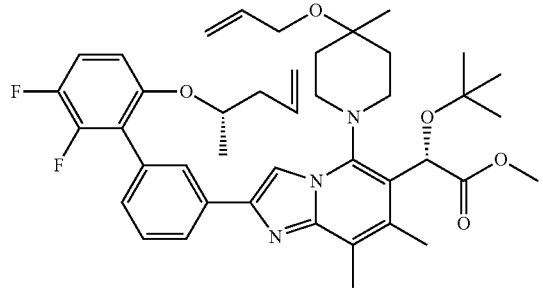 [SMILES: C=CCOC1(C)CCN(c2c([C@H](OC(C)(C)C)C(=O)OC)c(C)c(C)c3nc(-c4cccc(-c5c(O[C@@H](C)CC=C)ccc(F)c5F)c4)cn23)CC1]

(S)-Methyl 2-(5-(4-(allyloxy)-4-methylpiperidin-1-yl)-2-(2',3'-difluoro-6'-((S)-pent-4-en-2-yloxy)-[1,1'-biphenyl]-3-yl)-7,8-dimethylimidazo[1,2-a]pyridin-6-yl)-2-(tert-butoxy)acetate Prepared from (S)-methyl 2-(5-(4-(allyloxy)-4-methylpiperidin-1-yl)-2-(3-bromophenyl)-7,8-dimethylimidazo[1,2-a]pyridin-6-yl)-2-(tert-butoxy)acetate and (S)-2-(2,3-difluoro-6-(pent-4-en-2-yloxy)phenyl)-6-methyl-1,3,6,2-dioxazaborocane-4,8-dione in 45% yield following the same procedure as (S)-methyl 2-(5-(4-(allyloxy)-4-methylpiperidin-1-yl)-2-(4',5'-difluoro-2'-((S)-pent-4-en-2-yloxy)-[1,1'-biphenyl]-3-yl)-7,8-dimethylimidazo[1,2-a]pyridin-6-yl)-2-(tert-butoxy)acetate. LCMS (ESI, M+1): 716.7.

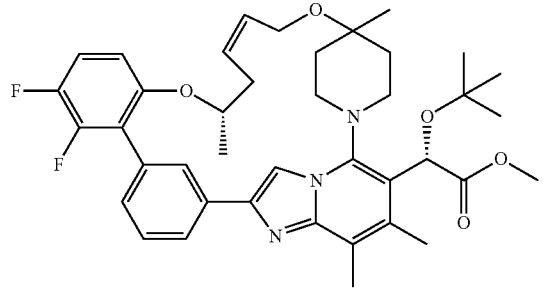 [SMILES: COC(=O)[C@@H](OC(C)(C)C)c1c(C)c(C)c2nc3cn2c1N1CCC(C)(CC1)OC/C=C\C[C@H](C)Oc1ccc(F)c(F)c1-c1cccc-3c1]

Methyl(2S)-2-(tert-butoxy)-2-[(22S,24Z)-16,17-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate Prepared in 41.6% yield from (S)-methyl 2-(5-(4-(allyloxy)-4-methylpiperidin-1-yl)-2-(2',3'-difluoro-6'-((S)-pent-4-en-2-yloxy)-[1,1'-biphenyl]-3-yl)-7,8-dimethylimidazo[1,2-a]pyridin-6-yl)-2-(tert-butoxy)acetate following the procedure for methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate. LCMS (ESI, M+1): 688.3.

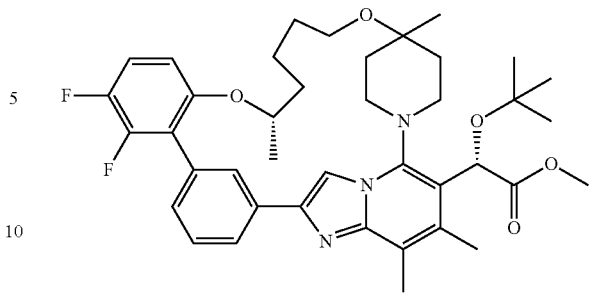

Methyl(2S)-2-(tert-butoxy)-2-[(22S)-16,17-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 80% yield from methyl(2S)-2-(tert-butoxy)-2-[(22S,24Z)-16,17-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate following the procedure for methyl(2S)-2-(tert-butoxy)-2-[(22S)-18-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. LCMS (ESI, M+1): 690.25.

Example 47

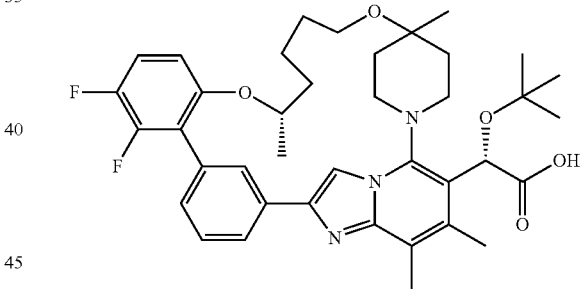

(2S)-2-(tert-Butoxy)-2-[(22S)-16,17-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 25.8% yield from methyl(2S)-2-(tert-butoxy)-2-[(22S)-16,17-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-$d_6$) δ 8.14 (d, J=8.1 Hz, 1H), 7.97 (s, 1H), 7.87 (s, 1H), 7.53 (t, J=7.7 Hz, 1H), 7.38 (q, J=9.4 Hz, 1H), 7.31 (d, J=7.7 Hz, 1H), 6.99 (d, J=6.6 Hz, 1H), 5.92 (br. s., 1H), 4.62 (br. s., 1H), 3.86 (t, J=11.2 Hz, 1H), 3.58 (t, J=10.6 Hz, 1H), 3.44 (br. s., 4H), 2.48 (s, 3H), 2.30 (s, 3H), 1.92-1.79 (m, 3H), 1.77-1.58 (m, 7H), 1.18 (s, 3H), 1.15 (s, 9H), 1.07 (d, J=5.9 Hz, 3H); LCMS (ESI, M): 675.3.

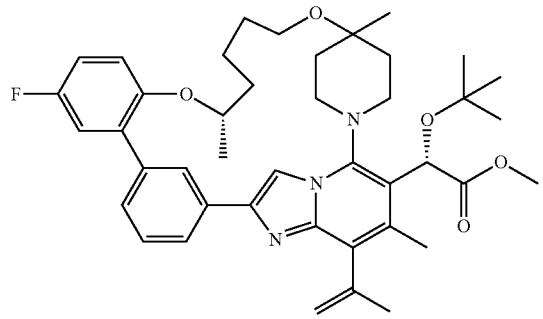 [SMILES: C=C(C)c1c(C)c([C@H](OC(C)(C)C)C(=O)OC)c2n3cc(nc13)-c1cccc(c1)-c1cc(F)ccc1O[C@@H](C)CCCCOC1(C)CCN2CC1]

Methyl(2S)-2-(tert-butoxy)-2-[(22S)-17-fluoro-4,22,28-trimethyl-5-(prop-1-en-2-yl)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 80% yield from methyl(2S)-2-[(22S)-5-bromo-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetate following the procedure for methyl(2S)-2-(tert-butoxy)-2-[(22S)-5-ethenyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. LCMS (ESI, M+1): 698.4.

Example 48

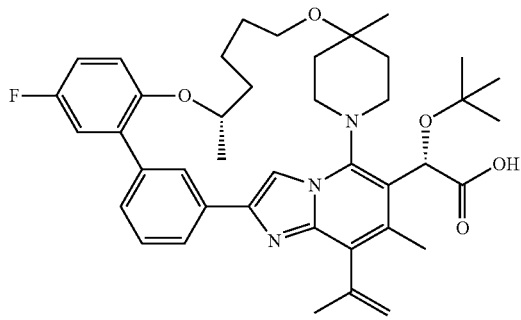 [SMILES: C=C(C)c1c(C)c([C@H](OC(C)(C)C)C(=O)O)c2n3cc(nc13)-c1cccc(c1)-c1cc(F)ccc1O[C@@H](C)CCCCOC1(C)CCN2CC1]

(2S)-2-(tert-Butoxy)-2-[(22S)-17-fluoro-4,22,28-trimethyl-5-(prop-1-en-2-yl)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 17.9% yield from methyl(2S)-2-(tert-butoxy)-2-[(22S)-17-fluoro-4,22,28-trimethyl-5-(prop-1-en-2-yl)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.12 (s, 1H), 8.08 (d, J=7.7 Hz, 1H), 7.98 (s, 1H), 7.52 (t, J=7.7 Hz, 1H), 7.33 (d, J=7.3 Hz, 1H), 7.22-7.12 (m, 3H), 5.98 (br. s., 1H), 5.43 (s, 1H), 4.89 (s, 1H), 4.61 (br. s., 1H), 3.83 (t, J=11.2 Hz, 1H), 3.63 (t, J=11.0 Hz, 1H), 3.44 (d, J=12.1 Hz, 4H), 3.20-3.11 (m, 1H), 2.66 (d, J=11.0 Hz, 1H), 2.32 (s, 3H), 2.15 (s, 3H), 1.91-1.59 (m, 9H), 1.52 (br. s., 1H), 1.19 (s, 3H), 1.17 (s, 9H), 1.06 (d, J=5.9 Hz, 3H); LCMS (ESI, M+1): 684.4.

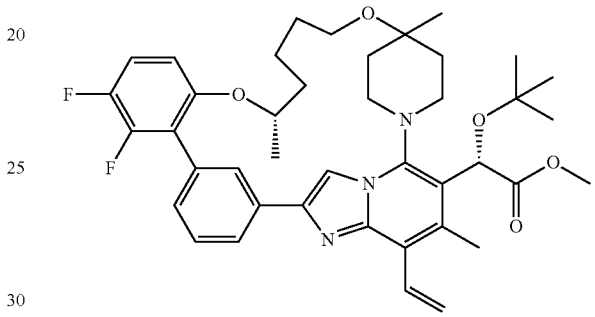

Methyl(2S)-2-(tert-butoxy)-2-[(22S)-5-ethenyl-16,17-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 52.5% yield from methyl(2S)-2-[(22S)-5-bromo-16,17-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetate following the procedure for methyl(2S)-2-(tert-butoxy)-2-[(22S)-5-ethenyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. LCMS (ESI, M+1): 702.4.

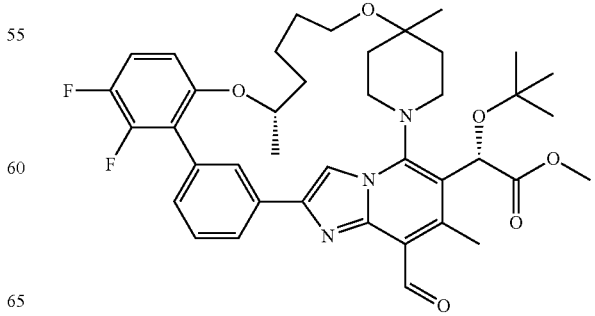

Methyl(2S)-2-(tert-butoxy)-2-[(22S)-16,17-difluoro-
5-formyl-4,22,28-trimethyl-21,27-dioxa-1,7,34-tri-
azahexacyclo[26.2.2.1$^{6,9}$.1$^{10,14}$.0$^{2,7}$.0$^{15,20}$]tetratria-
conta-2,4,6(34),8,10(33),11,13,15(20),16,18-decaen-
3-yl]acetate Methyl(2S)-2-(tert-butoxy)-2-[(22S)-5-ethenyl-16,17-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (0.15 g, 0.214 mmol, 1.0 equiv) was dissolved in dioxane (6.41 mL) and water (2.14 mL). To this solution was added sodium periodate (0.16 g, 0.748 mmol, 3.5 equiv) and 4% osmium tetroxide (0.136 g, 0.021 mmol, 0.1 equiv). The mixture was stirred at r.t. for 2 hours. Then it was diluted by EA, washed by water, dried over MgSO$_4$, concentrated to load onto 12 g ISCO column and purified with 0-100% EtOAc[2% TEA]/Hexane to afford the product (0.14 g, 93%). $^1$H NMR (400 MHz, CDCl$_3$) δ 11.23 (s, 1H), 8.28 (d, J=7.8 Hz, 1H), 8.07 (s, 1H), 7.92 (s, 1H), 7.58 (t, J=7.8 Hz, 1H), 7.39 (d, J=1.5 Hz, 1H), 7.10 (d, J=9.3 Hz, 1H), 6.72-6.65 (m, 1H), 6.19-5.95 (m, 1H), 4.53-4.43 (m, 1H), 4.05-3.93 (m, 1H), 3.80-3.74 (m, 1H), 3.71 (s, 3H), 3.50 (d, J=16.1 Hz, 2H), 3.21-3.13 (m, 1H), 2.77 (s, 3H), 2.74-2.66 (m, 1H), 1.96 (d, J=13.6 Hz, 2H), 1.86-1.69 (m, 8H), 1.29 (s, 3H), 1.25 (s, 9H), 1.13 (d, J=6.0 Hz, 3H); LCMS (ESI, M+1): 704.25.

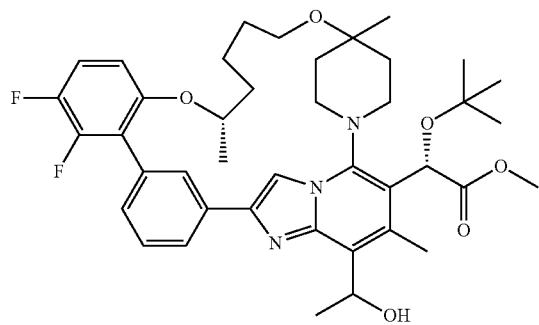 [SMILES: COC(=O)[C@@H](OC(C)(C)C)c1c(C)c(C(C)O)c2nc3cn2c1N1CCC(C)(CC1)OCCCC[C@H](C)Oc1ccc(F)c(F)c1-c1cccc-3c1]

Methyl(2S)-2-(tert-butoxy)-2-[(22S)-16,17-difluoro-
5-(1-hydroxyethyl)-4,22,28-trimethyl-21,27-dioxa-1,
7,34-triazahexacyclo[26.2.2.1$^{6,9}$.1$^{10,14}$.0$^{2,7}$.0$^{15,20}$]
tetratriaconta-2,4,6(34),8,10(33),11,13,15(20),16,18-
decaen-3-yl]acetate Methyl(2S)-2-(tert-butoxy)-2-[(22S)-16,17-difluoro-5-formyl-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (0.017 g, 0.024 mmol, 1.0 equiv) and (1-methylpiperidin-2-yl)methanol (3.12 mg, 0.024 mmol, 1.0 equiv) were mixed in 1 mL toluene and concentrated to remove water. Then the mixture was re-dissolved in toluene (1.2 mL). To this solution was added 1 M dimethyl zinc (0.097 mL, 4.0 equiv) and stirred for 1 hour. It was quenched by 1 mL methanol. After concentration, the residue was used as is for the next reaction. LCMS (ESI, M+1): 720.4.

Example 49

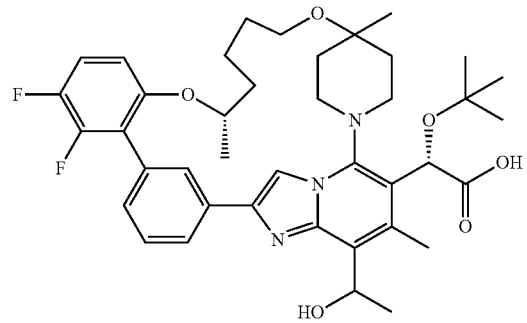 [SMILES: Cc1c([C@H](OC(C)(C)C)C(=O)O)c2n3cc(nc3c1C(C)O)-c1cccc(c1)-c1c(ccc(F)c1F)O[C@@H](C)CCCCOC1(C)CCN2CC1]

(2S)-2-(tert-Butoxy)-2-[(22S)-16,17-difluoro-5-(1-
hydroxyethyl)-4,22,28-trimethyl-21,27-dioxa-1,7,34-
triazahexacyclo[26.2.2.1$^{6,9}$.1$^{10,14}$.0$^{2,7}$.0$^{15,20}$]tetra-
triaconta-2,4,6(34),8,10(33),11,13,15(20),16,18-
decaen-3-yl]acetic acid Prepared in 19.0% yield from methyl(2S)-2-(tert-butoxy)-2-[(22S)-16,17-difluoro-5-(1-hydroxyethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.08 (d, J=7.7 Hz, 1H), 7.97 (s, 1H), 7.90 (s, 1H), 7.57 (t, J=7.7 Hz, 1H), 7.40 (q, J=9.8 Hz, 1H), 7.35 (d, J=7.3 Hz, 1H), 7.00 (d, J=7.3 Hz, 1H), 5.96 (br. s., 1H), 5.41 (br. s., 1H), 4.62 (br. s., 1H), 3.89-3.81 (m, 1H), 3.64-3.55 (m, 1H), 3.42-3.36 (m, 2H), 3.17 (br. s., 1H), 2.64 (d, J=7.3 Hz, 1H), 2.37 (s, 3H), 1.94-1.58 (m, 10H), 1.52 (d, J=6.6 Hz, 3H), 1.19 (s, 3H), 1.16 (s, 9H), 1.08 (d, J=5.9 Hz, 3H); LCMS (ESI, M+1): 706.05.

Example 50

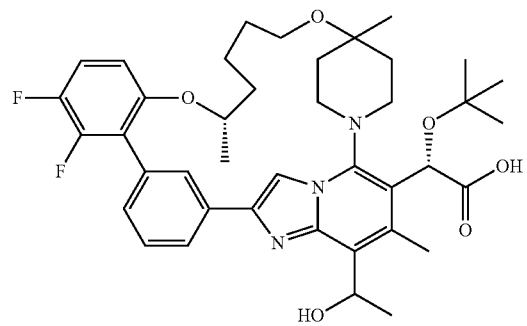 [SMILES: Cc1c([C@H](OC(C)(C)C)C(=O)O)c2n3cc(nc3c1C(C)O)-c1cccc(c1)-c1c(ccc(F)c1F)O[C@@H](C)CCCCOC1(C)CCN2CC1]

(2S)-2-(tert-Butoxy)-2-[(22S)-16,17-difluoro-5-(1-
hydroxyethyl)-4,22,28-trimethyl-21,27-dioxa-1,7,34-
triazahexacyclo[26.2.2.1$^{6,9}$.1$^{10,14}$.0$^{2,7}$.0$^{15,20}$]tetra-
triaconta-2,4,6(34),8,10(33),11,13,15(20),16,18-
decaen-3-yl]acetic acid Prepared in 25.9% yield from methyl(2S)-2-(tert-butoxy)-2-[(22S)-16,17-difluoro-5-(1-hydroxyethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-$d_6$) δ 8.08 (d, J=7.7 Hz, 1H), 7.98 (s, 1H), 7.90 (s, 1H), 7.56 (t, J=7.7 Hz, 1H), 7.39 (q, J=9.4 Hz, 1H), 7.34 (d, J=7.0 Hz, 1H), 7.00 (d, J=7.7 Hz, 1H), 5.97 (br. s., 1H), 5.50 (br. s., 1H), 4.62 (br. s., 1H), 3.89-3.83 (m, 1H), 3.60 (t, J=11.0 Hz, 1H), 3.42-3.34 (m, 2H), 3.15 (d, J=8.4 Hz, 1H), 2.64 (br. s., 1H), 2.41 (s, 3H), 1.92-1.82 (m, 2H), 1.77-1.58 (m, 8H), 1.51 (d, J=6.6 Hz, 3H), 1.19 (s, 3H), 1.17 (s, 9H), 1.07 (d, J=5.9 Hz, 3H); LCMS (ESI, M+1): 706.10.

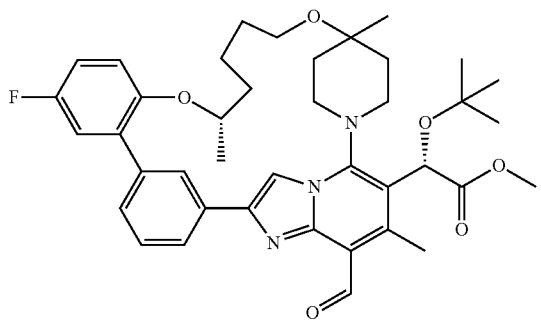 [SMILES: COC(=O)[C@@H](OC(C)(C)C)c1c(C)c(C=O)c2nc3cn2c1N1CCC(C)(CC1)OCCCC[C@H](C)Oc1ccc(F)cc1-c1cccc-3c1]

Methyl(2S)-2-(tert-butoxy)-2-[(22S)-17-fluoro-5-formyl-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 82.0% yield from Methyl(2S)-2-(tert-butoxy)-2-[(22S)-5-ethenyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for Methyl(2S)-2-(tert-butoxy)-2-[(22S)-16,17-difluoro-5-formyl-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. LCMS (ESI, M+1): 686.4.

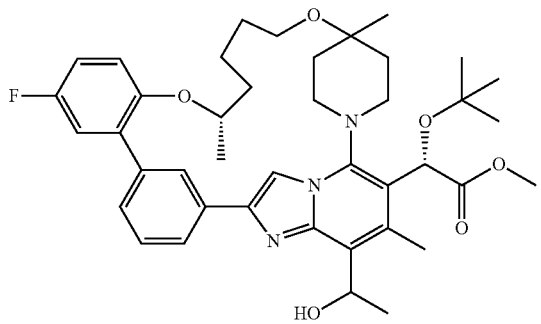 [SMILES: COC(=O)[C@@H](OC(C)(C)C)c1c(C)c(C(C)O)c2nc3cn2c1N1CCC(C)(CC1)OCCCC[C@H](C)Oc1ccc(F)cc1-c1cccc-3c1]

Methyl(2S)-2-(tert-butoxy)-2-[(22S)-17-fluoro-5-(1-hydroxyethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 46.9% yield from methyl(2S)-2-(tert-butoxy)-2-[(22S)-17-fluoro-5-formyl-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for methyl(2S)-2-(tert-butoxy)-2-[(22S)-16,17-difluoro-5-(1-hydroxyethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. LCMS (ESI, M+1): 702.4.

Example 51

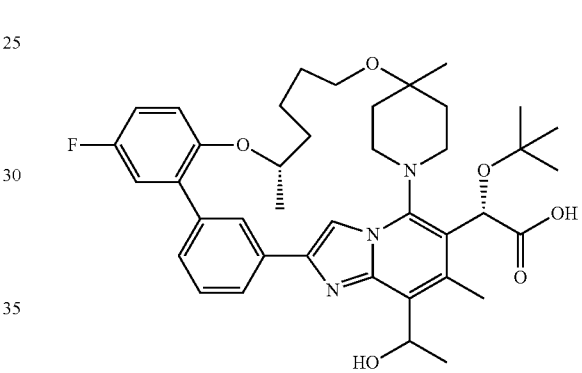

(2S)-2-(tert-Butoxy)-2-[(22S)-17-fluoro-5-(1-hydroxyethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 66.4% yield from methyl(2S)-2-(tert-butoxy)-2-[(22S)-17-fluoro-5-(1-hydroxyethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (400 MHz, DMSO-$d_6$) δ 8.18 (s, 1H), 8.06 (d, J=7.8 Hz, 1H), 7.95 (s, 1H), 7.54 (t, J=7.7 Hz, 1H), 7.36 (d, J=7.8 Hz, 1H), 7.23 (dd, J=9.4, 2.6 Hz, 1H), 7.19-7.14 (m, 2H), 6.44 (d, J=9.8 Hz, 1H), 5.57 (s, 1H), 5.29-5.15 (m, 1H), 4.70-4.58 (m, 1H), 3.84 (br. s., 2H), 3.56-3.42 (m, 3H), 2.68-2.58 (m, 1H), 2.33 (s, 3H), 1.99-1.53 (m, 10H), 1.50 (d, J=6.5 Hz, 3H), 1.20 (s, 3H), 1.12 (s, 9H), 1.09 (d, J=6.0 Hz, 3H); LCMS (ESI, M+1): 688.3.

Example 52

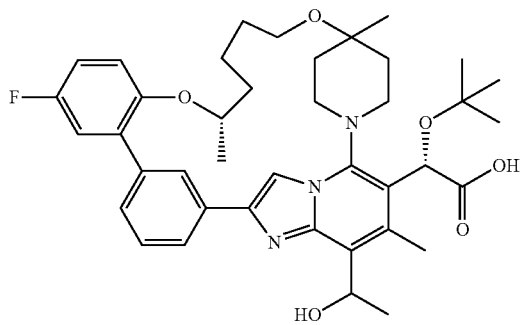 [SMILES: Cc1c([C@H](OC(C)(C)C)C(=O)O)c2n3cc(nc3c1C(C)O)-c1cccc(c1)-c1cc(F)ccc1O[C@@H](C)CCCCOC1(C)CCN2CC1]

(2S)-2-(tert-Butoxy)-2-[(22S)-17-fluoro-5-(1-hydroxyethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 66% yield from methyl(2S)-2-(tert-butoxy)-2-[(22S)-17-fluoro-5-(1-hydroxyethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (400 MHz, DMSO-d$_6$) δ 8.16 (s, 1H), 8.07 (d, J=7.8 Hz, 1H), 7.98 (s, 1H), 7.54 (t, J=7.8 Hz, 1H), 7.36 (d, J=7.8 Hz, 1H), 7.22 (dd, J=9.4, 2.6 Hz, 1H), 7.19-7.14 (m, 2H), 6.15 (br. s., 1H), 5.78 (br. s., 1H), 5.46 (br. s., 1H), 4.62 (br. s., 1H), 3.90-3.79 (m, 1H), 3.62-3.52 (m, 1H), 3.50-3.40 (m, 3H), 2.66 (d, J=9.0 Hz, 1H), 2.40 (s, 3H), 1.95-1.52 (m, 10H), 1.49 (d, J=6.8 Hz, 3H), 1.20 (s, 3H), 1.14 (s, 9H), 1.08 (d, J=6.0 Hz, 3H); LCMS (ESI, M+1): 688.3.

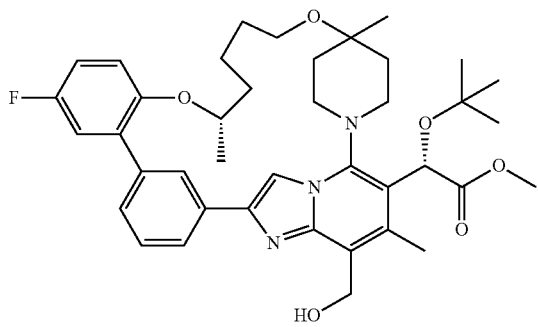 [SMILES: COC(=O)[C@@H](OC(C)(C)C)c1c(C)c(CO)c2nc3cn2c1N1CCC(C)(CC1)OCCCC[C@H](C)Oc1ccc(F)cc1-c1cccc-3c1]

Methyl(2S)-2-(tert-butoxy)-2-[(22S)-17-fluoro-5-(hydroxymethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Methyl(2S)-2-(tert-butoxy)-2-[(22S)-17-fluoro-5-formyl-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (15 mg, 0.022 mmol, 1.0 equiv) was dissolved in MeOH (437 µl). To this solution was added sodium borohydride (3.31 mg, 0.087 mmol, 4.0 equiv) and stirred at r.t. The solution turned to colorless immediately. It was stirred for ten minutes and quenched by water, extracted by Ethyl Acetate. The organic layer was concentrated to give the pure enough product for the next reaction.

Example 53

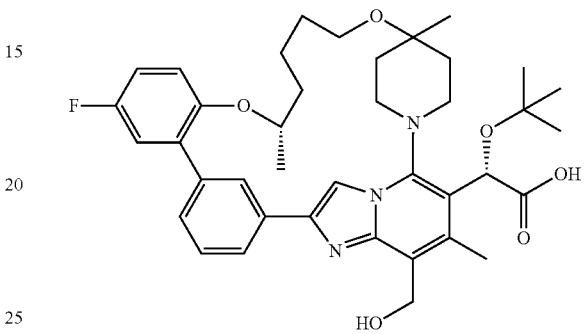

(2S)-2-(tert-Butoxy)-2-[(22S)-17-fluoro-5-(hydroxymethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 72.1% yield from methyl(2S)-2-(tert-butoxy)-2-[(22S)-17-fluoro-5-(hydroxymethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (400 MHz, DMSO-d$_6$) δ 8.16 (s, 1H), 8.13 (d, J=7.8 Hz, 1H), 7.97 (s, 1H), 7.52 (t, J=7.7 Hz, 1H), 7.33 (d, J=7.8 Hz, 1H), 7.22 (dd, J=9.4, 2.6 Hz, 1H), 7.19-7.13 (m, 2H), 5.58 (br. s., 1H), 5.03 (br. s., 1H), 5.00-4.93 (m, 1H), 4.90-4.82 (m, 1H), 4.63 (br. s., 1H), 3.91-3.75 (m, 2H), 3.57-3.43 (m, 3H), 2.63 (d, J=10.0 Hz, 1H), 2.42 (s, 3H), 1.96-1.52 (m, 10H), 1.20 (s, 3H), 1.13 (s, 9H), 1.09 (d, J=5.8 Hz, 3H); LCMS (ESI, M+1): 674.6.

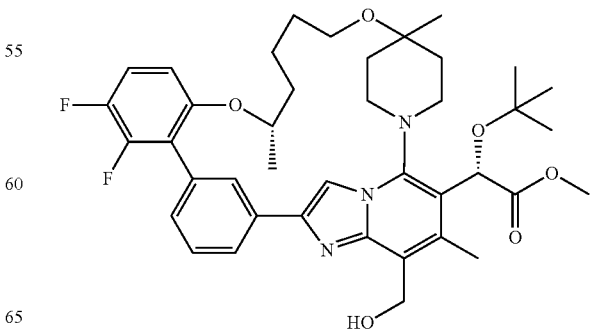

Methyl(2S)-2-(tert-butoxy)-2-[(22S)-16,17-difluoro-5-(hydroxymethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 76.0% yield from methyl(2S)-2-(tert-butoxy)-2-[(22S)-16,17-difluoro-5-formyl-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for methyl(2S)-2-(tert-butoxy)-2-[(22S)-17-fluoro-5-(hydroxymethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. $^1$H NMR (400 MHz, CDCl$_3$) δ 8.20 (d, J=7.8 Hz, 1H), 7.99 (s, 1H), 7.90 (s, 1H), 7.59-7.52 (m, 1H), 7.36 (d, J=7.8 Hz, 1H), 7.09 (q, J=9.0 Hz, 1H), 6.69 (d, J=9.3 Hz, 1H), 6.18 (br. s., 1H), 5.11 (s, 2H), 4.48 (br. s., 1H), 3.98 (t, J=11.2 Hz, 1H), 3.79-3.71 (m, 1H), 3.69 (s, 3H), 3.57-3.45 (m, 2H), 3.07 (d, J=11.3 Hz, 1H), 2.70 (d, J=8.0 Hz, 1H), 2.37 (s, 3H), 1.95 (br. s., 2H), 1.86-1.65 (m, 8H), 1.29 (s, 3H), 1.25 (s, 9H), 1.13 (d, J=6.0 Hz, 3H); LCMS (ESI, M+1): 706.3.

Example 54

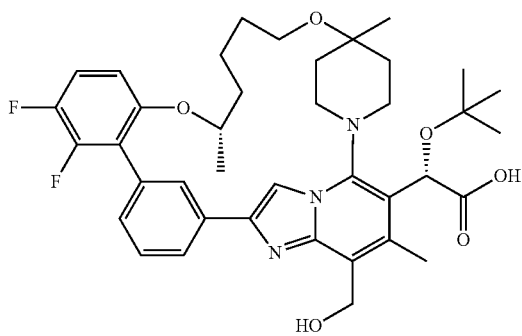 [SMILES: Cc1c([C@H](OC(C)(C)C)C(=O)O)c2n3cc(nc3c1CO)-c1cccc(c1)-c1c(ccc(F)c1F)O[C@@H](C)CCCCOC1(C)CCN2CC1]

(2S)-2-(tert-Butoxy)-2-[(22S)-16,17-difluoro-5-(hydroxymethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 80.0% yield from methyl(2S)-2-(tert-butoxy)-2-[(22S)-16,17-difluoro-5-(hydroxymethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (400 MHz, DMSO-d$_6$) δ 8.12 (d, J=7.8 Hz, 1H), 7.94 (s, 1H), 7.89 (s, 1H), 7.52 (t, J=7.7 Hz, 1H), 7.39 (q, J=9.6 Hz, 1H), 7.30 (d, J=7.5 Hz, 1H), 7.01 (d, J=7.0 Hz, 1H), 5.51 (s, 1H), 5.03 (br. s., 1H), 4.98 (d, J=11.3 Hz, 1H), 4.83 (d, J=11.3 Hz, 1H), 4.65 (br. s., 1H), 3.93-3.83 (m, 1H), 3.76 (br. s., 1H), 3.52-3.43 (m, 3H), 2.40 (s, 3H), 1.92 (d, J=12.0 Hz, 1H), 1.82-1.51 (m, 9H), 1.19 (s, 3H), 1.12 (s, 9H), 1.09 (d, J=6.0 Hz, 3H); LCMS (ESI, M+1): 692.20.

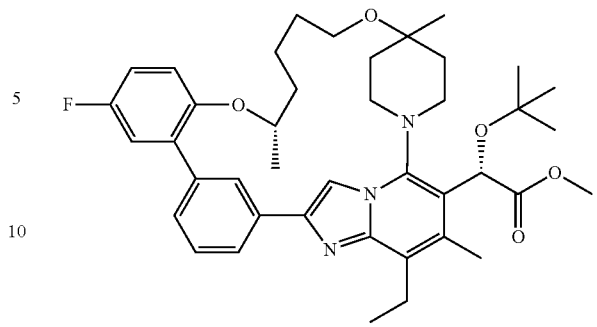

Methyl(2S)-2-(tert-butoxy)-2-[(22S)-5-ethyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Methyl(2S)-2-(tert-butoxy)-2-[(22S)-5-ethenyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (30 mg, 0.044 mmol, 1.0 equiv) was dissolved in MeOH (439 µl). To this solution was added Pd/C (4.67 mg, 4.39 µmol, 0.1 equiv) and stirred under H$_2$ balloon for 2 hours. The solid was filtered off through the celite. The filter was concentrated and the residue was used as is. LCMS (ESI, M+1): 686.4.

Example 55

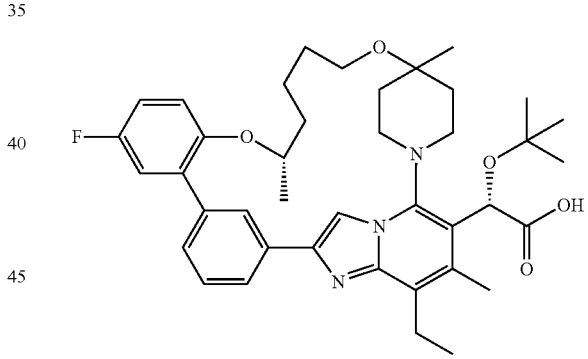

(2S)-2-(tert-Butoxy)-2-[(22S)-5-ethyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 6.81% yield from methyl(2S)-2-(tert-butoxy)-2-[(22S)-5-ethyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.17-8.10 (m, 1H), 7.99 (s, 1H), 7.53 (t, J=7.7 Hz, 1H), 7.34 (d, J=7.7 Hz, 1H), 7.23-7.13 (m, 3H), 6.00 (br. s., 1H), 4.61

(br. s., 1H), 3.83 (t, J=11.7 Hz, 1H), 3.63 (t, J=10.8 Hz, 1H), 3.44 (d, J=7.3 Hz, 2H), 3.12 (d, J=8.4 Hz, 1H), 3.07-2.97 (m, 2H), 2.64 (d, J=8.1 Hz, 1H), 2.33 (s, 3H), 1.90-1.59 (m, 9H), 1.52 (br. s., 1H), 1.19 (br. s., 5H), 1.16 (s, 9H), 1.07 (d, J=6.2 Hz, 3H); LCMS (ESI, M+1): 672.4.

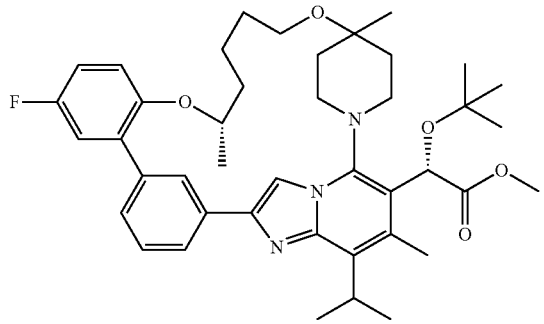 [SMILES: COC(=O)[C@@H](OC(C)(C)C)c1c(C)c(C(C)C)c2nc3cn2c1N1CCC(C)(CC1)OCCCC[C@H](C)Oc1ccc(F)cc1-c1cccc-3c1]

Methyl(2S)-2-(tert-butoxy)-2-[(22S)-17-fluoro-4,22,28-trimethyl-5-(propan-2-yl)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 91% yield from methyl(2S)-2-(tert-butoxy)-2-[(22S)-17-fluoro-4,22,28-trimethyl-5-(prop-1-en-2-yl)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for methyl(2S)-2-(tert-butoxy)-2-[(22S)-5-ethyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. LCMS (ESI, M+1): 700.4.

Example 56

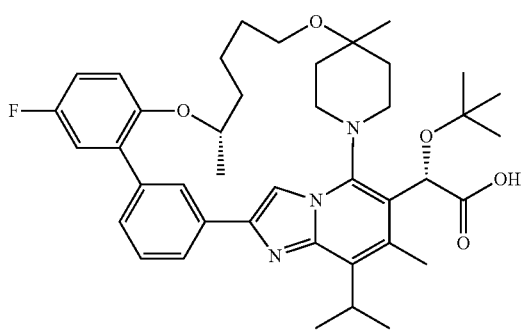 [SMILES: Cc1c([C@H](OC(C)(C)C)C(=O)O)c2n3cc(nc3c1C(C)C)-c1cccc(c1)-c1cc(F)ccc1O[C@@H](C)CCCCOC1(C)CCN2CC1]

(2S)-2-(tert-Butoxy)-2-[(22S)-17-fluoro-4,22,28-trimethyl-5-(propan-2-yl)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 98% yield from methyl(2S)-2-(tert-butoxy)-2-[(22S)-17-fluoro-4,22,28-trimethyl-5-(propan-2-yl)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, METHANOL-d$_4$) δ 8.15-8.10 (m, 2H), 8.00 (s, 1H), 7.51 (t, J=7.6 Hz, 1H), 7.28 (d, J=7.7 Hz, 1H), 7.13-7.07 (m, 2H), 7.06-7.00 (m, 1H), 6.01 (s, 1H), 4.55 (td, J=6.1, 3.6 Hz, 1H), 4.02 (t, J=11.2 Hz, 1H), 3.89-3.78 (m, 1H), 3.76-3.68 (m, 1H), 3.61-3.52 (m, 3H), 2.76 (d, J=10.2 Hz, 1H), 2.49 (s, 3H), 2.01-1.87 (m, 6H), 1.86-1.72 (m, 5H), 1.64 (d, J=5.2 Hz, 1H), 1.55 (dd, J=7.1, 0.9 Hz, 6H), 1.26 (s, 3H), 1.21 (s, 9H), 1.09 (d, J=6.0 Hz, 3H); LCMS (ESI, M+1): 686.4.

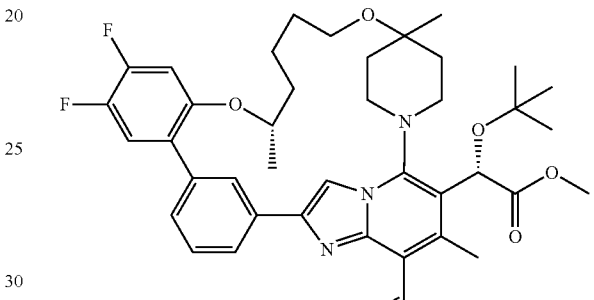

Methyl(2S)-2-(tert-butoxy)-2-[(22S)-5-ethenyl-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 84% yield from methyl(2S)-2-[(22S)-5-bromo-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetate following the procedure for methyl (2S)-2-(tert-butoxy)-2-[(22S)-5-ethenyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. LCMS (ESI, M+1): 702.4.

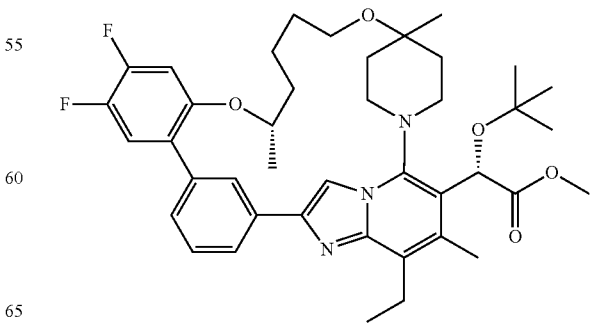

131

Methyl(2S)-2-(tert-butoxy)-2-[(22S)-5-ethyl-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 91% yield from methyl(2S)-2-(tert-butoxy)-2-[(22S)-5-ethenyl-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for methyl(2S)-2-(tert-butoxy)-2-[(22S)-5-ethyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. LCMS (ESI, M+1): 704.4.

Example 57

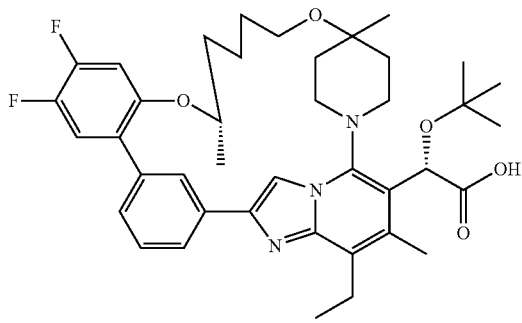 [SMILES: CCc1c(C)c([C@H](OC(C)(C)C)C(=O)O)c2n3cc(nc13)-c1cccc(c1)-c1cc(F)c(F)cc1O[C@@H](C)CCCCOC1(C)CCN2CC1]

(2S)-2-(tert-Butoxy)-2-[(22S)-5-ethyl-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 52.6% yield from methyl(2S)-2-(tert-butoxy)-2-[(22S)-5-ethyl-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.17-8.10 (m, 1H), 7.99 (s, 1H), 7.53 (t, J=7.7 Hz, 1H), 7.34 (d, J=7.7 Hz, 1H), 7.23-7.13 (m, 3H), 6.00 (br. s., 1H), 4.61 (br. s., 1H), 3.83 (t, J=11.7 Hz, 1H), 3.63 (t, J=10.8 Hz, 1H), 3.44 (d, J=7.3 Hz, 2H), 3.12 (d, J=8.4 Hz, 1H), 3.07-2.97 (m, 2H), 2.64 (d, J=8.1 Hz, 1H), 2.33 (s, 3H), 1.90-1.59 (m, 9H), 1.52 (br. s., 1H), 1.19 (d, J=2.9 Hz, 5H), 1.16 (s, 9H), 1.07 (d, J=6.2 Hz, 3H); LCMS (ESI, M+1): 690.4.

132

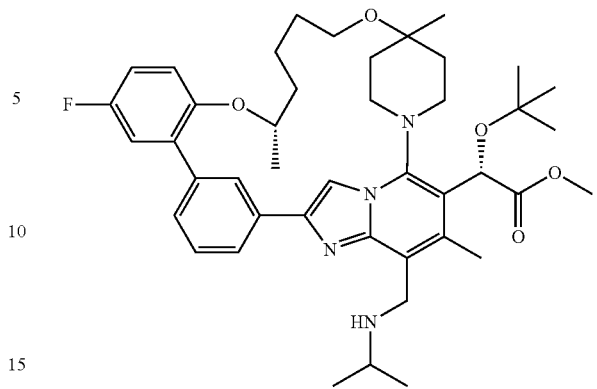

Methyl(2S)-2-(tert-butoxy)-2-[(22S)-17-fluoro-4,22,28-trimethyl-5-{[(propan-2-yl)amino]methyl}-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Methyl(2S)-2-(tert-butoxy)-2-[(22S)-17-fluoro-5-formyl-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (40 mg, 0.058 mmol, 1.0 equiv) was mixed with propan-2-amine (6.90 mg, 0.117 mmol, 2.0 equiv) in Tetrahydrofuran (583 µl) and Methanol (146 µl). The solution was stirred for 2 hours. LCMS show about 50% conversion to imine. Then to this solution was added sodium cyanoborohydride (21.99 mg, 0.350 mmol, 6.0 equiv) and stirred for 2 hours. The mixture was used for next reaction directly. LCMS (ESI, M+1): 729.4.

Example 58

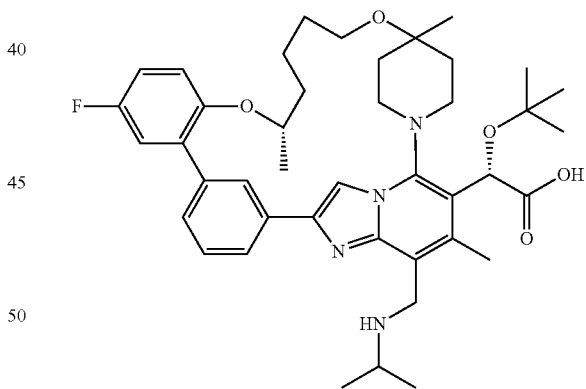

(2S)-2-(tert-Butoxy)-2-[(22S)-17-fluoro-4,22,28-trimethyl-5-{[(propan-2-yl)amino]methyl}-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 47.7% yield from methyl(2S)-2-(tert-butoxy)-2-[(22S)-17-fluoro-4,22,28-trimethyl-5-{[(propan-2-yl)amino]methyl}-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo

[26.2.2.1⁶,⁹.1¹⁰,¹⁴.0²,⁷.0¹⁵,²⁰]tetratriaconta-2,4,6(34),8,10 (33),11,13,15(20),16,18-decaen-3-yl]acetic acid. ¹H NMR (500 MHz, DMSO-d₆) δ 8.16 (s, 1H), 8.04 (d, J=7.7 Hz, 1H), 7.94 (s, 1H), 7.51 (t, J=7.9 Hz, 1H), 7.32 (d, J=7.3 Hz, 1H), 7.21 (d, J=9.2 Hz, 1H), 7.12 (d, J=5.9 Hz, 2H), 5.72 (br. s., 1H), 4.55 (br. s., 1H), 4.43 (d, J=12.5 Hz, 1H), 4.32 (d, J=11.7 Hz, 1H), 3.79 (br. s., 1H), 3.52-3.31 (m, 6H), 2.63 (d, J=8.4 Hz, 1H), 2.42 (s, 3H), 1.91-1.54 (m, 10H), 1.42 (d, J=5.5 Hz, 3H), 1.30 (d, J=6.2 Hz, 3H), 1.16 (s, 3H), 1.13 (s, 9H), 0.97 (d, J=5.9 Hz, 3H); LCMS (ESI, M+1): 715.4.

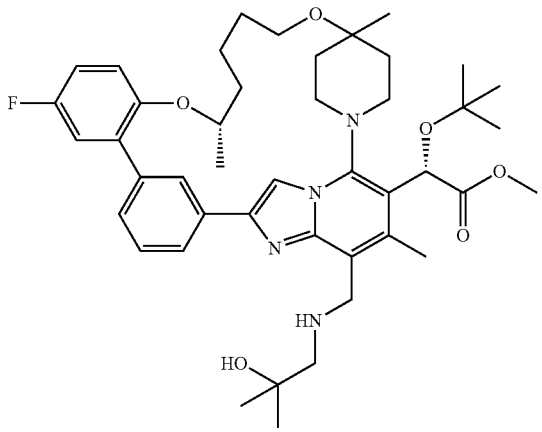 [SMILES: COC(=O)[C@@H](OC(C)(C)C)c1c(C)c(CNCC(C)(C)O)c2nc3cn2c1N1CCC(C)(CC1)OCCCC[C@H](C)Oc1ccc(F)cc1-c1cccc-3c1]

Methyl(2S)-2-(tert-butoxy)-2-[(22S)-17-fluoro-5-{[(2-hydroxy-2-methylpropyl)amino]methyl}-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetate Prepared from methyl(2S)-2-(tert-butoxy)-2-[(22S)-17-fluoro-5-formyl-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetate following the procedure for methyl(2S)-2-(tert-butoxy)-2-[(22S)-17-fluoro-4,22,28-trimethyl-5-{[(propan-2-yl)amino]methyl}-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetate. LCMS (ESI, M+1): 759.4.

Example 59

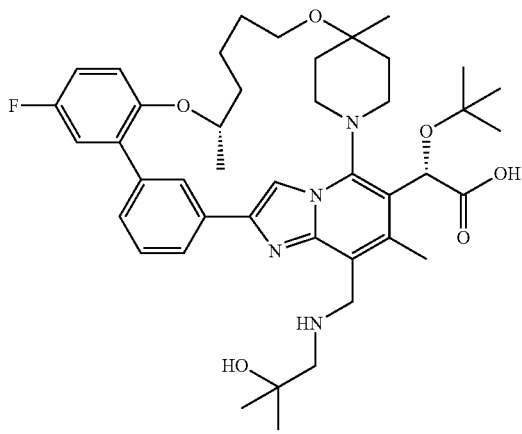 [SMILES: Cc1c([C@H](OC(C)(C)C)C(=O)O)c2n3cc(nc3c1CNCC(C)(C)O)-c1cccc(c1)-c1cc(F)ccc1O[C@@H](C)CCCCOC1(C)CCN2CC1]

(2S)-2-(tert-Butoxy)-2-[(22S)-17-fluoro-5-{[(2-hydroxy-2-methylpropyl)amino]methyl}-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetic acid Prepared in 89.0% yield from methyl(2S)-2-(tert-butoxy)-2-[(22S)-17-fluoro-5-{[(2-hydroxy-2-methylpropyl)amino]methyl}-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetic acid. ¹H NMR (500 MHz, DMSO-d₆) δ 8.18-8.11 (m, 2H), 7.98-7.93 (m, 1H), 7.52 (t, J=7.7 Hz, 1H), 7.33 (d, J=7.3 Hz, 1H), 7.25-7.12 (m, 3H), 5.71 (br. s., 1H), 4.62 (br. s., 1H), 4.14-4.02 (m, 2H), 3.92-3.81 (m, 1H), 3.74 (br. s., 1H), 3.56-3.41 (m, 6H), 2.64 (d, J=10.6 Hz, 1H), 2.39 (s, 3H), 1.93 (d, J=12.8 Hz, 1H), 1.81 (d, J=13.2 Hz, 4H), 1.74-1.72 (m, 1H), 1.63 (br. s., 4H), 1.19 (s, 3H), 1.11 (s, 9H), 1.08 (d, J=4.4 Hz, 9H); LCMS (ESI, M+1): 745.4.

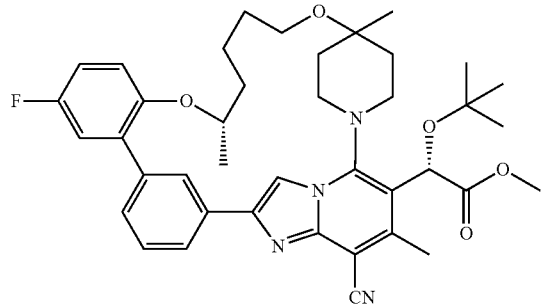 [SMILES: COC(=O)[C@@H](OC(C)(C)C)c1c(C)c(C#N)c2nc3cn2c1N1CCC(C)(CC1)OCCCC[C@H](C)Oc1ccc(F)cc1-c1cccc-3c1]

Methyl(2S)-2-(tert-butoxy)-2-[(22S)-5-cyano-17-fluoro-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetate Methyl(2S)-2-(tert-butoxy)-2-[(22S)-5,8-dibromo-17-fluoro-4,22,28-trimethyl-21,27-dioxa-1,7,34-triazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl]acetate (50 mg, 0.061 mmol, 1.0 equiv) was placed in a microwave tube, followed by zinc (0.401 mg, 6.13 μmol, 0.1 equiv), dicyanozinc (14.40 mg, 0.123 mmol, 2.0 equiv), and Pd(dppf)Cl₂ (50.1 mg, 0.061 mmol, 1.0 equiv). To this mixture was added DMAC (681 μl) and degassed, sealed, placed in microwave, and stirred for 2 hours at 150° C. Then it was diluted by 10 mL EA, washed by NaHCO3, dried over MgSO4, concentrated to give the pure enough product. LCMS (ESI, M+1): 683.4.

Example 60

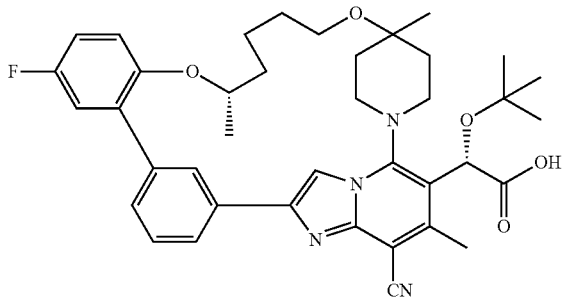 [SMILES: Cc1c([C@H](OC(C)(C)C)C(=O)O)c2n3cc(nc3c1C#N)-c1cccc(c1)-c1cc(F)ccc1O[C@@H](C)CCCCOC1(C)CCN2CC1]

(2S)-2-(tert-Butoxy)-2-[(22S)-5-cyano-17-fluoro-4, 22,28-trimethyl-21,27-dioxa-1,7,34-triazahexacyclo [26.2.2.1$^{6,9}$.1$^{10,14}$.0$^{2,7}$.0$^{15,20}$]tetratriaconta-2,4,6 (34),8,10(33),11,13,15(20),16,18-decaen-3-yl]acetic acid Prepared in 54.4% yield from methyl(2S)-2-(tert-butoxy)-2-[(22S)-5-cyano-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^{1}$H NMR (500 MHz, DMSO-d$_6$) δ 8.19 (s, 1H), 8.15-8.08 (m, 2H), 7.57 (t, J=7.7 Hz, 1H), 7.40 (d, J=7.3 Hz, 1H), 7.22 (d, J=9.5 Hz, 1H), 7.16 (d, J=5.5 Hz, 2H), 5.86 (br. s., 1H), 4.61 (br. s., 1H), 3.81 (t, J=12.3 Hz, 1H), 3.61 (t, J=11.4 Hz, 1H), 3.43 (br. s., 3H), 3.23-3.15 (m, 1H), 2.73 (br. s., 1H), 2.63 (s, 3H), 1.96-1.60 (m, 9H), 1.53 (br. s., 1H), 1.20 (s, 3H), 1.17 (s, 9H), 1.06 (d, J=5.9 Hz, 3H); LCMS (ESI, M+1): 669.3.

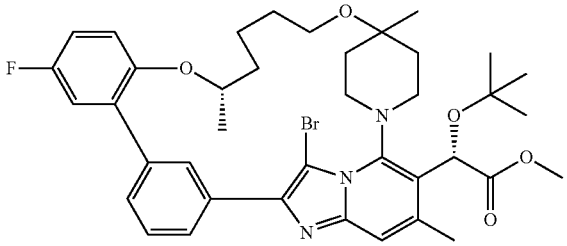 [SMILES: COC(=O)[C@@H](OC(C)(C)C)c1c(C)cc2nc3c(Br)n2c1N1CCC(C)(CC1)OCCCC[C@H](C)Oc1ccc(F)cc1-c1cccc-3c1]

Methyl(2S)-2-[(22S)-8-bromo-17-fluoro-4,22,28-trimethyl-21,27-dioxa-1,7,34-triazahexacyclo [26.2.2.1$^{6,9}$.1$^{10,14}$.0$^{2,7}$.0$^{15,20}$]tetratriaconta-2, 4, 6(34),8,10(33),11,13,15(20),16,18-decaen-3-yl]-2-(tert-butoxy)acetate Prepared in 87.0% yield from methyl(2S)-2-(tert-butoxy)-2-[(22S)-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for methyl(2S)-2-[(22S)-8-bromo-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2, 4,6(34),8,10(33),11,13,15(20),16,18-decaen-3-yl]-2-(tert-butoxy)acetate. LCMS (ESI, M+1): 736.3.

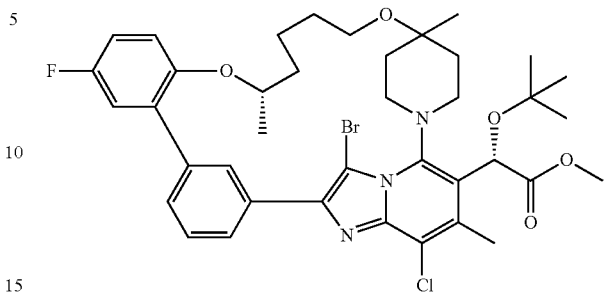

Methyl(2S)-2-[(22S)-8-bromo-5-chloro-17-fluoro-4, 22,28-trimethyl-21,27-dioxa-1,7,34-triazahexacyclo [26.2.2.1$^{6,9}$.1$^{10,14}$.0$^{2,7}$.0$^{15,20}$]tetratriaconta-2, 4, 6(34),8,10(33),11,13,15(20),16,18-decaen-3-yl]-2-(tert-butoxy)acetate Methyl(2S)-2-[(22S)-8-bromo-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20), 16,18-decaen-3-yl]-2-(tert-butoxy)acetate (50 mg, 0.068 mmol, 1.0 equiv) was dissolved in acetonitrile (1357 µl). To this solution was added 1-chloropyrrolidine-2,5-dione (9.06 mg, 0.068 mmol, 1.0 equiv) and stirred for 3 hours. The mixture was diluted by 15 mL Ethyl Acetate, washed by NaHCO3 and brine. The organic layer was dried, concentrated, and purified on ISCO 12 g column (0-100% EtOAc [2% TEA]/Hexane) to give the product (30 mg, 0.039 mmol, 57.3% yield).

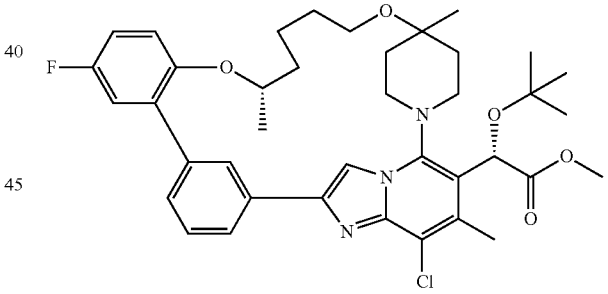

Methyl(2S)-2-(tert-butoxy)-2-[(22S)-5-chloro-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Methyl(2S)-2-[(22S)-8-bromo-5-chloro-17-fluoro-4,22, 28-trimethyl-21,27-dioxa-1,7,34-triazahexacyclo[26.2.2. 1$^{6,9}$.1$^{10,14}$.0$^{2,7}$.0$^{15,20}$]tetratriaconta-2,4,6(34),8,10(33),11, 13,15(20),16,18-decaen-3-yl]-2-(tert-butoxy)acetate (45 mg, 0.058 mmol, 1 equiv), 1-butanol (17.30 mg, 0.233 mmol, 4 equiv) were mixed in DMF (1.1 mL) and water (0.11 mL). To this solution was added Pd(OAc)$_2$ (13.10 mg, 0.058 mmol, 1.0 equiv), Sphos (48 mg, 0.12 mmol, 2 equiv) and cesium carbonate (28.5 mg, 0.088 mmol, 1.5 equiv). The solution was degassed by N2 for five minutes. Then it was stirred at 80° C. for 2 hours. The mixture was loaded onto 12 g ISCO column and purified by 0-100% Ethyl Acetate[2% TEA]/Hexane to provide the product (25 mg, 61.9%) as a brown oil. LCMS (ESI, M+1): 692.3

Example 61

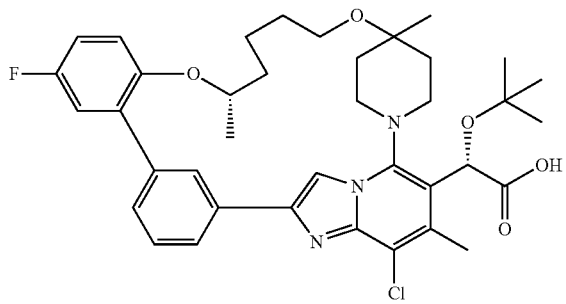 [SMILES: Cc1c([C@H](OC(C)(C)C)C(=O)O)c2n3cc(nc3c1Cl)-c1cccc(c1)-c1cc(F)ccc1O[C@@H](C)CCCCOC1(C)CCN2CC1]

(2S)-2-(tert-Butoxy)-2-[(22S)-5-chloro-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 19.1% yield from methyl(2S)-2-(tert-butoxy)-2-[(22S)-5-chloro-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.31 (s, 1H), 7.84 (d, J=7.7 Hz, 1H), 7.57 (t, J=7.9 Hz, 1H), 7.44 (d, J=7.7 Hz, 1H), 7.33 (s, 1H), 7.27-7.21 (m, 1H), 7.17 (d, J=8.8 Hz, 2H), 5.75 (br. s., 1H), 4.60 (d, J=4.4 Hz, 1H), 4.01-3.86 (m, 2H), 3.50 (br. s., 1H), 3.37 (br. s., 4H), 2.42 (s, 3H), 2.33 (br. s., 1H), 1.96 (d, J=13.2 Hz, 1H), 1.88-1.73 (m, 3H), 1.70-1.47 (m, 6H), 1.18 (s, 3H), 1.16 (s, 9H), 1.02 (d, J=5.9 Hz, 3H); LCMS (ESI, M+1): 678.3.

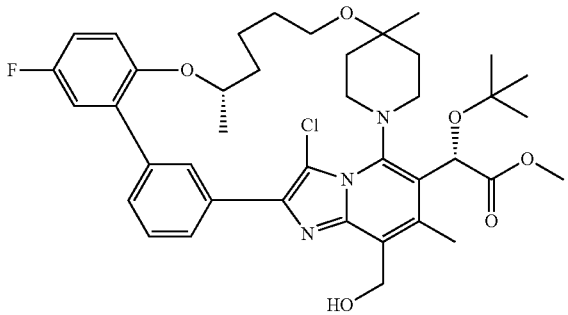 [SMILES: COC(=O)[C@@H](OC(C)(C)C)c1c(C)c(CO)c2nc3c(Cl)n2c1N1CCC(C)(CC1)OCCCC[C@H](C)Oc1ccc(F)cc1-c1cccc-3c1]

Methyl(2S)-2-(tert-butoxy)-2-[(22S)-8-chloro-17-fluoro-5-(hydroxymethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Prepared in 70.0% yield from Methyl(2S)-2-(tert-butoxy)-2-[(22S)-17-fluoro-5-(hydroxymethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for methyl(2S)-2-(tert-butoxy)-2-[(22S)-8-chloro-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate. LCMS (ESI, M+1): 722.3.

Example 62

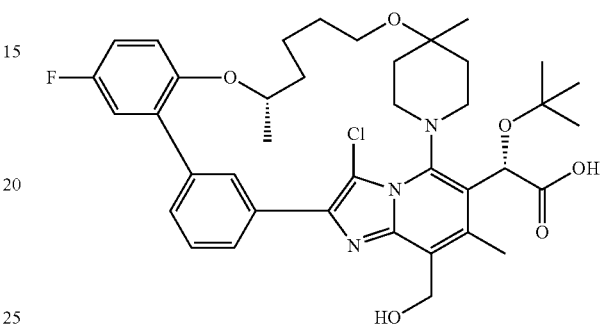

(2S)-2-(tert-Butoxy)-2-[(22S)-8-chloro-17-fluoro-5-(hydroxymethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 17.4% yield from methyl(2S)-2-(tert-butoxy)-2-[(22S)-8-chloro-17-fluoro-5-(hydroxymethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.33 (s, 1H), 7.90 (d, J=7.7 Hz, 1H), 7.60 (t, J=7.5 Hz, 1H), 7.47 (d, J=7.7 Hz, 1H), 7.25 (s, 2H), 7.20-7.13 (m, 3H), 7.05 (s, 1H), 5.96 (br. s., 1H), 5.01-4.95 (m, 1H), 4.93-4.88 (m, 1H), 4.61 (br. s., 1H), 4.05-3.90 (m, 2H), 3.52 (br. s., 1H), 3.38 (br. s., 2H), 2.46 (br. s., 3H), 2.35 (br. s., 1H), 2.02-1.59 (m, 8H), 1.21 (br. s., 3H), 1.19 (s, 9H), 1.04 (d, J=5.9 Hz, 3H); LCMS (ESI, M+1): 708.1.

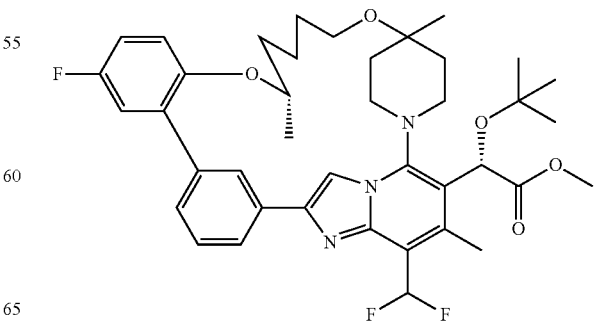

Methyl(2S)-2-(tert-butoxy)-2-[(22S)-5-(difluorom-
ethyl)-17-fluoro-4,22,28-trimethyl-21,27-dioxa-1,7,
34-triazahexacyclo[26.2.2.1⁶,⁹.1¹⁰,¹⁴.0²,⁷.0¹⁵,²⁰]
tetratriaconta-2,4,6(34),8,10(33),11,13,15(20),16,18-
decaen-3-yl]acetate Methyl(2S)-2-(tert-butoxy)-2-[(22S)-17-fluoro-5-formyl-
4,22,28-trimethyl-21,27-dioxa-1,7,34-triazahexacyclo
[26.2.2.1⁶,⁹.1¹⁰,¹⁴.0²,⁷.0¹⁵,²⁰]tetratriaconta-2,4,6(34),8,10
(33),11,13,15(20),16,18-decaen-3-yl]acetate (15 mg, 0.022
mmol, 1 equiv) was dissolved in DCE (0.2 mL). To this
solution was added DAST (24.19 µl, 0.131 mmol, 6 equiv)
and stirred for two hours. The mixture was diluted by 10 mL
ethyl acetate, washed by NaHCO3, dried over MgSO$_4$, and
concentrated down to afford a brown oil, which is used for the
next reaction without further purification. LCMS (ESI, M+1):
708.4.

Example 63

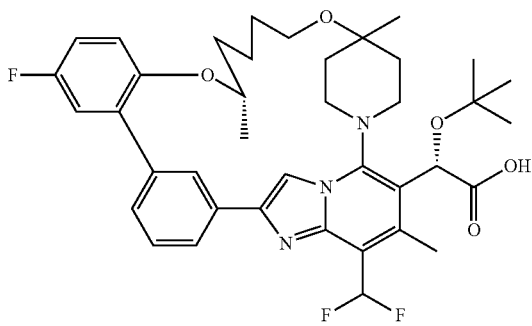 [SMILES: Cc1c([C@H](OC(C)(C)C)C(=O)O)c2n3cc(nc3c1C(F)F)-c1cccc(c1)-c1cc(F)ccc1O[C@@H](C)CCCCOC1(C)CCN2CC1]

(2S)-2-(tert-Butoxy)-2-[(22S)-5-(difluoromethyl)-
17-fluoro-4,22,28-trimethyl-21,27-dioxa-1,7,34-
triazahexacyclo[26.2.2.1⁶,⁹.1¹⁰,¹⁴.0²,⁷.0¹⁵,²⁰]tetra-
triaconta-2,4,6(34),8,10(33),11,13,15(20),16,18-
decaen-3-yl]acetic acid Prepared in 19.1% yield from methyl(2S)-2-(tert-butoxy)-
2-[(22S)-5-(difluoromethyl)-17-fluoro-4,22,28-trimethyl-
21,27-dioxa-1,7,34-triazahexacyclo[26.2.2.1⁶,⁹.1¹⁰,¹⁴.0²,⁷.
0¹⁵,²⁰]tetratriaconta-2,4,6(34),8,10(33),11,13,15(20),16,18-
decaen-3-yl]acetate following the procedure for (2S)-2-(tert-
butoxy)-2-[(22S)-8-chloro-4,17,22,28-tetramethyl-21,27-
dioxa-1,7,34-triazahexacyclo[26.2.2.1⁶,⁹.1¹⁰,¹⁴.0²,⁷.0¹⁵,²⁰]
tetratriaconta-2,4,6(34),8,10(33),11,13,15(20),16,18-
decaen-3-yl]acetic acid. $^1$H NMR (500 MHz, DMSO-d$_6$) δ
8.19 (s, 1H), 8.15 (d, J=7.7 Hz, 1H), 8.06 (s, 1H), 7.97-7.65
(m, 1H), 7.57-7.51 (m, 1H), 7.38 (d, J=7.7 Hz, 1H), 7.22 (d,
J=7.3 Hz, 1H), 7.17 (d, J=4.8 Hz, 2H), 5.83 (br. s., 1H), 4.62
(br. s., 1H), 3.83 (br. s., 1H), 3.57 (d, J=11.7 Hz, 1H), 3.44 (d,
J=9.2 Hz, 4H), 2.68 (d, J=10.6 Hz, 1H), 2.53 (br. s., 3H),
1.94-1.58 (m, 9H), 1.53 (br. s., 1H), 1.19 (s, 3H), 1.15 (s, 9H),
1.07 (d, J=5.9 Hz, 3H); LCMS (ESI, M+1): 678.3.

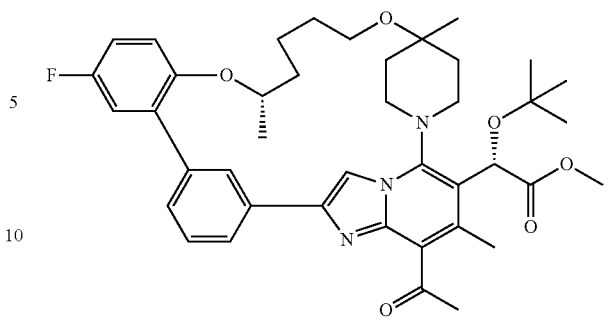

Methyl(2S)-2-[(22S)-5-acetyl-17-fluoro-4,22,28-
trimethyl-21,27-dioxa-1,7,34-triazahexacyclo
[26.2.2.1⁶,⁹.1¹⁰,¹⁴.0²,⁷.0¹⁵,²⁰]tetratriaconta-2, 4,
6(34),8,10(33),11,13,15(20),16,18-decaen-3-yl]-2-
(tert-butoxy)acetate Methyl(2S)-2-(tert-butoxy)-2-[(22S)-17-fluoro-4,22,28-
trimethyl-5-(prop-1-en-2-yl)-21,27-dioxa-1,7,34-triaza-
hexacyclo[26.2.2.1⁶,⁹.1¹⁰,¹⁴.0²,⁷.0¹⁵,²⁰]tetratriaconta-2,4,6
(34),8,10(33),11,13,15(20),16,18-decaen-3-yl]acetate (45
mg, 0.064 mmol, 1 equiv) was dissolved in dioxane (1934 µl)
and water (645 µl). To this solution was added sodium perio-
date (444 mg, 2.076 mmol, 3.5 equiv) and 4% osmium tet-
raoxide (372 µl, 0.030 mmol, 0.05 equiv). The mixture was
stirred at r.t. for 2 hours. Yellow solid was observed in the
meantime. To the mixture was added water (20 mL) and EA
(20 mL). The aqueous layer was separated. the organic layer
was washed by brine, dried over MgSO4, filtered and con-
centrated to give a yellow oil, which is used as is for the next
reaction. LCMS (ESI, M+1): 700.3.

Example 64

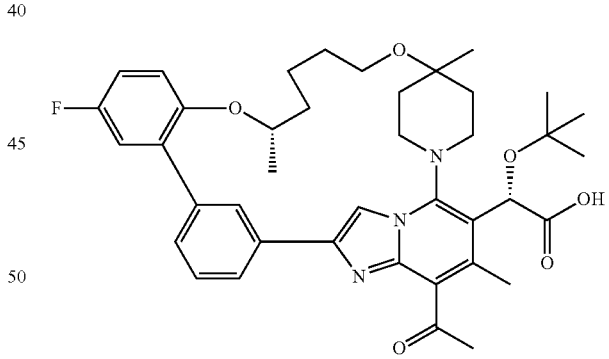

(2S)-2-[(22S)-5-Acetyl-17-fluoro-4,22,28-trimethyl-
21,27-dioxa-1,7,34-triazahexacyclo[26.2.2.1⁶,⁹.
1¹⁰,¹⁴.0²,⁷.0¹⁵,²⁰]tetratriaconta-2,4,6(34),8,10(33),
11,13,15(20),16,18-decaen-3-yl]-2-(tert-butoxy)ace-
tic acid Prepared in 4.3% yield from methyl(2S)-2-[(22S)-5-
acetyl-17-fluoro-4,22,28-trimethyl-21,27-dioxa-1,7,34-tri-
azahexacyclo[26.2.2.1⁶,⁹.1¹⁰,¹⁴.0²,⁷.0¹⁵,²⁰]tetratriaconta-2,
4,6(34),8,10(33),11,13,15(20),16,18-decaen-3-yl]-2-(tert-
butoxy)acetate following the procedure for (2S)-2-(tert-
butoxy)-2-[(22S)-8-chloro-4,17,22,28-tetramethyl-21,27- dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.16 (s, 1H), 8.09 (d, J=7.7 Hz, 1H), 8.03 (s, 1H), 7.53 (t, J=7.5 Hz, 1H), 7.36 (d, J=7.7 Hz, 1H), 7.23-7.13 (m, 3H), 5.85 (br. s., 1H), 4.61 (br. s., 1H), 3.87-3.79 (m, 1H), 3.63-3.55 (m, 1H), 3.45 (br. s., 3H), 3.33 (br. s., 1H), 2.76 (s, 3H), 2.67 (d, J=8.1 Hz, 1H), 2.28 (s, 3H), 1.89-1.61 (m, 9H), 1.51 (br. s., 1H), 1.19 (s, 3H), 1.15 (s, 9H), 1.06 (d, J=5.9 Hz, 3H); LCMS (ESI, M+1): 686.4.

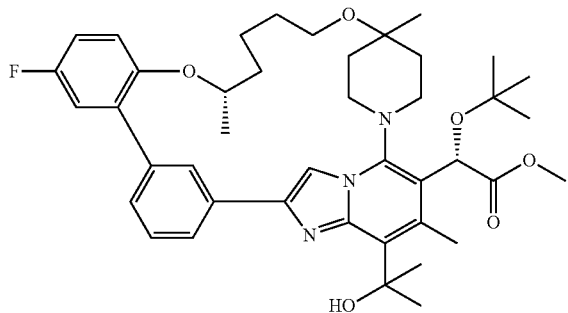 [SMILES: COC(=O)[C@@H](OC(C)(C)C)c1c(C)c(C(C)(C)O)c2nc3cn2c1N1CCC(C)(CC1)OCCCC[C@H](C)Oc1ccc(F)cc1-c1cccc-3c1]

Methyl(2S)-2-(tert-butoxy)-2-[(22S)-17-fluoro-5-(2-hydroxypropan-2-yl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate Methyl(2S)-2-(tert-butoxy)-2-[(22S)-17-fluoro-4,22,28-trimethyl-5-(prop-1-en-2-yl)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (50 mg, 0.072 mmol, 1 equiv) was dissolved in ethanol (0.86 mL). To this solution was added iron(II) phthalacyanine (4.07 mg, 7.16 μmol, 0.1 equiv) and sodium borohydride (5.42 mg, 0.143 mmol, 2 equiv). The reaction was stirred under air for 1 hour. No reaction. The mixture was then placed under oxygen balloon and stirred for 2 hours. To this solution was added 10 mg catalyst and 10 mg sodium borohydride and stirred under the oxygen balloon again. It was found that the vial emitted heat and the solution of the reaction turned to dark purple and back to blue again. The reaction was stirred overnight. The reaction completed 30% by LCMS. It was used as is for the next reaction. LCMS (ESI, M+1): 716.4.

Example 65

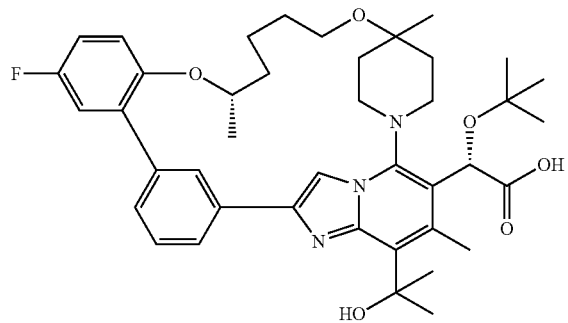 [SMILES: Cc1c([C@H](OC(C)(C)C)C(=O)O)c2n3cc(nc3c1C(C)(C)O)-c1cccc(c1)-c1cc(F)ccc1O[C@@H](C)CCCCOC1(C)CCN2CC1]

(2S)-2-(tert-Butoxy)-2-[(22S)-17-fluoro-5-(2-hydroxypropan-2-yl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid Prepared in 11.7% yield from methyl(2S)-2-(tert-butoxy)-2-[(22S)-17-fluoro-5-(2-hydroxypropan-2-yl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate following the procedure for (2S)-2-(tert-butoxy)-2-[(22S)-8-chloro-4,17,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid. $^1$H NMR (500 MHz, DMSO-d$_6$) δ 8.15 (s, 1H), 8.00 (d, J=7.3 Hz, 1H), 7.92 (s, 1H), 7.56 (t, J=7.7 Hz, 1H), 7.38 (d, J=7.3 Hz, 1H), 7.24-7.13 (m, 3H), 5.98 (br. s., 1H), 4.61 (br. s., 1H), 3.80 (t, J=11.6 Hz, 1H), 3.60 (t, J=12.1 Hz, 1H), 3.44 (d, J=14.7 Hz, 4H), 3.25 (br. s., 1H), 2.64 (d, J=9.5 Hz, 1H), 2.42 (s, 3H), 1.91-1.75 (m, 5H), 1.71 (s, 10H), 1.52 (br. s., 1H), 1.19 (s, 3H), 1.15 (s, 9H), 1.07 (d, J=5.9 Hz, 3H); LCMS (ESI, M+1): 686.4.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula I

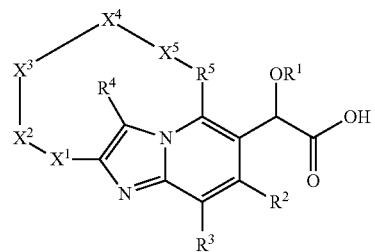

I where:
R$^1$ is hydrogen, alkyl, or cycloalkyl;
R$^2$ is hydrogen or alkyl;
R$^3$ is hydrogen, halo, alkyl, or (alkyl)SO$_2$NH—;
R$^4$ is hydrogen or alkyl;
R$^5$ is azetidinyl, pyrrolidinyl, piperidinyl, piperazinyl, morpholinyl, homopiperidinyl, homopiperazinyl, or homomorpholinyl substituted with 0-3 substituents selected from halo, alkyl, haloalkyl, hydroxy, alkoxy, and haloalkoxy;
Ar$^1$ is phenyl substituted with 0-3 substituents selected from cyano, halo, alkyl, haloalkyl, alkoxy, and haloalkoxy;
Ar$^2$ is imidazolyl or oxadiazolyl and is substituted with 0-3 substituents selected from halo and alkyl;
X$^1$ is CONHCH$_2$—, Ar$^1$, or —(Ar$^2$)CH$_2$—;
X$^2$ is phenyl substituted with 0-3 substituents selected from cyano, halo, alkyl, haloalkyl, alkoxy, and haloalkoxy;
X$^3$ is —CH—, —CH$_2$—, or —O—;

$X^4$ is alkylene or alkenylene; and
$X^5$ is —CH—, —CH$_2$—, or —O—;
or a pharmaceutically acceptable salt thereof.

2. A compound of claim 1 where IV is alkyl; $R^2$ is alkyl; $R^3$ is hydrogen, halo, alkyl, or (alkyl)SO$_2$NH—; $R^4$ is hydrogen; $R^5$ is azetidinyl, pyrrolidinyl, piperidinyl, piperazinyl, morpholinyl, homopiperidinyl, homopiperazinyl, or homomorpholinyl substituted with 0-3 substituents selected from halo, alkyl, haloalkyl, hydroxy, alkoxy, and haloalkoxy; $Ar^1$ is phenyl substituted with 0-3 substituents selected from cyano, halo, alkyl, haloalkyl, alkoxy, and haloalkoxy; $Ar^2$ is imidazolyl or oxadiazolyl and is substituted with 0-3 substituents selected from halo and alkyl; $X^1$ is CONHCH$_2$—, $Ar^1$, or $(Ar^2)$CH$_2$—; $X^2$ is phenyl substituted with 0-3 substituents selected from cyano, halo, alkyl, haloalkyl, alkoxy, and haloalkoxy; $X^3$ is —CH—, —CH$_2$—, or —O—; $X^4$ is alkylene or alkenylene; and $X^5$ is —CH—, —CH$_2$—, or —O—; or a pharmaceutically acceptable salt thereof.

3. A compound of claim 2 where $R^5$ is piperidinyl substituted with 0-3 alkyl substituents; $Ar^1$ is phenyl substituted with 0-3 substituents selected from cyano, halo, alkyl, haloalkyl, alkoxy, and haloalkoxy; $Ar^2$ is imidazolyl or oxadiazolyl substituted with 0-3 substituents selected from halo and alkyl; $X^1$ is CONHCH$_2$—, $Ar^1$, or $(Ar^2)$CH$_2$—; $X^2$ is phenyl substituted with 0-3 substituents selected from cyano, halo, alkyl, haloalkyl, alkoxy, and haloalkoxy; $X^3$ is —CH—, —CH$_2$—, or —O—; $X^4$ is alkylene or alkenylene; and $X^5$ is —CH—, —CH$_2$—, or —O—; or a pharmaceutically acceptable salt thereof.

4. A compound of claim 1 where $R^1$ is alkyl, $R^2$ is alkyl, $R^3$ is hydrogen, halo, alkyl, or (alkyl)SO$_2$NH—, and $R^4$ is hydrogen or alkyl.

5. A compound of claim 1 where $R^5$ is piperidinyl substituted with 0-3 substituents selected from halo, alkyl, haloalkyl, hydroxy, alkoxy, and haloalkoxy.

6. A compound of claim 5 where $R^5$ is piperidinyl substituted with 0-3 alkyl substituents.

7. A compound of claim 1 where $X^1$ is $Ar^1$.

8. A compound of claim 1 where $X^1$ is CONHCH$_2$— or $(Ar^2)$CH$_2$—.

9. A compound of claim 1 where $X^3$ is —O—, $X^4$ is alkylene or alkenylene; and $X^5$ is —O—.

10. A compound of claim 1 selected from the group consisting of
(2S)-2-(tert-Butoxy)-2-{4,25-dimethyl-10-oxo-19-oxa-1,7,11,30-tetraazapentacyclo[23.2.2.1$^{6,9}$.0$^{2,7}$.0$^{13,18}$]triaconta-2,4,6(3),8,13 (18),14,16-heptaen-3-yl}acetic acid;
(2S)-2-(tert-Butoxy)-2-{15-fluoro-4,26-dimethyl-10-oxo-19-oxa-1,7,11,31-tetraazapentacyclo[24.2.2.1$^{6,9}$.0$^{2,7}$.0$^{13,18}$]hentriaconta-2,4,6(31),8,13 (18),14,16-heptaen-3-yl}acetic acid;
(2S)-2-(tert-Butoxy)-2-{15-fluoro-4,26-dimethyl-10-oxo-19,25-dioxa-1,7,11,31-tetraazapentacyclo [24.2.2.1$^{6,9}$.0$^{2,7}$.0$^{13,18}$]hentriaconta-2,4,6(31),8,13 (18),14,16-heptaen-3-yl}acetic acid;
(2S)-2-(tert-Butoxy)-2-{4,28-dimethyl-21,27,33-trioxa-1,7,11,12,34-pentaazahexacyclo[26.2.2.1$^{6,9}$.1$^{10,13}$.0$^{2,7}$.0$^{15,20}$]tetratriaconta-2,4,6(34),8,10,12,15(20),16,18-nonaen-3-yl}acetic acid;
((2S)-2-(tert-Butoxy)-2-{12-chloro-17-fluoro-4,28-dimethyl-21,27-dioxa-1,7,11,33,34-pentaazahexacyclo [26.2.2.1$^{6,9}$.1$^{10,13}$.0$^{2,7}$.0$^{15,20}$]tetratriaconta-2,4,6(34),8,10(33),12,15(20),16,18-nonaen-3-yl}acetic acid;
(2S)-2-(tert-Butoxy)-2-[(22S)-18-fluoro-4,22,28-trimethyl-21,27-dioxa-1,7,34-triazahexacyclo[26.2.2. 1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid;
(2S)-2-(tert-Butoxy)-2-[(22S)-4,17,22,28-tetramethyl-21,27-dioxa-1,7,34-triazahexacyclo[26.2.2.1$^{6,9}$.1$^{10,14}$. 0$^{2,7}$.0$^{15,20}$]tetratriaconta-2,4,6(34),8,10(33),11,13,15 (20),16,18-decaen-3-yl]acetic acid;
(2S)-2-(tert-Butoxy)-2-[(22S)-4,17,22,28-tetramethyl-21,27-dioxa-1,7,34-triazahexacyclo[26.2.2.1$^{6,9}$.1$^{10,14}$. 0$^{2,7}$.0$^{15,20}$]tetratriaconta-2,4,6(34),8,10(33),11,13,15 (20),16,18-decaen-3-yl]acetic acid;
(2S)-2-(tert-Butoxy)-2-[(22S)-4,17,22,28-tetramethyl-21,27-dioxa-1,7,34-triazahexacyclo[26.2.2.1$^{6,9}$.1$^{10,14}$. 0$^{2,7}$.0$^{15,20}$]tetratriaconta-2,4,6(34),8,10(33),11,13,15 (20),16,18,24-undecaen-3-yl]acetic acid;
(2S)-2-(tert-Butoxy)-2-[(22S)-17-fluoro-4,22,28-trimethyl-21,27-dioxa-1,7,34-triazahexacyclo[26.2.2. 1$^{6,9}$.1$^{10,14}$.0$^{2,7}$.0$^{15,20}$]tetratriaconta-2,4,6(34),8,10(33), 11,13,15(20),16,18-decaen-3-yl]acetic acid;
(2S)-2-(tert-Butoxy)-2-[(22S)-17,18-difluoro-4,22,28-trimethyl-21,27-dioxa-1,7,34-triazahexacyclo[26.2.2. 1$^{6,9}$.1$^{10,13}$.0$^{2,7}$.0$^{15,20}$]tetratriaconta-2,4,6(34),8,10(33), 11,13,15(20),16,18,24-undecaen-3-yl]acetic acid;
(2S)-2-(tert-Butoxy)-2-[(22S)-17,18-difluoro-4,22,28-trimethyl-21,27-dioxa-1,7,34-triazahexacyclo[26.2.2. 1$^{6,9}$.1$^{10,14}$.0$^{2,7}$.0$^{15,20}$]tetratriaconta-2,4,6(34),8,10(33), 11,13,15(20),16,18,24-undecaen-3-yl]acetic acid;
(2S)-2-(tert-Butoxy)-2-[(22S)-17,18-difluoro-4,22,28-trimethyl-21,27-dioxa-1,7,34-triazahexacyclo[26.2.2. 1$^{6,9}$.1$^{10,14}$.0$^{2,7}$.0$^{15,20}$]tetratriaconta-2,4,6(34),8,10(33), 11,13,15(20),16,18-decaen-3-yl]acetic acid;
(2S)-2-(tert-Butoxy)-2-[(22S)-16,18-difluoro-4,22,28-trimethyl-21,27-dioxa-1,7,34-triazahexacyclo[26.2.2. 1$^{6,9}$.1$^{10,14}$.0$^{2,7}$.0$^{15,20}$]tetratriaconta-2,4,6(34),8,10(33), 11,13,15(20),16,18,24-undecaen-3-yl]acetic acid;
(2S)-2-(tert-Butoxy)-2-[(22S)-16,18-difluoro-4,22,28-trimethyl-21,27-dioxa-1,7,34-triazahexacyclo[26.2.2. 1$^{6,9}$.1$^{10,14}$.0$^{2,7}$.0$^{15,20}$]tetratriaconta-2,4,6 (34),8,10 (33),11,13,15(20),16,18,24-undecaen-3-yl]acetic acid;
(2S)-2-(tert-Butoxy)-2-[(22S)-16,18-difluoro-4,22,28-trimethyl-21,27-dioxa-1,7,34-triazahexacyclo[26.2.2. 1$^{6,9}$.1$^{10,14}$.0$^{2,7}$.0$^{15,20}$]tetratriaconta-2,4,6(34),8,10(33), 11,13,15(20),16,18-decaen-3-yl]acetic acid;
(2S)-2-(tert-Butoxy)-2-[(22S)-4,17,18,22,28-pentamethyl-21,27-dioxa-1,7,34-triazahexacyclo[26.2.2. 1$^{6,9}$.1$^{10,14}$.0$^{2,7}$.0$^{15,20}$]tetratriaconta-2,4,6(34),8,10(33), 11,13,15(20),16,18,24-undecaen-3-yl]acetic acid;
(2S)-2-(tert-Butoxy)-2-[(22S)-4,17,18,22,28-pentamethyl-21,27-dioxa-1,7,34-triazahexacyclo[26.2.2. 1$^{6,9}$.1$^{10,14}$.0$^{2,7}$.0$^{15,20}$]tetratriaconta-2,4,6(34),8,10(33), 11,13,15(20),16,18,24-undecaen-3-yl]acetic acid;
(2S)-2-(tert-Butoxy)-2-[(22S)-4,17,18,22,28-pentamethyl-21,27-dioxa-1,7,34-triazahexacyclo[26.2.2. 1$^{6,9}$.1$^{10,14}$.0$^{2,7}$.0$^{15,20}$]tetratriaconta-2,4,6(34),8,10(33), 11,13,15(20),16,18-decaen-3-yl]acetic acid;
(2S)-2-(tert-Butoxy)-2-[(22S)-17-fluoro-4,18,22,28-tetramethyl-21,27-dioxa-1,7,34-triazahexacyclo [26.2.2.1$^{6,9}$.1$^{10,14}$.0$^{2,7}$.0$^{15,20}$]tetratriaconta-2,4,6(34), 8,10(33),11,13,15(20),16,18-decaen-3-yl]acetic acid;
(2S)-2-(tert-Butoxy)-2-[(22S)-16-fluoro-4,18,22,28-tetramethyl-21,27-dioxa-1,7,34-triazahexacyclo [26.2.2.1$^{6,9}$.1$^{10,14}$.0$^{2,7}$.0$^{15,20}$]tetratriaconta-2,4,6(34), 8,10(33),11,13,15(20),16,18-decaen-3-yl]acetic acid;
(2S)-2-(tert-Butoxy)-2-[(22S)-8-chloro-4,17,22,28-tetramethyl-21,27-dioxa-1,7,34-triazahexacyclo [26.2.2.1$^{6,9}$.1$^{10,14}$.0$^{2,7}$.0$^{15,20}$]tetratriaconta-2,4,6(34), 8,10(33),11,13,15(20),16,18-decaen-3-yl]acetic acid;

(2S)-2-(tert-Butoxy)-2-[(22S)-8-chloro-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-8-chloro-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-8-chloro-4,17,18,22,28-pentamethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-8,17,18-trifluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-[(22S)-8-Bromo-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetic acid;

(2S)-2-[(22S)-8-Bromo-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetic acid;

(2S)-2-[(22S)-5-Bromo-8-chloro-17-fluoro-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetic acid;

(2S)-2-(tert-Butoxy)-2-[(22S)-17-fluoro-4,5,18,22,28-pentamethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-fluoro-5-methanesulfonamido-4,18,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-[(22S)-5-Bromo-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetic acid;

(2S)-2-(tert-Butoxy)-2-[(22S)-17-fluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S,24E)-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid;

(2S)-2-(tert-Butoxy)-2-[(22S)-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-[(22S)-5-Bromo-19-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetic acid;

(2S)-2-(tert-Butoxy)-2-[(22S)-19-fluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-5-ethenyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-fluoro-4,22,28-trimethyl-5-(pyridin-4-yl)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-fluoro-5-(4-fluorophenyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17,18-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-4,5,22,28-tetramethyl-17-(trifluoromethoxy)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-16,18-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-16,18-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17,19-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-butoxy)-2-[(22S)-16,17-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-16,17-difluoro-4,5,22,28-tetramethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-fluoro-4,22,28-trimethyl-5-(prop-1-en-2-yl)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-16,17-difluoro-5-(1-hydroxyethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-16,17-difluoro-5-(1-hydroxyethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-fluoro-5-(1-hydroxyethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-fluoro-5-(1-hydroxyethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-fluoro-5-(hydroxymethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-16,17-difluoro-5-(hydroxymethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-5-ethyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-fluoro-4,22,28-trimethyl-5-(propan-2-yl)-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-5-ethyl-17,18-difluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-fluoro-4,22,28-trimethyl-5-{[(propan-2-yl)amino]methyl}-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-fluoro-5-{[(2-hydroxy-2-methylpropyl)amino]methyl}-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-5-cyano-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-5-chloro-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-8-chloro-17-fluoro-5-(hydroxymethyl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-5-(difluoromethyl)-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-[(22S)-5-Acetyl-17-fluoro-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]-2-(tert-butoxy)acetic acid; and (2S)-2-(tert-Butoxy)-2-[(22S)-17-fluoro-5-(2-hydroxypropan-2-yl)-4,22,28-trimethyl-21,27-dioxa-1,7,34-triazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid or a pharmaceutically acceptable salt thereof.

11. A composition useful for treating HIV infection comprising a therapeutic amount of a compound of claim 1 and a pharmaceutically acceptable carrier.

12. A method for treating HIV infection comprising administering a therapeutically effective amount of a compound of claim 1, or a pharmaceutically acceptable salt thereof, to a patient in need thereof.

* * * * *